United States Patent
Huisman et al.

(10) Patent No.: US 10,975,367 B2
(45) Date of Patent: Apr. 13, 2021

(54) ENGINEERED PHENYLALANINE AMMONIA LYASE POLYPEPTIDES

(71) Applicant: Codexis, Inc., Redwood City, CA (US)

(72) Inventors: Gjalt W. Huisman, Redwood City, CA (US); Nicholas J. Agard, San Francisco, CA (US); Benjamin Mijts, San Carlos, CA (US); Jonathan Vroom, South San Francisco, CA (US); Xiyun Zhang, Fremont, CA (US)

(73) Assignee: Codexis, Inc., Redwood City, CA (US)

( * ) Notice: Subject to any disclaimer, the term of this patent is extended or adjusted under 35 U.S.C. 154(b) by 0 days.

(21) Appl. No.: 16/813,207

(22) Filed: Mar. 9, 2020

(65) Prior Publication Data

US 2020/0199566 A1    Jun. 25, 2020

Related U.S. Application Data

(60) Continuation of application No. 16/389,203, filed on Apr. 19, 2019, which is a continuation of application No. 16/176,896, filed on Oct. 31, 2018, now Pat. No. 10,294,468, which is a division of application No. 15/431,491, filed on Feb. 13, 2017, now Pat. No. 10,160,963, which is a division of application No. 14/255,539, filed on Apr. 17, 2014, now Pat. No. 9,611,468.

(60) Provisional application No. 61/813,586, filed on Apr. 18, 2013, provisional application No. 61/897,932, filed on Oct. 31, 2013.

(51) Int. Cl.
*C12N 9/88* (2006.01)
*A61K 38/00* (2006.01)

(52) U.S. Cl.
CPC ........ *C12N 9/88* (2013.01); *C12Y 403/01005* (2013.01); *C12Y 403/01024* (2013.01); *A61K 38/00* (2013.01)

(58) Field of Classification Search
None
See application file for complete search history.

(56) References Cited

U.S. PATENT DOCUMENTS

| | | |
|---|---|---|
| 5,605,793 A | 2/1997 | Stemmer |
| 5,753,487 A | 5/1998 | Eigtved et al. |
| 5,811,238 A | 9/1998 | Stemmer et al. |
| 5,830,721 A | 11/1998 | Stemmer et al. |
| 5,834,252 A | 11/1998 | Stemmer et al. |
| 5,837,458 A | 11/1998 | Minshull et al. |
| 5,928,905 A | 7/1999 | Stemmer et al. |
| 6,096,548 A | 8/2000 | Stemmer |
| 6,117,679 A | 9/2000 | Stemmer |
| 6,132,970 A | 10/2000 | Stemmer |
| 6,165,793 A | 12/2000 | Stemmer |
| 6,180,406 B1 | 1/2001 | Stemmer |
| 6,251,674 B1 | 6/2001 | Tobin et al. |
| 6,277,638 B1 | 8/2001 | Stemmer |
| 6,287,861 B1 | 9/2001 | Stemmer et al. |
| 6,287,862 B1 | 9/2001 | delCardayre et al. |
| 6,291,242 B1 | 9/2001 | Stemmer |
| 6,297,053 B1 | 10/2001 | Stemmer |
| 6,303,344 B1 | 10/2001 | Patten et al. |
| 6,309,883 B1 | 10/2001 | Minshull et al. |
| 6,319,713 B1 | 11/2001 | Patten et al. |
| 6,319,714 B1 | 11/2001 | Crameri et al. |
| 6,323,030 B1 | 11/2001 | Stemmer |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,344,356 B1 | 2/2002 | Stemmer |
| 6,352,859 B1 | 3/2002 | delCardayre et al. |
| 6,355,484 B1 | 3/2002 | Patten et al. |
| 6,358,740 B1 | 3/2002 | Patten et al. |
| 6,358,742 B1 | 3/2002 | Stemmer |
| 6,365,377 B1 | 4/2002 | Patten et al. |
| 6,365,408 B1 | 4/2002 | Stemmer |
| 6,368,861 B1 | 4/2002 | Crameri et al. |
| 6,372,497 B1 | 4/2002 | Stemmer |
| 6,376,246 B1 | 4/2002 | Crameri et al. |
| 6,379,964 B1 | 4/2002 | delCardayre et al. |
| 6,387,702 B1 | 5/2002 | Stemmer |
| 6,391,552 B2 | 5/2002 | Stemmer |
| 6,391,640 B1 | 5/2002 | Minshull et al. |
| 6,395,547 B1 | 5/2002 | Stemmer |
| 6,406,855 B1 | 6/2002 | Patten et al. |
| 6,406,910 B1 | 6/2002 | Patten et al. |
| 6,413,745 B1 | 7/2002 | Patten et al. |
| 6,413,774 B1 | 7/2002 | Stemmer |
| 6,420,175 B1 | 7/2002 | Stemmer |
| 6,423,542 B1 | 7/2002 | Crameri et al. |

(Continued)

FOREIGN PATENT DOCUMENTS

| | | |
|---|---|---|
| WO | 95/22625 A1 | 8/1995 |
| WO | 95/33836 A1 | 12/1995 |

(Continued)

OTHER PUBLICATIONS

Altschul, S.F., et al., "Gapped BLAST and PSI-BLAST: a new generation of protein database search programs," Nucleic Acids Res., 25(17):3389-3402 (1997).
Altschul, S., et al., "Basic local alignment search tool," J. Mol. Biol., 215: 403-410 (1990).
Ambrus, C.M., et al., "Phenylalanine depletion for the management of phenylketonuria: use of enzyme reactors with immobilized enzymes," Science, 201:837-839 [1978].

(Continued)

*Primary Examiner* — Kagnew H Gebreyesus
(74) *Attorney, Agent, or Firm* — Codexis, Inc.

(57) ABSTRACT

The present invention provides engineered phenylalanine ammonia-lyase (PAL) polypeptides and compositions thereof, as well as polynucleotides encoding the engineered phenylalanine ammonia-lyase (PAL) polypeptides.

31 Claims, 6 Drawing Sheets
Specification includes a Sequence Listing.

(56) References Cited

U.S. PATENT DOCUMENTS

| | | |
|---|---|---|
| 6,426,224 B1 | 7/2002 | Crameri et al. |
| 6,436,675 B1 | 8/2002 | Welch et al. |
| 6,444,468 B1 | 9/2002 | Stemmer et al. |
| 6,455,253 B1 | 9/2002 | Patten et al. |
| 6,479,652 B1 | 11/2002 | Crameri et al. |
| 6,482,647 B1 | 11/2002 | Stemmer |
| 6,489,146 B2 | 12/2002 | Stemmer et al. |
| 6,506,602 B1 | 1/2003 | Stemmer |
| 6,506,603 B1 | 1/2003 | Stemmer |
| 6,519,065 B1 | 2/2003 | Colbourne et al. |
| 6,521,453 B1 | 2/2003 | Crameri et al. |
| 6,528,311 B1 | 3/2003 | delCardayre et al. |
| 6,537,746 B2 | 3/2003 | Arnold et al. |
| 6,573,098 B1 | 6/2003 | Stemmer |
| 6,576,467 B1 | 6/2003 | Stemmer |
| 6,579,678 B1 | 6/2003 | Patten et al. |
| 6,586,182 B1 | 7/2003 | Patten et al. |
| 6,602,986 B1 | 8/2003 | Stemmer et al. |
| 6,613,514 B2 | 9/2003 | Patten et al. |
| 6,653,072 B1 | 11/2003 | Patten et al. |
| 6,716,631 B1 | 4/2004 | delCardayre et al. |
| 6,946,296 B2 | 9/2005 | Patten et al. |
| 6,961,664 B2 | 11/2005 | Selfinov et al. |
| 6,995,017 B1 | 2/2006 | Stemmer |
| 7,024,312 B1 | 4/2006 | Selfinov et al. |
| 7,058,515 B1 | 6/2006 | Selfinov et al. |
| 7,105,297 B2 | 9/2006 | Minshull et al. |
| 7,148,054 B2 | 12/2006 | delCardayre et al. |
| 7,288,375 B2 | 10/2007 | Stemmer et al. |
| 7,421,347 B2 | 9/2008 | Selfinov et al. |
| 7,430,477 B2 | 9/2008 | Selfinov et al. |
| 7,531,341 B1 | 5/2009 | Vellard et al. |
| 7,534,564 B2 | 5/2009 | Patten et al. |
| 7,534,595 B2 | 5/2009 | Vellard et al. |
| 7,537,923 B2 | 5/2009 | Kakkis et al. |
| 7,553,653 B2 | 6/2009 | Kakkis et al. |
| 7,560,263 B2 | 7/2009 | Kakkis et al. |
| 7,620,500 B2 | 11/2009 | Mundorff et al. |
| 7,620,502 B2 | 11/2009 | Selfinov et al. |
| 7,629,170 B2 | 12/2009 | delCardayre et al. |
| 7,702,464 B1 | 4/2010 | Emig et al. |
| 7,747,391 B2 | 6/2010 | Gustafsson et al. |
| 7,747,393 B2 | 6/2010 | Fox |
| 7,751,986 B2 | 7/2010 | Gustafsson et al. |
| 7,776,598 B2 | 8/2010 | Patten et al. |
| 7,783,428 B2 | 8/2010 | Gustafsson et al. |
| 7,790,433 B2 | 9/2010 | Kakkis et al. |
| 7,795,030 B2 | 9/2010 | Minshull et al. |
| 7,853,410 B2 | 12/2010 | Selfinov et al. |
| 7,868,138 B2 | 1/2011 | Stemmer et al. |
| 7,873,499 B2 | 1/2011 | Selfinov et al. |
| 7,904,249 B2 | 3/2011 | Selfinov et al. |
| 7,957,912 B2 | 6/2011 | Selfinov et al. |
| 8,383,346 B2 | 2/2013 | Colbeck et al. |
| 9,611,468 B2 | 4/2017 | Huisman et al. |
| 10,144,924 B2 | 12/2018 | Huisman et al. |
| 10,160,963 B2 | 12/2018 | Huisman et al. |
| 10,294,468 B2 | 5/2019 | Huisman et al. |
| 10,358,639 B2 | 7/2019 | Huisman et al. |
| 10,487,319 B2 | 11/2019 | Huisman et al. |
| 10,494,623 B2 | 12/2019 | Huisman et al. |
| 2005/0260724 A1 | 11/2005 | Ben-Bassat et al. |
| 2008/0008695 A1 | 1/2008 | Vellard et al. |
| 2008/0220990 A1 | 9/2008 | Fox |
| 2009/0312196 A1 | 12/2009 | Colbeck et al. |
| 2012/0177722 A1 | 7/2012 | Weiner et al. |
| 2013/0005012 A1 | 1/2013 | Yu |
| 2013/0039898 A1 | 2/2013 | Okhamafe et al. |
| 2013/0340119 A1 | 12/2013 | Plesch et al. |

FOREIGN PATENT DOCUMENTS

| | | |
|---|---|---|
| WO | 96/00787 A1 | 1/1996 |
| WO | 97/0078 A1 | 1/1997 |
| WO | 97/35966 A1 | 10/1997 |
| WO | 98/27230 A1 | 6/1998 |
| WO | 00/42651 A1 | 7/2000 |
| WO | 01/75767 A2 | 10/2001 |
| WO | 2003/018759 A2 | 3/2003 |
| WO | 2008/153776 A1 | 12/2008 |
| WO | 2009/152336 A1 | 12/2009 |
| WO | 2010/144103 A1 | 12/2010 |
| WO | 2011/097335 A2 | 8/2011 |
| WO | 2012/122333 A1 | 9/2012 |

OTHER PUBLICATIONS

Bartsch, S., et al., "Mutational analysis of phenylalanine ammonia lyase to improve reactions rates for various substrates," Prot. Eng. Des. Sel., 23:929-933 [2010].

Bate, N.J., et al., "Quantitative relationship between phenylalanine ammonia-lyase levels and phenylpropanoid accumulation in transgenic tobacco identifies a rate-determining step in natural product synthesis," Proc. Natl. Acad. Sci. USA, 91:7608-7612 [1994].

Beaucage, S.L., et al., "Deoxynucleoside phosphoamidites—A new class of key intermediates for deoxypolynucleotide synthesis," Tetrahedron Letters, 22(20):1859-62 (1981).

Bershtein, S., et al., "Protein Quality Control Acts on Folding Intermediates to Shape the Effects of Mutations on Organismal Fitness," Mol.Cell., 49:133-144 [2013].

Black, M.E., et al., "Creation of drug-specific herpes simplex virus type 1 thymidine kinase mutants for gene therapy," Proc Natl Acad Sci USA, 93:3525-3529 (1996).

Botstein, D., et al., "Strategies and applications of in vitro mutagenesis," Science, 229(4719):1193-1201, 1985.

Bourget, L., et al., "Artificial cell-microencapsulated phenylalanine ammonia-lyase," Appl. Biochem. Biotechnol., 10:57-59 [1984].

Carter, P., "Site-directed mutagenesis," Biochem. J., 237:1-7 (1986).

Chace, D.H., et al., "Rapid Diagnosis of Phenylketonuria by Quantitative Analysis for Phenylalanine and Tyrosine in Neonatal Blood Spots by Tandem Mass Spectrometry," Clin. Chem., 39/1:66-71 [1993].

Christians, F.C., et al., "Directed evolution of thymidine kinase for AZT phosphorylation using DNA family shuffling," Nat. Biotechnol., 17:259-264 (1999).

Crameri, A., et al., "DNA shuffling of a family of genes from diverse species accelerates directed evolution", Nature, 391:288-291 (1998).

Crameri, A., et al., "Improved green fluorescent protein by molecular evolution using DNA shuffling," Nat. Biotechnol., 14(3):315-319 (1996).

Crameri, A., et al., "Molecular evolution of an arsenate detoxification pathway by DNA shuffling," Nat. Biotechnol., 15 (5):436-438 (1997).

Dale, S.J., et al., "Oligonucleotide-directed random mutagenesis using the phosphorothioate method," Methods Mol. Biol., 57:369-74 (1996).

De Boer, H.A., et al., "The tac promoter: A functional hybrid derived from the trp and lac promoters," Proc. Natl Acad. Sci. USA, 80: 21-25 (1983).

Gloge, A., et al., "Phenylalanine ammonia-lyase: the use of its broad substrate specificity for mechanistic investigations and biocatalysis—synthesis of L-arylalanines," Chem., 6(18): 3386-3390 [2000].

Guo, Z., et al., "3'-End-Forming Signals of Yeast mRNA," Mol. Cell. Biol., 15(11):5983-5990 [1995].

Henikoff, S., et al., "Amino acid substitution matrices from protein blocks," Proc. Natl. Acad. Sci. USA, 89:10915-10919 [1992].

Ikeda, K., et al., "Phenylalanine ammonia-lyase modified with polyethylene glycol: potential therapeutic agent for phenylketonuria," Amino Acids, 29(3):283-287 [2005].

Kang, T.S., et al., "Converting an injectable protein therapeutic into an oral form: Phenylalanine ammonia lyase for phenylketonuria," Mol. Gen. Metabol., 99:4-9 [2010].

Kim, W., et al., "Trends in enzyme therapy for phenylketonuria," Molec. Therap., 10(2):220-224 [2004].

Kramer, B., et al., "Different base/base mismatches are corrected with different efficiencies by the methyl-directed DNA mismatch-repair system of E. coli," Cell, 38(3):879-887, 1984.

(56) References Cited

OTHER PUBLICATIONS

Ling, M.M., et al., "Approaches to DNA Mutagenesis: An Overview," Anal. Biochem., 254(2):157-78 [1997].
Matthes, H.W.D., et al., "Simultaneous rapid chemical synthesis of over one hundred oligonucleotides on a microscale," EMBO J., 3(4):801-05 (1984).
McDonald, J.D., et al., "Pahhph-5: a mouse mutant deficient in phenylalanine hydroxylase," Proc. Natl. Acad. Sci. USA, 87:1965-1967 [1990].
Minshull, J., et al., "Protein evolution by molecular breeding," Curr. Op. Chem. Biol., 3(3):284-290 (1999).
Nakamura, Y., et al., "Codon usage tabulated from international DNA sequence databases: status for the year 2000," Nucl. Acids Res., 28:292 [2000].
Needleman, S., et al., "A general method applicable to the search for similarities in the amino acid sequence of two proteins," J. Mol. Biol. 48:443-453 (1970).
Pearson, W.R., "Improved tools for biological sequence comparison," Proc. Nat'l. Acad. Sci. USA, 85:2444-2448 (1988).
Romanos, M.A., et al., "Foreign gene expression in yeast: a review," Yeast 8:423-488 [1992].
Sarkissian, C.N., et al., "A different approach to treatment of phenylketonuria: Phenylalanine degradation with recombinant phenylalanine ammonia lyase," Proc. Natl. Acad. Sci. USA, 96:2339-2344 [1999].
Shah, R.M., et al., "Strategies to maximize the encapsulation efficiency of phenylalanine ammonia lyase in microcapsules," Int. J. Pharmaceut., 356(102):61-68 [2008].
Simonen, M., et al., "Protein Secretion in *Bacillus* Species," Microbiological Reviews, 57:109-137 (1993).
Smith, M., "In vitro mutagenesis," Ann. Rev. Genet., 19:423-462 (1985).
Smith, T., et al., "Comparison of Biosequences," Adv. Appl. Math, 2:482-489 (1981).
Southwood, S., et al., "Several Common HLA-DR Types Share Largely Overlapping Peptide Binding Repertoires1,2," J. Immunol., 160:3363-3373 [1998].
Stemmer, W., "DNA Shuffling by Random Fragmentation and Reassembly: In vitro Recombination for Molecular Evolution," Proc. Natl. Acad. Sci. USA, 91:10747-10751 (1994).
Stemmer, W.P.C., "Rapid evolution of a protein in vitro by DNA shuffling", Nature, 370:389-391 (1994).
Turner, N.J., "Ammonia lyases and aminomutases as biocatalysts for the synthesis of alpha-amino and beta-amino acids," Curr. Opin. Chem. Biol., 15(2):234-240 [2011].
Villa-Komaroff, L., et al., "A bacterial clone synthesizing proinsulin," Proc. Natl Acad. Sci. USA, 75:3727-3731 (1978).
Vita, R., et al., "The Immune Epitope Database 2.0," Nucl. Acids Res., 38:D854-62 [2010].
Wells, J.A., et al., "Cassette mutagenesis: an efficient method for generation of multiple mutations at defined sites," Gene, 34:315-323 (1985).
Zhang, J-H., et al., "Directed evolution of a fucosidase from a galactosidase by DNA shuffling and screening ,"Proc. Nat. Acad. Sci., U.S.A., 94:4504-4509 (1997).
Zhao, H., et al., "Molecular evolution by staggered extension process (StEP) in vitro recombination," Nat. Biotechnol., 16:258-261 (1998).
NCBI Accession No. YP_001865631.1 dated Jun. 10, 2013.
NCBI Accession No. YP_007056096.1 dated Jun. 11, 2013.
NCBI Accession No. YP_007127054.1 dated Jun. 11, 2013.
NCBI Accession No. ZP_07108482.1 dated Nov. 9, 2010.
NCBI Accession No. YP_324488.1 dated Jun. 10, 2013.
Moffitt, M.G., et al., "Discovery of two cyanobacterial phenylalanine ammonia lyases: kinetic and structural characterization," Biochemistry, 46(4):1004-1012 [2007].
Sarkissian, C.N., et al., "Preclinical evaluation of multiple species of PEGylated recombinant phenylalanine ammonia lyase for the treatment of phenylketonuria," PNAS, 105(52):20897-20899 [2008].
UNIPROT Accession No. K9TV53 dated Mar. 6, 2013.

ENGINEERED PHENYLALANINE AMMONIA LYASE POLYPEPTIDES

CROSS-REFERENCE TO RELATED APPLICATIONS

The present application is a Continuation of U.S. patent application Ser. No. 16/389,203, filed Apr. 19, 2019, which is a Continuation of Ser. No. 16/176,896, filed Oct. 31, 2018, now U.S. Pat. No. 10,294,468, which is a Divisional of U.S. patent application Ser. No. 15/431,491, filed Feb. 13, 2017, now U.S. Pat. No. 10,160,963, which is a Divisional of U.S. patent application Ser. No. 14/255,539, filed Apr. 17, 2014, now U.S. Pat. No. 9,611,468, which claims priority to U.S. Prov. Pat. Appln. Ser. No. 61/813,586 filed Apr. 18, 2013, and U.S. Prov. Pat. Appln. Ser. No. 61/897,932, filed Oct. 31, 2013, all of which are incorporated by reference in their entireties for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file CX7-131US2_ST25.TXT, created on Apr. 15, 2014, 127,412 bytes, machine format IBM-PC, MS-Windows operating system, is hereby incorporated by reference.

FIELD OF THE INVENTION

The present invention provides engineered phenylalanine ammonia-lyase (PAL) polypeptides and compositions thereof, as well as polynucleotides encoding the engineered phenylalanine ammonia-lyase (PAL) polypeptides. In some embodiments, the engineered PAL polypeptides are optimized to provide enhanced catalytic activity, as well as reduced sensitivity to proteolysis and increased tolerance to acidic pH levels. In some embodiments the engineered PAL polypeptides are deimmunized. The invention also relates to the use of the compositions comprising the engineered PAL polypeptides for therapeutic and industrial purposes.

BACKGROUND OF THE INVENTION

Phenylalanine ammonia-lyase (PAL) along with histidine ammonia-lyase (HAL) and tyrosine ammonia-lyase (TAL) are members of the aromatic amino acid lyase family (EC 4.3.1.23-1.25 and 4.3.1.3). More specifically the enzymes having PAL activity (EC 4.3.1.23-1.25 and previously classified as EC4.3.1.5) catalyze the nonoxidative deamination of L-phenylalanine into (E)-cinnamic acid. PAL is a non-mammalian enzyme that is widely distributed in plants and has also been identified in fungi and a limited number of bacteria. PAL enzymes may be used as a therapeutic protein for the treatment of the metabolic disorder, phenylketonuria (PKU). PKU is an autosomal metabolic genetic disorder in which the hepatic enzyme phenylalanine hydroxylase (PAH) or one or more of the enzymes involved in the synthesis or recycling of the co-factor tetrahydrobiopterin, is nonfunctional due to a mutation in one of the corresponding genes. This lack of functionality results in high levels of phenylalanine in the bloodstream. The phenylalanine is converted into phenylpyruvate (phenylketone) and other derivatives. In humans, if PKU is not treated early, high levels of phenylalanine and some of its breakdown products can cause significant medical problems including intellectual disability, microcephaly and seizures. Numerous studies have focused on the use of PAL in the treatment of PKU by enzyme substitution (Ambrus et al., Science 201:837-839 [1978]; Bourget et al., Appl. Biochem. Biotechnol., 10:57-59 [1984]; and Sarkissian et al., Proc. Natl. Acad. Sci. USA 96:2339-2344 [1999]).

One method of detoxifying phenylalanine in the blood stream is the use of injectable recombinant PAL and PAL variants modified by pegylation (PEG-PAL). Pegylation has been shown to improve enzyme half-life and reduce subject antigenic response (See e.g., WO 2008/153776, WO 2011/097335, and U.S. Pat. No. 7,531,341). PAL variants useful in PEG-PAL compositions have been described as variants of wild-type *Nostoc punctiforme* (NpPAL); *Anabaena variabilis* (AvPAL) and *Rhodosporidium toruloides* (RtPAL). In particular, variants of wild-type AvPAL have been described wherein the cysteine residues at positions 64, 318, 503 and 565 have been substituted with serine (See e.g., U.S. Pat. Nos.: 7,790,433; 7,560,263; and 7,537,923).

An alternative route of PAL administration as a means of reducing plasma concentration of L-phenylalanine in PKU subjects is a non-invasive formulation such as an oral formulation (Sarkissian et al., Proc. Natl. Acad. Sci. USA 96:2339-2344 [1999]). A key advantage of oral delivery of PAL is the reduced exposure of the enzyme to the immune system thereby minimizing the immune response which is observed with injectable PEG-PAL. However, a major limitation for the oral formulation of PAL is loss of enzyme activity in the stomach and intestinal lumen. In order to be effective and functional PAL must resist degradation by acidic pHs and proteases such as trypsin, chymotrypsin, carboxypeptidases and pepsin that normally degrade proteinaceous foods to oligopeptides and amino acids. In some previous studies (Sarkissian, supra) in order to achieve a significant effect for the oral administration of PAL, a large amount of the enzyme was required partly due to enzymatic degradation by proteases and partly due to relatively low specific activity at pH 7.0. Various means have been explored to suppress PAL degradation upon digestion (Kim et al., Molec. Therap., 10:220-224 [2004]; and Shah et al., Int. J. Pharmaceut., 356:61-68 [2008]).

One approach to increase the effectiveness of PAL under the harsh conditions of the digestive tract is to provide engineered PAL polypeptides that are tolerant to the inherent harsh conditions. Kang et al. used site directed mutagenesis of a chymotrypsin cleavage site and pegylation of surface lysines of an AvPAL to reduce proteolytic inactivation (See, Kang et al., Mol. Gen. Metabol., 99:4-9 [2010]). In these studies ten cleavage sites were specifically mutated and all but two of these resulting mutants (F18A and R94G) lost more than 50% of the original enzyme activity. None of the mutants showed increased activity and the F18A mutant showed a slight increase in trypsin resistance (Kang et al., supra). Further studies with PAL, while effective, generally have not resulted in a longer lived enzyme. Therefore, oral administration of previously described PAL mutants and derivatives thereof does not result in effective treatment of PKU.

Despite the progress made with various formulations of PAL there remains a need for PAL polypeptides having improved properties for oral administration. These improved properties include without limitation a greater half-life, increased catalytic activity, improved stability to the conditions in the digestive track and reduced aggregation.

In addition to therapeutic applications PAL enzymes may also be used in the industrial synthesis of L-phenylalanine and other substituted L-phenylalanine derivatives. These derivatives may then be used as pharmaceutical precursors (Gloge et al., Chem., 6: 3386-3390 [2000]; Bartsch et al., Prot. Eng. Des. Sel., 23:929-933 [2010]; and Turner, Curr. Opin. Chem. Biol., 234-240 [2011]).

PAL enzymes may also be used in agricultural applications. PAL plays a significant role in biosynthesis of phenylpropanoids (such as flavonoids and lignin) in plants, fungi and bacteria and can act as a defense related enzyme (Bate et al., Proc. Natl. Acad. Sci. USA 91:7608-7612 [1994]). Modulation of PAL activity by using recombinant polypeptides having PAL activity could potentially lead to effective herbicides.

SUMMARY OF THE INVENTION

The present invention provides engineered phenylalanine ammonia-lyase (PAL) polypeptides and compositions thereof, as well as polynucleotides encoding the engineered phenylalanine ammonia-lyase (PAL) polypeptides. In some embodiments, the engineered PAL polypeptides are optimized to provide enhanced catalytic activity, as well as reduced sensitivity to proteolysis and increased tolerance to acidic pH levels. In some embodiments the engineered PAL polypeptides are deimmunized. The invention also relates to the use of the compositions comprising the engineered PAL polypeptides for therapeutic and industrial purposes. In some embodiments, the present invention is directed to engineered phenylalanine ammonia-lyase (PAL) polypeptides and biologically active fragments and analogs thereof having improved properties such an increased tolerance to acidic pH and/or reduced sensitivity to proteolysis.

The present invention is directed to engineered PAL polypeptides and biologically active fragments and analogs thereof having improved properties when compared to a wild-type PAL enzyme or a reference PAL polypeptide under essentially the same conditions. The invention is further directed to methods of using the engineered PAL polypeptides and biologically active fragments and analogs thereof in therapeutic and/or industrial compositions and methods of using such compositions for therapeutic and/or industrial purposes.

In a first aspect, the invention provides engineered phenylalanine ammonia-lyase (PAL) polypeptides wherein the engineered PAL polypeptide has an improved property selected from the group of i) enhanced catalytic activity, ii) reduced sensitivity to proteolysis, iii) increased tolerance to acidic pH, iv) reduced aggregation, or a combination of any of i), ii), iii) or iv) as compared to the reference sequence when measured under essentially the same conditions. In some specific embodiments, the engineered PAL polypeptides have two improved properties. In other specific embodiments, the improved property is reduced sensitivity to proteolysis and in yet in other specific embodiments, the improved property is increased tolerance to acidic pH.

In a second aspect, the engineered PAL polypeptides include proteins comprising at least 85% amino acid sequence identity to SEQ ID NO:4, or a functional fragment thereof and an amino acid residue difference at a position corresponding to positions X39; X91; X158; X180; X195; X243; X245; X256; X257; X270; X290; X307; X308; X326; X349; X364; X394; X399; X400; X404; X407; X443; X453; X459; X460; X463; X474; X522; X524; and X528, when optimally aligned with the polypeptide of SEQ ID NO:4.

In some specific embodiments of the first and second aspects, the engineered PAL polypeptides comprise at least an amino acid residue difference of one or more amino acid residue positions corresponding to A39; A91; Y158; S180; K195; T243; I245; A256; L257; N270; N290; H307; E308; I326; L349; L364; A394; S399; N400; P404; L407; F443; N453; Y459; T460; T463; N474; K522; T524; and P528, when optimally aligned with the polypeptide of SEQ ID NO:4. In some specific embodiments, the engineered PAL polypeptides comprise at least 2, at least 3, at least 4, at least 5, at least 6, at least 7, at least 8, at least 9, at least 10, at least 15, and at least 20 amino acid residue differences from the reference polypeptide comprising the amino acid sequence of SEQ ID NO:4.

In other specific embodiments of the first and second aspects, the engineered PAL polypeptides comprise at least 90%, (at least 91%, 92%, 93%, 94%, 95%, 96%, 97%, 98% and 99%) amino acid sequence identity to SEQ ID NO:4. In yet further specific embodiments, the engineered PAL polypeptides comprise at least 90%, (at least 91%, 92%, 93%, 94%, 95%, 96%, 97%, 98% and 99%) amino acid sequence identity to SEQ ID NO:4, and comprise one or more of the following substitutions A39V; A91V; Y158H; S180A; K195E; T243I/L; I245L; A256G; L257W/A; N270K; N290G; H307G/Q/M; E308Q; I326F; L349M; L364Q; A394V; S399N; N400K; P404A; L407V; F443H; N453G; Y459F; T460G; T463N; N474Q; K522Y/F/N; T524S; and P528L.

In other specific embodiments, the engineered PAL polypeptides are derived from a wild-type *Anabaena variabilis* PAL (such as ATCC29413; NCBI protein reference sequence YP_324488.1; SEQ ID NO:4).

In a third aspect, the engineered polypeptides having phenylalanine ammonia-lyase (PAL) activity encompassed by the invention comprises an amino acid sequence having at least 99% sequence identity to SEQ ID NO:10, or a functional fragment thereof.

In a fourth aspect, the engineered polypeptides having phenylalanine ammonia-lyase (PAL) activity encompassed by the invention comprise an amino acid sequence having at least 95% sequence identity to SEQ ID NO:10, or a functional fragment thereof and further comprising an amino acid residue difference as compared to SEQ ID NO:10, at one, two, three, four, five, or six more amino acid positions.

In a fifth aspect, the invention provides a polynucleotide sequence encoding any one of the engineered PAL polypeptides as described herein.

In a sixth aspect, the invention provides a pharmaceutical composition or an industrial composition comprising any one of the engineered PAL polypeptides as described herein.

In some embodiments, the present invention provides engineered polypeptides having phenylalanine ammonia-lyase (PAL) activity comprising a) an amino acid sequence having at least 85% sequence identity to reference sequence SEQ ID NO:4 or a functional fragment thereof; b) an amino acid residue difference as compared to SEQ ID NO:4 or the functional fragment thereof at one or more amino acid positions; and c) which exhibits an improved property selected from i) enhanced catalytic activity, ii) reduced sensitivity to proteolysis, iii) increased tolerance to acidic pH, iv) reduced aggregation or a combination of any of i), ii), iii) or iv) as compared to the reference sequence. In some embodiments, one or more amino acid positions are selected from X39; X54; X59; X73; X91; X158; X112, X134, X180; X195; X240; X243; X245; X256; X257; X270; X290; X304, X305; X307; X308; X326; X349; X353; X364; X394; X399; X400; X404; X407; X443; X453; X459; X460; X463; X474; X509; X521; X522; X524; X528; X546; X564; and/or combinations thereof when optimally aligned with the amino acid sequence of SEQ ID NO: 4. In some additional embodiments, the improved property is selected from reduced sensitivity to proteolysis and/or increased tolerance to acidic pH. In yet additional embodiments, the reference sequence is a wild-type PAL derived from *Anabaena variabilis*. In some further embodiments, the amino acid residue of the reference sequence of SEQ ID NO:4 corresponds to A39; T54; G59, S73; A91; Y158; S180; K195; A112; R134; Q240; T243; I245; A256; L257; N270; N290; Y304; R305; H307; E308; I326; L349; D353; L364; A394; S399; N400; P404; L407; F443; N453; Y459; T460; T463; N474; E509; Q521; K522; T524; P528; S546; and/or P564. In some embodiments, the amino acid residue difference as compared to SEQ ID NO:4 is selected from one or more of the following substitutions A39V; T54K; G59R; S73K; A112C; R134Q; A91V; Y158H; S180A; K195E; Q240R/W; T243I/L; I245L; A256G; L257W/A; N270K; N290G; Y304H; R305M; H307G/Q/M; E308Q; I326F; L349M; D353A/N; L364Q; A394V; S399N; N400K; P404A; L407V; F443H; N453G; Y459F; T460G; T463N; N474Q; E509L; Q521K/S; K522Y/F/N; T524S; P528L; S546R; and P564 G/L/M; when optimally aligned with the polypeptide of SEQ ID NO:4. In some further embodiments, the engineered polypeptide has at least about 90%, at least about 91%, at least about 92%, at least about 93%, at least about 94%, at least about 95%, at least about 96%, at least about 97%, at least about 98%, at least about 99%, or about 100% sequence identity to reference sequence SEQ ID NO:4. In some further embodiments, the engineered polypeptide has at least 90%, at least 91%, at least 92%, at least 93%, at least 94%, at least 95%, at least 96%, at least 97%, at least 98%, at least 99%, or 100% sequence identity to reference sequence SEQ ID NO:4. In some additional embodiments, the engineered polypeptide has at least about 90% sequence identity to reference sequence SEQ ID NO:4. In some additional embodiments, the engineered polypeptide has at least about 95% sequence identity to reference sequence SEQ ID NO:4. In some further embodiments, the engineered polypeptide has at least about 90% sequence identity to SEQ ID NO:4; and an amino acid residue difference at position H307. In some further embodiments, the engineered polypeptide has at least 90% sequence identity to reference sequence SEQ ID NO:4. In some additional embodiments, the engineered polypeptide has at least 95% sequence identity to reference sequence SEQ ID NO:4. In some further embodiments, the engineered polypeptide has at least 90% sequence identity to SEQ ID NO:4; and an amino acid residue difference at position H307. In some additional embodiments, the amino acid residue difference is H307G/Q/M. In some further embodiments, the amino acid residue difference is selected from a combination of one or more of A39; A91; Q240; A256; N290; Y304; R305; H307; D353 A394; S399; P404; L407; Q521; K522; and T524.

The present invention also provides engineered polypeptides having phenylalanine ammonia-lyase (PAL) activity comprising an amino acid sequence having at least about 90%, at least about 91%, at least about 92%, at least about 93%, at least about 94%, at least about 95%, at least about 96%, at least about 97%, at least about 98%, at least about 99%, or at least about 100% sequence identity to SEQ ID NO:6, 8, 10, 12, and/or 14, or a functional fragment thereof. In some embodiments, the engineered polypeptides having phenylalanine ammonia-lyase (PAL) activity comprise an amino acid sequence having at least about 95% sequence identity to SEQ ID NO:6, 8, 10, 12, and/or 14, or a functional fragment thereof. In some further embodiments, the engineered polypeptides having phenylalanine ammonia-lyase (PAL) activity comprise an amino acid sequence having at least about 99% sequence identity to SEQ ID NO:6, 8, 10, 12, and/or 14, or a functional fragment thereof.

The present invention also provides engineered polypeptides having phenylalanine ammonia-lyase (PAL) activity comprising an amino acid sequence having at least about at least 90%, at least 91%, at least 92%, at least 93%, at least 94%, at least 95%, at least 96%, at least 97%, at least 98%, at least 99%, or at 100% sequence identity to SEQ ID NO:6, 8, 10, 12, and/or 14, or a functional fragment thereof. In some embodiments, the engineered polypeptides having phenylalanine ammonia-lyase (PAL) activity comprise an amino acid sequence having at least about 95% sequence identity to SEQ ID NO:6, 8, 10, 12, and/or 14, or a functional fragment thereof. In some further embodiments, the engineered polypeptides having phenylalanine ammonia-lyase (PAL) activity comprise an amino acid sequence having at least about 99% sequence identity to SEQ ID NO:6, 8, 10, 12, and/or 14, or a functional fragment thereof. In some embodiments, the engineered polypeptides having phenylalanine ammonia-lyase (PAL) activity comprise an amino acid sequence having at least 95% sequence identity to SEQ ID NO:6, 8, 10, 12, and/or 14, or a functional fragment thereof. In some further embodiments, the engineered polypeptides having phenylalanine ammonia-lyase (PAL) activity comprise an amino acid sequence having at least 99% sequence identity to SEQ ID NO:6, 8, 10, 12, and/or 14, or a functional fragment thereof.

The present invention also provides engineered polypeptides having phenylalanine ammonia-lyase (PAL) activity comprising an amino acid sequence having at least about 90%, at least about 91%, at least about 92%, at least about 93%, at least about 94%, at least about 95%, at least about 96%, at least about 97%, at least about 98%, at least about 99%, or at least about 100% sequence identity to SEQ ID NO:4, or a functional fragment thereof, wherein the engineered polypeptide is deimmunized. The present invention also provides engineered polypeptides having phenylalanine ammonia-lyase (PAL) activity comprising an amino acid sequence having at least 90%, at least 91%, at least 92%, at least 93%, at least 94%, at least 95%, at least 96%, at least 97%, at least 98%, at least 99%, or 100% sequence identity to SEQ ID NO:4, or a functional fragment thereof, wherein the engineered polypeptide is deimmunized. In some embodiments, the engineered polypeptides having phenylalanine ammonia-lyase (PAL) activity comprise an amino acid sequence having at least 95% sequence identity to SEQ ID NO:4, or a functional fragment thereof, wherein the engineered polypeptide is deimmunized. In some additional embodiments, the engineered polypeptide having phenylalanine ammonia-lyase (PAL) activity is a variant PAL provided in any of Tables 9-1 through 9-7. In some embodiments, the deimmunized engineered having phenylalanine ammonia-lyase (PAL) activity comprises an amino acid sequence having at least 95% sequence identity to SEQ ID NO:6, 8, 10, 12, and/or 14.

The present invention also provides polynucleotide sequences encoding the engineered polypeptides having PAL activity provided herein. In some embodiments, the polynucleotide sequence is operably linked to a control sequence. The present invention further provides vectors comprising at least one polynucleotide sequence encoding at least on engineered polypeptide having PAL activity. The present invention also provides host cells transformed with at least one polynucleotide sequence encoding an engineered polypeptide having PAL activity, as provided herein.

The present invention further provides methods of producing an engineered PAL polypeptide in a host cell, comprising culturing a host cell comprising at least one polynucleotide encoding at least one engineered PAL polypeptide under suitable culture conditions. The present invention further provides methods of producing an engineered PAL polypeptide in a host cell, comprising culturing a host cell comprising a polynucleotide encoding the engineered PAL polypeptide under suitable culture conditions. In some embodiments, the methods further comprise recovering the engineered PAL polypeptide from the culture and/or host cells.

The present invention also provides compositions comprising at least one engineered polypeptide having PAL activity, as provided herein. In some embodiments, the composition is a pharmaceutical composition further comprising a pharmaceutically acceptable carrier. The present invention further provides uses of these compositions.

The present invention also provides engineered polypeptides having phenylalanine ammonia-lyase (PAL) activity comprising: a) an amino acid sequence having at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or greater sequence identity to a reference sequence having phenylalanine ammonia-lyase (PAL) activity, or a functional fragment thereof; b) a polypeptide sequence comprising at least one amino acid residue difference as compared to a reference sequence having phenylalanine ammonia-lyase (PAL) activity, or the functional fragment thereof at one or more amino acid positions; and c) which exhibits an improved property selected from i) enhanced catalytic activity, ii) reduced sensitivity to proteolysis, iii) increased tolerance to acidic pH, iv) reduced aggregation, v) reduced immunogenicity, or a combination of any of i), ii), iii), iv), or v), as compared to the reference sequence having phenylalanine ammonia-lyase (PAL) activity. In some embodiments, the reference sequence is a prokaryotic PAL, while in some other embodiments, the reference sequence is a eukaryotic PAL. In some embodiments, the reference sequence is a bacterial PAL (e.g., *Anabaena variabilis* PAL), while in some other embodiments it is a human or other PAL. In some further embodiments, the reference sequence is a wild-type sequence (e.g., wild-type *A. variabilis* PAL), while in some alternative embodiments, the reference sequence is a variant enzyme (e.g., an engineered polypeptide having PAL activity).

In some embodiments, the engineered polypeptides having phenylalanine ammonia-lyase (PAL) activity of the present invention comprise: a) an amino acid sequence having at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or greater sequence identity to reference sequence SEQ ID NO:4 or a functional fragment thereof; b) a polypeptide sequence comprising at least one amino acid residue difference as compared to SEQ ID NO:4, or the functional fragment thereof at one or more amino acid positions; and c) which exhibits an improved property selected from i) enhanced catalytic activity, ii) reduced sensitivity to proteolysis, iii) increased tolerance to acidic pH, iv) reduced aggregation, v) reduced immunogenicity, or a combination of any of i), ii), iii), iv), or v), as compared to the reference sequence SEQ ID NO:4.

In some additional embodiments, the engineered polypeptides having phenylalanine ammonia-lyase (PAL) activity comprise: a) an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or greater sequence identity to reference sequence SEQ ID NO:4 or a functional fragment thereof; b) a polypeptide sequence comprising at least one amino acid residue difference as compared to SEQ ID NO:4 or the functional fragment thereof at one or more amino acid positions; and c) which exhibits an improved property selected from i) enhanced catalytic activity, ii) reduced sensitivity to proteolysis, iii) increased tolerance to acidic pH, iv) reduced aggregation, v) reduced immunogenicity, or a combination of any of i), ii), iii), iv), or v), as compared to the reference sequence SEQ ID NO:4.

In some embodiments, the engineered polypeptides having phenylalanine ammonia lyase activity (PAL) comprise at least one substitution(s) at one or more of the following amino acid positions: 20, 24, 27, 39, 43, 45, 47, 54, 58, 59, 62, 70, 73, 80, 82, 91, 94, 98, 104, 105, 110, 112, 115, 117, 118, 119, 121, 123, 124, 125, 126, 127, 128, 129, 130, 131, 133, 134, 135, 139, 140, 141, 142, 143, 144, 145, 146, 147, 149, 150, 151, 153, 154, 156, 157, 158, 159, 172, 174, 175, 176, 177, 178, 180, 187, 191, 195, 199, 205, 206, 210, 212, 213, 214, 232, 240, 243, 245, 247, 248, 250, 256, 257, 266, 270, 275, 278, 279, 285, 286, 289, 290, 292, 304, 305, 307, 308, 309, 319, 321, 326, 331, 332, 334, 349, 353, 355, 364, 365, 369, 370, 371, 372, 374, 375, 377, 378, 379, 381, 382, 383, 384, 385, 387, 389, 394, 396, 399, 400, 403, 404, 407, 417, 418, 425, 431, 432, 433, 434, 435, 436, 437, 438, 439, 443, 446, 447, 453, 456, 459, 460, 461, 463, 471, 472, 473, 474, 475, 476, 477, 478, 479, 482, 483, 503, 507, 509, 521, 522, 524, 525, 528, 538, 546, 547, 551, 558, 560, 564, 565, and/or any combinations thereof, wherein the amino acid positions are numbered with reference to SEQ ID NO:4. In some embodiments, the amino acid residue of the reference sequence of SEQ ID NO:4 corresponds to A39, T54, G59, S73, A91, Y158, S180, K195, A112, R134, Q240, T243, I245, A256, L257, N270, N290, Y304, R305, H307, E308, I326, L349, D353, L364, A394, S399, N400, P404, L407, F443, N453, Y459, T460, T463, N474, E509, Q521, K522, T524, P528, S546, and/or P564. In some additional embodiments, the amino acid residue difference as compared to SEQ ID NO:4 is selected from one or more of the following substitutions A39V, T54K, G59R, S73K, A112C, R134Q, A91V, Y158H, S180A, K195E, Q240R/W, T243I/L, I245L, A256G, L257W/A, N270K, N290G, Y304H, R305M, H307G/Q/M, E308Q, I326F, L349M, D353A/N, L364Q, A394V, S399N, N400K, P404A, L407V, F443H, N453G, Y459F, T460G, T463N, N474Q, E509L, Q521K/S, K522Y/F/N, T524S, P528L, S546R, and P564 G/L/M, when optimally aligned with the polypeptide of SEQ ID NO:4. In some further embodiments, the engineered polypeptide has at least about 90% sequence identity to SEQ ID NO:4; and an amino acid residue difference at position H307. In some embodiments, the amino acid residue difference is H307G/Q/M. In some still further embodiments, the amino acid residue difference is selected from a combination of one or more of A39, A91, Q240, A256, N290, Y304, R305, H307, D353, A394, S399, P404, L407, Q521, K522, and T524. In some additional embodiments, the improved property of the engineered polypeptides having phenylalanine ammonia lyase activity (PAL) is selected from reduced sensitivity to proteolysis and/or increased tolerance to acidic pH.

The present invention also provides engineered polypeptides having phenylalanine ammonia-lyase (PAL) activity comprising: a) an amino acid sequence having at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or greater sequence identity to reference sequence SEQ ID NO:10 or a functional fragment thereof; b) a polypeptide sequence comprising at least one amino acid residue difference as compared to SEQ ID NO:10 or the functional fragment thereof at one or more amino acid positions; and c) which exhibits an improved property selected from i) enhanced catalytic activity, ii) reduced sensitivity to proteolysis, iii) increased tolerance to acidic pH, iv) reduced aggregation, v) reduced immunogenicity, or a combination of any of i), ii), iii), iv), or v), as compared to the reference sequence SEQ ID NO:10.

In some embodiments, the present invention also provides engineered polypeptides having phenylalanine ammonia-lyase (PAL) activity comprising: a) an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or greater sequence identity to reference sequence SEQ ID NO:10 or a functional fragment thereof; b) a polypeptide sequence comprising at least one amino acid residue difference as compared to SEQ ID NO:10 or the functional fragment thereof at one or more amino acid positions; and c) which exhibits an improved property selected from i) enhanced catalytic activity, ii) reduced sensitivity to proteolysis, iii) increased tolerance to acidic pH, iv) reduced aggregation, v) reduced immunogenicity, or a combination of any of i), ii), iii), iv), or v), as compared to the reference sequence SEQ ID NO:10.

In some embodiments, the present invention also provides engineered polypeptides having phenylalanine ammonia-lyase (PAL) activity comprising: a) an amino acid sequence having at least 85% sequence identity to reference sequence SEQ ID NO:10 or a functional fragment thereof; b) a polypeptide sequence comprising at least one amino acid residue difference as compared to SEQ ID NO:10 or the functional fragment thereof at one or more amino acid positions; and c) which exhibits an improved property selected from i) enhanced catalytic activity, ii) reduced sensitivity to proteolysis, iii) increased tolerance to acidic pH, iv) reduced aggregation, v) reduced immunogenicity, or a combination of any of i), ii), iii), iv), or v), as compared to the reference sequence SEQ ID NO:10.

In some embodiments, the present invention also provide engineered polypeptides having phenylalanine ammonia-lyase (PAL) activity comprising an amino acid sequence having at least 85% sequence identity to reference sequence SEQ ID NO:10 and at least one amino acid residue difference as compared to SEQ ID NO:10 and that exhibits at least one improved property selected from enhanced catalytic activity, reduced sensitivity to proteolysis, increased tolerance to acidic pH, reduced aggregation, and/or reduced immunogenicity, as compared to the SEQ ID NO:10.

In some embodiments, the present invention also provides engineered polypeptides having phenylalanine ammonia-lyase (PAL) activity, wherein the amino acid residue difference as compared to SEQ ID NO:10, is selected from one or more of the following substitutions or substitution sets: I27E/V39A; I27E/V39A/R43L/V105C/A153R/L214E/P266H/L278D/C503Q; I27E/V39A/R43L/L214E/A547D; I27E/V39A/V105C/A112C/R134Q/L214E/L278D/C503Q/A547D/C565N; I27E/V39A/V105C/A112C/R134Q/A547D/C565N; I27E/V39A/V105C/A112C/R134Q/A153R/Q205T/L214E/P266H/L278D/C503Q/A551D; I27E/V39A/V105C/A112C/Q205T/P210C/P266H/C503Q/A547D; I27E/V39A/V105C/A112C/Q205T/P266H/I285E/C503Q/A551D; I27E/V39A/V105C/A112C/L214E/I285E/C503Q/A547D; I27E/V39A/V105C/S131N/R134Q/Q205T/L214E/C503Q/A547D/C565N; I27E/V39A/V105C/R134Q/A153R/P210C/L278D/I285E/C503Q/A547D/A551D; I27E/V39A/V105C/R134Q/Q205T/P210C/L278D/C503Q/A547D; I27E/V39A/V105C/R134Q/Q205T/L214E; I27E/V39A/V105C/R134Q/Q205T/L214E/A551D/C565N; I27E/V39A/V105C/R134Q/Q205T/L278D/I285E/C503Q/A547D/A551D/C565N; I27E/V39A/V105C/R134Q/P210C; I27E/V39A/V105C/R134Q/P210C/L214E; I27E/V39A/V105C/R134Q/P210C/L214E/I285E/A547D; I27E/V39A/V105C/R134Q/P210C/L214E/C503Q/A551D/C565N; I27E/V39A/V105C/R134Q/L214E/L278D/A547D/A551D; I27E/V39A/V105C/R134Q/L214E/I285E/C503Q/A547D/A551D; I27E/V39A/V105C/R134Q/P266H/C503Q; I27E/V39A/V105C/R134Q/P266H/C503Q/A547D/A551D; I27E/V39A/V105C/R134Q/L278D/C503Q/C565N; I27E/V39A/V105C/R134Q/L278D/I285E/C503Q; I27E/V39A/V105C/R134Q/L278D/A551D; I27E/V39A/V105C/R134Q/I285E/A547D/A551D; I27E/V39A/V105C/R134Q/C503Q/A551D; I27E/V39A/V105C/A153R/Q205T/L278D/C503Q/A547D/A551D; I27E/V39A/V105C/A153R/L214E; I27E/V39A/V105C/A153R/I285E; I27E/V39A/V105C/A153R/C503Q/A547D/C565N; I27E/V39A/V105C/A153R/A551D/C565N; I27E/V39A/V105C/Q205T/P210C/L214E/L278D/A547D; I27E/V39A/V105C/Q205T/P210C/L278D/C503Q; I27E/V39A/V105C/Q205T/P210C/L278D/A547D; I27E/V39A/V105C/Q205T/L214E/L278D/C503Q/A547D; I27E/V39A/V105C/Q205T/L278D/C503Q/A547D; I27E/V39A/V105C/P210C/I285E/C503Q/A547D/A551D/C565N; I27E/V39A/V105C/P210C/L214E/P266H/L278D; I27E/V39A/V105C/L214E/P266H/C503Q/A547D/C565N; I27E/V39A/V105C/L214E/L278D/L309P/C503Q/A547D/A551D; I27E/V39A/V105C/L278D/C503Q/A547D/C565N; I27E/V39A/V105C/I285E/A547D; I27E/V39A/V105C/C503Q/A551D; I27E/V39A/V105C/C503Q/A547D/A551D/C565N; I27E/V39A/A112C/R134Q/Q205T/P210C/L214E/A551D/C565N; I27E/V39A/A112C/R134Q/L214E/P266H/A551D; I27E/V39A/A112C/R134Q/L214E/C503Q/A547D; I27E/V39A/A112C/R134Q/P266H/I285E; I27E/V39A/A112C/Q205T/L214E/P266H/C503Q/A551D/C565N; I27E/V39A/A112C/Q205T/L278D/I285E; I27E/V39A/A112C/L214E; I27E/V39A/A112C/L214E/L278D/C503Q/A547D/A551D; I27E/V39A/A112C/I285E; I27E/V39A/A112C/A547D; I27E/V39A/R134Q; I27E/V39A/R134Q/A153R/Q205T/L214E/P266H/C503Q; I27E/V39A/R134Q/A153R/P210C/L214E/L278D/I285E/A547D/C565N; I27E/V39A/R134Q/A153R/L214E/P266H/L278D/C503Q/A547D/C565N; I27E/V39A/R134Q/A153G/L214E/P266H/I285E/C503Q/A551D/C565N; I27E/V39A/R134Q/A153R/L214E/C503Q/A547D; I27E/V39A/R134Q/A153R/L278D; I27E/V39A/R134Q/A153R/L278D/A547D/A551D; I27E/V39A/R134Q/A153R/A547D; I27E/V39A/R134Q/Q205T/L214E/P266H/I285E/C503Q/A551D/C565N; I27E/V39A/R134Q/Q205T/P266H/C503Q/A551D/C565N; I27E/V39A/R134Q/P210C/L214E/C503Q; I27E/V39A/R134Q/P210C/C503Q/A551D; I27E/V39A/R134Q/L214E/P266H/A551D; I27E/V39A/R134Q/L278D/I285E/C503Q/A547D/A551D; I27E/V39A/R134Q/L278D/C503Q/A547D; I27E/V39A/

R134Q/C503Q/A547D; I27E/V39A/R134Q/A547D/C565N; I27E/V39A/Q205T/L214E/C503Q/C565N; I27E/V39A/Q205T/P266H/I285E/A547D/A551D/C565N; I27E/V39A/Q205T/P266H/A551D; I27E/V39A/Q205T/L278D/C503Q/A551D/C565N; I27E/V39A/Q205T/L278D/C503Q/C565N; I27E/V39A/Q205T/C503Q/A547D/C565N; I27E/V39A/P210C/T212S; I27E/V39A/P210C/L214E/L278D/C503Q/A551D; I27E/V39A/P210C/L214E/I285E/C503Q/A551D; I27E/V39A/P210C/P266H/I285E/C503Q/A547D; I27E/V39A/P210C/P266H/C503Q/A551D; I27E/V39A/L214E; I27E/V39A/L214E/P266H/L278D/C503Q/A547D/A551D/C565N; I27E/V39A/L214E/L278D/C503Q; I27E/V39A/L214E/L278D/C503Q/A547D/C565N; I27E/V39A/L214E/C503Q/A551D; I27E/V39A/P266H; I27E/V39A/P266H/L278D; I27E/V39A/L278D; I27E/V39A/L278D/A547D; I27E/V39A/L278D/I285E/C503Q/A547D; I27E/V39A/L278D/C503Q/C565N; I27E/V39A/C503Q; I27E/G45D/Q205T/P266H/C565N; I27E/V105C; I27E/V105C/R134Q/A153R/P210C/L214E/C503Q/A547D; I27E/V105C/R134Q/A153R/I285E/A547D; I27E/V105C/R134Q/A153R/C503Q; I27E/V105C/R134Q/Q205T/P210C/C503Q; I27E/V105C/R134Q/Q205T/L214E/P266H/L278D/C503Q/C565N; I27E/V105C/Q205T/P266H/C503Q; I27E/V105C/R134Q/P210C/L214E/P266H/L278D/A551D/C565N; I27E/V105C/R134Q/P210C/L214E/C503Q/A551D/C565N; I27E/V105C/R134Q/P210C/P266H/L278D/I285E/C503Q/A551D/C565N; I27E/V105C/R134Q/L214E/L278D/C503Q/A547D; I27E/V105C/R134Q/L214E/L278D/C503Q/A547D/A551D/C565N; I27E/V105C/Q205T; I27E/V105C/Q205T/L214E/P266H; I27E/V105C/Q205T/L214E/P266H/A551D/C565N; I27E/V105C/Q205T/L214E/L278D/I285E/C503Q/A547D/A551D/C565N; I27E/V105C/Q205T/C503Q/A547D/A551D/C565N; I27E/V105C/L214E; I27E/V105C/L214E/P266H/C503Q; I27E/V105C/L214E/I285E/A551D/C565N; I27E/V105C/L214E/A547D/A551D/C565N; I27E/V105C/L214E/A551D/C565N; I27E/V105C/P266H; I27E/V105C/P266H/I285E/C503Q/A547D/C565N; I27E/V105C/L278D/A547D; I27E/V105C/I285E/C503Q/A547D/A551D/C565N; I27E/V105C/C503Q/A547D/C565N; I27E/V105C/C503Q/A547D/A551D/C565N; I27E/A112C/R134Q/A153R/L214E/P266H/C503Q; I27E/A112C/R134Q/L278D/I285E/C503Q/A551D/C565N; I27E/A112C/R134Q/Q205T/L278D/C503Q; I27E/A112C/R134Q/Q205T/I285E/C503Q; I27E/A112C/Q205T/P266H/L278D/I285E/C503Q; I27E/A112C/P210C/L214E/C503Q/A547D; I27E/R134Q; I27E/R134Q/A153R/I285E/C503Q/A547D; I27E/R134Q/Q205T/I285E/C503Q/A551D; I27E/R134Q/Q205T/P266H/L278D/A547D; I27E/R134Q/P210C; I27E/R134Q/L214E/C503Q; I27E/R134Q/L214E/C503Q/A547D; I27E/R134Q/L214E/C503Q/A547D/A551D; I27E/R134Q/L214E/C503Q/C565N; I27E/R134Q/L278D/I285E/A551D/C565N; I27E/R134Q/I285E/C503Q; I27E/A153R/L214E/L278D/I285E/A551D/C565N; I27E/A153R/L214E/L278D/A551D; I27E/Q205T; I27E/Q205T/L214E/L278D/I285E/C503Q/C565N; I27E/Q205T/L214E/C503Q/A547D/C565N; I27E/Q205T/P266H/L278D/I285E/A551D/C565N; I27E/Q205T/L278D/A551D; I27E/P210C; I27E/P210C/L214E/C503Q/A547D; I27E/P210C/L278D/C503Q; I27E/P210C/C503Q; I27E/P210C/C503Q/C565N; I27E/P210C/A551D; I27E/L214E; I27E/L214E/P266H/L278D/I285E/A551D; I27E/L214E/L278D; I27E/L214E/L278D/C503Q; I27E/L214E/C503Q; I27E/L214E/C503Q/A547D; I27E/L214E/C503Q/A547D/C565N; I27E/L214E/A551D; I27E/P266H/L278D/C503Q; I27E/P266H/A547D/A551D; I27E/L278D/C503Q/A551D; I27E/L278D/C503Q/A551D/C565N; I27E/A547D/C565N; V39A/G45S/L278D/C503Q/A551D; V39A/V105C/R134Q/A153R/Q205T/A551D; V39A/V105C/R134Q/P210C/L214E/A551D; V39A/V105C/R134Q/L214E/C503Q/A547D/A551D; V39A/V105C/A153R/P266H/A547D/A551D; V39A/V105C/Q205T/C503Q; V39A/V105C/Q205T/A551D; V39A/V105C/P210C/A547D; V39A/V105C/L214E/P266H/A547D/C565N; V39A/V105C/L214E/I285E/C503Q/A551D/C565N; V39A/A112C/R134Q/Q205T/L214E/L278D; V39A/A112C/R134Q/L214E/C503Q/A547D/A551D; V39A/A112C/A153R/Q205T/L278D/C503Q/A547D; V39A/R134Q; V39A/R134Q/Q205T/L214E/C503Q/C565N; V39A/R134Q/P210C/L214E/A547D/C565N; V39A/A153R/C503Q/A547D; V39A/Q205T/L278D/A547D/A551D; V39A/P210C/L214E/L278D/I285E/C503Q/A551D; V39A/P266H; V39A/P275R/L278D/C503Q/A551D; V39A/C503Q; V39A/C503Q/A551D/C565N; V105C; V105C/A112C/R134Q/Q205T/L214E/Y492H/C503Q/A547D; V105C/R134Q/A153R/Q205T/L214E/C503Q; V105C/R134Q/Q205T/L214E/A547D; V105C/R134Q/Q205T/P266H/L278D; V105C/R134Q/L214E/P266H/I285E/C503Q/A551D/C565N; V105C/R134Q/L214E/L278D/C565N; V105C/R134Q/L214E/C503Q/A547D; V105C/R134Q/L214E/C503Q/A547D/A551D; V105C/R134Q/C503Q; V105C/R134Q/C503Q/A547D; V105C/R134Q/C503Q/A547D/C565N; V105C/A153R/Q205T/L214E/P266H/C503Q/A547D; V105C/A153R/Q205T/P266H/I285E/A547D/C565N; V105C/Q205T/P210C/L214E/C503Q/A547D; V105C/Q205T/L214E/L278D; V105C/Q205T/L214E/C503Q/A547D/A551D/C565N; V105C/Q205T/C503Q/A551D; V105C/L214E/P266H/L278D/A547D; V105C/L214E/L278D/C503Q/A547D/A551D; V105C/L214E/I285E; V105C/L214E/I285E/C503Q/A547D/A551D/C565N; V105C/L214E/I285E/A547D/C565N; V105C/L278D/C503Q/A551D; V105C/I285E; V105C/I285E/A547D; V105C/C503Q; V105C/A547D/A551D; A112C/R134Q/A153R/L214E/L278D/I285E/C503Q/A547D/A551D/C565N; A112C/R134Q/L214E/C503Q/A547D/A551D/C565N; A112C/L214E/L278D; A112C/L278D/C503Q/A547D; R134Q/Q205T/L214E/I285E/C503Q/A551D/C565N; R134Q/Q205T/C503Q; R134Q/P210C/L214E/L278D/C503Q/A547D/C565N; R134Q/P210C/L214E/C503Q/A547D/A551D; R134Q/L214E; R134Q/L214E/L278D/C503Q; R134Q/L214E/L278D/C503Q/A551D; R134Q/L214E/I285E/C503Q; R134Q/C503Q; R134Q/C503Q/A547D/A551D; A153R; Q205T/L214E/I285E/C503Q/A551D; Q205T/L214E/I285E/C503Q/C565N; Q205T/L214E/C503Q/A547D/C565N; Q205T/L278D/I285E/A547D/A551D; P210C/L214E; P210C/L214E/P266H; L214E/P266H; L214E/P266H/C503Q/A547D/A551D/C565N; L214E/C503Q/A547D; L214E/A547D; P266H/L278D/C503Q; P266H/C565N; L278D/A547D/C503Q; C503Q/A547D; C503Q/A547D/A551D/C565N; C503Q/A547D/C565N; C503Q/A551D; C503Q/A551D/C565N; A547D; and/or C565N.

In some additional embodiments, the present invention also provides engineered polypeptides having phenylalanine ammonia-lyase (PAL) activity, wherein the amino acid residue difference as compared to SEQ ID NO:10, is selected from one or more of the following substitutions or substitution sets: V80I/R134C/P564Q; V121C; A123G; A124G; M125L; L126I/T; L126M/R134L; L127A; A129G/L; N130Q; N130C/M370I R134W; M133R; R134I; R134N/G307C; G135C/S; and/or G135A/A394E.

In some additional embodiments, the present invention also provides engineered polypeptides having phenylalanine ammonia-lyase (PAL) activity, wherein the amino acid residue difference as compared to SEQ ID NO:10, is selected from one or more of the following substitutions or substitution sets: G20S/I144L; R43S; L47M/I144L; L47M/R146E; L47M/M147G/A383E; L47M/P157C; Q58H/L143V; Q58K/P157D/G369C; A62S/M147V; S82I/G135C/P157F/W279L; R94C/I149E; T110I/I139R; L118M/L141H; A119E/T156H/A289D; I139M/V; R140D/G/M; R140N/A199E; R140E/A334S/A551D; L141K/Q/P/T; E142H/P/V; E142D/G371D; L143F/M; I144L/N/V; K145N/Q/R; K145G/P157T; R146H/L; R146W/D191Y; M147A; I149L/R; F150K/L/M; L151M; A153C/G; A153S/H250N; G154R; G154Y/L174M/Q321K/S456I/G483C; T156K/G483C; P157D/F/H/Y; Y158E; V159C/H/L/M; M247I; L319M; and/or Q389K.

In still some additional embodiments, the present invention also provides engineered polypeptides having phenylalanine ammonia-lyase (PAL) activity, wherein the amino acid residue difference as compared to SEQ ID NO:10, is selected from one or more of the following substitutions or substitution sets: P117T/Y176Q; V172I/C/L; L174M; S175G; Y176E/I/M/R/V; I177M/V; T178L/A477S; and/or S180C/T.

In some additional embodiments, the present invention also provides engineered polypeptides having phenylalanine ammonia-lyase (PAL) activity, wherein the amino acid residue difference as compared to SEQ ID NO:10, is selected from one or more of the following substitutions or substitution sets: R43S/H374K; R43S/H374R; A112S/M370A/A507E; M147I/H374S; S187R/L381V; D191Y/H385N; A232S; Q240K/H374R; A256S/L381N; P275Q/M370S; P275T/H374R; Q332K/Y377M; A334S/H374V; L349M; Q355K/H374S; M370G/I/S; G371H/N/Q/S; M372A/V; H374A/D/G/L/N/R/S/T; H374Q/P396Q; H374R/G417C; L375I; L375M; Y377C/I/N; Y378C/D/E/I/L/N/S; Y378F/P404Q; I379C/H/L/M/N; L381G/V; L381M/Q560K; L382C/H/I/M/S; A383S/V; K384R; H385C/G/N; H385M/P403H; H385S/P403H; D387S; L418M; G425V; A447S; S461G; and/or S525L.

In some additional embodiments, the present invention also provides engineered polypeptides having phenylalanine ammonia-lyase (PAL) activity, wherein the amino acid residue difference as compared to SEQ ID NO:10, is selected from one or more of the following substitutions or substitution sets: A24S/F434M; A62S/T433N; S98I; L213M/S438L; Q240K/T433Y; S286R/Y435T; A289S/L431E; S331I; L431C/E/G/P/S/V; L432C/V; T433A/I/L/N/P/Q/R/S/V/W; F434C; Y435L; Y435Q/H446N; G436M; G436D/T; N437E/G/Q; N437T/L538M; S438C/F/M/R/T; I439C/F/L/V; and/or A477S.

In some additional embodiments, the present invention also provides engineered polypeptides having phenylalanine ammonia-lyase (PAL) activity, wherein the amino acid residue difference as compared to SEQ ID NO:10, is selected from one or more of the following substitutions or substitution sets: A24E; Q58R/Y475H; A70S/N474E; L104M/V476L; A119E/G365A; L206M; P275Q; G276V; Q292H/A479G; Q355H/I478C; P404T/A477V; I471F/G/K/M/N/R/V/W; F472G; Q473H/K/M/R/S; Q473H/A507S; N474A/H/R/W; N474D/R490H; Y475C/F/L/Q; V476C/I/L; I478N/S; A479G/S; F482C/L; G483C/H/S; G483A/S524I; G483R/G537C; and/or A558S.

In some additional embodiments, the present invention also provides engineered polypeptides having phenylalanine ammonia-lyase (PAL) activity, wherein the amino acid residue difference as compared to SEQ ID NO:10, is selected from one or more of the following substitutions or substitution sets: V39A/K115E/M133R/C565N; V39A/M133R/F472G/C503Q/C565N; V39A/M133R/F472G/C565N; V39A/M133R/C503Q; V39A/M133R/C503Q/C565N; V39A/M147A/Y378E/C503Q/C565N; V39A/M147A/Y378E/C565N; V39A/M147A/L381F/F472G/C503Q/C565N; V39A/M147A/L381G/C503Q/C565N; V39A/M147A/F472G/C503Q/C565N; V39A/M147A/F472G/C565N; V39A/M147A/C565N; V39A/G248C/L381G/F472G/C503Q/C565N; V39A/Y378E/C503Q/C565N; V39A/Y378E/C565N; V39A/L381G; V39A/F472G/C503Q/C565N; V39A/C503Q/C565N; M133R/L381G/C565N; M133R/C503Q; Y378D/C503Q; Y378E/F472G/C503Q/C565N; L381G/F472GC503Q/C565N; and/or F472G/C503Q/C565N.

In still some further embodiments, the present invention also provides engineered polypeptides having phenylalanine ammonia-lyase (PAL) activity, wherein the amino acid residue difference as compared to SEQ ID NO:10, is selected from one or more of the following substitutions or substitution sets: I27E/V39A; I27E/V39A/R43L/V105C/A153R/L214E/P266H/L278D/C503Q; I27E/V39A/R43L/L214E/A547D; I27E/V39A/V105C/A112C/R134Q/L214E/L278D/C503Q/A547D/C565N; I27E/V39A/V105C/A112C/R134Q/A153R/Q205T/L214E/P266H/L278D/C503Q/A551D; I27E/V39A/V105C/A112C/Q205T/P210C/P266H/C503Q/A547D; I27E/V39A/V105C/A112C/Q205T/P266H/I285E/C503Q/A551D; I27E/V39A/V105C/A112C/L214E/I285E/C503Q/A547D; I27E/V39A/V105C/S131N/R134Q/Q205T/L214E/C503Q/A547D/C565N; I27E/V39A/V105C/R134Q/A153R/P210C/L278D/I285E/C503Q/A547D/A551D; I27E/V39A/V105C/R134Q/Q205T/P210C/L278D/C503Q/A547D; I27E/V39A/V105C/R134Q/Q205T/L214E; I27E/V39A/V105C/R134Q/Q205T/L214E/A551D/C565N; I27E/V39A/V105C/R134Q/Q205T/L278D/I285E/C503Q/A547D/A551D/C565N; I27E/V39A/V105C/R134Q/P210C; I27E/V39A/V105C/R134Q/P210C/L214E; I27E/V39A/V105C/R134Q/P210C/L214E/I285E/A547D; I27E/V39A/V105C/R134Q/P210C/L214E/C503Q/A551D/C565N; I27E/V39A/V105C/R134Q/L214E/L278D/A547D/A551D; I27E/V39A/V105C/R134Q/L214E/I285E/C503Q/A547D/A551D; I27E/V39A/V105C/R134Q/P266H/C503Q; I27E/V39A/V105C/R134Q/P266H/C503Q/A547D/A551D; I27E/V39A/V105C/R134Q/L278D/C503Q/C565N; I27E/V39A/V105C/R134Q/L278D/I285E/C503Q; I27E/V39A/V105C/R134Q/L278D/A551D; I27E/V39A/V105C/R134Q/I285E/A547D/A551D; I27E/V39A/V105C/R134Q/C503Q/A551D; I27E/V39A/V105C/A153R/Q205T/L278D/C503Q/A547D/A551D; I27E/V39A/V105C/A153R/L214E; I27E/V39A/V105C/A153R/I285E; I27E/V39A/V105C/A153R/C503Q/A547D/C565N; I27E/V39A/V105C/A153R/A551D/C565N; I27E/V39A/V105C/Q205T/P210C/L214E/L278D/A547D; I27E/V39A/V105C/Q205T/P210C/L278D/C503Q; I27E/V39A/V105C/Q205T/P210C/L278D/A547D; I27E/V39A/V105C/Q205T/L214E/L278D/C503Q/A547D; I27E/V39A/V105C/Q205T/L278D/C503Q/A547D; I27E/V39A/V105C/P210C/I285E/C503Q/A547D/A551D/C565N; I27E/V39A/V105C/P210C/L214E/P266H/L278D; I27E/V39A/V105C/L214E/P266H/C503Q/A547D/C565N; I27E/V39A/V105C/L214E/L278D/L309P/C503Q/A547D/A551D; I27E/V39A/V105C/L278D/C503Q/A547D/C565N; I27E/V39A/V105C/I285E/A547D; I27E/V39A/V105C/C503Q/A551D; I27E/V39A/V105C/C503Q/A547D/A551D/C565N; I27E/V39A/A112C/R134Q/Q205T/P210C/L214E/A551D/C565N; I27E/V39A/A112C/R134Q/L214E/P266H/A551D; I27E/V39A/A112C/R134Q/L214E/C503Q/A547D; I27E/V39A/A112C/R134Q/P266H/I285E; I27E/V39A/A112C/Q205T/

L214E/P266H/C503Q/A551D/C565N; I27E/V39A/A112C/ Q205T/L278D/I285E; I27E/V39A/A112C/L214E; I27E/ V39A/A112C/L214E/L278D/C503Q/A547D/A551D; I27E/ V39A/A112C/I285E; I27E/V39A/A112C/A547D; I27E/ V39A/R134Q; I27E/V39A/R134Q/A153R/Q205T/L214E/ P266H/C503Q; I27E/V39A/R134Q/A153R/P210C/L214E/ L278D/I285E/A547D/C565N; I27E/V39A/R134Q/A153R/ L214E/P266H/L278D/C503Q/A547D/C565N; I27E/V39A/ R134Q/A153G/L214E/P266H/I285E/C503Q/A551D/ C565N; I27E/V39A/R134Q/A153R/L214E/C503Q/ A547D; I27E/V39A/R134Q/A153R/L278D; I27E/V39A/ R134Q/A153R/L278D/A547D/A551D; I27E/V39A/ R134Q/A153R/A547D; I27E/V39A/R134Q/Q205T/L214E/ P266H/I285E/C503Q/A551D/C565N; I27E/V39A/R134Q/ Q205T/P266H/C503Q/A551D/C565N; I27E/V39A/ R134Q/P210C/L214E/C503Q; I27E/V39A/R134Q/P210C/ C503Q/A551D; I27E/V39A/R134Q/L214E/P266H/A551D; I27E/V39A/R134Q/L278D/I285E/C503Q/A547D/A551D; I27E/V39A/R134Q/L278D/C503Q/A547D; I27E/V39A/ R134Q/C503Q/A547D; I27E/V39A/R134Q/A547D/ C565N; I27E/V39A/Q205T/L214E/C503Q/C565N; I27E/ V39A/Q205T/P266H/I285E/A547D/A551D/C565N; I27E/ V39A/Q205T/P266H/A551D; I27E/V39A/Q205T/L278D/ C503Q/A551D/C565N; I27E/V39A/Q205T/L278D/ C503Q/C565N; I27E/V39A/Q205T/C503Q/A547D/ C565N; I27E/V39A/P210C/T212S; I27E/V39A/P210C/ L214E/L278D/C503Q/A551D; I27E/V39A/P210C/L214E/ I285E/C503Q/A551D; I27E/V39A/P210C/P266H/I285E/ C503Q/A547D; I27E/V39A/P210C/P266H/C503Q/A551D; I27E/V39A/L214E; I27E/V39A/L214E/P266H/L278D/ C503Q/A547D/A551D/C565N; I27E/V39A/L214E/ L278D/C503Q; I27E/V39A/L214E/L278D/C503Q/A547D/ C565N; I27E/V39A/L214E/C503Q/A551D; I27E/V39A/ P266H; I27E/V39A/P266H/L278D; I27E/V39A/L278D; I27E/V39A/L278D/A547D; I27E/V39A/L278D/I285E/ C503Q/A547D; I27E/V39A/L278D/C503Q/C565N; I27E/ V39A/C503Q; I27E/G45D/Q205T/P266H/C565N; I27E/ V105C; I27E/V105C/R134Q/A153R/P210C/L214E/ C503Q/A547D; I27E/V105C/R134Q/A153R/I285E/ A547D; I27E/V105C/R134Q/A153R/C503Q; I27E/V105C/ R134Q/Q205T/P210C/C503Q; I27E/V105C/R134Q/ Q205T/L214E/P266H/L278D/C503Q/C565N; I27E/ V105C/Q205T/P266H/C503Q; I27E/V105C/R134Q/ P210C/L214E/P266H/L278D/A551D/C565N; I27E/ V105C/R134Q/P210C/L214E/C503Q/A551D/C565N; I27E/V105C/R134Q/P210C/P266H/L278D/I285E/C503Q/ A551D/C565N; I27E/V105C/R134Q/L214E/L278D/ C503Q/A547D; I27E/V105C/R134Q/L214E/L278D/ C503Q/A547D/A551D/C565N; I27E/V105C/Q205T; I27E/ V105C/Q205T/L214E/P266H; I27E/V105C/Q205T/ L214E/P266H/A551D/C565N; I27E/V105C/Q205T/ L214E/L278D/I285E/C503Q/A547D/A551D/C565N; I27E/V105C/Q205T/C503Q/A547D/A551D/C565N; I27E/ V105C/L214E; I27E/V105C/L214E/P266H/C503Q; I27E/ V105C/L214E/I285E/A551D/C565N; I27E/V105C/L214E/ A547D/A551D/C565N; I27E/V105C/L214E/A551D/ C565N; I27E/V105C/P266H; I27E/V105C/P266H/I285E/ C503Q/A547D/C565N; I27E/V105C/L278D/A547D; I27E/ V105C/I285E/C503Q/A547D/A551D/C565N; I27E/ V105C/C503Q/A547D/C565N; I27E/V105C/C503Q/ A547D/A551D/C565N; I27E/A112C/R134Q/A153R/ L214E/P266H/C503Q; I27E/A112C/R134Q/L278D/I285E/ C503Q/A551D/C565N; I27E/A112C/L214E/Q205T/ L278D/C503Q; I27E/A112C/R134Q/Q205T/I285E/C503Q; I27E/A112C/Q205T/P266H/L278D/I285E/C503Q; I27E/ A112C/P210C/L214E/C503Q/A547D; I27E/R134Q; I27E/ R134Q/A153R/C503Q/A547D; I27E/R134Q/ Q205T/I285E/C503Q/A551D; I27E/R134Q/Q205T/P266H/ L278D/A547D; I27E/R134Q/P210C; I27E/R134Q/L214E/ C503Q; I27E/R134Q/L214E/C503Q/A547D; I27E/R134Q/ L214E/C503Q/A547D/A551D; I27E/R134Q/L214E/ C503Q/C565N; I27E/R134Q/L278D/I285E/A551D/ C565N; I27E/R134Q/I285E/C503Q; I27E/A153R/L214E/ L278D/I285E/A551D/C565N; I27E/A153R/L214E/L278D/ A551D; I27E/Q205T; I27E/Q205T/L214E/L278D/I285E/ C503Q/C565N; I27E/Q205T/L214E/C503Q/A547D/ C565N; I27E/Q205T/P266H/L278D/I285E/A551D/C565N; I27E/Q205T/L278D/A551D; I27E/P210C; I27E/P210C/ L214E/C503Q/A547D; I27E/P210C/L278D/C503Q; I27E/ P210C/C503Q; I27E/P210C/C503Q/C565N; I27E/P210C/ A551D; I27E/L214E; I27E/L214E/P266H/L278D/I285E/ A551D; I27E/L214E/L278D; I27E/L214E/L278D/C503Q; I27E/L214E/C503Q; I27E/L214E/C503Q/A547D; I27E/ L214E/C503Q/A547D/C565N; I27E/L214E/A551D; I27E/ P266H/L278D/C503Q; I27E/P266H/A547D/A551D; I27E/ L278D/C503Q/A551D; I27E/L278D/C503Q/A551D/ C565N; I27E/A547D/C565N; V39A/G45S/L278D/C503Q/ A551D; V39A/V105C/R134Q/A153R/Q205T/A551D; V39A/V105C/R134Q/P210C/L214E/A551D; V39A/ V105C/R134Q/L214E/C503Q/A547D/A551D; V39A/ V105C/A153R/P266H/A547D/A551D; V39A/V105C/ Q205T/C503Q; V39A/V105C/Q205T/A551D; V39A/ V105C/P210C/A547D; V39A/V105C/L214E/P266H/ A547D/C565N; V39A/V105C/L214E/I285E/C503Q/ A551D/C565N; V39A/A112C/R134Q/Q205T/L214E/ L278D; V39A/A112C/L214E/C503Q/A547D/ A551D; V39A/A112C/A153R/Q205T/L278D/C503Q/ A547D; V39A/R134Q; V39A/R134Q/Q205T/L214E/ C503Q/C565N; V39A/R134Q/P210C/L214E/A547D/ C565N; V39A/A153R/C503Q/A547D; V39A/Q205T/ L278D/A547D/A551D; V39A/P210C/L214E/L278D/ I285E/C503Q/A551D; V39A/P266H; V39A/P275R/ L278D/A551D; V39A/C503Q; V39A/C503Q/ A551D/C565N; V105C; V105C/A112C/R134Q/Q205T/ L214E/Y492H/C503Q/A547D; V105C/R134Q/A153R/ Q205T/L214E/C503Q; V105C/R134Q/Q205T/L214E/ A547D; V105C/R134Q/Q205T/P266H/L278D; V105C/ R134Q/L214E/P266H/I285E/C503Q/A551D/C565N; V105C/R134Q/L214E/L278D/C565N; V105C/R134Q/ L214E/C503Q/A547D; V105C/R134Q/L214E/C503Q/ A547D/A551D; V105C/R134Q/C503Q; V105C/R134Q/ C503Q/A547D; V105C/R134Q/C503Q/A547D/C565N; V105C/A153R/Q205T/L214E/P266H/C503Q/A547D; V105C/A153R/Q205T/P266H/I285E/A547D/C565N; V105C/Q205T/P210C/L214E/C503Q/A547D; V105C/ Q205T/L214E/L278D; V105C/Q205T/L214E/C503Q/ A547D/A551D/C565N; V105C/Q205T/C503Q/A551D; V105C/L214E/P266H/L278D/A547D; V105C/L214E/ L278D/C503Q/A547D/A551D; V105C/L214E/I285E; V105C/L214E/I285E/C503Q/A547D/A551D/C565N; V105C/L214E/I285E/A547D/C565N; V105C/L278D/ C503Q/A551D; V105C/I285E; V105C/I285E/A547D; V105C/C503Q; V105C/A547D/A551D; A112C/R134Q/ A153R/L214E/L278D/I285E/C503Q/A547D/A551D/ C565N; A112C/R134Q/L214E/C503Q/A547D/A551D/ C565N; A112C/L214E/L278D; A112C/L278D/C503Q/ A547D; R134Q/Q205T/L214E/I285E/C503Q/A551D/ C565N; R134Q/Q205T/C503Q; R134Q/P210C/L214E/ L278D/C503Q/A547D/C565N; R134Q/P210C/L214E/ C503Q/A547D/A551D; R134Q/L214E; R134Q/L214E/ L278D/C503Q; R134Q/L214E/L278D/C503Q/A551D; R134Q/L214E/I285E/C503Q; R134Q/C503Q; R134Q/ C503Q/A547D/A551D; A153R; Q205T/L214E/I285E/ C503Q/A551D; Q205T/L214E/I285E/C503Q/C565N;

Q205T/L214E/C503Q/A547D/C565N; Q205T/L278D/ I285E/A547D/A551D; P210C/L214E; P210C/L214E/ P266H; L214E/P266H; L214E/P266H/C503Q/A547D/ A551D/C565N; L214E/C503Q/A547D; L214E/A547D; P266H/L278D/C503Q; P266H/C565N; L278D/A547D; C503Q; C503Q/A547D; C503Q/A547D/A551D/C565N; C503Q/A547D/C565N; C503Q/A551D; C503Q/A551D/ C565N; A547D; C565N; V80I/R134C/P564Q; V121C; A123G; A124G; M125L; L126I/T; L126M/R134L; L127A; A129G/L; N130Q; N130C/M370I R134W; M133R; R134I; R134N/G307C; G135C/S; G135A/A394E; G20S/I144L; R43S; L47M/I144L; L47M/R146E; L47M/M147G/A383E; L47M/P157C; Q58H/L143V; Q58K/P157D/G369C; A62S/ M147V; S82I/G135C/P157F/W279L; R94C/I149E; T110I/ I139R; L118M/L141H; A119E/T156H/A289D; I139M/V; R140D/G/M; R140N/A199E; R140E/A334S/A551D; L141K/Q/P/T; E142H/P/V; E142D/G371D; L143F/M; I144L/N/V; K145N/Q/R; K145G/P157T; R146H/L; R146W/D191Y; M147A; I149L/R; F150K/L/M; L151M; A153C/G; A153S/H250N; G154R; G154Y/L174M/Q321K/ S456I/G483C; T156K/G483C; P157D/F/H/Y; Y158E; V159C/H/L/M; M247I; L319M; Q389K; P117T/Y176Q; V172I/C/L; L174M; S175G; Y176E/I/M/R/V; I177M/V; T178L/A477S; S180C/T; R43S/H374K; R43S/H374R; A112S/M370A/A507E; M147I/H374S; S187R/L381V; D191Y/H385N; A232S; Q240K/H374R; A256S/L381N; P275Q/M370S; P275T/H374R; Q332K/Y377M; A334S/ H374V; L349M; Q355K/H374S; M370G/I/S; G371H/N/Q/ S; M372A/V; H374A/D/G/L/N/R/S/T; H374Q/P396Q; H374R/G417C; L375I; L375M; Y377C/I/N; Y378C/D/E/I/ L/N/S; Y378F/P404Q; I379C/H/L/M/N; L381G/V; L381M/ Q560K; L382C/H/I/M/S; A383S/V; K384R; H385C/G/N; H385M/P403H; H385S/P403H; D387S; L418M; G425V; A447S; S461G; S525L; A24S/F434M; A62S/T433N; S98I; L213M/S438L; Q240K/T433Y; S286R/Y435T; A289S/ L431E; S331I; L431C/E/G/P/S/V; L432C/V; T433A/I/L/N/ P/Q/R/S/V/W; F434C; Y435L; Y435Q/H446N; G436M; G436D/T; N437E/G/Q; N437T/L538M; S438C/F/M/R/T; I439C/F/L/V; A477S; A24E; Q58R/Y475H; A70S/N474E; L104M/V476L; A119E/G365A; L206M; P275Q; G276V; Q292H/A479G; Q355H/I478C; P404T/A477V; I471F/G/K/ M/N/R/V/W; F472G; Q473H/K/M/R/S; Q473H/A507S; N474A/H/R/W; N474D/R490H; Y475C/F/L/Q; V476C/I/L; I478N/S; A479G/S; F482C/L; G483C/H/S; G483A/S524I; G483R/G537C; A558S; V39A/K115E/M133R/C565N; V39A/M133R/F472G/C503Q/C565N; V39A/M133R/ F472G/C565N; V39A/M133R/C503Q; V39A/M133R/ C503Q/C565N; V39A/M147A/Y378E/C503Q/C565N; V39A/M147A/Y378E/C565N; V39A/M147A/L381G/ F472G/C503Q/C565N; V39A/M147A/L381G/C503Q/ C565N; V39A/M147A/F472G/C503Q/C565N; V39A/ M147A/F472G/C565N; V39A/M147A/C565N; V39A/ G248C/L381G/F472G/C503Q/C565N; V39A/Y378E/ C503Q/C565N; V39A/Y378E/C565N; V39A/L381G; V39A/F472G/C503Q/C565N; V39A/C503Q/C565N; M133R/L381G/C565N; M133R/C503Q; Y378D/C503Q; Y378E/F472G/C503Q/C565N; L381G/F472GC503Q/ C565N; and/or F472G/C503Q/C565N.

The present invention also provides engineered polypeptides having phenylalanine ammonia-lyase (PAL) activity comprising: a) an amino acid sequence having at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or greater sequence identity to reference sequence SEQ ID NO:26 or a functional fragment thereof; b) a polypeptide sequence comprising at least one amino acid residue difference as compared to SEQ ID NO:26 or the functional fragment thereof at one or more amino acid positions; and c) which exhibits an improved property selected from i) enhanced catalytic activity, ii) reduced sensitivity to proteolysis, iii) increased tolerance to acidic pH, iv) reduced aggregation, v) reduced immunogenicity, or a combination of any of i), ii), iii), iv), or v), as compared to the reference sequence SEQ ID NO:26.

In some embodiments, the present invention also provides engineered polypeptides having phenylalanine ammonia-lyase (PAL) activity comprising: a) an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or greater sequence identity to reference sequence SEQ ID NO:26 or a functional fragment thereof; b) a polypeptide sequence comprising at least one amino acid residue difference as compared to SEQ ID NO:26 or the functional fragment thereof at one or more amino acid positions; and c) which exhibits an improved property selected from i) enhanced catalytic activity, ii) reduced sensitivity to proteolysis, iii) increased tolerance to acidic pH, iv) reduced aggregation, v) reduced immunogenicity, or a combination of any of i), ii), iii), iv), or v), as compared to the reference sequence SEQ ID NO:26.

In some additional embodiments, the present invention provides engineered polypeptides having phenylalanine ammonia-lyase (PAL) activity comprising: a) an amino acid sequence having at least 85% sequence identity to reference sequence SEQ ID NO:26 or a functional fragment thereof; b) a polypeptide sequence comprising at least one amino acid residue difference as compared to SEQ ID NO:26 or the functional fragment thereof at one or more amino acid positions; and c) which exhibits an improved property selected from i) enhanced catalytic activity, ii) reduced sensitivity to proteolysis, iii) increased tolerance to acidic pH, iv) reduced aggregation, v) reduced immunogenicity, or a combination of any of i), ii), iii), iv), or v), as compared to the reference sequence SEQ ID NO:26. In some embodiments, the engineered polypeptides having phenylalanine ammonia-lyase (PAL) activity of the present invention comprise an amino acid sequence having at least 85% sequence identity to reference sequence SEQ ID NO:26, and at least one amino acid residue difference as compared to SEQ ID NO:126, and that exhibit at least one improved property selected from enhanced catalytic activity, reduced sensitivity to proteolysis, increased tolerance to acidic pH, reduced aggregation, and/or reduced immunogenicity, as compared to SEQ ID NO:26. In some embodiments of the engineered polypeptides, the amino acid residue difference as compared to SEQ ID NO:26 is selected from one or more of the following substitutions or substitution sets A24E/G381L; L127V; A129I/V; S131C/T; H132L/S; R134C/F/H/K; R134H/Y378E/G381L; R134H/Y378E/G381L/V388T; R134H/V388T; A136K; A289S; M372L; H374G/M/Q; G381A/C/F/I/L/M/N/Q/S/T; A383C/M; V388C/T; L431M; and/or L563M.

In some embodiments, the engineered polypeptide having phenylalanine ammonia lyase (PAL) activity of the present invention has at least about 90%, at least about 91%, at least about 92%, at least about 93%, at least about 94%, at least about 95%, at least about 96%, at least about 97%, at least about 98%, or at least about 99% sequence identity to reference sequence SEQ ID NO:4. In some embodiments, the engineered polypeptide having phenylalanine ammonia lyase (PAL) activity of the present invention has at least about 90% sequence identity to reference sequence SEQ ID NO:4, while in some further embodiments, the engineered polypeptide has at least about 95% sequence identity to reference sequence SEQ ID NO:4. In some embodiments, the engineered polypeptide having phenylalanine ammonia lyase (PAL) activity of the present invention has at least 90%, at least 91%, at least 92%, at least 93%, at least 94%, at least 95%, at least 96%, at least 97%, at least 98%, or at least 99% sequence identity to reference sequence SEQ ID NO:4. In some embodiments, the engineered polypeptide having phenylalanine ammonia lyase (PAL) activity of the present invention has at least 90% sequence identity to reference sequence SEQ ID NO:4, while in some further embodiments, the engineered polypeptide has at least 95% sequence identity to reference sequence SEQ ID NO:4. In some further embodiments, the engineered polypeptides comprise functional fragments of polypeptides (e.g., any of the variant provided in the Tables, herein) having phenylalanine ammonia lyase (PAL) activity of the present invention.

In some embodiments, the engineered polypeptide having phenylalanine ammonia lyase (PAL) activity of the present invention has at least about 90%, at least about 91%, at least about 92%, at least about 93%, at least about 94%, at least about 95%, at least about 96%, at least about 97%, at least about 98%, or at least about 99% sequence identity to SEQ ID NO:6, 8, 10, 12, 14, 16, 18, 20, 22, 24, and/or 26. In some embodiments, the engineered polypeptide having phenylalanine ammonia lyase (PAL) activity of the present invention has at least 90%, at least 91%, at least 92%, at least 93%, at least 94%, at least 95%, at least 96%, at least 97%, at least 98%, or at least 99% sequence identity to SEQ ID NO:6, 8, 10, 12, 14, 16, 18, 20, 22, 24, and/or 26. In some embodiments, the engineered polypeptide having phenylalanine ammonia-lyase (PAL) activity comprise an amino acid sequence having at least about 90% sequence identity to SEQ ID NO:6, 8, 10, 12, 14, 16, 18, 20, 22, 24, and/or 26. In some embodiments, the engineered polypeptide having phenylalanine ammonia-lyase (PAL) activity comprises an amino acid sequence having at least about 99% sequence identity to SEQ ID NO:6, 8, 10, 12, 14, 16, 18, 20, 22, 24, and/or 26, or a functional fragment thereof. In some further embodiments, the engineered polypeptides comprise functional fragments of polypeptides (e.g., functional fragments of SEQ ID NO:6, 8, 10, 12, 14, 16, 18, 20, 22, 24, and/or 26, as well as any of the variants provided in the Tables, herein) having phenylalanine ammonia lyase (PAL) activity of the present invention.

The present invention also provides engineered polypeptides having phenylalanine ammonia-lyase (PAL) activity, wherein the engineered polypeptides are variant PALs provided in any of Tables 2-1 through 2-5 and/or Tables 9-1 through 9-7.

In some embodiments, the engineered polypeptide having phenylalanine ammonia-lyase (PAL) activity is an *Anabaena variabilis* enzyme. In some additional embodiments, the engineered polypeptides having phenylalanine ammonia-lyase (PAL) activity are thermostable. In some embodiments, the engineered polypeptides having phenylalanine ammonia-lyase (PAL) activity are resistant to proteolysis. In some additional embodiments, the engineered polypeptides having phenylalanine ammonia-lyase (PAL) activity are resistant to proteolysis by at least one digestive tract enzyme. In some further embodiments, the engineered polypeptides having phenylalanine ammonia-lyase (PAL) activity are resistant to proteolysis by chymotrypsin, trypsin, carboxypeptidases, and/or elastases. In some further embodiments, the engineered polypeptide having phenylalanine ammonia-lyase (PAL) activity is acid stable.

The present invention also provides engineered polypeptides having phenylalanine ammonia-lyase (PAL) activity that are deimmunized. In some embodiments, the deimmunized engineered polypeptides comprise an amino acid sequence having at least about 90%, at least about 91%, at least about 92%, at least about 93%, at least about 94%, at least about 95%, at least about 96%, at least about 97%, at least about 98%, at least about 99%, or greater, sequence identity to SEQ ID NO:6, 8, 10, 12, 14, 16, 18, 20, 22, 24, and/or 26. In some additional embodiments, the deimmunized engineered polypeptides comprise an amino acid sequence having at least 90%, at least 91%, at least 92%, at least 93%, at least 94%, at least 95%, at least 96%, at least 97%, at least 98%, at least 99%, or greater, sequence identity to SEQ ID NO:6, 8, 10, 12, 14, 16, 18, 20, 22, 24, and/or 26. In some embodiments, the deimmunized engineered polypeptides comprise an amino acid sequence having at least 95% sequence identity to SEQ ID NO:6, 8, 10, 12, 14, 16, 18, 20, 22, 24, and/or 26. In some embodiments, the deimmunized engineered polypeptides comprise an amino acid sequence having 95% sequence identity to SEQ ID NO:6, 8, 10, 12, 14, 16, 18, 20, 22, 24, and/or 26.

In still some further embodiments, the present invention provides purified engineered polypeptides having phenylalanine ammonia lyase (PAL) activity.

The present invention also provides polynucleotide sequences encoding at least one engineered polypeptide having phenylalanine ammonia lyase (PAL), as set forth herein. In some embodiments, the polynucleotide sequence is operably linked to a control sequence. In some additional embodiments, the polynucleotide sequence is codon-optimized.

The present invention also provides expression vectors comprising at least one polynucleotide sequence encoding at least one engineered polypeptide having phenylalanine ammonia-lyase (PAL) activity, as provided herein. In some embodiments, the expression vector further comprises at least one control sequence. In some embodiments, the control sequence is a promoter. In some additional embodiments, the promoter is a heterologous promoter.

The present invention also provides host cells transformed with at least one polynucleotide sequence encoding at least one engineered polypeptides having phenylalanine ammonia-lyase (PAL) activity, and/or at least one expression vector comprising at least one polynucleotide sequence encoding at least one engineered polypeptide having phenylalanine ammonia-lyase (PAL) activity and at least one control sequence. In some embodiments, the host cells comprise at least one engineered polypeptide having phenylalanine ammonia-lyase (PAL) activity that is codon-optimized. In some embodiments, the host cell is *E. coli*.

The present invention also provides methods of producing at least one engineered PAL polypeptide in a host cell comprising culturing a host cell comprising at least one polynucleotide encoding at least one engineered polypeptide having phenylalanine ammonia-lyase (PAL) activity, and/or at least one expression vector comprising at least one polynucleotide sequence encoding at least one engineered polypeptide having phenylalanine ammonia-lyase (PAL) activity and at least one control sequence, under suitable culture conditions, such that the engineered PAL polypeptide is produced. In some embodiments, the methods further comprise the step of recovering at least one engineered polypeptide having phenylalanine ammonia-lyase (PAL)

from the culture and/or host cells. In some further embodiments, the methods further comprise the step of purifying at least one engineered polypeptide having phenylalanine ammonia-lyase (PAL).

The present invention also provides compositions comprising at least one engineered polypeptide having phenylalanine ammonia-lyase (PAL) activity as provided herein. In some embodiments, the composition is a pharmaceutical composition. In some embodiments, the composition is a dietary and/or nutritional supplement. In some further embodiments, the pharmaceutical compositions further comprise at least one pharmaceutically acceptable excipient and/or carrier. In some additional embodiments, the composition is suitable for the treatment of phenylketonuria. In some further embodiments, the pharmaceutical composition is suitable for oral administration to a human. In some embodiments, the composition is in the form of a pill, tablet, capsule, gelcap, liquid, or emulsion. In yet some further embodiments, the pill, tablet, capsule, or gelcap further comprises an enteric coating. In some additional embodiments, the pharmaceutical composition is suitable for parenteral injection into a human. In some embodiments, the pharmaceutical composition is coadministered with at least one additional therapeutically effective compound. In some further embodiments, the pharmaceutical composition comprises at least one additional therapeutically effective compound. In some additional embodiments, the pharmaceutical composition is present in a dietary and/or nutritional supplement.

The present invention also provides methods for treating and/or preventing the symptoms of phenylketonuria in a subject, comprising providing a subject having phenylketonuria, and providing at least one composition provided herein to the subject. In some embodiments, the composition comprises a pharmaceutical composition, while in some alternative embodiments, the composition comprises a dietary/nutritional supplement. In some embodiments of the methods, the symptoms of phenylketonuria are ameliorated. In some additional embodiments, the treated subject is able to eat a diet that is less restricted in its methionine, phenylalanine, and/or tyrosine content than diets required by subjects exhibiting the symptoms of phenylalanine. In some embodiments, the treated subject (i.e., a subject who has been provided with at least one composition comprising at least one engineered polypeptide having phenylalanine ammonia-lyase (PAL) activity as provided herein) is able to eat a diet that is less restricted in its methionine, phenylalanine and/or tyrosine content than diets required by subjects who have not been provided at least one composition as provided herein. In some embodiments, the composition provided to the subjects comprises a pharmaceutical composition, while in some alternative embodiments, the composition comprises a dietary/nutritional supplement. The present invention also provides treated subjects, wherein the subject has been administered at least one composition and/or pharmaceutical composition comprising at least one engineered polypeptide having phenylalanine ammonia-lyase (PAL) activity as provided herein. In some embodiments, the subject is an animal selected from primates, rodents, and lagamorphs. In some additional embodiments, the subject is a mouse. In some further embodiments, the subject is a human. In still some further embodiments, the subject is a human infant or child, while in some alternative embodiments, the subject is a human adult or young adult.

The present invention also provides uses of the compositions comprising at least one engineered polypeptide having phenylalanine ammonia-lyase (PAL) activity provided herein.

DESCRIPTION OF THE INVENTION

Figure 1:
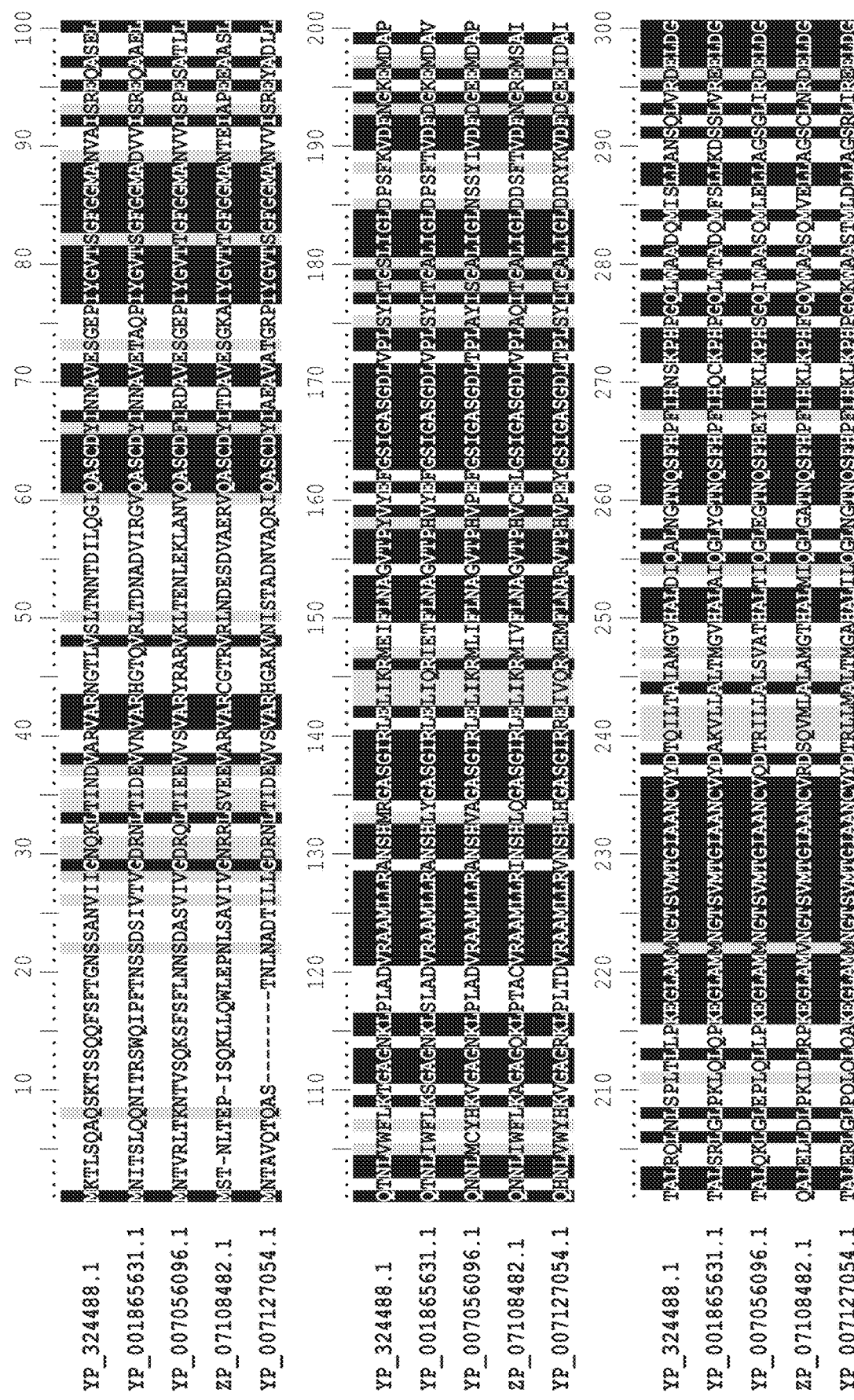
FIG. 1 provides an alignment of wild-type PAL protein sequences: *Anabaena variabilis* PAL (NCBI YP_324488.1 (SEQ ID NO:4)); *Nostoc punctiforme* phenylalanine/histidine ammonia lyase "NpPHAL" (NCBI YP_001865631.1 (SEQ ID NO:30); *Rivularia* sp. histidine ammonia-lyase "RspHAL" (NCBI YP_007056096.1 (SEQ ID NO:31); *Oscillatoria* sp. histidine ammonia-lyase "Osp HAL" (NCBI YP_07108482.1 (SEQ ID NO:32); and *Gloeocapsa* sp. histidine ammonia-lyase "GspHAL" (NCBI YP_007127054.1) (SEQ ID NO:33).
Figure 1:
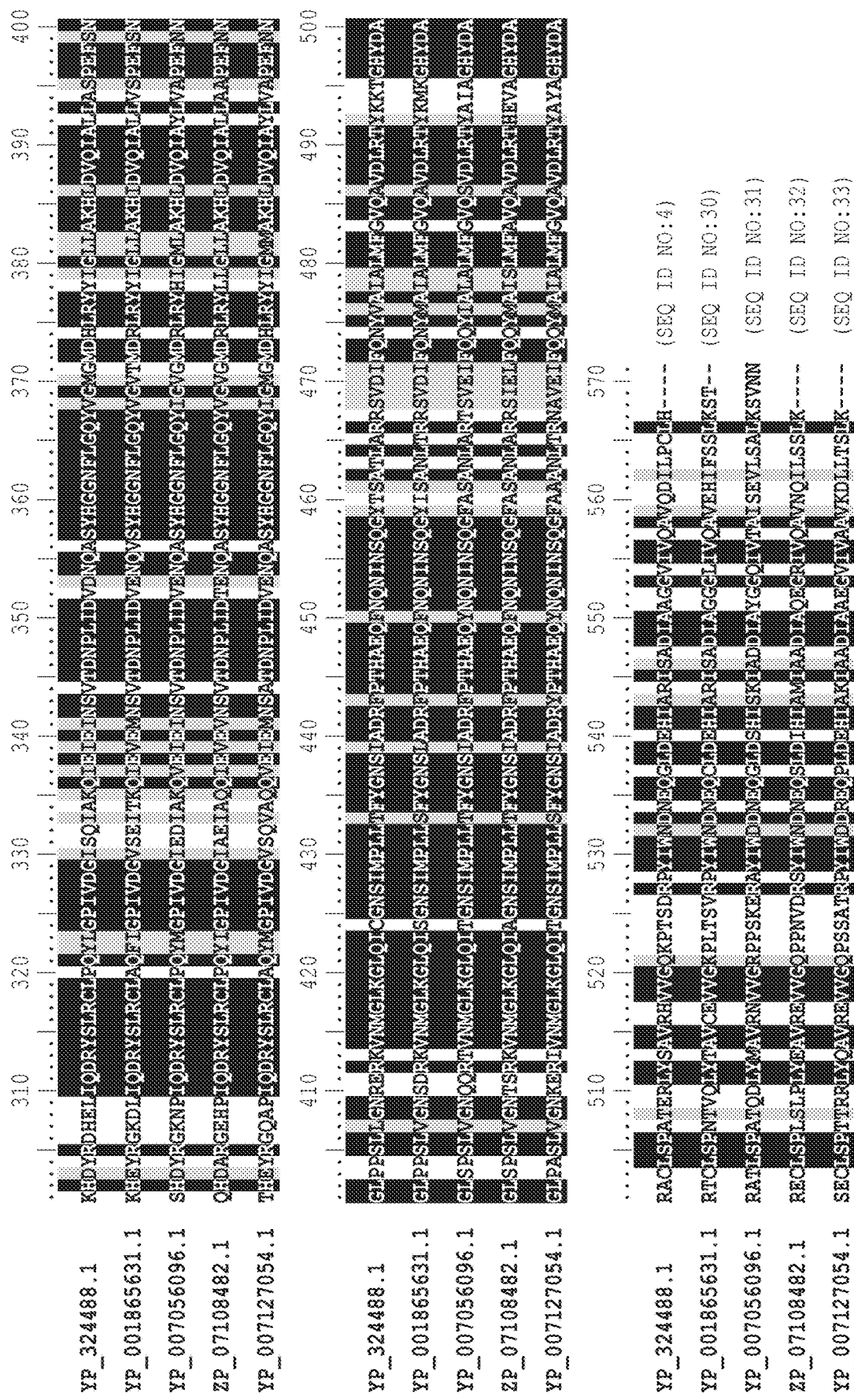

The present invention provides engineered PAL polypeptides, mutants, biologically active fragments and analogues thereof, and pharmaceutical and industrial compositions comprising the same.

The invention provides engineered phenylalanine ammonia-lyase (PAL) polypeptides and compositions thereof, as well as polynucleotides encoding the engineered phenylalanine ammonia-lyase (PAL) polypeptides. In some embodiments, the engineered PAL polypeptides are optimized to provide enhanced catalytic activity, as well as reduced sensitivity to proteolysis and increased tolerance to acidic pH levels. In some embodiments the engineered PAL polypeptides are deimmunized. The invention also relates to the use of the compositions comprising the engineered PAL polypeptides for therapeutic and industrial purposes.

Abbreviations and Definitions:

Unless defined otherwise, all technical and scientific terms used herein generally have the same meaning as commonly understood by one of ordinary skill in the art to which this invention pertains. Generally, the nomenclature used herein and the laboratory procedures of cell culture, molecular genetics, microbiology, organic chemistry, analytical chemistry and nucleic acid chemistry described below are those well-known and commonly employed in the art. Such techniques are well-known and described in numerous texts and reference works well known to those of skill in the art. Standard techniques, or modifications thereof, are used for chemical syntheses and chemical analyses. All patents, patent applications, articles and publications mentioned herein, both supra and infra, are hereby expressly incorporated herein by reference.

Although any suitable methods and materials similar or equivalent to those described herein find use in the practice of the present invention, some methods and materials are described herein. It is to be understood that this invention is not limited to the particular methodology, protocols, and reagents described, as these may vary, depending upon the context they are used by those of skill in the art. Accordingly, the terms defined immediately below are more fully described by reference to the application as a whole. All patents, patent applications, articles and publications mentioned herein, both supra and infra, are hereby expressly incorporated herein by reference.

Also, as used herein, the singular "a", "an," and "the" include the plural references, unless the context clearly indicates otherwise.

Numeric ranges are inclusive of the numbers defining the range. Thus, every numerical range disclosed herein is intended to encompass every narrower numerical range that falls within such broader numerical range, as if such narrower numerical ranges were all expressly written herein. It is also intended that every maximum (or minimum) numerical limitation disclosed herein includes every lower (or higher) numerical limitation, as if such lower (or higher) numerical limitations were expressly written herein.

The term "about" means an acceptable error for a particular value. In some instances "about" means within 0.05%, 0.5%, 1.0%, or 2.0%, of a given value range. In some instances, "about" means within 1, 2, 3, or 4 standard deviations of a given value.

Furthermore, the headings provided herein are not limitations of the various aspects or embodiments of the invention which can be had by reference to the application as a whole. Accordingly, the terms defined immediately below are more fully defined by reference to the application as a whole. Nonetheless, in order to facilitate understanding of the invention, a number of terms are defined below.

Unless otherwise indicated, nucleic acids are written left to right in 5' to 3' orientation; amino acid sequences are written left to right in amino to carboxy orientation, respectively.

As used herein, the term "comprising" and its cognates are used in their inclusive sense (i.e., equivalent to the term "including" and its corresponding cognates).

"EC" number refers to the Enzyme Nomenclature of the Nomenclature Committee of the International Union of Biochemistry and Molecular Biology (NC-IUBMB). The IUBMB biochemical classification is a numerical classification system for enzymes based on the chemical reactions they catalyze.

"ATCC" refers to the American Type Culture Collection whose biorepository collection includes genes and strains.

"NCBI" refers to National Center for Biological Information and the sequence databases provided therein.

As used herein, the term "phenylalanine ammonia-lyase (PAL) polypeptide" refers to a class of enzymes within the aromatic amino acid lyase family (EC 4.3.1.23, EC 4.3.1.24 and EC4.3.1.25) which also includes histidine ammonia-lyase, and tyrosine ammonia-lyase. The PAL polypeptides are also sometimes referred to as phenylalanine/tyrosine ammonia-lyases because some PAL enzymes may use tyrosine as well as phenylalanine as a substrate. However, the AvPAL and variants disclosed and claimed herein do not use tyrosine as a substrate. PAL polypeptides catalyze the conversion of L-phenylalanine to trans-cinnamic acid and ammonia. PAL activity refers to the enzymatic activity of PAL polypeptides. In some preferred embodiments, a PAL enzyme also contains the cofactor 3,5-dihydro-5-methylidene-4H-imidazol-4-one (MIO). This cofactor maybe required for catalytic activity and is formed by cyclization and dehydration of a conserved active site Ala167-Ser168-Gly169 tripeptide segment.

"Protein," "polypeptide," and "peptide" are used interchangeably herein to denote a polymer of at least two amino acids covalently linked by an amide bond, regardless of length or post-translational modification (e.g., glycosylation or phosphorylation).

"Amino acids" are referred to herein by either their commonly known three-letter symbols or by the one-letter symbols recommended by IUPAC-IUB Biochemical Nomenclature Commission. Nucleotides, likewise, may be referred to by their commonly accepted single letter codes.

The term "engineered," "recombinant," "non-naturally occurring," and "variant," when used with reference to a cell, a polynucleotide or a polypeptide refers to a material or a material corresponding to the natural or native form of the material that has been modified in a manner that would not otherwise exist in nature or is identical thereto but produced or derived from synthetic materials and/or by manipulation using recombinant techniques.

As used herein, "wild-type" and "naturally-occurring" refer to the form found in nature. For example a wild-type polypeptide or polynucleotide sequence is a sequence present in an organism that can be isolated from a source in nature and which has not been intentionally modified by human manipulation.

"Deimmunized" as used herein, refers to the manipulation of a protein to create a variant that is not as immunogenic as the wild-type or reference protein. In some embodiments, the deimmunization is complete, in that the variant protein does not stimulate an immune response in patients to whom the variant protein is administered. This response can be measured by various methods including but not limited to, the presence or abundance of neutralizing (i.e., anti-drug antibodies), the presence of an anaphylactic response, or the prevalence or intensity of cytokine release upon administration of the protein. In some embodiments, the variant protein is less immunogenic than the wild-type or reference protein. In some embodiments, deimmunization involves modifications to proteins (e.g., epitopes) that are recognized by T-cell receptors. In some embodiments, the T-cell epitopes are removed from a wild-type or reference protein in order to produce a deimmunized variant protein. In some embodiments, the deimmunized protein shows lower levels of response in biochemical and cell-biological predictors of human immunological responses including dendritic-cell T-cell activation assays, or human leukocyte antigen (HLA) peptide binding assays.

"Coding sequence" refers to that part of a nucleic acid (e.g., a gene) that encodes an amino acid sequence of a protein.

The term "percent (%) sequence identity" is used herein to refer to comparisons among polynucleotides and polypeptides, and are determined by comparing two optimally aligned sequences over a comparison window, wherein the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman (Smith and Waterman, Adv. Appl. Math., 2:482 [1981]), by the homology alignment algorithm of Needleman and Wunsch (Needleman and Wunsch, J. Mol. Biol., 48:443 [1970]), by the search for similarity method of Pearson and Lipman (Pearson and Lipman, Proc. Natl. Acad. Sci. USA 85:2444 [1988]), by computerized implementations of these algorithms (e.g., GAP, BESTFIT, FASTA, and TFASTA in the GCG Wisconsin Software Package), or by visual inspection, as known in the art. Examples of algorithms that are suitable for determining percent sequence identity and sequence similarity include, but are not limited to the BLAST and BLAST 2.0 algorithms (See e.g., Altschul et al., J. Mol. Biol., 215: 403-410 [1990]; and Altschul et al., Nucleic Acids Res., 3389-3402 [1977]). Software for performing BLAST analyses is publicly available through the National Center for Biotechnology Information website. This algorithm involves first identifying high scoring sequence pairs (HSPs) by identifying short words of length "W" in the query sequence, which either match or satisfy some positive-valued threshold score "T," when aligned with a word of the same length in a database sequence. T is referred to as the neighborhood word score threshold (See, Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (reward score for a pair of matching residues; always >0) and "N" (penalty score for mismatching residues; always <0). For amino acid sequences, a scoring matrix is used to calculate the cumulative score. Extension of the word hits in each direction are halted when: the cumulative alignment score falls off by the quantity "X" from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (See e.g., Henikoff and Henikoff, Proc. Natl. Acad. Sci. USA 89:10915 [1989]). Exemplary determination of sequence alignment and % sequence identity can employ the BESTFIT or GAP programs in the GCG Wisconsin Software package (Accelrys, Madison Wis.), using default parameters provided.

"Reference sequence" refers to a defined sequence used as a basis for a sequence comparison. A reference sequence may be a subset of a larger sequence, for example, a segment of a full-length gene or polypeptide sequence. Generally, a reference sequence is at least 20 nucleotide or amino acid residues in length, at least 25 residues in length, at least 50 residues in length, at least 100 residues in length or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptide are typically performed by comparing sequences of the two polynucleotides or polypeptides over a "comparison window" to identify and compare local regions of sequence similarity. In some embodiments, a "reference sequence" can be based on a primary amino acid sequence, where the reference sequence is a sequence that can have one or more changes in the primary sequence. For instance, the phrase "reference sequence based on SEQ ID NO:4 having a valine at the residue corresponding to X39" refers to a reference sequence in which the corresponding residue at position X39 in SEQ ID NO:4 (e.g., an alanine), has been changed to valine.

"Comparison window" refers to a conceptual segment of at least about 20 contiguous nucleotide positions or amino acids residues wherein a sequence may be compared to a reference sequence of at least 20 contiguous nucleotides or amino acids and wherein the portion of the sequence in the comparison window may comprise additions or deletions (i.e., gaps) of 20 percent or less as compared to the reference sequence (which does not comprise additions or deletions) for optimal alignment of the two sequences. The comparison window can be longer than 20 contiguous residues, and includes, optionally 30, 40, 50, 100, or longer windows.

"Corresponding to", "reference to," and "relative to" when used in the context of the numbering of a given amino acid or polynucleotide sequence refer to the numbering of the residues of a specified reference sequence when the given amino acid or polynucleotide sequence is compared to the reference sequence. In other words, the residue number or residue position of a given polymer is designated with respect to the reference sequence rather than by the actual numerical position of the residue within the given amino acid or polynucleotide sequence. For example, a given amino acid sequence, such as that of an engineered PAL, can be aligned to a reference sequence by introducing gaps to optimize residue matches between the two sequences. In these cases, although the gaps are present, the numbering of the residue in the given amino acid or polynucleotide sequence is made with respect to the reference sequence to which it has been aligned.

"Amino acid difference" and "residue difference" refer to a difference in the amino acid residue at a position of a polypeptide sequence relative to the amino acid residue at a corresponding position in a reference sequence. The positions of amino acid differences generally are referred to herein as "Xn," where n refers to the corresponding position in the reference sequence upon which the residue difference is based. For example, a "residue difference at position X91 as compared to SEQ ID NO:4" refers to a difference of the amino acid residue at the polypeptide position corresponding to position 91 of SEQ ID NO:4. Thus, if the reference polypeptide of SEQ ID NO:4 has a alanine at position 91, then a "residue difference at position X91 as compared to SEQ ID NO:4" refers to an amino acid substitution of any residue other than alanine at the position of the polypeptide corresponding to position 91 of SEQ ID NO:4. In most instances herein, the specific amino acid residue difference at a position is indicated as "XnY" where "Xn" specified the corresponding residue and position of the reference polypeptide (as described above), and "Y" is the single letter identifier of the amino acid found in the engineered polypeptide (i.e., the different residue than in the reference polypeptide). In some instances (e.g., in the Tables in the Examples), the present disclosure also provides specific amino acid differences denoted by the conventional notation "AnB", where A is the single letter identifier of the residue in the reference sequence, "n" is the number of the residue position in the reference sequence, and B is the single letter identifier of the residue substitution in the sequence of the engineered polypeptide. In some instances, a polypeptide of the present disclosure can include one or more amino acid residue differences relative to a reference sequence, which is indicated by a list of the specified positions where residue differences are present relative to the reference sequence. In some embodiments, where more than one amino acid can be used in a specific residue position of a polypeptide, the various amino acid residues that can be used are separated by a "/" (e.g., X307G/X307Q or X307G/Q). The present disclosure includes engineered polypeptide sequences comprising one or more amino acid differences that include either/or both conservative and non-conservative amino acid substitutions.

The terms "amino acid substitution set" and "substitution set" refers to a group of amino acid substitutions within a polypeptide sequence. In some embodiments, substitution sets comprise 1, 2, 3, 4, 5, 6, 7, 8, 9, 10, 11, 12, 13, 14, 15, or more amino acid substitutions. In some embodiments, a substitution set refers to the set of amino acid substitutions that is present in any of the variant AvPAL polypeptides listed in any of the Tables in the Examples. For example, the substitution set present in Variant 36 is A39V/A91V/N290G/H307G/L407V/T524S, wherein the amino acid positions are relative to SEQ ID NO:4.

"Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid (e.g., alanine, valine, leucine, and isoleucine); an amino acid with hydroxyl side chain is substituted with another amino acid with a hydroxyl side chain (e.g., serine and threonine); an amino acids having aromatic side chains is substituted with another amino acid having an aromatic side chain (e.g., phenylalanine, tyrosine, tryptophan, and histidine); an amino acid with a basic side chain is substituted with another amino acid with a basis side chain (e.g., lysine and arginine); an amino acid with an acidic side chain is substituted with another amino acid with an acidic side chain (e.g., aspartic acid or glutamic acid); and a hydrophobic or hydrophilic amino acid is replaced with another hydrophobic or hydrophilic amino acid, respectively.

"Non-conservative substitution" refers to substitution of an amino acid in the polypeptide with an amino acid with significantly differing side chain properties. Non-conservative substitutions may use amino acids between, rather than within, the defined groups and affect: (a) the structure of the peptide backbone in the area of the substitution (e.g., proline for glycine); (b) the charge or hydrophobicity; and/or (c) the bulk of the side chain. By way of example and not limitation, exemplary non-conservative substitutions include an acidic amino acid substituted with a basic or aliphatic amino acid; an aromatic amino acid substituted with a small amino acid; and a hydrophilic amino acid substituted with a hydrophobic amino acid.

"Deletion" refers to modification to the polypeptide by removal of one or more amino acids from the reference polypeptide. Deletions can comprise removal of 1 or more amino acids, 2 or more amino acids, 5 or more amino acids, 10 or more amino acids, 15 or more amino acids, or 20 or more amino acids, up to 10% of the total number of amino acids, or up to 20% of the total number of amino acids making up the reference enzyme while retaining enzymatic activity and/or retaining the improved properties of an engineered transaminase enzyme. Deletions can be directed to the internal portions and/or terminal portions of the polypeptide. In various embodiments, the deletion can comprise a continuous segment or can be discontinuous.

"Insertion" refers to modification to the polypeptide by addition of one or more amino acids from the reference polypeptide. Insertions can be in the internal portions of the polypeptide, or to the carboxy or amino terminus. Insertions as used herein include fusion proteins as is known in the art. The insertion can be a contiguous segment of amino acids or separated by one or more of the amino acids in the naturally occurring polypeptide.

The terms "functional fragment" and "biologically active fragment" are used interchangeably herein, to refer to a polypeptide that has an amino-terminal and/or carboxy-terminal deletion(s) and/or internal deletions, but where the remaining amino acid sequence is identical to the corresponding positions in the sequence to which it is being compared (e.g., a full length engineered PAL of the present invention) and that retains substantially all of the activity of the full-length polypeptide.

"Isolated polypeptide" refers to a polypeptide which is substantially separated from other contaminants that naturally accompany it (e.g., protein, lipids, and polynucleotides). The term embraces polypeptides which have been removed or purified from their naturally-occurring environment or expression system (e.g., host cell or in vitro synthesis). The recombinant PAL polypeptides may be present within a cell, present in the cellular medium, or prepared in various forms, such as lysates or isolated preparations. As such, in some embodiments, the recombinant PAL polypeptides provided herein are isolated polypeptides.

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure PAL composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species. In some embodiments, the isolated recombinant PAL polypeptides are substantially pure polypeptide compositions.

"Improved enzyme property" refers to an engineered PAL polypeptide that exhibits an improvement in any enzyme property as compared to a reference PAL polypeptide, such as a wild-type PAL polypeptide (e.g., AvPAL wild-type having SEQ ID NO:4) or another engineered PAL polypeptide. Improved properties include but are not limited to such properties as increased protein expression, increased thermoactivity, increased thermostability, increased pH activity, increased stability, increased enzymatic activity, increased substrate specificity and/or affinity, increased specific activity, increased resistance to substrate and/or end-product inhibition, increased chemical stability, improved chemoselectivity, improved solvent stability, increased tolerance to acidic pH, increased tolerance to proteolytic activity (i.e., reduced sensitivity to proteolysis), reduced aggregation, increased solubility, reduced immunogenicity, and altered temperature profile.

"Increased enzymatic activity" and "enhanced catalytic activity" refer to an improved property of the engineered PAL polypeptides, which can be represented by an increase in specific activity (e.g., product produced/time/weight protein) and/or an increase in percent conversion of the substrate to the product (e.g., percent conversion of starting amount of substrate to product in a specified time period using a specified amount of PAL) as compared to the reference PAL enzyme (e.g., wild-type AvPAL and/or another engineered AvPAL). Exemplary methods to determine enzyme activity are provided in the Examples. Any property relating to enzyme activity may be affected, including the classical enzyme properties of $K_m$, $V_{max}$ or $k_{cat}$, changes of which can lead to increased enzymatic activity. Improvements in enzyme activity can be from about 1.1 fold the enzymatic activity of the corresponding wild-type enzyme, to as much as 2-fold, 5-fold, 10-fold, 20-fold, 25-fold, 50-fold, 75-fold, 100-fold, 150-fold, 200-fold or more enzymatic activity than the naturally occurring PAL or another engineered PAL from which the PAL polypeptides were derived.

In some embodiments, the engineered PAL polypeptides have a $k_{cat}$ of at least 0.1/sec, at least 0.2/sec, at least 0.3/sec, at least 0.5/sec, at least 1.0/sec and in some preferred embodiments greater than 1.0/sec. In some embodiments, the $K_m$ is in the range of about 1 μm to about 5 mM; in the range of about 5 μm to about 2 mM; in the range of about 10 μm to about 2 mM; or in the range of about 10 μm to about 1 mM. In some specific embodiments, the engineered PAL enzyme exhibits improved enzymatic activity in the range of 1.5 to 10 fold, 1.5 to 25 fold, 1.5 to 50 fold, 1.5 to 100 fold or greater, than that of the reference PAL enzyme. PAL activity can be measured by any standard assay known in the art, (e.g., by monitoring changes in spectrophotometric properties of reactants or products). In some embodiments, the amount of products produced is measured by High-Performance Liquid Chromatography (HPLC) separation combined with UV absorbance or fluorescent detection directly or following o-phthaldialdehyde (OPA) derivatization. In some embodiments, comparisons of enzyme activities are made using a defined preparation of enzyme, a defined assay under a set condition, and one or more defined substrates, as further described in detail herein. Generally, when lysates are compared, the numbers of cells and the amount of protein assayed are determined as well as use of identical expression systems and identical host cells, in order to minimize variations in amount of enzyme produced by the host cells and present in the lysates.

The term "improved tolerance to acidic pH" means that a recombinant PAL according to the invention exhibits increased stability (i.e., higher retained activity at about pH 7.0, after exposure to acidic pH for a specified period of time [1 hour, up to 24 hours]) as compared to a reference PAL.

"Physiological pH" as used herein means the pH range generally found in a subject's (e.g., human) small intestine. There normally is a gradient pH from the pyloric valve to the large intestine, in the range of about 6.0 to 7.5.

The term "acidic pH" used with reference to improved stability to acidic pH conditions or increased tolerance to acidic pH means a pH range of about 1.5 to 6.8.

The terms "proteolytic activity" and "proteolysis" used interchangeably herein refer to the breakdown of proteins into smaller polypeptides or amino acids. The breakdown of proteins is generally the result of hydrolysis of the peptide bond by protease (proteinase) enzymes. Protease enzymes include but are not limited to pepsin, trypsin, chymotrypsin, elastase; carboxypeptidase A and B, and peptidases (e.g., amino peptidase, dipeptidase and enteropeptidase).

The phrases "reducing sensitivity to proteolysis" and "reducing proteolytic sensitivity" are used interchangeably herein mean that an engineered PAL polypeptide according to the invention will have a higher enzyme activity compared to a reference PAL in a standard assay (e.g., as disclosed in the Examples) after treatment with one or more proteases.

"Aggregation" means clumping or precipitation of a PAL polypeptide. Aggregation can lead to inactivation of the enzyme. The term "reduced aggregation" means an engineered PAL polypeptide will be less prone to aggregation, as compared to a reference PAL. Methods for assessing aggregation are known in the art, including but not limited to the use of fluorescent microscopy with appropriate dyes (e.g., thioflavin T or Nile Red), dynamic light scattering, flow cytometry with appropriate dyes (e.g., Bodipy), filtration and analysis by SDS-PAGE, and/or Western blotting, fluorescent correlation spectroscopy, and electron microscopy. There are commercially available kits to assess aggregation (e.g., the ProteoStat® Protein Aggregation Assay kit [Enzo]).

"Conversion" refers to the enzymatic conversion (or biotransformation) of substrate(s) to the corresponding product(s). "Percent conversion" refers to the percent of the substrate that is converted to the product within a period of time under specified conditions. Thus, the "enzymatic activity" or "activity" of a PAL polypeptide can be expressed as "percent conversion" of the substrate to the product in a specific period of time.

"Hybridization stringency" relates to hybridization conditions, such as washing conditions, in the hybridization of nucleic acids. Generally, hybridization reactions are performed under conditions of lower stringency, followed by washes of varying but higher stringency. The term "moderately stringent hybridization" refers to conditions that permit target-DNA to bind a complementary nucleic acid that has about 60% identity, preferably about 75% identity, about 85% identity to the target DNA, with greater than about 90% identity to target-polynucleotide. Exemplary moderately stringent conditions are conditions equivalent to hybridization in 50% formamide, 5× Denhart's solution, 5×SSPE, 0.2% SDS at 42° C., followed by washing in 0.2×SSPE, 0.2% SDS, at 42° C. "High stringency hybridization" refers generally to conditions that are about 10° C. or less from the thermal melting temperature $T_m$ as determined under the solution condition for a defined polynucleotide sequence. In some embodiments, a high stringency condition refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in conditions equivalent to 50% formamide, 5× Denhart's solution, 5×SSPE, 0.2% SDS at 42° C., followed by washing in 0.1×SSPE, and 0.1% SDS at 65° C. Another high stringency condition is hybridizing in conditions equivalent to hybridizing in 5×SSC containing 0.1% (w:v) SDS at 65° C. and washing in 0.1×SSC containing 0.1% SDS at 65° C. Other high stringency hybridization conditions, as well as moderately stringent conditions, are described in the references cited above.

"Codon optimized" refers to changes in the codons of the polynucleotide encoding a protein to those preferentially used in a particular organism such that the encoded protein is more efficiently expressed in that organism. Although the genetic code is degenerate, in that most amino acids are represented by several codons, called "synonyms" or "synonymous" codons, it is well known that codon usage by particular organisms is nonrandom and biased towards particular codon triplets. This codon usage bias may be higher in reference to a given gene, genes of common function or ancestral origin, highly expressed proteins versus low copy number proteins, and the aggregate protein coding regions of an organism's genome. In some embodiments, the polynucleotides encoding the PAL enzymes are codon optimized for optimal production from the host organism selected for expression.

"Control sequence" refers herein to include all components that are necessary or advantageous for the expression of a polynucleotide and/or polypeptide of the present disclosure. Each control sequence may be native or foreign to the nucleic acid sequence encoding the polypeptide. Such control sequences include, but are not limited to, leaders, polyadenylation sequences, propeptide sequences, promoter sequences, signal peptide sequences, initiation sequences, and transcription terminators. At a minimum, the control sequences include a promoter, and transcriptional and translational stop signals. In some embodiments, the control sequences are provided with linkers for the purpose of introducing specific restriction sites facilitating ligation of the control sequences with the coding region of the nucleic acid sequence encoding a polypeptide.

"Operably linked" is defined herein as a configuration in which a control sequence is appropriately placed (i.e., in a functional relationship) at a position relative to a polynucleotide of interest such that the control sequence directs or regulates the expression of the polynucleotide encoding a polypeptide of interest.

"Promoter sequence" refers to a nucleic acid sequence that is recognized by a host cell for expression of a polynucleotide of interest, such as a coding sequence. The promoter sequence contains transcriptional control sequences that mediate the expression of a polynucleotide of interest. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

"Suitable reaction conditions" refers to those conditions in the enzymatic conversion reaction solution (e.g., ranges of enzyme loading, substrate loading, temperature, pH, buffers, co-solvents, etc.) under which a PAL polypeptide of the present disclosure is capable of converting a substrate to the desired product compound, Exemplary "suitable reaction conditions" are provided herein (See, the Examples).

"Loading", such as in "compound loading" or "enzyme loading" refers to the concentration or amount of a component in a reaction mixture at the start of the reaction. "Substrate" in the context of an enzymatic conversion reaction process refers to the compound or molecule acted on by the PAL polypeptide. "Product" in the context of an enzymatic conversion process refers to the compound or molecule resulting from the action of the PAL polypeptide on the substrate.

As used herein the term "culturing" refers to the growing of a population of microbial cells under suitable conditions using any suitable medium (e.g., liquid, gel, or solid).

Recombinant polypeptides (e.g., PAL enzyme variants) can be produced using any suitable methods known the art. For example, there is a wide variety of different mutagenesis techniques well known to those skilled in the art. In addition, mutagenesis kits are also available from many commercial molecular biology suppliers. Methods are available to make specific substitutions at defined amino acids (site-directed), specific or random mutations in a localized region of the gene (regio-specific), or random mutagenesis over the entire gene (e.g., saturation mutagenesis). Numerous suitable methods are known to those in the art to generate enzyme variants, including but not limited to site-directed mutagenesis of single-stranded DNA or double-stranded DNA using PCR, cassette mutagenesis, gene synthesis, error-prone PCR, shuffling, and chemical saturation mutagenesis, or any other suitable method known in the art. Non-limiting examples of methods used for DNA and protein engineering are provided in the following patents: U.S. Pat. Nos. 6,117,679; 6,420,175; 6,376,246; 6,586,182; 7,747,391; 7,747,393; 7,783,428; and 8,383,346. After the variants are produced, they can be screened for any desired property (e.g., high or increased activity, or low or reduced activity, increased thermal activity, increased thermal stability, and/or acidic pH stability, etc.). In some embodiments, "recombinant PAL polypeptides" (also referred to herein as "engineered PAL polypeptides," "variant PAL enzymes," and "PAL variants") find use.

As used herein, a "vector" is a DNA construct for introducing a DNA sequence into a cell. In some embodiments, the vector is an expression vector that is operably linked to a suitable control sequence capable of effecting the expression in a suitable host of the polypeptide encoded in the DNA sequence. In some embodiments, an "expression vector" has a promoter sequence operably linked to the DNA sequence (e.g., transgene) to drive expression in a host cell, and in some embodiments, also comprises a transcription terminator sequence.

As used herein, the term "expression" includes any step involved in the production of the polypeptide including, but not limited to, transcription, post-transcriptional modification, translation, and post-translational modification. In some embodiments, the term also encompasses secretion of the polypeptide from a cell.

As used herein, the term "produces" refers to the production of proteins and/or other compounds by cells. It is intended that the term encompass any step involved in the production of polypeptides including, but not limited to, transcription, post-transcriptional modification, translation, and post-translational modification. In some embodiments, the term also encompasses secretion of the polypeptide from a cell.

As used herein, an amino acid or nucleotide sequence (e.g., a promoter sequence, signal peptide, terminator sequence, etc.) is "heterologous" to another sequence with which it is operably linked if the two sequences are not associated in nature.

As used herein, the terms "host cell" and "host strain" refer to suitable hosts for expression vectors comprising DNA provided herein (e.g., a polynucleotide sequences encoding at least one AvPAL variant). In some embodiments, the host cells are prokaryotic or eukaryotic cells that have been transformed or transfected with vectors constructed using recombinant DNA techniques as known in the art.

The term "analogue" means a polypeptide having more than 70% sequence identity but less than 100% sequence identity (e.g., more than 75%, 78%, 80%, 83%, 85%, 88%, 90%, 91%, 92%, 93%, 94%, 95%, 96%, 97%, 98%, 99% sequence identity) with a reference polypeptide. In some embodiments, analogues include non-naturally occurring amino acid residues including, but not limited, to homoarginine, ornithine and norvaline, as well as naturally occurring amino acids. In some embodiments, analogues also include one or more D-amino acid residues and non-peptide linkages between two or more amino acid residues.

The term "therapeutic" refers to a compound administered to a subject who shows signs or symptoms of pathology having beneficial or desirable medical effects.

The term "pharmaceutical composition" refers to a composition suitable for pharmaceutical use in a mammalian subject (e.g., human) comprising a pharmaceutically effective amount of an engineered PAL polypeptide encompassed by the invention and an acceptable carrier.

The term "effective amount" means an amount sufficient to produce the desired result. One of general skill in the art may determine what the effective amount by using routine experimentation.

The terms "isolated" and "purified" are used to refer to a molecule (e.g., an isolated nucleic acid, polypeptide, etc.) or other component that is removed from at least one other component with which it is naturally associated. The term "purified" does not require absolute purity, rather it is intended as a relative definition.

The term "subject" encompasses mammals such as humans, non-human primates, livestock, companion animals, and laboratory animals (e.g., rodents and lagamorphs). It is intended that the term encompass females as well as males.

As used herein, the term "patient" means any subject that is being assessed for, treated for, or is experiencing disease.

The term "infant" refers to a child in the period of the first month after birth to approximately one (1) year of age. As used herein, the term "newborn" refers to child in the period from birth to the 28th day of life. The term "premature infant" refers to an infant born after the twentieth completed week of gestation, yet before full term, generally weighing ~500 to ~2499 grams at birth. A "very low birth weight infant" is an infant weighing less than 1500 g at birth.

As used herein, the term "child" refers to a person who has not attained the legal age for consent to treatment or research procedures. In some embodiments, the term refers to a person between the time of birth and adolescence.

As used herein, the term "adult" refers to a person who has attained legal age for the relevant jurisdiction (e.g., 18 years of age in the United States). In some embodiments, the term refers to any fully grown, mature organism. In some embodiments, the term "young adult" refers to a person less than 18 years of age, but who has reached sexual maturity.

As used herein, "composition" and "formulation" encompass products comprising at least one engineered PAL of the present invention, intended for any suitable use (e.g., pharmaceutical compositions, dietary/nutritional supplements, feed, etc.).

The terms "administration" and "administering" a composition mean providing a composition of the present invention to a subject (e.g., to a person suffering from the effects of PKU).

The term "carrier" when used in reference to a pharmaceutical composition means any of the standard pharmaceutical carrier, buffers, and excipients, such as stabilizers, preservatives, and adjuvants.

The term "pharmaceutically acceptable" means a material that can be administered to a subject without causing any undesirable biological effects or interacting in a deleterious manner with any of the components in which it is contained and that possesses the desired biological activity.

As used herein, the term "excipient" refers to any pharmaceutically acceptable additive, carrier, diluent, adjuvant, or other ingredient, other than the active pharmaceutical ingredient (API; e.g., the engineered PAL polypeptides of the present invention). Excipients are typically included for formulation and/or administration purposes.

The term "therapeutically effective amount" when used in reference to symptoms of disease/condition refers to the amount and/or concentration of a compound (e.g., engineered PAL polypeptides) that ameliorates, attenuates, or eliminates one or more symptom of a disease/condition or prevents or delays the onset of symptom(s) (e.g., PKU). In some embodiments, the term is use in reference to the amount of a composition that elicits the biological (e.g., medical) response by a tissue, system, or animal subject that is sought by the researcher, physician, veterinarian, or other clinician.

The term "therapeutically effective amount" when used in reference to a disease/condition refers to the amount and/or concentration of a composition that ameliorates, attenuates, or eliminates the disease/condition.

It is intended that the terms "treating," "treat" and "treatment" encompass preventative (e.g., prophylactic), as well as palliative treatment.

Engineered PAL Polypeptides:

The parent PAL polypeptides from which the engineered PAL polypeptides of the invention are derived from include bacterial strains such as *Anabaena* (e.g., *A. variabilis*), *Nostoc* (e.g., *N. punctiforme*), *Rhodosporidium* (e.g., *R. toruloides*), *Streptomyces* (e.g., *S. maritimus* or *S. verticillatus*), *Oscillatoria* sp., *Gloeocapsa* sp., and *Rivularia* sp. PAL enzymes from these strains have been identified and are well known. Homologous enzyme sequences from *Anabaena* (*A. variabilis*) ATCC 29413 and NCBI YP_324488.1; *Nostoc* (*N. punctiforme*) ATCC 29133 and NCBI YP_00186563.1; *Oscillatoria* sp. PCC 6506 and NCBI ZP_07108482.1 and *Gloeocapsa* sp. PCC7428 and NCBI YP_007127054.1 are provided in FIG. 1. The *Nostoc punctiforme* phenylalanine/histidine ammonia lyase "NpPHAL" (NCBI YP_001865631.1 (SEQ ID NO:30); *Rivularia* sp. histidine ammonia-lyase "RspHAL" (NCBI YP_007056096.1 (SEQ ID NO:31); *Oscillatoria* sp. histidine ammonia-lyase "Osp HAL" (NCBI YP_07108482.1 (SEQ ID NO:32); and *Gloeocapsa* sp. histidine ammonia-lyase "GspHAL" (NCBI YP_007127054.1) (SEQ ID NO:33) have more than 70% homology with AvPAL (SEQ ID NO:4).

Furthermore, when a particular PAL variant (i.e., an engineered PAL polypeptide) is referred to by reference to modification of particular amino acids residues in the sequence of a wild-type PAL or reference PAL it is to be understood that variants of another PAL modified in the equivalent position(s) (as determined from the optional amino acid sequence alignment between the respective amino acid sequences) are encompassed herein. In some embodiments, the engineered PAL polypeptide is derived from any one of the polypeptides listed from the bacterial strains above (i.e., Nostoc [N. punctiforme], Rhodosporidium [R. toruloides], Streptomyces [S. maritimus or S. verticillatus], Oscillatoria sp., Gloeocapsa sp and Rivularia sp.). In some additional embodiments, the engineered PAL polypeptide of the present invention comprises the conserved active site Ala167-Ser168-Gly169 and comprises at least 70%, at least 75%, at least 80%, at least 85%, at least 90%, at least 91%, at least 92%, at least 93%, at least 94%, at least 95%, at least 96%, at least 97%, at least 98%, or at least 99% sequence identity to SEQ ID NO:4. In some embodiments, the engineered PAL polypeptides comprise not only PAL activity but are also active on tyrosine and/or histidine substrates.

In some embodiments, engineered PAL polypeptides are produced by cultivating a microorganism comprising at least one polynucleotide sequence encoding at least one engineered PAL polypeptide under conditions which are conducive for producing the engineered PAL polypeptide. In some embodiments, the engineered PAL polypeptide is subsequently recovered from the resulting culture medium and/or cells.

The present invention provides exemplary engineered PAL polypeptides having PAL activity. The Examples provide Tables showing sequence structural information correlating specific amino acid sequence features with the functional activity of the engineered PAL polypeptides. This structure-function correlation information is provided in the form of specific amino acid residue differences relative to the reference engineered polypeptide of SEQ ID NO:4, as well as associated experimentally determined activity data for the exemplary engineered PAL polypeptides.

In some embodiments, the engineered PAL polypeptides of the present invention having PAL activity comprise a) an amino acid sequence having at least 85% sequence identity to reference sequence SEQ ID NO:4; b) an amino acid residue difference as compared to SEQ ID NO:4 at one or more amino acid positions; and c) which exhibits an improved property selected from i) enhanced catalytic activity, ii) reduced proteolytic sensitivity, iii) increased tolerance to acidic pH, iv) reduced aggregation or a combination of any of i), ii), iii) or iv) as compared to the reference sequence.

In some embodiments the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:4, and an amino acid residue difference as compared to SEQ ID NO:4, at one or more amino acid positions (such as at 1, 2, 3, 4, 5, 6, 7, 8, 9, 10, 11, 12, 14, 15, 20 or more amino acid positions compared to SEQ ID NO:4 or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:4). In some embodiments, the residue difference as compared to SEQ ID NO:4, at one or more positions includes at least 1, 2, 3, 4, 5, 6, 7, 8, 9, 10 or more conservative amino acid substitutions. In some embodiments, the engineered PAL polypeptide is a polypeptide listed in the Tables provided in the Examples.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:4 and an amino acid residue difference as compared to SEQ ID NO:4 at one or more amino acid positions are selected from X39; X54; X59; X73; X91; X158; X112, X134, X180; X195; X240; X243; X245; X256; X257; X270; X290; X304; X305; X307; X308; X326; X349; X353; X364; X394; X399; X400; X404; X407; X443; X453; X459; X460; X463; X474; X509; X521; X522; X524; X528; X546; X564; or any combination thereof, when optimally aligned with the amino acid sequence of SEQ ID NO:4. In some embodiments the amino acid difference is 1, 2, 3, 4, 5, 6, 7, 8, 9, 10, 15, or 20 or greater amino acid positions.

In some embodiments, the engineered PAL polypeptides exhibiting at least one improved property have at least 85% (at least 88%, 90%, 91%, 92%, 93%, 94%, 95%, 96%, 97%, 98%, 99%) sequence identity to SEQ ID NO:4 and comprise an amino acid residue difference at position H307 and optionally an amino acid residue difference at 1, 2, 3, 4, 5, 6, 7, 8, 9, 10 or more amino acid positions. In some embodiments the amino acid residue difference at position 307 is H307/G/Q/M.

In some embodiments, the engineered PAL polypeptides exhibiting at least one improved property have at least 85% (at least 88%, 90%, 91%, 92%, 93%, 94%, 95%, 96%, 97%, 98%, 99%) sequence identity to SEQ ID NO:4 and comprise at least one amino acid residue difference selected from a combination of one or more of A39; T54; G59; S73; A91; Y158; S180; K195; A112; R134; Q240; T243; I245; A256; L257; N270; N290; Y304; R305; H307; E308; I326; L349; D353; L364; A394; S399; N400; P404; L407; F443; N453; Y459; T460; T463; N474; E509; Q521; K522; T524; P528; S546; and/or P564. In some additional embodiments, there are amino acid residue differences at 1, 2, 3, 4, 5, 6, 7, 8, 9, 10 or more amino acid positions.

In some embodiments, the engineered PAL polypeptides exhibiting an improved property have at least 85% (at least 88%, 90%, 91%, 92%, 93%, 94%, 95%, 96%, 97%, 98%, 99%) sequence identity to SEQ ID NO:4 and comprise an amino acid residue difference selected from a combination of one or more of A39V; T54K; G59R; S73K; A112C; R134Q; A91V; Y158H; S180A; K195E; Q240R/W; T243I/L; I245L; A256G; L257W/A; N270K; N290G; Y304H; R305M; H307G/Q/M; E308Q; I326F; L349M; D353A/N; L364Q; A394V; S399N; N400K; P404A; L407V; F443H; N453G; Y459F; T460G; T463N; N474Q; E509L; Q521K/S; K522Y/F/N; T524S; P528L; S546R; and P564 G/L/M, when optimally aligned with SEQ ID NO:4.

In some embodiments, the amino acid residue difference is selected from a combination of one or more of A39V; A91V; A256G; N290G; A394V; S399N; P404A; L407V; K522Y/F/N; and/or T524S, when optimally aligned with SEQ ID NO:4.

In some embodiments, the present invention provides functional fragments of engineered PAL polypeptides. In some embodiments, functional fragments comprise at least about 90%, at least about 95%, at least about 96%, at least about 97%, at least about 98%, or at least about 99% of the activity of the engineered PAL polypeptide from which it was derived (i.e., the parent engineered PAL). In some embodiments, functional fragments comprise at least about 90%, at least about 91%, at least about 92%, at least about 93%, at least about 94%, at least about 95%, at least about 96%, at least about 97%, at least about 98%, or at least about 99% of the parent sequence of the engineered PAL. In some embodiments the functional fragment will be truncated by less than 5, less than 10, less than 15, less than 10, less than 25, less than 30, less than 35, less than 40, less than 45, and less than 50 amino acids.

In some embodiments, the present invention provides functional fragments of engineered PAL polypeptides. In some embodiments, functional fragments comprise at least about 95%, 96%, 97%, 98%, or 99% of the activity of the engineered PAL polypeptide from which it was derived (i.e., the parent engineered PAL). In some embodiments, functional fragments comprise at least 90%, 91%, 92%, 93%, 94%, 95%, 96%, 97%, 98%, or 99% of the parent sequence of the engineered PAL. In some embodiments the functional fragment will be truncated by less than 5, less than 10, less than 15, less than 10, less than 25, less than 30, less than 35, less than 40, less than 45, less than 50, less than 55, less than 60, less than 65, or less than 70 amino acids.

In some embodiments, the engineered PAL polypeptides exhibiting at least one improved property has at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:6 and an amino acid residue difference as compared to SEQ ID NO:6, at one or more amino acid positions (such as at 1, 2, 3, 4, 5, 6, 7, 8, 9, 10, 11, 12, 14, 15 or more amino acid positions) compared to SEQ ID NO:6, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:6. In some embodiments, the engineered PALs comprise at least 90% sequence identity to SEQ ID NO:6 and comprise an amino acid difference as compared to SEQ ID NO:6 of at least 1, 2, 3, 4, 5, 6, 7, 8, 9, 10 or more amino acid positions. In some embodiments, the engineered PAL polypeptide consists of the sequence of SEQ ID NO:6.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:10, or a functional fragment thereof and an amino acid residue difference as compared to SEQ ID NO:10, at one or more amino acid positions (such as at 1, 2, 3, 4, 5, 6, 7, 8, 9, 10, 11, 12, 14, 15 or more amino acid positions) compared to SEQ ID NO:10, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:10. In some embodiments, the engineered PALs comprise at least 95% sequence identity to SEQ ID NO:10, and comprise an amino acid difference as compared to SEQ ID NO:10, of at least 1, 2, 3, 4, 5, 6, 7, 8, 9, 10 or more amino acid positions. In some embodiments, the engineered PAL polypeptide consists of the sequence of SEQ ID NO:10.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:12 or a functional fragment thereof and an amino acid residue difference as compared to SEQ ID NO:12 at one or more amino acid positions (such as at 1, 2, 3, 4, 5, 6, 7, 8, 9, 10, 11, 12, 14, 15 or more amino acid positions) compared to SEQ ID NO:12, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:12. In some embodiments, the engineered PALs comprise at least 95% sequence identity to SEQ ID NO:12, and comprise an amino acid difference as compared to SEQ ID NO:12, of at least 1, 2, 3, 4, 5, 6, 7, 8, 9, 10 or more amino acid positions. In some embodiments, the engineered PAL polypeptide consists of the sequence of SEQ ID NO:12.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:14 or a functional fragment thereof and an amino acid residue difference as compared to SEQ ID NO:14 at one or more amino acid positions (such as at 1, 2, 3, 4, 5, 6, 7, 8, 9, 10, 11, 12, 14, 15 or more amino acid positions) compared to SEQ ID NO:14, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:14. In some embodiments, the engineered PALs comprise at least 95% sequence identity to SEQ ID NO:14, and comprise an amino acid difference as compared to SEQ ID NO:14, of at least 1, 2, 3, 4, 5, 6, 7, 8, 9, 10 or more amino acid positions. In some embodiments, the engineered PAL polypeptide consists of the sequence of SEQ ID NO:14.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:16 or a functional fragment thereof and an amino acid residue difference as compared to SEQ ID NO:16 at one or more amino acid positions (such as at 1, 2, 3, 4, 5, 6, 7, 8, 9, 10, 11, 12, 14, 15 or more amino acid positions) compared to SEQ ID NO:16, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:16. In some embodiments, the engineered PALs comprise at least 95% sequence identity to SEQ ID NO:16, and comprise an amino acid difference as compared to SEQ ID NO:16, of at least 1, 2, 3, 4, 5, 6, 7, 8, 9, 10 or more amino acid positions. In some embodiments, the engineered PAL polypeptide consists of the sequence of SEQ ID NO:16.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:18 or a functional fragment thereof and an amino acid residue difference as compared to SEQ ID NO:18 at one or more amino acid positions (such as at 1, 2, 3, 4, 5, 6, 7, 8, 9, 10, 11, 12, 14, 15 or more amino acid positions) compared to SEQ ID NO:18, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:18. In some embodiments, the engineered PALs comprise at least 95% sequence identity to SEQ ID NO:18, and comprise an amino acid difference as compared to SEQ ID NO:18, of at least 1, 2, 3, 4, 5, 6, 7, 8, 9, 10 or more amino acid positions. In some embodiments, the engineered PAL polypeptide consists of the sequence of SEQ ID NO:18.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:20 or a functional fragment thereof and an amino acid residue difference as compared to SEQ ID NO:20 at one or more amino acid positions (such as at 1, 2, 3, 4, 5, 6, 7, 8, 9, 10, 11, 12, 14, 15 or more amino acid positions) compared to SEQ ID NO:20, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:20. In some embodiments, the engineered PALs comprise at least 95% sequence identity to SEQ ID NO:20, and comprise an amino acid difference as compared to SEQ ID NO:20, of at least 1, 2, 3, 4, 5, 6, 7, 8, 9, 10 or more amino acid positions. In some embodiments, the engineered PAL polypeptide consists of the sequence of SEQ ID NO:20.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:22 or a functional fragment thereof and an amino acid residue difference as compared to SEQ ID NO:22 at one or more amino acid positions (such as at 1, 2, 3, 4, 5, 6, 7, 8, 9, 10, 11, 12, 14, 15 or more amino acid positions) compared to SEQ ID NO:22, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:22. In some embodiments, the engineered PALs comprise at least 95% sequence identity to SEQ ID NO:22, and comprise an amino acid difference as compared to SEQ ID NO:22, of at least 1, 2, 3, 4, 5, 6, 7, 8, 9, 10 or more amino acid positions. In some embodiments, the engineered PAL polypeptide consists of the sequence of SEQ ID NO:22.

In some embodiments, the engineered PAL polypeptides exhibiting at least one improved property have at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:24 or a functional fragment thereof and an amino acid residue difference as compared to SEQ ID NO:24 at one or more amino acid positions (such as at 1, 2, 3, 4, 5, 6, 7, 8, 9, 10, 11, 12, 14, 15 or more amino acid positions) compared to SEQ ID NO:24, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:24. In some embodiments, the engineered PALs comprise at least 95% sequence identity to SEQ ID NO:24, and comprise an amino acid difference as compared to SEQ ID NO:24, of at least 1, 2, 3, 4, 5, 6, 7, 8, 9, 10 or more amino acid positions. In some embodiments, the engineered PAL polypeptide consists of the sequence of SEQ ID NO:24.

Variants with Reduced Sensitivity to Proteolysis:

In some embodiments, the engineered PAL polypeptides of the present invention have PAL activity, exhibit reduced sensitivity to proteolysis, and comprise: a) an amino acid sequence having at least 85% sequence identity to reference sequence SEQ ID NO:4; an b) an amino acid residue difference as compared to SEQ ID NO:4 at one or more amino acid positions.

In some embodiments, the engineered PAL polypeptides that exhibit reduced sensitivity to proteolysis have at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:4 and an amino acid residue difference as compared to SEQ ID NO:4 at one or more amino acid positions (such as at 1, 2, 3, 4, 5, 6, 7, 8, 9, 10, 11, 12, 14, 15, 20 or more amino acid positions compared to SEQ ID NO:4 or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NO:4).

In some embodiments, the engineered PAL polypeptides that exhibit reduced sensitivity to proteolysis have at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:4 and an amino acid residue difference as compared to SEQ ID NO:4, at one or more amino acid positions are selected from X39; X54; X59; X73; X91; X158; X112, X134, X180; X195; X240; X243; X245; X256; X257; X270; X290; X304, X305; X307; X308; X326; X349; X353; X364; X394; X399; X400; X404; X407; X443; X453; X459; X460; X463; X474; X509; X521; X522; X524; X528; X546; X564; or any combination thereof, when optimally aligned with the amino acid sequence of SEQ ID NO: 4. In some embodiments the amino acid difference is 1, 2, 3, 4, 5, 6, 7, 8, 9, 10, 15, or 20 or greater amino acid positions.

In some embodiments, the engineered PAL polypeptides that exhibit reduced sensitivity to proteolysis have at least 85%, at least 88%, 90%, 91%, 92%, 93%, 94%, 95%, 96%, 97%, 98%, or 99% sequence identity to SEQ ID NO:4, and comprise an amino acid residue difference at position X307; X326; X460; X307; and/or X528 and optionally an amino acid residue difference at 1, 2, 3, 4, 5, 6, 7, 8, 9, 10 or more amino acid positions. In some embodiments, the amino acid residue difference is selected from Y304H/W; R305L/M; H307G/M/Q; I326F; Q240W; T460G; P528L; and any of these substitutions in combination, when aligned with SEQ ID NO:4.

In some embodiments, the engineered PAL polypeptides that exhibit reduced sensitivity to proteolysis have at least 85%, at least 88%, at least 90%, at least 91%, at least 92%, at least 93%, at least 94%, at least 95%, at least 96%, at least 97%, at least 98%, at least 99%, or greater amino acid sequence identity with any of SEQ ID NOS:10, 12, 14, 16, 18, 20, 22, and/or 24, or a functional fragment thereof and an amino acid residue difference as compared to SEQ ID NOS:10, 12, 14, 16, 18, 20, 22, and/or 24, at one or more amino acid positions (such as at 1, 2, 3, 4, 5, 6, 7, 8, 9, 10, 11, 12, 14, 15 or more amino acid positions) compared to SEQ ID NOS:10, 12, 14, 16, 18, 20, 22, and/or 24, or a sequence having at least 85%, at least 88%, at least 90%, at least 91%, at least 92%, at least 93%, at least 94%, at least 95%, at least 96%, at least 97%, at least 98%, at least 99% or greater amino acid sequence identity with SEQ ID NOS:10, 12, 14, 16, 18, 20, 22, and/or 24. In some embodiments, the engineered PAL comprises at least 95% sequence identity to SEQ ID NOS:10, 12, 14, 16, 18, 20, 22, and/or 24, and comprise an amino acid difference as compared to SEQ ID NOS:10, 12, 14, 16, 18, 20, 22, and/or 24, of at least 1, 2, 3, 4, 5, 6, 7, 8, 9, 10 or more amino acid positions. In some embodiments, the PAL comprises or consists of the sequence of SEQ ID NO:10, 12, 14, 16, 18, 20, 22, and/or 24.

In some embodiments, the proteolytic sensitivity of the engineered PAL polypeptides is reduced by at least 5%, at least 10%, at least 15%, at least 20%, at least 25%, at least 30%, at least 40%, at least 50%, at least 60%, at least 70%, at least 80%, at least 85%, at least 90%, or at least 95%, of that of the wild-type PAL (e.g., AvPAL having SEQ ID NO:4) or as compared to a reference PAL polypeptide under essentially the same conditions. The proteolytic activity can be measured using any suitable methods known in the art, including but not limited to those described in the Examples.

In some embodiments, the engineered PAL polypeptides having reduced sensitivity to proteolysis have reduced sensitivity to a composition comprising one or more proteases, including, but not limited to pepsin, trypsin, chymotrypsin, carboxypeptidase A and B, peptidases (e.g., amino peptidase, dipeptidase and enteropeptidase) when both the reference PAL and the engineered PAL having the reduced sensitivity are compared and exposed to essentially the same amount and kind of protease under essentially the same conditions.

In some embodiments, the engineered PAL polypeptide having reduced sensitivity to proteolysis have enzyme activity levels that are about 1.0 fold, 2-fold, 5-fold, 10-fold, 20-fold, 25-fold, 50-fold, 75-fold, 100-fold, 150-fold, 200-fold or more of the enzymatic activity of the reference PAL (e.g., AvPAL). In some embodiments, the engineered polypeptides have more enzyme activity, as compared to a reference PAL, when activity is measured at a pH range of 4.5 to 7.5; when activity is measured at a pH range of 4.5 to 6.5; when activity is measured at a pH range of 5.0 to 7.5; when activity is measured at a pH range of 5.0 to 6.5; when activity is measured at a pH range of 5.5 to 7.5; and/or also when activity is measured at a pH range of 5.5 to 6.5. In some other embodiments, the engineered PAL polypeptides have $K_m$ values in the range of 1 µM to 5 mM.

Variants with Increased Tolerance to Acidic pH:

In some embodiments, the engineered PAL polypeptides of the invention have PAL activity, are tolerant to acidic pH levels and comprise: a) an amino acid sequence having at least 85% sequence identity to reference sequence SEQ ID NO:4, or a fragment thereof; and b) an amino acid residue difference as compared to SEQ ID NO:4, at one or more amino acid positions.

In some embodiments, the engineered PAL polypeptides that exhibit increased tolerance to acidic pH as compared to wild-type AvPAL and/or another reference polypeptide have at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:4 and an amino acid residue difference as compared to SEQ ID NO:4, at one or more amino acid positions (such as at 1, 2, 3, 4, 5, 6, 7, 8, 9, 10, 11, 12, 14, 15, 20 or more amino acid positions compared to SEQ ID NO:4, or a sequence having at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:4.

In some embodiments, the engineered PAL polypeptides that exhibit increased tolerance to acidic pH as compared to wild-type AvPAL and/or another reference polypeptide, have at least 85%, at least 88%, at least 90%, at least 91%, at least 92%, at least 93%, at least 94%, at least 95%, at least 96%, at least 97%, at least 98%, at least 99%, or greater amino acid sequence identity with SEQ ID NO:4, and an amino acid residue difference as compared to SEQ ID NO:4, at one or more amino acid positions are selected from X39; X54; X59; X73; X91; X158; X112, X134, X180; X195; X240; X243; X245; X256; X257; X270; X290; X304, X305; X307; X308; X326; X349; X353; X364; X394; X399; X400; X404; X407; X443; X453; X459; X460; X463; X474; X509; X521; X522; X524; X528; X546; X564; or any combination thereof when optimally aligned with the amino acid sequence of SEQ ID NO:4. In some embodiments the amino acid difference is 1, 2, 3, 4, 5, 6, 7, 8, 9, 10, 15, or 20 or greater amino acid positions.

In some embodiments, the engineered PAL polypeptides that exhibit increased tolerance to acidic pH as compared to wild-type AvPAL and/or another reference polypeptide have at least 85%, at least 88%, 90%, 91%, 92%, 93%, 94%, 95%, 96%, 97%, 98%, or 99% sequence identity to SEQ ID NO:4, and comprise an amino acid residue difference at position X39; X54; X59; X73; X91; X158; X112, X134, X180; X195; X240; X243; X245; X256; X257; X270; X290; X304, X305; X307; X308; X326; X349; X353; X364; X394; X399; X400; X404; X407; X443; X453; X459; X460; X463; X474; X509; X521; X522; X524; X528; X546; X564; or any combination thereof; and optionally an amino acid residue difference at 1, 2, 3, 4, 5, 6, 7, 8, 9, 10 or more amino acid positions. In some embodiments the amino acid residue difference is A39; T54; G59, S73; A91; Y158; S180; K195; A112; R134; Q240; T243; I245; A256; L257; N270; N290; Y304; R305; H307; E308; I326; L349; D353; L364; A394; S399; N400; P404; L407; F443; N453; Y459; T460; T463; N474; E509; Q521; K522; T524; P528; S546; and/or P564, when aligned with SEQ ID NO:4. In some embodiments, the engineered PAL polypeptides that exhibit increased tolerance to acidic pH have at least 85%, at least 88%, 90%, 91%, 92%, 93%, 94%, 95%, 96%, 97%, 98%, or 99% sequence identity to SEQ ID NO:4, and comprise an amino acid residue difference at one or more positions A39V; T54K; G59R; S73K; A112C; R134Q; A91V; Y158H; S180A; K195E; Q240R/W; T243I/L; I245L; A256G; L257W/A; N270K; N290G; Y304H; R305M; H307G/Q/M; E308Q; I326F; L349M; D353A/N; L364Q; A394V; S399N; N400K; P404A; L407V; F443H; N453G; Y459F; T460G; T463N; N474Q; E509L; Q521K/S; K522Y/F/N; T524S; P528L; S546R; and/or P564 G/L/M; when aligned with SEQ ID NO:4.

In some embodiments, when all other assay conditions are essentially the same, the engineered PAL polypeptides having increased tolerance to acidic pH as compared to a reference PAL polypeptide have an increased tolerance at a pH range between 1.5 to 6.5; between 1.5 and 5.0; between 2.0 to 5.5; between 3.0 and 6.8; between 3.0 and 5.5; between 4.0 and 6.5; between 4.0 and 4.5; between 4.5 and 5.0; between 4.5 and 5.5, between 4.5 and 6.0; between 4.5 and 6.5; between 5.0 and 6.5; between 5.0 and 6.0; between 5.0 and 5.5; between 5.5 and 6.0; between 6.0 and 6.5; and/or between 6.5 and 7.0. In some embodiments, the increased tolerance to acidic pH is exhibited at a pH of about 3.5, 4.0, 4.5, 5.0, 5.5, 6.0 and/or 6.5.

In some embodiments, the engineered PAL polypeptides that have increased tolerance to acidic pH also exhibit greater PAL activity as compared to a reference PAL when measure by a standard assay. Any suitable assay finds use in the present invention, including, but not limited to those provided herein.

It is further contemplated that any of the exemplary engineered polypeptides (i.e., Variant No. 1-Variant No. 1010) find use as the starting amino acid sequence for synthesizing other engineered PAL polypeptides, for example by subsequent rounds of evolution by adding new combinations of various amino acid differences from other polypeptides and other residue positions described herein. In some embodiments, additional improvements are generated by including amino acid differences at residue positions that were maintained as unchanged throughout earlier rounds of evolution. It is not intended that the present invention be limited to any particular method for producing engineered PAL polypeptides, as any suitable method finds use, including but not limited to the methods provided herein.

Polynucleotides Encoding Engineered Polypeptides, Expression Vectors and Host Cells:

The present invention provides polynucleotides encoding the engineered PAL polypeptides described herein. In some embodiments, the polynucleotides are operatively linked to one or more heterologous regulatory sequences that control gene expression to create a recombinant polynucleotide capable of expressing the polypeptide. In some embodiments, expression constructs containing at least one heterologous polynucleotide encoding the engineered PAL polypeptide(s) is introduced into appropriate host cells to express the corresponding PAL polypeptide(s).

As will be apparent to the skilled artisan, availability of a protein sequence and the knowledge of the codons corresponding to the various amino acids provide a description of all the polynucleotides capable of encoding the subject polypeptides. The degeneracy of the genetic code, where the same amino acids are encoded by alternative or synonymous codons, allows an extremely large number of nucleic acids to be made, all of which encode an engineered PAL polypeptide. Thus, the present invention provides methods and compositions for the production of each and every possible variation of PAL polynucleotides that could be made that encode the PAL polypeptides described herein by selecting combinations based on the possible codon choices, and all such variations are to be considered specifically disclosed for any polypeptide described herein, including the amino acid sequences presented in the Examples (e.g., in the various Tables).

In some embodiments, the codons are preferably optimized for utilization by the chosen host cell for protein production. For example, preferred codons used in bacteria are typically used for expression in bacteria. Consequently, codon optimized polynucleotides encoding the engineered PAL polypeptides contain preferred codons at about 40%, 50%, 60%, 70%, 80%, 90%, or greater than 90% of the codon positions in the full length coding region.

In some embodiments, the PAL polynucleotide encodes an engineered polypeptide having PAL activity with the properties disclosed herein, wherein the polypeptide comprises an amino acid sequence having at least 80%, 85%, 86%, 87%, 88%, 89%, 90%, 91%, 92%, 93%, 94%, 95%, 96%, 97%, 98%, 99% or more identity to a reference sequence selected from SEQ ID NOS:3, 5, 7, 9, 11, 13, 15, 17, 19, 21, and/or 23, or the amino acid sequence of any variant (e.g., those provided in the Examples), and one or more residue differences as compared to the reference polynucleotide of SEQ ID NOs:3, 5, 7, 9, 11, 13, 15, 17, 19, 21 and/or 23, or the amino acid sequence of any variant as disclosed in the Examples (for example 1, 2, 3, 4, 5, 6, 7, 8, 9, 10 or more amino acid residue positions). In some embodiments, the reference sequence is selected from SEQ ID NOS:3, 5, 7, 9, 11, 13, 15, 17, 19, 21, and/or 23.

In some embodiments, the PAL polynucleotide encodes an engineered polypeptide having PAL activity with the properties disclosed herein, wherein the polypeptide comprises an amino acid sequence having at least 80%, 85%, 86%, 87%, 88%, 89%, 90%, 91%, 92%, 93%, 94%, 95%, 96%, 97%, 98%, 99%, or more sequence identity to reference sequence SEQ ID NO:4 and one or more residue differences as compared to SEQ ID NO:4 at residue positions from X39; X54; X59; X73; X91; X158; X112, X134, X180; X195; X240; X243; X245; X256; X257; X270; X290; X304; X305; X307; X308; X326; X349; X353; X364; X394; X399; X400; X404; X407; X443; X453; X459; X460; X463; X474; X509; X521; X522; X524; X528; X546; and/or X564; when optimally aligned with the polypeptide of SEQ ID NO:4.

In some embodiments, the polynucleotide encoding the engineered PAL polypeptides comprises a polynucleotide sequence selected from a polynucleotide sequence selected from SEQ ID NOS:3, 5, 7, 9, 11, 13, 15, 17, 19, 21, and/or 23. In some embodiments, the polynucleotide encoding an engineered PAL polypeptide has at least 80%, 85%, 90%, 93%, 95%, 96%, 97%, 98%, 99% nucleotide residue identity to SEQ ID NOS:2, 3, 5, 7, 9, 11, 13, 15, 17, 19, 21, and/or 23.

In some embodiments, the polynucleotides are capable of hybridizing under highly stringent conditions to a reference polynucleotide sequence selected from SEQ ID NOS:2, 3, 5, 7, 9, 11, 13, 15, 17, 19, 21, and/or 23, or a complement thereof, or a polynucleotide sequence encoding any of the variant PAL polypeptides provided herein. In some embodiments, the polynucleotide capable of hybridizing under highly stringent conditions encodes a PAL polypeptide comprising an amino acid sequence that has one or more residue differences as compared to SEQ ID NO:4, at residue positions selected from X39; X54; X59; X73; X91; X158; X112, X134, X180; X195; X240; X243; X245; X256; X257; X270; X290; X304; X305; X307; X308; X326; X349; X353; X364; X394; X399; X400; X404; X407; X443; X453; X459; X460; X463; X474; X509; X521; X522; X524; X528; X546; and/or X564.

In some embodiments, an isolated polynucleotide encoding any of the engineered PAL polypeptides herein is manipulated in a variety of ways to facilitate expression of the PAL polypeptide. In some embodiments, the polynucleotides encoding the PAL polypeptides comprise expression vectors where one or more control sequences is present to regulate the expression of the PAL polynucleotides and/or polypeptides. Manipulation of the isolated polynucleotide prior to its insertion into a vector may be desirable or necessary depending on the expression vector utilized. Techniques for modifying polynucleotides and nucleic acid sequences utilizing recombinant DNA methods are well known in the art. In some embodiments, the control sequences include among others, promoters, leader sequences, polyadenylation sequences, propeptide sequences, signal peptide sequences, and transcription terminators. In some embodiments, suitable promoters are selected based on the host cells selection. For bacterial host cells, suitable promoters for directing transcription of the nucleic acid constructs of the present disclosure, include, but are not limited to promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (See e.g., Villa-Kamaroff et al., Proc. Natl Acad. Sci. USA 75: 3727-3731 [1978]), as well as the tac promoter (See e.g., DeBoer et al., Proc. Natl Acad. Sci. USA 80: 21-25 [1983]). Exemplary promoters for filamentous fungal host cells, include, but are not limited to promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (See e.g., WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof. Exemplary yeast cell promoters can be from the genes can be from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are known in the art (See e.g., Romanos et al., Yeast 8:423-488 [1992]).

In some embodiments, the control sequence is also a suitable transcription terminator sequence (i.e., a sequence recognized by a host cell to terminate transcription). In some embodiments, the terminator sequence is operably linked to the 3' terminus of the nucleic acid sequence encoding the PAL polypeptide. Any suitable terminator which is functional in the host cell of choice finds use in the present invention. Exemplary transcription terminators for filamentous fungal host cells can be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Exemplary terminators for yeast host cells can be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are known in the art (See e.g., Romanos et al., supra).

In some embodiments, the control sequence is also a suitable leader sequence (i.e., a non-translated region of an mRNA that is important for translation by the host cell). In some embodiments, the leader sequence is operably linked to the 5' terminus of the nucleic acid sequence encoding the PAL polypeptide. Any suitable leader sequence that is functional in the host cell of choice find use in the present invention. Exemplary leaders for filamentous fungal host cells are obtained from the genes for *Aspergillus oryzae* TAKA amylase, and *Aspergillus nidulans* triose phosphate isomerase. Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

In some embodiments, the control sequence is also a polyadenylation sequence (i.e., a sequence operably linked to the 3' terminus of the nucleic acid sequence and which, when transcribed, is recognized by the host cell as a signal to add polyadenosine residues to transcribed mRNA). Any suitable polyadenylation sequence which is functional in the host cell of choice finds use in the present invention. Exemplary polyadenylation sequences for filamentous fungal host cells include, but are not limited to the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase. Useful polyadenylation sequences for yeast host cells are known (See e.g., Guo and Sherman, Mol. Cell. Bio., 15:5983-5990 [1995]).

In some embodiments, the control sequence is also a signal peptide (i.e., a coding region that codes for an amino acid sequence linked to the amino terminus of a polypeptide and directs the encoded polypeptide into the cell's secretory pathway). In some embodiments, the 5' end of the coding sequence of the nucleic acid sequence inherently contains a signal peptide coding region naturally linked in translation reading frame with the segment of the coding region that encodes the secreted polypeptide. Alternatively, in some embodiments, the 5' end of the coding sequence contains a signal peptide coding region that is foreign to the coding sequence. Any suitable signal peptide coding region which directs the expressed polypeptide into the secretory pathway of a host cell of choice finds use for expression of the engineered polypeptide(s). Effective signal peptide coding regions for bacterial host cells are the signal peptide coding regions include, but are not limited to those obtained from the genes for *Bacillus* NClB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are known in the art (See e.g., Simonen and Palva, Microbiol. Rev., 57:109-137 [1993]). In some embodiments, effective signal peptide coding regions for filamentous fungal host cells include, but are not limited to the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase. Useful signal peptides for yeast host cells include, but are not limited to those from the genes for *Saccharomyces cerevisiae* alpha-factor and *Saccharomyces cerevisiae* invertase.

In some embodiments, the control sequence is also a propeptide coding region that codes for an amino acid sequence positioned at the amino terminus of a polypeptide. The resultant polypeptide is referred to as a "proenzyme," "propolypeptide," or "zymogen." A propolypeptide can be converted to a mature active polypeptide by catalytic or autocatalytic cleavage of the propeptide from the propolypeptide. The propeptide coding region may be obtained from any suitable source, including, but not limited to the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* lactase (See e.g., WO 95/33836). Where both signal peptide and propeptide regions are present at the amino terminus of a polypeptide, the propeptide region is positioned next to the amino terminus of a polypeptide and the signal peptide region is positioned next to the amino terminus of the propeptide region.

In some embodiments, regulatory sequences are also utilized. These sequences facilitate the regulation of the expression of the polypeptide relative to the growth of the host cell. Examples of regulatory systems are those that cause the expression of the gene to be turned on or off in response to a chemical or physical stimulus, including the presence of a regulatory compound. In prokaryotic host cells, suitable regulatory sequences include, but are not limited to the lac, tac, and trp operator systems. In yeast host cells, suitable regulatory systems include, but are not limited to the ADH2 system or GAL1 system. In filamentous fungi, suitable regulatory sequences include, but are not limited to the TAKA alpha-amylase promoter, *Aspergillus niger* glucoamylase promoter, and *Aspergillus oryzae* glucoamylase promoter.

In another aspect, the present invention is directed to a recombinant expression vector comprising a polynucleotide encoding an engineered PAL polypeptide, and one or more expression regulating regions such as a promoter and a terminator, a replication origin, etc., depending on the type of hosts into which they are to be introduced. In some embodiments, the various nucleic acid and control sequences described herein are joined together to produce recombinant expression vectors which include one or more convenient restriction sites to allow for insertion or substitution of the nucleic acid sequence encoding the PAL polypeptide at such sites. Alternatively, in some embodiments, the nucleic acid sequence of the present invention is expressed by inserting the nucleic acid sequence or a nucleic acid construct comprising the sequence into an appropriate vector for expression. In some embodiments involving the creation of the expression vector, the coding sequence is located in the vector so that the coding sequence is operably linked with the appropriate control sequences for expression.

The recombinant expression vector may be any suitable vector (e.g., a plasmid or virus), that can be conveniently subjected to recombinant DNA procedures and bring about the expression of the PAL polynucleotide sequence. The choice of the vector typically depends on the compatibility of the vector with the host cell into which the vector is to be introduced. The vectors may be linear or closed circular plasmids.

In some embodiments, the expression vector is an autonomously replicating vector (i.e., a vector that exists as an extra-chromosomal entity, the replication of which is independent of chromosomal replication, such as a plasmid, an extra-chromosomal element, a minichromosome, or an artificial chromosome). The vector may contain any means for assuring self-replication. In some alternative embodiments, the vector is one in which, when introduced into the host cell, it is integrated into the genome and replicated together with the chromosome(s) into which it has been integrated. Furthermore, in some embodiments, a single vector or plasmid, or two or more vectors or plasmids which together contain the total DNA to be introduced into the genome of the host cell, and/or a transposon is utilized.

In some embodiments, the expression vector contains one or more selectable markers, which permit easy selection of transformed cells. A "selectable marker" is a gene, the product of which provides for biocide or viral resistance, resistance to heavy metals, prototrophy to auxotrophs, and the like. Examples of bacterial selectable markers include, but are not limited to the dal genes from *Bacillus subtilis* or *Bacillus licheniformis*, or markers, which confer antibiotic resistance such as ampicillin, kanamycin, chloramphenicol or tetracycline resistance. Suitable markers for yeast host cells include, but are not limited to ADE2, HIS3, LEU2, LYS2, MET3, TRP1, and URA3. Selectable markers for use in filamentous fungal host cells include, but are not limited to, amdS (acetamidase; e.g., from *A. nidulans* or *A. oryzae*), argB (ornithine carbamoyltransferases), bar (phosphinothricin acetyltransferase; e.g., from *S. hygroscopicus*), hph (hygromycin phosphotransferase), niaD (nitrate reductase), pyrG (orotidine-5'-phosphate decarboxylase; e.g., from *A. nidulans* or *A. oryzae*), sC (sulfate adenyltransferase), and trpC (anthranilate synthase), as well as equivalents thereof.

In another aspect, the present invention provides a host cell comprising at least one polynucleotide encoding at least one engineered PAL polypeptide of the present invention, the polynucleotide(s) being operatively linked to one or more control sequences for expression of the engineered PAL enzyme(s) in the host cell. Host cells suitable for use in expressing the polypeptides encoded by the expression vectors of the present invention are well known in the art and include but are not limited to, bacterial cells, such as *E. coli*, *Vibrio fluvialis*, *Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, BHK, 293, and Bowes melanoma cells; and plant cells. Exemplary host cells also include various *Escherichia coli* strains (e.g., W3110 (ΔfhuA) and BL21).

Accordingly, in another aspect, the present invention provides methods of producing the engineered PAL polypeptides, where the methods comprise culturing a host cell capable of expressing a polynucleotide encoding the engineered PAL polypeptide under conditions suitable for expression of the polypeptide. In some embodiments, the methods further comprise the steps of isolating and/or purifying the PAL polypeptides, as described herein.

Appropriate culture media and growth conditions for host cells are well known in the art. It is contemplated that any suitable method for introducing polynucleotides for expression of the PAL polypeptides into cells will find use in the present invention. Suitable techniques include, but are not limited to electroporation, biolistic particle bombardment, liposome mediated transfection, calcium chloride transfection, and protoplast fusion.

Engineered PAL polypeptides with the properties disclosed herein can be obtained by subjecting the polynucleotide encoding the naturally occurring or engineered PAL polypeptide to any suitable mutagenesis and/or directed evolution methods known in the art, and/or as described herein. An exemplary directed evolution technique is mutagenesis and/or DNA shuffling (See e.g., Stemmer, Proc. Natl. Acad. Sci. USA 91:10747-10751 [1994]; WO 95/22625; WO 97/0078; WO 97/35966; WO 98/27230; WO 00/42651; WO 01/75767 and U.S. Pat. No. 6,537,746). Other directed evolution procedures that can be used include, among others, staggered extension process (StEP), in vitro recombination (See e.g., Zhao et al., Nat. Biotechnol., 16:258-261 [1998]), mutagenic PCR (See e.g., Caldwell et al., PCR Methods Appl., 3:S136-S140 [1994]), and cassette mutagenesis (See e.g., Black et al., Proc. Natl. Acad. Sci. USA 93:3525-3529 [1996]).

Mutagenesis and directed evolution methods can be readily applied to PAL-encoding polynucleotides to generate variant libraries that can be expressed, screened, and assayed. Any suitable mutagenesis and directed evolution methods find use in the present invention and are well known in the art (See e.g., U.S. Pat. Nos. 5,605,793, 5,830,721, 6,132,970, 6,420,175, 6,277,638, 6,365,408, 6,602,986, 7,288,375, 6,287,861, 6,297,053, 6,576,467, 6,444,468, 5,811238, 6,117,679, 6,165,793, 6,180,406, 6,291,242, 6,995,017, 6,395,547, 6,506,602, 6,519,065, 6,506,603, 6,413,774, 6,573,098, 6,323,030, 6,344,356, 6,372,497, 7,868,138, 5,834,252, 5,928,905, 6,489,146, 6,096,548, 6,387,702, 6,391,552, 6,358,742, 6,482,647, 6,335,160, 6,653,072, 6,355,484, 6,03,344, 6,319,713, 6,613,514, 6,455,253, 6,579,678, 6,586,182, 6,406,855, 6,946,296, 7,534,564, 7,776,598, 5,837,458, 6,391,640, 6,309,883, 7,105,297, 7,795,030, 6,326,204, 6,251,674, 6,716,631, 6,528,311, 6,287,862, 6,335,198, 6,352,859, 6,379,964, 7,148,054, 7,629,170, 7,620,500, 6,365,377, 6,358,740, 6,406,910, 6,413,745, 6,436,675, 6,961,664, 7,430,477, 7,873,499, 7,702,464, 7,783,428, 7,747,391, 7,747,393, 7,751,986, 6,376,246, 6,426,224, 6,423,542, 6,479,652, 6,319,714, 6,521,453, 6,368,861, 7,421,347, 7,058,515, 7,024,312, 7,620,502, 7,853,410, 7,957,912, 7,904,249, and all related non-US counterparts; Ling et al., Anal. Biochem., 254(2):157-78 [1997]; Dale et al., Meth. Mol. Biol., 57:369-74 [1996]; Smith, Ann. Rev. Genet., 19:423-462 [1985]; Botstein et al., Science, 229:1193-1201 [1985]; Carter, Biochem. J., 237:1-7 [1986]; Kramer et al., Cell, 38:879-887 [1984]; Wells et al., Gene, 34:315-323 [1985]; Minshull et al., Curr. Op. Chem. Biol., 3:284-290 [1999]; Christians et al., Nat. Biotechnol., 17:259-264 [1999]; Crameri et al., Nature, 391:288-291 [1998]; Crameri, et al., Nat. Biotechnol., 15:436-438 [1997]; Zhang et al., Proc. Nat. Acad. Sci. U.S.A., 94:4504-4509 [1997]; Crameri et al., Nat. Biotechnol., 14:315-319 [1996]; Stemmer, Nature, 370:389-391 [1994]; Stemmer, Proc. Nat. Acad. Sci. USA, 91:10747-10751 [1994]; WO 95/22625; WO 97/0078; WO 97/35966; WO 98/27230; WO 00/42651; WO 01/75767; WO 2009/152336, and U.S. Pat. No. 6,537, 746, all of which are incorporated herein by reference).

In some embodiments, the enzyme clones obtained following mutagenesis treatment are screened by subjecting the enzyme preparations to a defined temperature (or other assay conditions) and measuring the amount of enzyme activity remaining after heat treatments or other suitable assay conditions. Clones containing a polynucleotide encoding a PAL polypeptide are then isolated from the gene, sequenced to identify the nucleotide sequence changes (if any), and used to express the enzyme in a host cell. Measuring enzyme activity from the expression libraries can be performed using any suitable method known in the art (e.g., standard biochemistry techniques, such as HPLC analysis).

For engineered polypeptides of known sequence, the polynucleotides encoding the enzyme can be prepared by standard solid-phase methods, according to known synthetic methods. In some embodiments, fragments of up to about 100 bases can be individually synthesized, then joined (e.g., by enzymatic or chemical litigation methods, or polymerase mediated methods) to form any desired continuous sequence. For example, polynucleotides and oligonucleotides disclosed herein can be prepared by chemical synthesis using the classical phosphoramidite method (See e.g., Beaucage et al., Tet. Lett., 22:1859-69 [1981]; and Matthes et al., EMBO J., 3:801-05 [1984]), as it is typically practiced in automated synthetic methods. According to the phosphoramidite method, oligonucleotides are synthesized (e.g., in an automatic DNA synthesizer, purified, annealed, ligated and cloned in appropriate vectors).

Accordingly, in some embodiments, a method for preparing the engineered PAL polypeptide can comprise: (a) synthesizing a polynucleotide encoding a polypeptide comprising an amino acid sequence selected from the amino acid sequence of any variant as described herein, and (b) expressing the PAL polypeptide encoded by the polynucleotide. In some embodiments of the method, the amino acid sequence encoded by the polynucleotide can optionally have one or several (e.g., up to 3, 4, 5, or up to 10) amino acid residue deletions, insertions and/or substitutions. In some embodiments, the amino acid sequence has optionally 1-2, 1-3, 1-4, 1-5, 1-6, 1-7, 1-8, 1-9, 1-10, 1-15, 1-20, 1-21, 1-22, 1-23, 1-24, 1-25, 1-30, 1-35, 1-40, 1-45, or 1-50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 17, 18, 19, 20, 21, 22, 23, 24, 25, 30, 30, 35, 40, 45, or 50 amino acid residue deletions, insertions and/or substitutions. In some embodiments, the amino acid sequence has optionally 1, 2, 3, 4, 5, 6, 7, 8, 9, 10, 11, 12, 13, 14, 15, 16, 18, 20, 21, 22, 23, 24, or 25 amino acid residue deletions, insertions and/or substitutions. In some embodiments, the substitutions are conservative or non-conservative substitutions.

The expressed engineered PAL polypeptide can be evaluated for any desired improved property or combination of properties (e.g., activity, selectivity, stability, acid tolerance, protease sensitivity, etc.) using any suitable assay known in the art, including but not limited to the assays and conditions described herein.

In some embodiments, any of the engineered PAL polypeptides expressed in a host cell are recovered from the cells and/or the culture medium using any one or more of the well-known techniques for protein purification, including, among others, lysozyme treatment, sonication, filtration, salting-out, ultra-centrifugation, and chromatography.

Chromatographic techniques for isolation of the PAL polypeptides include, among others, reverse phase chromatography, high-performance liquid chromatography, ion-exchange chromatography, hydrophobic-interaction chromatography, size-exclusion chromatography, gel electrophoresis, and affinity chromatography. Conditions for purifying a particular enzyme depends, in part, on factors such as net charge, hydrophobicity, hydrophilicity, molecular weight, molecular shape, etc., and will be apparent to those having skill in the art. In some embodiments, affinity techniques may be used to isolate the improved PAL enzymes. For affinity chromatography purification, any antibody that specifically binds a PAL polypeptide of interest may find use. For the production of antibodies, various host animals, including but not limited to rabbits, mice, rats, etc., are immunized by injection with a PAL polypeptide, or a fragment thereof. In some embodiments, the PAL polypeptide or fragment is attached to a suitable carrier, such as BSA, by means of a side chain functional group or linkers attached to a side chain functional group.

In some embodiments, the engineered PAL polypeptide is produced in a host cell by a method comprising culturing a host cell (e.g., an *E. coli* strain) comprising a polynucleotide sequence encoding an engineered PAL polypeptide as described herein under conditions conducive to the production of the engineered PAL polypeptide and recovering the engineered PAL polypeptide from the cells and/or culture medium. In some embodiments, the host cell produces more than one engineered PAL polypeptide.

In some embodiments, the present invention provides a method of producing an engineered PAL polypeptide comprising culturing a recombinant bacterial cell comprising a polynucleotide sequence encoding an engineered PAL polypeptide having at least 85%, 90%, 95%, 96%, 97%, 98%, or 99% sequence identity to reference sequences SEQ ID NO:4, and one or more amino acid residue differences as compared to SEQ ID NO:4 selected from X39; X91; X158; X180; X195; X243; X245; X256; X257; X270; X290; X307; X308; X326; X349; X364; X394; X399; X400; X404; X407; X443; X453; X459; X460; X463; X474; X522; X524; and X528, or combinations thereof, when optimally aligned with the amino acid sequence of SEQ ID NO:4 under suitable culture conditions to allow the production of the engineered PAL polypeptide and optionally recovering the engineered PAL polypeptide from the culture and/or cultured bacterial cells. In some embodiments, the host cell produces more than one engineered PAL polypeptide.

In some embodiments, once the engineered PAL polypeptides are recovered from the recombinant host cells and/or culture medium, they are further purified by any suitable method(s) known in the art. In some additional embodiments, the purified TAL polypeptides are combined with other ingredients and compounds to provide compositions and formulations comprising the engineered PAL polypeptide as appropriate for different applications and uses (e.g., pharmaceutical compositions).

Compositions:

The present invention provides engineered PAL polypeptides suitable for use in numerous compositions. These compositions find use in many fields, including but not limited to pharmaceuticals, dietary/nutritional supplements, food, feed, and fine chemical production. For example, in some embodiments, the present invention provides food and/or feeds comprising at least one engineered PAL variant and/or at least one polynucleotide sequence encoding at least one PAL variant. In some embodiments, the present invention provides beverages comprising at least one engineered PAL variant.

In some embodiments, the engineered PAL variant in food, feed, and/or nutritional/dietary supplement is glycosylated. Furthermore, the engineered PAL variants find use in any suitable edible enzyme delivery matrix. In some embodiments, the engineered PAL variants are present in an edible enzyme delivery matrix designed for rapid dispersal of the PAL variant within the digestive tract of an animal upon ingestion of the variant.

The present invention also provides engineered PAL polypeptides suitable for use in production of fine chemicals and other industrially important compounds (See e.g., US Pat. Appln. Nos. 2013/0340119, 2013/0005012, and 2005/0260724, and WO 2012/122333).

Pharmaceutical and Other Compositions

The present invention provides engineered PAL polypeptides suitable for use in pharmaceutical and other compositions, such as dietary/nutritional supplements.

Depending on the mode of administration, these compositions comprising a therapeutically effective amount of an engineered PAL according to the invention are in the form of a solid, semi-solid, or liquid. In some embodiments, the compositions include other pharmaceutically acceptable components such as diluents, buffers, excipients, salts, emulsifiers, preservatives, stabilizers, fillers, and other ingredients. Details on techniques for formulation and administration are well known in the art and described in the literature.

In some embodiments, the engineered PAL polypeptides are formulated for use in oral pharmaceutical compositions. Any suitable format for use in delivering the engineered PAL polypeptides find use in the present invention, including but not limited to pills, tablets, gel tabs, capsules, lozenges, dragees, powders, soft gels, sol-gels, gels, emulsions, implants, patches, sprays, ointments, liniments, creams, pastes, jellies, paints, aerosols, chewing gums, demulcents, sticks, suspensions (including but not limited to oil-based suspensions, oil-in water emulsions, etc.), slurries, syrups, controlled release formulations, suppositories, etc. In some embodiments, the engineered PAL polypeptides are provided in a format suitable for injection (i.e., in an injectable formulation). In some embodiments, the engineered PAL polypeptides are provided in biocompatible matrices such as sol-gels, including silica-based (e.g., oxysilane) sol-gels. In some embodiments, the engineered PAL polypeptides are encapsulated. In some alternative embodiments, the engineered PAL polypeptides are encapsulated in nanostructures (e.g., nanotubes, nanotubules, nanocapsules, or microcapsules, microspheres, liposomes, etc.). Indeed, it is not intended that the present invention be limited to any particular delivery formulation and/or means of delivery. It is intended that the engineered PAL polypeptides be administered by any suitable means known in the art, including but not limited to parenteral, oral, topical, transdermal, intranasal, intraocular, intrathecal, via implants, etc.

In some embodiments, the engineered PAL polypeptides are chemically modified by glycosylation, pegylation (i.e., modified with polyethylene glycol [PEG] or activated PEG, etc.) or other compounds (See e.g., Ikeda, Amino Acids 29:283-287 [2005]; U.S. Pat. Nos. 7,531,341, 7,534,595, 7,560,263, and 7,53,653; US Pat. Appln. Publ. Nos. 2013/0039898, 2012/0177722, etc.). Indeed, it is not intended that the present invention be limited to any particular delivery method and/or mechanism.

In some additional embodiments, the engineered PAL polypeptides are provided in formulations comprising matrix-stabilized enzyme crystals. In some embodiments, the formulation comprises a cross-linked crystalline engineered PAL enzyme and a polymer with a reactive moiety that adheres to the enzyme crystals. The present invention also provides engineered PAL polypeptides in polymers.

In some embodiments, compositions comprising the engineered PAL polypeptides of the present invention include one or more commonly used carrier compounds, including but not limited to sugars (e.g., lactose, sucrose, mannitol, and/or sorbitol), starches (e.g., corn, wheat, rice, potato, or other plant starch), cellulose (e.g., methyl cellulose, hydroxypropylmethyl cellulose, sodium carboxy-methylcellulose), gums (e.g., arabic, tragacanth, guar, etc.), and/or proteins (e.g., gelatin, collagen, etc.). Additional components in oral formulations may include coloring and or sweetening agents (e.g., glucose, sucrose, and mannitol) and lubricating agents (e.g., magnesium stearate), as well as enteric coatings (e.g., methacrylate polymers, hydroxyl propyl methyl cellulose phthalate, and/or any other suitable enteric coating known in the art). In some embodiments, disintegrating or solubilizing agents are included (e.g., cross-linked polyvinyl pyrrolidone, agar, alginic acid or salts thereof, such as sodium alginate). In some embodiments, the engineered PAL polypeptide are combined with various additional components, including but not limited to preservatives, suspending agents, thickening agents, wetting agents, alcohols, fatty acids, and/or emulsifiers, particularly in liquid formulations.

In some embodiments, the engineered PAL polypeptide are be combined with various additional components, including but not limited to preservatives, suspending agents, thickening agents, wetting agents, alcohols, fatty acids, and/or emulsifiers, particularly in liquid formulations. In some embodiments, the engineered PAL polypeptides are administered to subjects in combination with other compounds used in the treatment of PKU, including but not limited to KUVAN® tetrahydrobiopterin (BioMarin Pharmaceutical, Inc., Novato, Calif.), antacids (e.g., omeprazole, esomeprazole and other prazoles), as well as any other suitable compounds.

In some embodiments, the present invention provides engineered PAL polypeptides suitable for use in decreasing the concentration of phenylalanine in fluids such as blood, cerebrospinal fluid, etc. The dosage of engineered PAL polypeptide(s) administered to an animal depend upon the condition or disease, the general condition of the animal, and other factors known to those in the art. In some embodiments, the compositions are intended for single or multiple administration to an animal. In some embodiments, it is contemplated that the concentration of engineered PAL polypeptide(s) in the composition(s) administered to an animal (e.g., a human with PKU) is sufficient to effectively treat, ameliorate and/or prevent disease (e.g., PKU and/or PKU-related conditions, diseases and/or symptoms), In some embodiments, the engineered PAL polypeptides are administered in combination with other pharmaceutical and/or dietary compositions.

Industrial Compositions

It is contemplated that the engineered PAL polypeptides of the present invention will find use in industrial compositions. In some embodiments, the engineered PAL polypeptides are formulated for use in the food and/or feed industries. In some embodiments, the engineered PAL polypeptides are formulated in granulated or pelleted products which are mixed with animal feed components such as additional enzymes (for example, cellulases, laccases, and amylases). In some alternative embodiments, the engineered PAL polypeptides are used in liquid animal feed compositions (e.g., aqueous or oil based slurries). Thus, in some embodiments, the engineered PAL variants of the present invention are sufficiently thermotolerant and thermostable to withstand the treatment used to produce pellets and other processed feed/foods.

The engineered PAL variants of the present invention also find use in the production of phenylalanine and/or phenylalanine derivatives.

The foregoing and other aspects of the invention may be better understood in connection with the following non-limiting examples. The examples are provided for illustrative purposes only and are not intended to limit the scope of the present invention in any way.

EXPERIMENTAL

The following examples, including experiments and results achieved, are provided for illustrative purposes only and are not to be construed as limiting the present invention.

In the experimental disclosure below, the following abbreviations apply: ppm (parts per million); M (molar); mM (millimolar), uM and µM (micromolar); nM (nanomolar); mol (moles); gm and g (gram); mg (milligrams); ug and µg (micrograms); L and l (liter); ml and mL (milliliter); cm (centimeters); mm (millimeters); um and µm (micrometers); sec. (seconds); min(s) (minute(s)); h(s) and hr(s) (hour(s)); U (units); MW (molecular weight); rpm (rotations per minute); psi and PSI (pounds per square inch); ° C. (degrees Centigrade); RT and rt (room temperature); CDS (coding sequence); DNA (deoxyribonucleic acid); RNA (ribonucleic acid); E. coli W3110 (commonly used laboratory E. coli strain, available from the Coli Genetic Stock Center [CGSC], New Haven, Conn.); HTP (high throughput); HPLC (high pressure liquid chromatography); CFSE (carboxyfluorescein succinimidyl ester); IPTG (isopropyl β-D-1-thiogalactopyranoside); PES (polyethersulfone); PHE and phe (phenylalanine); BSA (bovine serum albumin); PBMC (peripheral blood mononuclear cells); PKU (phenylketonuria); MHC (major histocompatibility complex); HLA (human leukocyte antigen); HLA-DR (an MHC Class II cell surface receptor encoded by the HLA complex on chromosome #6); FIOPC (fold improvements over positive control); LB (Luria broth); Athens Research (Athens Research Technology, Athens, Ga.); ProSpec (ProSpec Tany Technogene, East Brunswick, N.J.); Sigma-Aldrich (Sigma-Aldrich, St. Louis, Mo.); Ram Scientific (Ram Scientific, Inc., Yonkers, N.Y.); Pall Corp. (Pall, Corp., Pt. Washington, N.Y.); Millipore (Millipore, Corp., Billerica Mass.); Difco (Difco Laboratories, BD Diagnostic Systems, Detroit, Mich.); Molecular Devices (Molecular Devices, LLC, Sunnyvale, Calif.); Kuhner (Adolf Kuhner, AG, Basel, Switzerland); Cambridge Isotope Laboratories, (Cambridge Isotope Laboratories, Inc., Tewksbury, Mass.); Applied Biosystems (Applied Biosystems, part of Life Technologies, Corp., Grand Island, N.Y.), Agilent (Agilent Technologies, Inc., Santa Clara, Calif.); Thermo Scientific (part of Thermo Fisher Scientific, Waltham, Mass.); Corning (Corning, Inc., Palo Alto, Calif.); Constant Systems (Constant Systems Ltd., Daventry, United Kingdom); Megazyme (Megazyme International, Wicklow, Ireland); Enzo (Enzo Life Sciences, Inc., Farmingdale, N.Y.); GE Healthcare (GE Healthcare Biosciences, Piscataway, N.J.); Harlan (Harlan Laboratories, Indianapolis, Ind.); AB Sciex (AB Sciex, Framingham, Mass.); and Bio-Rad (Bio-Rad Laboratories, Hercules, Calif.).

The following polynucleotide and polypeptide sequences find use in the present invention. In some cases (as shown below), the polynucleotide sequence is followed by the encoded polypeptide.

```
Polynucleotide Sequence of pET16b-AvPAL Expression Vector (SEQ ID NO: 1):
                                                                    (SEQ ID NO: 1)
TCTCATGTTTGACAGCTTATCATCGATAAGCTTTAATGCGGTAGTTTATCACAGTTAAATT

GCTAACGCAGTCAGGCACCGTGTATGAAATCTAACAATGCGCTCATCGTCATCCTCGGCA

CCGTCACCCTGGATGCTGTAGGCATAGGCTTGGTTATGCCGGTACTGCCGGGCCTCTTGC

GGGATATCCGGATATAGTTCCTCCTTTCAGCAAAAAACCCCTCAAGACCCGTTTAGAGGC

CCCAAGGGGTTATGCTAGTTATTGCTCAGCGGTGGCAGCAGCCAACTCAGCTTCCTTTCG

GGCTTTGTTAGCAGCCGGATCCTTAATGCAGACACGGCAGAATGTCCTGAACGGCCTGA

ACAATAACACCACCGGCTGCAATATCTGCACTAATACGTGCAATATGTTCATCCAGACCC
```

-continued

```
TGTTCATTATCATTCCAAATATACGGACGATCTGAGGTCGGTTTCTGACCAACAACATGA
CGAACTGCGCTATACAGACGTTCGGTTGCCGGTGACAGACAGGCACGTGCATCATAATG
ACCGGTTTTTTGTAGGTACGCAGATCAACTGCCTGAACACCAAACATCAGGGCAATGGC
AACATAATTCTGAAAAATATCAACGCTACGACGTGCCAGGGTTGCGCTGGTATAACCCTG
GCTGTTAATATTCTGGTTAAACTGTTCGGCATGGGTCGGAAAACGATCTGCAATACTATT
ACCATAAAAGGTCAGCAGCGGCATAATGCTATTACCGCAAATCTGCAGACCTTTCAGAC
CCATATTAACTTTACGTTCACGATTACCCAGCAGACTCGGAGGCAGACCATTGCTAAATT
CCGGTGATGCCAGCAGTGCAATCTGAACATCCAGATGTTTTGCCAGCAGACCGATATAAT
AGCGCAGATGATCCATACCCATACCAACATACTGACCCAGAAAATTACCACCATGATAG
CTTGCCTGATTATCAACATCAATCAGCGGGTTATCGGTAACGCTGTTAATCTCAATTTCG
ATTTGTTTGGCAATCTGGCTAATACCATCAACAATCGGACCCAGATACTGCGGCAGACAA
CGCAGGCTATAACGATCCTGGATCAGTTCATGATCACGATAATCATGTTTACCATCCAGT
TCATCACGAACCAGCTGGCTATTGGCCAGCAGGCTAATCATCTGATCTGCTGCCCACAGC
TGACCCGGATGCGGTTTGCTGTTATGGATAAACGGATGAAAGCTCTGATTTGTACCATTC
AGTGCCTGAATATCCAGTGCATGAACACCCATTGCAATTGCGGTCAGAATCTGGGTATCA
TAAACACAATTTGCTGCAATACCGGTCATAACGCTGGTGCCATTCATCATTGCCAGACCT
TCTTTCGGCAGCAGGGTCAGCGGACTCAGATTCAGCTGACGCAGTGCGGTCGGTGCGTCC
ATTTCTTTGCCATTAAAATCAACTTTAAAGCTCGGGTCCAGGCCAATCAGGCTACCGGTA
ATATAGCTCAGCGGAACCAGATCACCGCTGGCACCAATGCTACCAAATTCATAAACATA
CGGGGTAACACCGGCATTCAGAAAGATTTCCATGCGTTTAATCAGTTCCAGACGAATACC
GCTTGCACCACGCATGTGGCTATTTGCACGCAGCAGCATTGCTGCACGAACATCTGCCAG
CGGCAGTTTATTACCTGCACCGGTTTTCAGAAACCAAACCAGATTGGTCTGCAGTTCGCT
TGCCTGTTCACGGCTAATTGCAACATTTGCCATACCACCAAAACCGCTGGTAACACCATA
AATCGGTTCACCGCTTTCAACTGCATTATTGATATAATCACAGCTGGCCTGAATACCCTG
CAGAATATCGGTATTATTGGTCAGGCTAACCAGGGTGCCATTACGGGCAACACGTGCAA
CATCATTGATGGTCAGTTTCTGATTACCAATAATCACATTTGCGCTGCTATTGCCGGTAAA
GCTAAACTGCTGGCTGCTGGTTTTGCTCTGTGCCTGGCTCAGGGTTTTCATATGACGACCT
TCGATATGGCCGCTGCTGTGATGATGATGATGATGATGATGATGGCCCATGGTATAT
CTCCTTCTTAAAGTTAAACAAAATTATTTCTAGAGGGGAATTGTTATCCGCTCACAATTCC
CCTATAGTGAGTCGTATTAATTTCGCGGGATCGAGATCTCGATCCTCTACGCCGGACGCA
TCGTGGCCGGCATCACCGGCGCCACAGGTGCGGTTGCTGGCGCCTATATCGCCGACATCA
CCGATGGGGAAGATCGGGCTCGCCACTTCGGGCTCATGAGCGCTTGTTTCGGCGTGGGTA
TGGTGGCAGGCCCCGTGGCCGGGGGACTGTTGGGCGCCATCTCCTTGCATGCACCATTCC
TTGCGGCGGCGGTGCTCAACGGCCTCAACCTACTACTGGGCTGCTTCCTAATGCAGGAGT
CGCATAAGGGAGAGCGTCGAGATCCCGGACACCATCGAATGGCGCAAAACCTTTCGCGG
TATGGCATGATAGCGCCCGGAAGAGAGTCAATTCAGGGTGGTGAATGTGAAACCAGTAA
CGTTATACGATGTCGCAGAGTATGCCGGTGTCTCTTATCAGACCGTTTCCCGCGTGGTGA
ACCAGGCCAGCCACGTTTCTGCGAAAACGCGGGAAAAAGTGGAAGCGGCGATGGCGGA
GCTGAATTACATTCCCAACCGCGTGGCACAACAACTGGCGGGCAAACAGTCGTTGCTGA
TTGGCGTTGCCACCTCCAGTCTGGCCCTGCACGCGCCGTCGCAAATTGTCGCGGCGATTA
AATCTCGCGCCGATCAACTGGGTGCCAGCGTGGTGGTGTCGATGGTAGAACGAAGCGGC
```

-continued

```
GTCGAAGCCTGTAAAGCGGCGGTGCACAATCTTCTCGCGCAACGCGTCAGTGGGCTGAT
CATTAACTATCCGCTGGATGACCAGGATGCCATTGCTGTGGAAGCTGCCTGCACTAATGT
TCCGGCGTTATTTCTTGATGTCTCTGACCAGACACCCATCAACAGTATTATTTTCTCCCAT
GAAGACGGTACGCGACTGGGCGTGGAGCATCTGGTCGCATTGGGTCACCAGCAAATCGC
GCTGTTAGCGGGCCCATTAAGTTCTGTCTCGGCGCGTCTGCGTCTGGCTGGCTGGCATAA
ATATCTCACTCGCAATCAAATTCAGCCGATAGCGGAACGGGAAGGCGACTGGAGTGCCA
TGTCCGGTTTTCAACAAACCATGCAAATGCTGAATGAGGGCATCGTTCCCACTGCGATGC
TGGTTGCCAACGATCAGATGGCGCTGGGCGCAATGCGCGCCATTACCGAGTCCGGGCTG
CGCGTTGGTGCGGATATCTCGGTAGTGGGATACGACGATACCGAAGACAGCTCATGTTAT
ATCCCGCCGTTAACCACCATCAAACAGGATTTTCGCCTGCTGGGGCAAACCAGCGTGGAC
CGCTTGCTGCAACTCTCTCAGGGCCAGGCGGTGAAGGGCAATCAGCTGTTGCCCGTCTCA
CTGGTGAAAAGAAAAACCACCCTGGCGCCCAATACGCAAACCGCCTCTCCCCGCGCGTT
GGCCGATTCATTAATGCAGCTGGCACGACAGGTTTCCCGACTGGAAAGCGGGCAGTGAG
CGCAACGCAATTAATGTAAGTTAGCTCACTCATTAGGCACCGGGATCTCGACCGATGCCC
TTGAGAGCCTTCAACCCAGTCAGCTCCTTCCGGTGGGCGCGGGGCATGACTATCGTCGCC
GCACTTATGACTGTCTTCTTTATCATGCAACTCGTAGGACAGGTGCCGGCAGCGCTCTGG
GTCATTTTCGGCGAGGACCGCTTTCGCTGGAGCGCGACGATGATCGGCCTGTCGCTTGCG
GTATTCGGAATCTTGCACGCCCTCGCTCAAGCCTTCGTCACTGGTCCCGCCACCAAACGT
TTCGGCGAGAAGCAGGCCATTATCGCCGGCATGGCGGCCGACGCGCTGGGCTACGTCTT
GCTGGCGTTCGCGACGCGAGGCTGGATGGCCTTCCCCATTATGATTCTTCTCGCTTCCGG
CGGCATCGGGATGCCCGCGTTGCAGGCCATGCTGTCCAGGCAGGTAGATGACGACCATC
AGGGACAGCTTCAAGGATCGCTCGCGGCTCTTACCAGCCTAACTTCGATCACTGGACCGC
TGATCGTCACGGCGATTTATGCCGCCTCGGCGAGCACATGGAACGGGTTGGCATGGATTG
TAGGCGCCGCCCTATACCTTGTCTGCCTCCCCGCGTTGCGTCGCGGTGCATGGAGCCGGG
CCACCTCGACCTGAATGGAAGCCGGCGGCACCTCGCTAACGGATTCACCACTCCAAGAA
TTGGAGCCAATCAATTCTTGCGGAGAACTGTGAATGCGCAAACCAACCCTTGGCAGAAC
ATATCCATCGCGTCCGCCATCTCCAGCAGCCGCACGCGGCGCATCTCGGGCAGCGTTGGG
TCCTGGCCACGGGTGCGCATGATCGTGCTCCTGTCGTTGAGGACCCGGCTAGGCTGGCGG
GGTTGCCTTACTGGTTAGCAGAATGAATCACCGATACGCGAGCGAACGTGAAGCGACTG
CTGCTGCAAAACGTCTGCGACCTGAGCAACAACATGAATGGTCTTCGGTTTCCGTGTTTC
GTAAAGTCTGGAAACGCGGAAGTCAGCGCCCTGCACCATTATGTTCCGGATCTGCATCGC
AGGATGCTGCTGGCTACCCTGTGGAACACCTACATCTGTATTAACGAAGCGCTGGCATTG
ACCCTGAGTGATTTTTCTCTGGTCCCGCCGCATCCATACCGCCAGTTGTTTACCCTCACAA
CGTTCCAGTAACCGGGCATGTTCATCATCAGTAACCCGTATCGTGAGCATCCTCTCTCGTT
TCATCGGTATCATTACCCCCATGAACAGAAATCCCCCTTACACGGAGGCATCAGTGACCA
AACAGGAAAAACCGCCCTTAACATGGCCCGCTTTATCAGAAGCCAGACATTAACGCTT
CTGGAGAAACTCAACGAGCTGGACGCGGATGAACAGGCAGACATCTGTGAATCGCTTCA
CGACCACGCTGATGAGCTTTACCGCAGCTGCCTCGCGCGTTTCGGTGATGACGGTGAAAA
CCTCTGACACATGCAGCTCCCGGAGACGGTCACAGCTTGTCTGTAAGCGGATGCCGGGA
GCAGACAAGCCCGTCAGGGCGCGTCAGCGGGTGTTGGCGGGTGTCGGGGCGCAGCCATG
```

-continued

```
ACCCAGTCACGTAGCGATAGCGGAGTGTATACTGGCTTAACTATGCGGCATCAGAGCAG

ATTGTACTGAGAGTGCACCATATATGCGGTGTGAAATACCGCACAGATGCGTAAGGAGA

AAATACCGCATCAGGCGCTCTTCCGCTTCCTCGCTCACTGACTCGCTGCGCTCGGTCGTTC

GGCTGCGGCGAGCGGTATCAGCTCACTCAAAGGCGGTAATACGGTTATCCACAGAATCA

GGGGATAACGCAGGAAAGAACATGTGAGCAAAAGGCCAGCAAAAGGCCAGGAACCGTA

AAAAGGCCGCGTTGCTGGCGTTTTTCCATAGGCTCCGCCCCCCTGACGAGCATCACAAAA

ATCGACGCTCAAGTCAGAGGTGGCGAAACCCGACAGGACTATAAAGATACCAGGCGTTT

CCCCCTGGAAGCTCCCTCGTGCGCTCTCCTGTTCCGACCCTGCCGCTTACCGGATACCTGT

CCGCCTTTCTCCCTTCGGGAAGCGTGGCGCTTTCTCATAGCTCACGCTGTAGGTATCTCAG

TTCGGTGTAGGTCGTTCGCTCCAAGCTGGGCTGTGTGCACGAACCCCCCGTTCAGCCCGA

CCGCTGCGCCTTATCCGGTAACTATCGTCTTGAGTCCAACCCGGTAAGACACGACTTATC

GCCACTGGCAGCAGCCACTGGTAACAGGATTAGCAGAGCGAGGTATGTAGGCGGTGCTA

CAGAGTTCTTGAAGTGGTGGCCTAACTACGGCTACACTAGAAGGACAGTATTTGGTATCT

GCGCTCTGCTGAAGCCAGTTACCTTCGGAAAAAGAGTTGGTAGCTCTTGATCCGGCAAAC

AAACCACCGCTGGTAGCGGTGGTTTTTTTGTTTGCAAGCAGCAGATTACGCGCAGAAAAA

AAGGATCTCAAGAAGATCCTTTGATCTTTTCTACGGGGTCTGACGCTCAGTGGAACGAAA

ACTCACGTTAAGGGATTTTGGTCATGAGATTATCAAAAAGGATCTTCACCTAGATCCTTT

TAAATTAAAAATGAAGTTTTAAATCAATCTAAAGTATATATGAGTAAACTTGGTCTGACA

GTTACCAATGCTTAATCAGTGAGGCACCTATCTCAGCGATCTGTCTATTTCGTTCATCCAT

AGTTGCCTGACTCCCCGTCGTGTAGATAACTACGATACGGGAGGGCTTACCATCTGGCCC

CAGTGCTGCAATGATACCGCGAGACCCACGCTCACCGGCTCCAGATTTATCAGCAATAA

ACCAGCCAGCCGGAAGGGCCGAGCGCAGAAGTGGTCCTGCAACTTTATCCGCCTCCATC

CAGTCTATTAATTGTTGCCGGGAAGCTAGAGTAAGTAGTTCGCCAGTTAATAGTTTGCGC

AACGTTGTTGCCATTGCTGCAGGCATCGTGGTGTCACGCTCGTCGTTTGGTATGGCTTCAT

TCAGCTCCGGTTCCCAACGATCAAGGCGAGTTACATGATCCCCCATGTTGTGCAAAAAAG

CGGTTAGCTCCTTCGGTCCTCCGATCGTTGTCAGAAGTAAGTTGGCCGCAGTGTTATCAC

TCATGGTTATGGCAGCACTGCATAATTCTCTTACTGTCATGCCATCCGTAAGATGCTTTTC

TGTGACTGGTGAGTACTCAACCAAGTCATTCTGAGAATAGTGTATGCGGCGACCGAGTTG

CTCTTGCCCGGCGTCAACACGGGATAATACCGCGCCACATAGCAGAACTTTAAAAGTGCT

CATCATTGGAAAACGTTCTTCGGGGCGAAAACTCTCAAGGATCTTACCGCTGTTGAGATC

CAGTTCGATGTAACCCACTCGTGCACCCAACTGATCTTCAGCATCTTTTACTTTCACCAGC

GTTTCTGGGTGAGCAAAAACAGGAAGGCAAAATGCCGCAAAAAAGGGAATAAGGGCGA

CACGGAAATGTTGAATACTCATACTCTTCCTTTTTCAATATTATTGAAGCATTTATCAGGG

TTATTGTCTCATGAGCGGATACATATTTGAATGTATTTAGAAAAATAAACAAATAGGGGT

TCCGCGCACATTTCCCCGAAAAGTGCCACCTGACGTCTAAGAAACCATTATTATCATGAC

ATTAACCTATAAAAATAGGCGTATCACGAGGCCCTTTCGTCTTCAAGAAT
```

Polynucleotide Sequence of the AvPAL ORF (SEQ ID NO: 2):

(SEQ ID NO: 2)

```
ATGAAAACCCTGAGCCAGGCACAGAGCAAAACCAGCAGCCAGCAGTTTAGCTTTACCGG

CAATAGCAGCGCAAATGTGATTATTGGTAATCAGAAACTGACCATCAATGATGTTGCAC

GTGTTGCCCGTAATGGCACCCTGGTTAGCCTGACCAATAATACCGATATTCTGCAGGGTA

TTCAGGCCAGCTGTGATTATATCAATAATGCAGTTGAAAGCGGTGAACCGATTTATGGTG
```

-continued

```
TTACCAGCGGTTTTGGTGGTATGGCAAATGTTGCAATTAGCCGTGAACAGGCAAGCGAA
CTGCAGACCAATCTGGTTTGGTTTCTGAAAACCGGTGCAGGTAATAAACTGCCGCTGGCA
GATGTTCGTGCAGCAATGCTGCTGCGTGCAAATAGCCACATGCGTGGTGCAAGCGGTATT
CGTCTGGAACTGATTAAACGCATGGAAATCTTTCTGAATGCCGGTGTTACCCCGTATGTT
TATGAATTTGGTAGCATTGGTGCCAGCGGTGATCTGGTTCCGCTGAGCTATATTACCGGT
AGCCTGATTGGCCTGGACCCGAGCTTTAAAGTTGATTTTAATGGCAAAGAAATGGACGC
ACCGACCGCACTGCGTCAGCTGAATCTGAGTCCGCTGACCCTGCTGCCGAAAGAAGGTCT
GGCAATGATGAATGGCACCAGCGTTATGACCGGTATTGCAGCAAATTGTGTTTATGATAC
CCAGATTCTGACCGCAATTGCAATGGGTGTTCATGCACTGGATATTCAGGCACTGAATGG
TACAAATCAGAGCTTTCATCCGTTTATCCATAACAGCAAACCGCATCCGGGTCAGCTGTG
GGCAGCAGATCAGATGATTAGCCTGCTGGCCAATAGCCAGCTGGTTCGTGATGAACTGG
ATGGTAAACATGATTATCGTGATCATGAACTGATCCAGGATCGTTATAGCCTGCGTTGTC
TGCCGCAGTATCTGGGTCCGATTGTTGATGGTATTAGCCAGATTGCCAAACAAATCGAAA
TTGAGATTAACAGCGTTACCGATAACCCGCTGATTGATGTTGATAATCAGGCAAGCTATC
ATGGTGGTAATTTTCTGGGTCAGTATGTTGGTATGGGTATGGATCATCTGCGCTATTATAT
CGGTCTGCTGGCAAAACATCTGGATGTTCAGATTGCACTGCTGGCATCACCGGAATTTAG
CAATGGTCTGCCTCCGAGTCTGCTGGGTAATCGTGAACGTAAAGTTAATATGGGTCTGAA
AGGTCTGCAGATTTGCGGTAATAGCATTATGCCGCTGCTGACCTTTTATGGTAATAGTAT
TGCAGATCGTTTTCCGACCCATGCCGAACAGTTTAACCAGAATATTAACAGCCAGGGTTA
TACCAGCGCAACCCTGGCACGTCGTAGCGTTGATATTTTTCAGAATTATGTTGCCATTGC
CCTGATGTTTGGTGTTCAGGCAGTTGATCTGCGTACCTACAAAAAAACCGGTCATTATGA
TGCACGTGCCTGTCTGTCACCGGCAACCGAACGTCTGTATAGCGCAGTTCGTCATGTTGT
TGGTCAGAAACCGACCTCAGATCGTCCGTATATTTGGAATGATAATGAACAGGGTCTGG
ATGAACATATTGCACGTATTAGTGCAGATATTGCAGCCGGTGGTGTTATTGTTCAGGCCG
TTCAGGACATTCTGCCGTGTCTGCAT
```

Polynucleotide Sequence of WT AvPAL (SEQ ID NO: 3):

(SEQ ID NO: 3)

```
ATGAAAACCCTGAGCCAGGCACAGAGCAAAACCAGCAGCCAGCAGTTTAGCTTTACCGG
CAATAGCAGCGCAAATGTGATTATTGGTAATCAGAAACTGACCATCAATGATGTTGCAC
GTGTTGCCCGTAATGGCACCCTGGTTAGCCTGACCAATAATACCGATATTCTGCAGGGTA
TTCAGGCCAGCTGTGATTATATCAATAATGCAGTTGAAAGCGGTGAACCGATTTATGGTG
TTACCAGCGGTTTTGGTGGTATGGCAAATGTTGCAATTAGCCGTGAACAGGCAAGCGAA
CTGCAGACCAATCTGGTTTGGTTTCTGAAAACCGGTGCAGGTAATAAACTGCCGCTGGCA
GATGTTCGTGCAGCAATGCTGCTGCGTGCAAATAGCCACATGCGTGGTGCAAGCGGTATT
CGTCTGGAACTGATTAAACGCATGGAAATCTTTCTGAATGCCGGTGTTACCCCGTATGTT
TATGAATTTGGTAGCATTGGTGCCAGCGGTGATCTGGTTCCGCTGAGCTATATTACCGGT
AGCCTGATTGGCCTGGACCCGAGCTTTAAAGTTGATTTTAATGGCAAAGAAATGGACGC
ACCGACCGCACTGCGTCAGCTGAATCTGAGTCCGCTGACCCTGCTGCCGAAAGAAGGTCT
GGCAATGATGAATGGCACCAGCGTTATGACCGGTATTGCAGCAAATTGTGTTTATGATAC
CCAGATTCTGACCGCAATTGCAATGGGTGTTCATGCACTGGATATTCAGGCACTGAATGG
TACAAATCAGAGCTTTCATCCGTTTATCCATAACAGCAAACCGCATCCGGGTCAGCTGTG
```

-continued

```
GGCAGCAGATCAGATGATTAGCCTGCTGGCCAATAGCCAGCTGGTTCGTGATGAACTGG

ATGGTAAACATGATTATCGTGATCATGAACTGATCCAGGATCGTTATAGCCTGCGTTGTC

TGCCGCAGTATCTGGGTCCGATTGTTGATGGTATTAGCCAGATTGCCAAACAAATCGAAA

TTGAGATTAACAGCGTTACCGATAACCCGCTGATTGATGTTGATAATCAGGCAAGCTATC

ATGGTGGTAATTTTCTGGGTCAGTATGTTGGTATGGGTATGGATCATCTGCGCTATTATAT

CGGTCTGCTGGCAAAACATCTGGATGTTCAGATTGCACTGCTGGCATCACCGGAATTTAG

CAATGGTCTGCCTCCGAGTCTGCTGGGTAATCGTGAACGTAAAGTTAATATGGGTCTGAA

AGGTCTGCAGATTTGCGGTAATAGCATTATGCCGCTGCTGACCTTTTATGGTAATAGTAT

TGCAGATCGTTTTCCGACCCATGCCGAACAGTTTAACCAGAATATTAACAGCCAGGGTTA

TACCAGCGCAACCCTGGCACGTCGTAGCGTTGATATTTTTCAGAATTATGTTGCCATTGC

CCTGATGTTTGGTGTTCAGGCAGTTGATCTGCGTACCTACAAAAAAACCGGTCATTATGA

TGCACGTGCCTGTCTGTCACCGGCAACCGAACGTCTGTATAGCGCAGTTCGTCATGTTGT

TGGTCAGAAACCGACCTCAGATCGTCCGTATATTTGGAATGATAATGAACAGGGTCTGG

ATGAACATATTGCACGTATTAGTGCAGATATTGCAGCCGGTGGTGTTATTGTTCAGGCCG

TTCAGGACATTCTGCCGTGTCTGCAT
```

Polypeptide Sequence of WT AvPAL (SEQ ID NO: 4):

(SEQ ID NO: 4)

```
MKTLSQAQSKTSSQQFSFTGNSSANVIIGNQKLTINDVARVARNGTLVSLTNNTDILQGIQAS

CDYINNAVESGEPIYGVTSGFGGMANVAISREQASELQTNLVWFLKTGAGNKLPLADVRAA

MLLRANSHMRGASGIRLELIKRMEIFLNAGVTPYVYEFGSIGASGDLVPLSYITGSLIGLDPSF

KVDFNGKEMDAPTALRQLNLSPLTLLPKEGLAMMNGTSVMTGIAANCVYDTQILTAIAMGV

HALDIQALNGTNQSFHPFIHNSKPHPGQLWAADQMISLLANSQLVRDELDGKHDYRDHELIQ

DRYSLRCLPQYLGPIVDGISQIAKQIEIEINSVTDNPLIDVDNQASYHGGNFLGQYVGMGMDH

LRYYIGLLAKHLDVQIALLASPEFSNGLPPSLLGNRERKVNMGLKGLQICGNSIMPLLTFYGN

SIADRFPTHAEQFNQNINSQGYTSATLARRSVDIFQNYVAIALMFGVQAVDLRTYKKTGHYD

ARACLSPATERLYSAVRHVVGQKPTSDRPYIWNDNEQGLDEHIARISADIAAGGVIVQAVQDI

LPCLH
```

Polynucleotide Sequence of AvPAL Variant No. 30 (SEQ ID NO: 5):

(SEQ ID NO: 5)

```
ATGAAAACCCTGAGTCAGGCACAGAGCAAAACCAGCAGCCAGCAGTTTAGCTTTACCGG

CAATAGCAGCGCAAATGTGATTATTGGTAATCAGAAACTGACCATCAATGATGTTGTACG

TGTTGCCCGTAATGGCACCCTGGTTAGCCTGACCAATAATACCGATATTCTGCAGGGTAT

TCAGGCCAGCTGTGATTATATCAATAATGCAGTTGAAAGCGGTGAACCGATTTATGGTGT

TACCAGCGGTTTTGGTGGTATGGCAAATGTTGTAATTAGCCGTGAACAGGCAAGCGAACT

GCAGACCAATCTGGTTTGGTTTCTGAAAACCGGTGCAGGTAATAAACTGCCGCTGGCAG

ATGTTCGTGCAGCAATGCTGCTGCGTGCAAATAGCCACATGCGTGGTGCAAGCGGTATTC

GTCTGGAACTGATTAAACGCATGGAAATCTTTCTGAATGCCGGTGTTACCCCGTATGTTT

ATGAATTTGGTAGCATTGGTGCCAGCGGTGATCTGGTTCCGCTGAGCTATATTACCGGTA

GCCTGATTGGCCTGGACCCGAGCTTTAAAGTTGATTTTAATGGCAAAGAAATGGACGCAC

CGACCGCACTGCGTCAGCTGAATCTGAGTCCGCTGACCCTGCTGCCGAAAGAAGGTCTG

GCAATGATGAATGGCACCAGCGTTATGACCGGTATTGCAGCAAATTGTGTTTATGATACC

CAGATTCTGACCGCAATTGCAATGGGTGTTCATGCACTGGATATTCAGGGACTGAATGGT

ACAAATCAGAGCTTTCATCCGTTTATCCATAACAGCAAACCGCATCCGGGTCAGCTGTGG
```

-continued

GCAGCAGATCAGATGATTAGCCTGCTGGCCGGTAGCCAGCTGGTTCGTGATGAACTGGA
TGGTAAACATGATTATCGTGATCATGAACTGATCCAGGATCGTTATAGCCTGCGTTGTCT
GCCGCAGTATCTGGGTCCGATTGTTGATGGTATTAGCCAGATTGCCAAACAAATCGAAAT
TGAGATTAACAGCGTTACCGATAACCCGCTGATTGATGTTGATAATCAGGCAAGCTATCA
TGGTGGTAATTTTCTGGGTCAGTATGTTGGTATGGGTATGGATCATCTGCGCTATTATATC
GGTCTGCTGGCAAAACATCTGGATGTTCAGATTGCACTGCTGGTATCACCGGAATTTAAC
AATGGTCTGCCTGCGAGTCTGGTGGGTAATCGTGAACGTAAAGTTAATATGGGTCTGAAA
GGTCTGCAGATTTGCGGTAATAGCATTATGCCGCTGCTGACCTTTTATGGTAATAGTATT
GCAGATCGTTTTCCGACCCATGCCGAACAGTTTAACCAGAATATTAACAGCCAGGGTTAT
ACCAGCGCAACCCTGGCACGTCGTAGCGTTGATATTTTTCAGAATTATGTTGCCATTGCC
CTGATGTTTGGTGTTCAGGCAGTTGATCTGCGTACCTACAAAAAAACCGGTCATTATGAT
GCACGTGCCTGTCTGTCACCGGCAACCGAACGTCTGTATAGCGCAGTTCGTCATGTTGTT
GGTCAGTATCCGAGCTCAGATCGTCCGTATATTTGGAATGATAATGAACAGGGTCTGGAT
GAACATATTGCACGTATTAGTGCAGATATTGCAGCCGGTGGTGTTATTGTTCAGGCCGTT
CAGGACATTCTGCCGTGTCTGCAT

Polypeptide Sequence of AvPAL Variant No. 30 (SEQ ID NO: 6):

(SEQ ID NO: 6)

MKTLSQAQSKTSSQQFSFTGNSSANVIIGNQKLTINDVVRVARNGTLVSLTNNTDILQGIQAS
CDYINNAVESGEPIYGVTSGFGGMANVVISREQASELQTNLVWFLKTGAGNKLPLADVRAA
MLLRANSHMRGASGIRLELIKRMEIFLNAGVTPYVYEFGSIGASGDLVPLSYITGSLIGLDPSF
KVDFNGKEMDAPTALRQLNLSPLTLLPKEGLAMMNGTSVMTGIAANCVYDTQILTAIAMGV
HALDIQGLNGTNQSFHPFIHNSKPHPGQLWAADQMISLLAGSQLVRDELDGKHDYRDHELIQ
DRYSLRCLPQYLGPIVDGISQIAKQIEIEINSVTDNPLIDVDNQASYHGGNFLGQYVGMGMDH
LRYYIGLLAKHLDVQIALLVSPEFNNGLPASLVGNRERKVNMGLKGLQICGNSIMPLLTFYG
NSIADRFPTHAEQFNQNINSQGYTSATLARRSVDIFQNYVAIALMFGVQAVDLRTYKKTGHY
DARACLSPATERLYSAVRHVVGQYPSSDRPYIWNDNEQGLDEHIARISADIAAGGVIVQAVQ
DILPCLH

Polynucleotide Sequence of AvPAL Variant No. 22 (SEQ ID NO: 7):

(SEQ ID NO: 7)

ATGAAAACCCTGAGCCAGGCACAGAGCAAAACCAGCAGCCAGCAGTTTAGCTTTACCGG
CAATAGCAGCGCAAATGTGATTATTGGTAATCAGAAACTGACCATCAATGATGTTGCAC
GTGTTGCCCGTAATGGCACCCTGGTTAGCCTGACCAATAATACCGATATTCTGCAGGGTA
TTCAGGCCAGCTGTGATTATATCAATAATGCAGTTGAAAGCGGTGAACCGATTTATGGTG
TTACCAGCGGTTTTGGTGGTATGGCAAATGTTGCAATTAGCCGTGAACAGGCAAGCGAA
CTGCAGACCAATCTGGTTTGGTTTCTGAAAACCGGTGCAGGTAATAAACTGCCGCTGGCA
GATGTTCGTGCAGCAATGCTGCTGCGTGCAAATAGCCACATGCGTGGTGCAAGCGGTATT
CGTCTGGAACTGATTAAACGCATGGAAATCTTTCTGAATGCCGGTGTTACCCCGTATGTT
TATGAATTTGGTAGCATTGGTGCCAGCGGTGATCTGGTTCCGCTGAGCTATATTACCGGT
AGCCTGATTGGCCTGGACCCGAGCTTTAAAGTTGATTTTAATGGCAAAGAAATGGACGC
ACCGACCGCACTGCGTCAGCTGAATCTGAGTCCGCTGACCCTGCTGCCGAAAGAAGGTCT
GGCAATGATGAATGGCACCAGCGTTATGACCGGTATTGCAGCAAATTGTGTTTATGATAC
CCAGATTCTGACCGCAATTGCAATGGGTGTTCATGCACTGGATATTCAGGCACTGAATGG

-continued

```
TACAAATCAGAGCTTTCATCCGTTTATCCATAACAGCAAACCGCATCCGGGTCAGCTGTG

GGCAGCAGATCAGATGATTAGCCTGCTGGCCAATAGCCAGCTGGTTCGTGATGAACTGG

ATGGTAAACATGATTATCGTGATGGTGAACTGATCCAGGATCGTTATAGCCTGCGTTGTC

TGCCGCAGTATCTGGGTCCGATTGTTGATGGTATTAGCCAGATTGCCAAACAAATCGAAA

TTGAGATTAACAGCGTTACCGATAACCCGCTGATTGATGTTGATAATCAGGCAAGCTATC

ATGGTGGTAATTTTCTGGGTCAGTATGTTGGTATGGGTATGGATCATCTGCGCTATTATAT

CGGTCTGCTGGCAAAACATCTGGATGTTCAGATTGCACTGCTGGCATCACCGGAATTTAG

CAATGGTCTGCCTCCGAGTCTGCTGGGTAATCGTGAACGTAAAGTTAATATGGGTCTGAA

AGGTCTGCAGATTTGCGGTAATAGCATTATGCCGCTGCTGACCTTTTATGGTAATAGTAT

TGCAGATCGTTTTCCGACCCATGCCGAACAGTTTAACCAGAATATTAACAGCCAGGGTTA

TACCAGCGCAACCCTGGCACGTCGTAGCGTTGATATTTTTCAGAATTATGTTGCCATTGC

CCTGATGTTTGGTGTTCAGGCAGTTGATCTGCGTACCTACAAAAAAACCGGTCATTATGA

TGCACGTGCCTGTCTGTCACCGGCAACCGAACGTCTGTATAGCGCAGTTCGTCATGTTGT

TGGTCAGAAACCGACCTCAGATCGTCCGTATATTTGGAATGATAATGAACAGGGTCTGG

ATGAACATATTGCACGTATTAGTGCAGATATTGCAGCCGGTGGTGTTATTGTTCAGGCCG

TTCAGGACATTCTGCCGTGTCTGCAT
```

Polypeptide Sequence of AvPAL Variant No. 22 (SEQ ID NO: 8):
                                          (SEQ ID NO: 8)

```
MKTLSQAQSKTSSQQFSFTGNSSANVIIGNQKLTINDVARVARNGTLVSLTNNTDILQGIQAS

CDYINNAVESGEPIYGVTSGFGGMANVAISREQASELQTNLVWFLKTGAGNKLPLADVRAA

MLLRANSHMRGASGIRLELIKRMEIFLNAGVTPYVYEFGSIGASGDLVPLSYITGSLIGLDPSF

KVDFNGKEMDAPTALRQLNLSPLTLLPKEGLAMMNGTSVMTGIAANCVYDTQILTAIAMGV

HALDIQALNGTNQSFHPFIHNSKPHPGQLWAADQMISLLANSQLVRDELDGKHDYRDGELIQ

DRYSLRCLPQYLGPIVDGISQIAKQIEIEINSVTDNPLIDVDNQASYHGGNFLGQYVGMGMDH

LRYYIGLLAKHLDVQIALLASPEFSNGLPPSLLGNRERKVNMGLKGLQICGNSIMPLLTFYGN

SIADRFPTHAEQFNQNINSQGYTSATLARRSVDIFQNYVAIALMFGVQAVDLRTYKKTGHYD

ARACLSPATERLYSAVRHVVGQKPTSDRPYIVVNDNEQGLDEHIARISADIAAGGVIVQAVQDI

LPCLH
```

Polynucleotide Sequence of AvPAL Variant No. 36 (SEQ ID NO: 9):
                                          (SEQ ID NO: 9)

```
ATGAAAACCCTGAGTCAGGCACAGAGCAAACCAGCAGCCAGCAGTTTAGCTTTACCGG

CAATAGCAGCGCAAATGTGATTATTGGTAATCAGAAACTGACCATCAATGATGTTGTACG

TGTTGCCCGTAATGGCACCCTGGTTAGCCTGACCAATAATACCGATATTCTGCAGGGTAT

TCAGGCCAGCTGTGATTATATCAATAATGCAGTTGAAAGCGGTGAACCGATTTATGGTGT

TACCAGCGGTTTTGGTGGTATGGCAAATGTTGTAATTAGCCGTGAACAGGCAAGCGAACT

GCAGACCAATCTGGTTTGGTTTCTGAAAACCGGTGCAGGTAATAAACTGCCGCTGGCAG

ATGTTCGTGCAGCAATGCTGCTGCGTGCAAATAGCCACATGCGTGGTGCAAGCGGTATTC

GTCTGGAACTGATTAAACGCATGGAAATCTTTCTGAATGCCGGTGTTACCCCGTATGTTT

ATGAATTTGGTAGCATTGGTGCCAGCGGTGATCTGGTTCCGCTGAGCTATATTACCGGTA

GCCTGATTGGCCTGGACCCGAGCTTTAAAGTTGATTTTAATGGCAAAGAAATGGACGCAC

CGACCGCACTCGCTCAGCTGAATCTGAGTCCGCTGACCCTGCTGCCGAAAGAAGGTCTG

GCAATGATGAATGGCACCAGCGTTATGACCGGTATTGCAGCAAATTGTGTTTATGATACC

CAGATTCTGACCGCAATTGCAATGGGTGTTCATGCACTGGATATTCAGGCACTGAATGGT
```

-continued

```
ACAAATCAGAGCTTTCATCCGTTTATCCATAACAGCAAACCGCATCCGGGTCAGCTGTGG

GCAGCAGATCAGATGATTAGCCTGCTGGCCGGTAGCCAGCTGGTTCGTGATGAACTGGA

TGGTAAACATGATTATCGTGATGGTGAACTGATCCAGGATCGTTATAGCCTGCGTTGTCT

GCCGCAGTATCTGGGTCCGATTGTTGATGGTATTAGCCAGATTGCCAAACAAATCGAAAT

TGAGATTAACAGCGTTACCGATAACCCGCTGATTGATGTTGATAATCAGGCAAGCTATCA

TGGTGGTAATTTTCTGGGTCAGTATGTTGGTATGGGTATGGATCATCTGCGCTATTATATC

GGTCTGCTGGCAAAACATCTGGATGTTCAGATTGCACTGCTGGCATCACCGGAATTTAGC

AATGGTCTGCCTCCGAGTCTGGTGGGTAATCGTGAACGTAAAGTTAATATGGGTCTGAAA

GGTCTGCAGATTTGCGGTAATAGCATTATGCCGCTGCTGACCTTTTATGGTAATAGTATT

GCAGATCGTTTTCCGACCCATGCCGAACAGTTTAACCAGAATATTAACAGCCAGGGTTAT

ACCAGCGCAACCCTGGCACGTCGTAGCGTTGATATTTTTCAGAATTATGTTGCCATTGCC

CTGATGTTTGGTGTTCAGGCAGTTGATCTGCGTACCTACAAAAAAACCGGTCATTATGAT

GCACGTGCCTGTCTGTCACCGGCAACCGAACGTCTGTATAGCGCAGTTCGTCATGTTGTT

GGTCAGAAACCGAGCTCAGATCGTCCGTATATTTGGAATGATAATGAACAGGGTCTGGA

TGAACATATTGCACGTATTAGTGCAGATATTGCAGCCGGTGGTGTTATTGTTCAGGCCGT

TCAGGACATTCTGCCGTGTCTGCAT
```

Polypeptide Sequence of AvPAL Variant No. 36 (SEQ ID NO: 10):
(SEQ ID NO: 10)

```
MKTLSQAQSKTSSQQFSFTGNSSANVIIGNQKLTINDVVRVARNGTLVSLTNNTDILQGIQAS

CDYINNAVESGEPIYGVTSGFGGMANVVISREQASELQTNLVWFLKTGAGNKLPLADVRAA

MLLRANSHMRGASGIRLELIKRMEIFLNAGVTPYVYEFGSIGASGDLVPLSYITGSLIGLDPSF

KVDFNGKEMDAPTALRQLNLSPLTLLPKEGLAMMNGTSVMTGIAANCVYDTQILTAIAMGV

HALDIQALNGTNQSFHPFIHNSKPHPGQLWAADQMISLLAGSQLVRDELDGKHDYRDGELIQ

DRYSLRCLPQYLGPIVDGISQIAKQIEIEINSVTDNPLIDVDNQASYHGGNFLGQYVGMGMDH

LRYYIGLLAKHLDVQIALLASPEFSNGLPPSLVGNRERKVNMGLKGLQICGNSIMPLLTFYGN

SIADRFPTHAEQFNQNINSQGYTSATLARRSVDIFQNYVAIALMFGVQAVDLRTYKKTGHYD

ARACLSPATERLYSAVRHVVGQKPSSDRPYIVVNDNEQGLDEHIARISADIAAGGVIVQAVQDI

LPCLH
```

Polynucleotide Sequence of AvPAL Variant No. 42 (SEQ ID NO: 11):
(SEQ ID NO: 11)

```
ATGAAAACCCTGAGTCAGGCACAGAGCAAAACCAGCAGCCAGCAGTTTAGCTTTACCGGC

AATAGCAGCGCAAATGTGATTATTGGTAATCAGAAACTGACCATCAATGATGTTGTACGT

GTTGCCCGTAATGGCACCCTGGTTAGCCTGACCAATAATAAAGATATTCTGCAGCGTATT

CAGGCCAGCTGTGATTATATCAATAATGCAGTTGAAAAAGGTGAACCGATTTATGGTGTT

ACCAGCGGTTTTGGTGGTATGGCAAATGTTGTAATTAGCCGTGAACAGGCAAGCGAACT

GCAGACCAATCTGGTTTGGTTTCTGAAAACCGGTGCAGGTAATAAACTGCCGCTGGCAG

ATGTTCGTGCAGCAATGCTGCTGCGTGCAAATAGCCACATGCGTGGTGCAAGCGGTATTC

GTCTGGAACTGATTAAACGCATGGAAATCTTTCTGAATGCCGGTGTTACCCCGTATGTTT

ATGAATTTGGTAGCATTGGTGCCAGCGGTGATCTGGTTCCGCTGAGCTATATTACCGGTA

GCCTGATTGGCCTGGACCCGAGCTTTAAAGTTGATTTTAATGGCAAAGAAATGGACGCA

CCGACCGCACTGCGTCAGCTGAATCTGAGTCCGCTGACCCTGCTGCCGAAAGAAGGTCT

GGCAATGATGAATGGCACCAGCGTTATGACCGGTATTGCAGCAAATTGTGTTTATGATAC
```

-continued

```
CCAGATTCTGACCGCAATTGCAATGGGTGTTCATGCACTGGATATTCAGGCACTGAATGG

TACAAATCAGAGCTTTCATCCGTTTATCCATAACAGCAAACCGCATCCGGGTCAGCTGTG

GGCAGCAGATCAGATGATTAGCCTGCTGGCCGGTAGCCAGCTGGTTCGTGATGAACTGG

ATGGTAAACATGATTATATGGATGGTGAACTGATCCAGGATCGTTATAGCCTGCGTTGTC

TGCCGCAGTATCTGGGTCCGATTGTTGATGGTATTAGCCAGATTGCCAAACAAATCGAAA

TTGAGATTAACAGCGTTACCGATAACCCGCTGATTGATGTTGATAATCAGGCAAGCTATC

ATGGTGGTAATTTTCTGGGTCAGTATGTTGGTATGGGTATGGATCATCTGCGCTATTATA

TCGGTCTGCTGGCAAAACATCTGGATGTTCAGATTGCACTGCTGGCATCACCGGAATTTA

GCAATGGTCTGCCTCCGAGTCTGGTGGGTAATCGTGAACGTAAAGTTAATATGGGTCTGA

AAGGTCTGCAGATTTGCGGTAATAGCATTATGCCGCTGCTGACCTTTTATGGTAATAGTA

TTGCAGATCGTTTTCCGACCCATGCCGAACAGTTTAACCAGAATATTAACAGCCAGGGTT

ATACCAGCGCAACCCTGGCACGTCGTAGCGTTGATATTTTTCAGAATTATGTTGCCATTG

CCCTGATGTTTGGTGTTCAGGCAGTTGATCTGCGTACCTACAAAAAAACCGGTCATTATG

ATGCACGTGCCCAGCTGTCACCGGCAACCGAACGTCTGTATAGCGCAGTTCGTCATGTTG

TTGGTAAAAAACCGAGCTCAGATCGTCCGTATATTTGGAATGATAATGAACAGGGTCTG

GATGAACATATTGCACGTATTAGTGCAGATATTGCAGCCGGTGGTGTTATTGTTCA

GGCCGTTCAGGACATTCTGCCGCCGCTGCAT
```

Polypeptide Sequence of AvPAL Variant No. 42 (SEQ ID NO: 12):
(SEQ ID NO: 12)

```
MKTLSQAQSKTSSQQFSFTGNSSANVIIGNQKLTINDVVRVARNGTLVSLTNNKDILQRIQAS

CDYINNAVEKGEPIYGVTSGFGGMANVVISREQASELQTNLVWFLKTGAGNKLPLADVRAA

MLLRANSHMRGASGIRLELIKRMEIFLNAGVTPYVYEFGSIGASGDLVPLSYITGSLIGLDPSF

KVDFNGKEMDAPTALRQLNLSPLTLLPKEGLAMMNGTSVMTGIAANCVYDTQILTAIAMGV

HALDIQALNGTNQSFHPFIHNSKPHPGQLWAADQMISLLAGSQLVRDELDGKHDYMDGELI

QDRYSLRCLPQYLGPIVDGISQIAKQIEIEINSVTDNPLIDVDNQASYHGGNFLGQYVGMGMDHLRYYIGLLA

KHLDVQIALLASPEFSNGLPPSLVGNRERKVNMGLKGLQICGNSIMPLLTFYGNSIADRFPTH

AEQFNQNINSQGYTSATLARRSVDIFQNYVAIALMFGVQAVDLRTYKKTGHYDARAQLSPA

TERLYSAVRHVVGKKPSSDRPYIVVNDNEQGLDEHIARISADIAAGGVIVQAVQDILPPLH
```

Polynucleotide Sequence of AvPAL Variant No. 43 (SEQ ID NO: 13):
(SEQ ID NO: 13)

```
ATGAAAACCCTGAGTCAGGCACAGAGCAAAACCAGCAGCCAGCAGTTTAGCTTTACCGG

CAATAGCAGCGCAAATGTGATTATTGGTAATCAGAAACTGACCATCAATGATGTTGTAC

GTGTTGCCCGTAATGGCACCCTGGTTAGCCTGACCAATAATAAAGATATTCTGCAGCGTA

TTCAGGCCAGCTGTGATTATATCAATAATGCAGTTGAAAGCGGTGAACCGATTTATGGTG

TTACCAGCGGTTTTGGTGGTATGGCAAATGTTGTAATTAGCCGTGAACAGGCAAGCGAA

CTGCAGACCAATCTGGTTTGGTTTCTGAAAACCGGTGCAGGTAATAAACTGCCGCTGGCA

GATGTTCGTGCAGCAATGCTGCTGCGTGCAAATAGCCACATGCGTGGTGCAAGCGGTAT

TCGTCTGGAACTGATTAAACGCATGGAAATCTTTCTGAATGCCGGTGTTACCCCGTATGT

TTATGAATTTGGTAGCATTGGTGCCAGCGGTGATCTGGTTCCGCTGAGCTATATTACCGG

TAGCCTGATTGGCCTGGACCCGAGCTTTAAAGTTGATTTTAATG

GCAAAGAAATGGACGCACCGACCGCACTGC

GTCAGCTGAATCTGAGTCCGCTGACCCTGCTGCCGAAAGAAGGTCTGGCAATGATGAAT

GGCACCAGCGTTATGACCGGTATTGCAGCAAATTGTGTTTATGATACCCAGATTCTGACC
```

-continued

```
GCAATTGCAATGGGTGTTCATGCACTGGATATTCAGGCACTGAATGGTACAAATCAGAG
CTTTCATCCGTTTATCCATAACAGCAAACCGCATCCGGGTCAGCTGTGGGCAGCAGATCA
GATGATTAGCCTGCTGGCCGGTAGCCAGCTGGTTCGTGATGAACTGGATGGTAAACATG
ATTATATGGATGGTGAACTGATCCAGGATCGTTATAGCCTGCGTTGTCTGCCGCAGTATC
TGGGTCCGATTGTTGATGGTATTAGCCAGATTGCCAAACAAATCGAAATTGAGATTAAC
AGCGTTACCGATAACCCGCTGATTGATGTTGATAATCAGGCAAGCTATCATGGTGGTAAT
TTTCTGGGTCAGTA
TGTTGGTATGGGTATGGATCATCTGCGCTATTATATCGGTCTGCTGGCAAAACATCTGGA
TGTTCAGATTGCACTGCTGGCATCACCGGAATTTAGCAATGGTCTGCCTCCGAGTCTGGT
GGGTAATCGTGAACGTAAAGTTAATATGGGTCTGAAAGGTCTGCAGATTTGCGGTAATA
GCATTATGCCGCTGCTGACCTTTTATGGTAATAGTATTGCAGATCGTTTTCCGACCCATGC
CGAACAGTTTAACCAGAATATTAACAGCCAGGGTTATACCAGCGCAACCCTGGCACGTC
GTAGCGTTGATATTTTTCAGAATTATGTTGCCATTGCCCTGATGTTTGGTGTTCAGGCAGT
TGATCTGCGTACCTACAAAAAAACCGGTCATTATGATGCACGTGCCCAGCTGTCACCGGC
AACCGAACGTCTGTATAGCGCAGTTCGTCATGTTGTTGGTAAAAAACCGAGCTCAGATC
GTCCGTATATTTGGAATGATAATGAACAGGGTCTGGATGAACATATTGCACGTATTAGTG
CAGATATTGCAGCCGGTGGTGTTATTGTTCAGGCCGTTCAGGACATTCTGCCGAACCTGC
AT
```

Polypeptide Sequence of AvPAL Variant No. 43 (SEQ ID NO: 14):

(SEQ ID NO: 14)

```
MKTLSQAQSKTSSQQFSFTGNSSANVIIGNQKLTINDVVRVARNGTLVSLTNNKDILQRIQAS
CDYINNAVESGEPIYGVTSGFGGMANVVISREQASELQTNLVWFLKTGAGNKLPLADVRAA
MLLRANSHMRGASGIRLELIKRMEIFLNAGVTPYVYEFGSIGASGDLVPLSYITGSLIGLDPSF
KVDFNGKEMDAPTALRQLNLSPLTLLPKEGLAMMNGTSVMTGIAANCVYDTQILTAIAMGV
HALDIQALNGTNQSFHPFIHNSKPHPGQLWAADQMISLLAGSQLVRDELDGKHDYMDGELI
QDRYSLRCLPQYLGPIVDGISQIAKQIEIEINSVTDNPLIDVDNQASYHGGNFLGQYVGMGMD
HLRYYIGLLAKHLDVQIALLASPEFSNGLPPSLVGNRERKVNMGLKGLQICGNSIMPLLTFYG
NSIADRFPTHAEQFNQNINSQGYTSATLARRSVDIFQNYVAIALMFGVQAVDLRTYKKTGHY
DARAQLSPATERLYSAVRHVVGKKPSSDRPYIVVNDNEQGLDEHIARISADIAAGGVIVQAVQ
DILPNLH
```

Polynucleotide Sequence of AvPAL Variant No. 1002 (SEQ ID NO: 15):

(SEQ ID NO: 15)

```
ATGAAAACCCTGAGTCAGGCACAGAGCAAAACCAGCAGCCAGCAGTTTAGCTTTACCGG
CAATAGCAGCGCAAATGTGATTATTGGTAATCAGAAACTGACCATCAATGATGTTGCGC
GTGTTGCCCGTAATGGCACCCTGGTTAGCCTGACCAATAATACCGATATTCTGCAGGGTA
TTCAGGCCAGCTGTGATTATATCAATAATGCAGTTGAAAGCGGTGAACCGATTTATGGTG
TTACCAGCGGTTTTGGTGGTATGGCAAATGTTGTAATTAGCCGTGAACAGGCAAGCGAA
CTGCAGACCAATCTGGTTTGGTTTCTGAAAACCGGTGCAGGTAATAAACTGCCGCTGGCA
GATGTTCGTGCAGCAATGCTGCTGCGTGCAAATAGCCACATGCATGGTGCAAGCGGTAT
TCGTCTGGAACTGATTAAACGCGCGGAAATCTTTCTGAATGCCGGTGTTACCCCGTATGT
TTATGAATTTGGTAGCATTGGTGCCAGCGGTGATCTGGTTCCGCTGAGCTATATTACCGG
TAGCCTGATTGGCCTGGACCCGAGCTTTAAAGTTGATTTTAATGGCAAAGAAATGGACG
```

-continued

```
CACCGACCGCACTGCGTCAGCTGAATCTGAGTCCGCTGACCCTGCTGCCGAAAGAAGGT
CTGGCAATGATGAATGGCACCAGCGTTATGACCGGTATTGCAGCAAATTGTGTTTATGAT
ACCCAGATTCTGACCGCAATTGCAATGGGTGTTCATGCACTGGATATTCAGGCACTGAAT
GGTACAAATCAGAGCTTTCATCCGTTTATCCATAACAGCAAACCGCATCCGGGTCAGCTG
TGGGCAGCAGATCAGATGATTAGCCTGCTGGCCGGTAGCCAGCTGGTTCGTGATGAACT
GGATGGTAAACATGATTATCGTGATGGTGAACTGATCCAGGATCGTTATAGCCTGCGTTG
TCTGCCGCAGTATCTGGGTCCGATTGTTGATGGTATTAGCCAGATTGCCAAACAAATCGA
AATTGAGATTAACAGCGTTACCGATAACCCGCTGATTGATGTTGATAATCAGGCAAGCT
ATCATGGTGGTAATTTTCTGGGTCAGTATGTTGGTATGGGTATGGATCATCTGCGCTATT
ATATCGGTGGCCTGGCAAAACATCTGGATGTTCAGATTGCACTGCTGGCATCACCGGAAT
TTAGCAATGGTCTGCCTCCGAGTCTGGTGGGTAATCGTGAACGTAAAGTTAATATGGGTC
TGAAAGGTCTGCAGATTTGCGGTAATAGCATTATGCCGCTGCTGACCTTTTATGGTAATA
GTATTGCAGATCGTTTTCCGACCCATGCCGAACAGTTTAACCAGAATATTAACAGCCAGG
GTTATACCAGCGCAACCCTGGCACGTCGTAGCGTTGATATTGGCCAGAATTATGTTGCCA
TTGCCCTGATGTTTGGTGTTCAGGCAGTTGATCTGCGTACCTACAAAAAAACCGGTCATT
ATGATGCACGTGCCCAGCTGTCACCGGCAACCGAACGTCTGTATAGCGCAGTTCGTCATG
TTGTTGGTCAGAAACCGAGCTCAGATCGTCCGTATATTTGGAATGATAATGAACAGGGTC
TGGATGAACATATTGCACGTATTAGTGCAGATATTGCAGCCGGTGGTGTTATTGTTCAGG
CCGTTCAGGACATTCTGCCGAACCTGCAT
```

Polypeptide Sequence of AvPAL Variant No. 1002 (SEQ ID NO: 16):
(SEQ ID NO: 16)
```
MKTLSQAQSKTSSQQFSFTGNSSANVIIGNQKLTINDVARVARNGTLVSLTNNTDILQGIQAS
CDYINNAVESGEPIYGVTSGFGGMANVVISREQASELQTNLVWFLKTGAGNKLPLADVRAA
MLLRANSHMHGASGIRLELIKRAEIFLNAGVTPYVYEFGSIGASGDLVPLSYITGSLIGLDPSF
KVDFNGKEMDAPTALRQLNLSPLTLLPKEGLAMMNGTSVMTGIAANCVYDTQILTAIAMGV
HALDIQALNGTNQSFHPFIHNSKPHPGQLWAADQMISLLAGSQLVRDELDGKHDYRDGELIQ
DRYSLRCLPQYLGPIVDGISQIAKQIEIEINSVTDNPLIDVDNQASYHGGNFLGQYVGMGMDH
LRYYIGGLAKHLDVQIALLASPEFSNGLPPSLVGNRERKVNMGLKGLQICGNSIMPLLTFYGN
SIADRFPTHAEQFNQNINSQGYTSATLARRSVDIGQNYVAIALMFGVQAVDLRTYKKTGHYD
ARAQLSPATERLYSAVRHVVGQKPSSDRPYIVVNDNEQGLDE
HIARISADIAAGGVIVQAVQDILPNLH
```

Polynucleotide Sequence of AvPAL Variant No. 1008 (SEQ ID NO: 17):
(SEQ ID NO: 17)
```
ATGAAAACCCTGAGTCAGGCACAGAGCAAAACCAGCAGCCAGCAGTTTAGCTTTACCGG
CAATAGCAGCGCAAATGTGATTATTGGTAATCAGAAACTGACCATCAATGATGTTGCGC
GTGTTGCCCGTAATGGCACCCTGGTTAGCCTGACCAATAATACCGATATTCTGCAGGGTA
TTCAGGCCAGCTGTGATTATATCAATAATGCAGTTGAAAGCGGTGAACCGATTTATGGTG
TTACCAGCGGTTTTGGTGGTATGGCAAATGTTGTAATTAGCCGTGAACAGGCAAGCGAA
CTGCAGACCAATCTGGTTTGGTTTCTGAAAACCGGTGCAGGTAATAAACTGCCGCTGGCA
GATGTTCGTGCAGCAATGCTGCTGCGTGCAAATAGCCACATGCATGGTGCAAGCGGTAT
TCGTCTGGAACTGATTAAACGCGCGGAAATCTTTCTGAATGCCGGTGTTACCCCGTATGT
TTATGAATTTGGTAGCATTGGTGCCAGCGGTGATCTGGTTCCGCTGAGCTATATTACCGG
TAGCCTGATTGGCCTGGACCCGAGCTTTAAAGTTGATTTTAATGGCAAAGAAATGGACG
```

-continued

```
CACCGACCGCACTGCGTCAGCTGAATCTGAGTCCGCTGACCCTGCTGCCGAAAGAAGGT
CTGGCAATGATGAATGGCACCAGCGTTATGACCGGTATTGCAGCAAATTGTGTTTATGAT
ACCCAGATTCTGACCGCAATTGCAATGGGTGTTCATGCACTGGATATTCAGGCACTGAAT
GGTACAAATCAGAGCTTTCATCCGTTTATCCATAACAGCAAACCGCATCCGGGTCAGCTG
TGGGCAGCAGATCAGATGATTAGCCTGCTGGCCGGTAGCCAGCTGGTTCGTGATGAACT
GGATGGTAAACATGATTATCGTGATGGTGAACTGATCCAGGATCGTTATAGCCTGCGTTG
TCTGCCGCAGTATCTGGGTCCGATTGTTGATGGTATTAGCCAGATTGCCAAACAAATCGA
AATTGAGATTAACAGCGTTACCGATAACCCGCTGATTGATGTTGATAATCAGGCAAGCT
ATCATGGTGGTAATTTTCTGGGTCAGTATGTTGGTATGGGTATGGATCATCTGCGCTATT
ATATCGGTGGCCTGGCAAAACATCTGGATACCCAGATTGCACTGCTGGCATCACCGGAA
TTTAGCAATGGTCTGCCTCCGAGTCTGGTGGGTAATCGTGAACGTAAAGTTAATATGGGT
CTGAAAGGTCTGCAGATTTGCGGTAATAGCATTATGCCGCTGCTGACCTTTTATGGTAAT
AGTATTGCAGATCGTTTTCCGACCCATGCCGAACAGTTTAACCAGAATATTAACAGCCAG
GGTTATACCAGCGCAACCCTGGCACGTCGTAGCGTTGATATTGGCCAGAATTATGTTGCC
ATTGCCCTGATGTTTGGTGTTCAGGCAGTTGATCTGCGTACCTACAAAAAAACCGGTCAT
TATGATGCACGTGCCCAGCTGTCACCGGCAACCGAACGTCTGTATAGCGCAGTTCGTCAT
GTTGTTGGTCAGAAACCGAGCTCAGATCGTCCGTATATTTGGAATGATAATGAACAGGG
TCTGGATGAACATATTGCACGTATTAGTGCAGATATTGCAGCCGGTGGTGTTATTGTTCA
GGCCGTTCAGGACATTCTGCCGAACCTGCAT
```

Polypeptide Sequence of AvPAL Variant No. 1008 (SEQ ID NO: 18):

(SEQ ID NO: 18)

```
MKTLSQAQSKTSSQQFSFTGNSSANVIIGNQKLTINDVARVARNGTLVSLTNNTDILQGI
QASCDYINNAVESGEPIYGVTSGFGGMANVVISREQASELQTNLVWFLKTGAGNKLPLADVR
AAMLLRANSHMHGASGIRLELIKRAEIFLNAGVTPYVYEFGSIGASGDLVPLSYITGSLIGLDP
SFKVDFNGKEMDAPTALRQLNLSPLTLLPKEGLAMMNGTSVMTGIAANCVYDTQILTAIAM
GVHALDIQALNGTNQSFHPFIHNSKPHPGQLWAADQMISLLAGSQLVRDELDGKHDYRDGE
LIQDRYSLRCLPQYLGPIVDGISQIAKQIEIEINSVTDNPLIDVDNQASYHGGNFLGQYVGMGM
DHLRYYIGGLAKHLDTQIALLASPEFSNGLPPSLVGNRERKVNMGLKGLQICGNSIMPLLTFY
GNSIADRFPTHAEQFNQNINSQGYTSATLARRSVDIGQNYVAIALMFGVQAVDLRTYKKTGH
YDARAQLSPATERLYSAVRHVVGQKPSSDRPYIVVNDNEQGLDEHIARISADIAAGGVIVQAVQDILPNLH
```

Polynucleotide Sequence of AvPAL Variant No. 1009 (SEQ ID NO: 19):

(SEQ ID NO: 19)

```
ATGAAAACCCTGAGTCAGGCACAGAGCAAAACCAGCAGCCAGCAGTTTAGCTTTACCGG
CAATAGCAGCGCAAATGTGATTATTGGTAATCAGAAACTGACCATCAATGATGTTGCGC
GTGTTGCCCGTAATGGCACCCTGGTTAGCCTGACCAATAATACCGATATTCTGCAGGGTA
TTCAGGCCAGCTGTGATTATATCAATAATGCAGTTGAAAGCGGTGAACCGATTTATGGTG
TTACCAGCGGTTTTGGTGGTATGGCAAATGTTGTAATTAGCCGTGAACAGGCAAGCGAA
CTGCAGACCAATCTGGTTTGGTTTCTGAAAACCGGTGCAGGTAATAAACTGCCGCTGGCA
GATGTTCGTGCAGCAATGCTGCTGCGTGCAAATAGCCACATGCATGGTGCAAGCGGTAT
TCGTCTGGAACTGATTAAACGCGCGGAAATCTTTCTGAATGCCGGTGTTACCCCGTATGT
TTATGAATTTGGTAGCATTGGTGCCAGCGGTGATCTGGTTCCGCTGAGCTATATTACCGG
TAGCCTGATTGGCCTGGACCCGAGCTTTAAAGTTGATTTTAATGGCAAAGAAATGGACG
```

-continued
```
CACCGACCGCACTGCGTCAGCTGAATCTGAGTCCGCTGACCCTGCTGCCGAAAGAAGGT

CTGGCAATGATGAATGGCACCAGCGTTATGACCGGTATTGCAGCAAATTGTGTTTATGAT

ACCCAGATTCTGACCGCAATTGCAATGGGTGTTCATGCACTGGATATTCAGGCACTGAAT

GGTACAAATCAGAGCTTTCATCCGTTTATCCATAACAGCAAACCGCATCCGGGTCAGCTG

TGGGCAGCAGATCAGATGATTAGCCTGCTGGCCGGTAGCCAGCTGGTTCGTGATGAACT

GGATGGTAAACATGATTATCGTGATGGTGAACTGATCCAGGATCGTTATAGCCTGCGTTG

TCTGCCGCAGTATCTGGGTCCGATTGTTGATGGTATTAGCCAGATTGCCAAACAAATCGA

AATTGAGATTAACAGCGTTACCGATAACCCGCTGATTGATGTTGATAATCAGGCAAGCT

ATCATGGTGGTAATTTTCTGGGTCAGTATGTTGGTATGGGTATGGATCATCTGCGCTATG

AAATCGGTCTGCTGGCAAAACATCTGGATGTTCAGATTGCACTGCTGGCATCACCGGAAT

TTAGCAATGGTCTGCCTCCGAGTCTGGTGGGTAATCGTGAACGTAAAGTTAATATGGGTC

TGAAAGGTCTGCAGATTTGCGGTAATAGCATTATGCCGCTGCTGACCTTTTATGGTAATA

GTATTGCAGATCGTTTTCCGACCCATGCCGAACAGTTTAACCAGAATATTAACAGCCAGG

GTTATACCAGCGCAACCCTGGCACGTCGTAGCGTTGATATTGGCCAGAATTATGTTGCCA

TTGCCCTGATGTTTGGTGTTCAGGCAGTTGATCTGCGTACCTACAAAAAAACCGGTCATT

ATGATGCACGTGCCCAGCTGTCACCGGCAACCGAACGTCTGTATAGCGCAGTTCGTCATG

TTGTTGGTCAGAAACCGAGCTCAGATCGTCCGTATATTTGGAATGATAATGAACAGGGTC

TGGATGAACATATTGCACGTATTAGTGCAGATATTGCAGCCGGTGGTGTTATTGTTCAGG

CCGTTCAGGACATTCTGCCGAACCTGCAT
```

Polypeptide Sequence of AvPAL Variant No. 1009 (SEQ ID NO: 20):
(SEQ ID NO: 20)
```
MKTLSQAQSKTSSQQFSFTGNSSANVIIGNQKLTINDVARVARNGTLVSLTNNTDILQGI

QASCDYINNAVESGEPIYGVTSGFGGMANVVISREQASELQTNLVWFLKTGAGNKLPLADVR

AAMLLRANSHMHGASGIRLELIKRAEIFLNAGVTPYVYEFGSIGASGDLVPLSYITGSLIGLDP

SFKVDFNGKEMDAPTALRQLNLSPLTLLPKEGLAMMNGTSVMTGIAANCVYDTQILTAIAM

GVHALDIQALNGTNQSFHPFIHNSKPHPGQLWAADQMISLLAGSQLVRDELDGKHDYRDGE

LIQDRYSLRCLPQYLGPIVDGISQIAKQIEIEINSVTDNPLIDVDNQASYHGGNFLGQYVGMGM

DHLRYEIGLLAKHLDVQIALLASPEFSNGLPPSLVGNRERKVNMGLKGLQICGNSIMPLLTFY

GNSIADRFPTHAEQFNQNINSQGYTSATLARRSVDIGQNYVAIALMFGVQAVDLRTYKKTGH

YDARAQLSPATERLYSAVRHVVGQKPSSDRPYIVVNDNEQGLDEHIARISADIAAGGVIVQAV

QDILPNLH
```

Polynucleotide Sequence of AvPAL Variant No. 1010 (SEQ ID NO: 21):
(SEQ ID NO: 21)
```
ATGAAAACCCTGAGTCAGGCACAGAGCAAAACCAGCAGCCAGCAGTTTAGCTTTACCGG

CAATAGCAGCGCAAATGTGATTATTGGTAATCAGAAACTGACCATCAATGATGTTGCGC

GTGTTGCCCGTAATGGCACCCTGGTTAGCCTGACCAATAATACCGATATTCTGCAGGGTA

TTCAGGCCAGCTGTGATTATATCAATAATGCAGTTGAAAGCGGTGAACCGATTTATGGTG

TTACCAGCGGTTTTGGTGGTATGGCAAATGTTGTAATTAGCCGTGAACAGGCAAGCGAA

CTGCAGACCAATCTGGTTTGGTTTCTGAAAACCGGTGCAGGTAATAAACTGCCGCTGGCA

GATGTTCGTGCAGCAATGCTGCTGCGTGCAAATAGCCACATGCATGGTGCAAGCGGTAT

TCGTCTGGAACTGATTAAACGCGCGGAAATCTTTCTGAATGCCGGTGTTACCCCGTATGT

TTATGAATTTGGTAGCATTGGTGCCAGCGGTGATCTGGTTCCGCTGAGCTATATTACCGG

TAGCCTGATTGGCCTGGACCCGAGCTTTAAAGTTGATTTTAATGGCAAAGAAATGGACG
```

-continued

```
CACCGACCGCACTGCGTCAGCTGAATCTGAGTCCGCTGACCCTGCTGCCGAAAGAAGGT

CTGGCAATGATGAATGGCACCAGCGTTATGACCGGTATTGCAGCAAATTGTGTTTATGAT

ACCCAGATTCTGACCGCAATTGCAATGGGTGTTCATGCACTGGATATTCAGGCACTGAAT

GGTACAAATCAGAGCTTTCATCCGTTTATCCATAACAGCAAACCGCATCCGGGTCAGCTG

TGGGCAGCAGATCAGATGATTAGCCTGCTGGCCGGTAGCCAGCTGGTTCGTGATGAACT

GGATGGTAAACATGATTATCGTGATGGTGAACTGATCCAGGATCGTTATAGCCTGCGTTG

TCTGCCGCAGTATCTGGGTCCGATTGTTGATGGTATTAGCCAGATTGCCAAACAAATCGA

AATTGAGATTAACAGCGTTACCGATAACCCGCTGATTGATGTTGATAATCAGGCAAGCT

ATCATGGTGGTAATTTTCTGGGTCAGTATGTTGGTATGGGTATGGATCATCTGCGCTATG

AAATCGGTCTGCTGGCAAAACATCTGGATACCCAGATTGCACTGCTGGCATCACCGGAA

TTTAGCAATGGTCTGCCTCCGAGTCTGGTGGGTAATCGTGAACGTAAAGTTAATATGGGT

CTGAAAGGTCTGCAGATTTGCGGTAATAGCATTATGCCGCTGCTGACCTTTTATGGTAAT

AGTATTGCAGATCGTTTTCCGACCCATGCCGAACAGTTTAACCAGAATATTAACAGCCAG

GGTTATACCAGCGCAACCCTGGCACGTCGTAGCGTTGATATTGGCCAGAATTATGTTGCC

ATTGCCCTGATGTTTGGTGTTCAGGCAGTTGATCTGCGTACCTACAAAAAAACCGGTCAT

TATGATGCACGTGCCCAGCTGTCACCGGCAACCGAACGTCTGTATAGCGCAGTTCGTCAT

GTTGTTGGTCAGAAACCGAGCTCAGATCGTCCGTATATTTGGAATGATAATGAACAGGG

TCTGGATGAACATATTGCACGTATTAGTGCAGATATTGCAGCCGGTGGTGTTATTGTTCA

GGCCGTTCAGGACATTCTGCCGAACCTGCAT
```

Polypeptide Sequence of AvPAL Variant No. 1010 (SEQ ID NO: 22):

(SEQ ID NO: 22)

```
MKTLSQAQSKTSSQQFSFTGNSSANVIIGNQKLTINDVARVARNGTLVSLTNNTDILQGI

QASCDYINNAVESGEPIYGVTSGFGGMANVVISREQASELQTNLVWFLKTGAGNKLPLADVR

AAMLLRANSHMHGASGIRLELIKRAEIFLNAGVTPYVYEFGSIGASGDLVPLSYITGSLIGLDP

SFKVDFNGKEMDAPTALRQLNLSPLTLLPKEGLAMMNGTSVMTGIAANCVYDTQILTAIAM

GVHALDIQALNGTNQSFHPFIHNSKPHPGQLWAADQMISLLAGSQLVRDELDGKHDYRDGE

LIQDRYSLRCLPQYLGPIVDGISQIAKQIEIEINSVTDNPLIDVDNQASYHGGNFLGQYVGMGM

DHLRYEIGLLAKHLDTQIALLASPEFSNGLPPSLVGNRERKVNMGLKGLQICGNSIMPLLTFY

GNSIADRFPTHAEQFNQNINSQGYTSATLARRSVDIGQNYVAIALMFGVQAVDLRTYKKTGH

YDARAQLSPATERLYSAVRHVVGQKPSSDRPYIVVNDNEQGLDE

HIARISADIAAGGVIVQAVQDILPNLH
```

Polynucleotide Sequence of AvPAL Variant No. 1084 (SEQ ID NO: 23):

(SEQ ID NO: 23)

```
ATGAAAACCCTGAGTCAGGCACAGAGCAAAACCAGCAGCCAGCAGTTTAGCCATACCGG

CAATAGCAGCGCAAATGTGATTATTGGTAATCAGAAACTGACCATCAATGATGTTGTAC

GTGTTGCCCGTAATGGCACCGCGGTTAGCCTGACCAATAATAAAGATATTCTGCAGCGTA

TTCAGGCCAGCTGTGATTATATCAATAATGCAGTTGAAAAAGGTGAACCGATTTATGGTG

TTACCAGCGGTTTTGGTGGTATGGCAAATGTTGTAATTAGCCGTGAACAGGCAAGCGAA

CTGCAGACCAATCTGGTTTGGTTTCTGAAAACCGGTGCAGGTAATAAACTGCCGCTGGCA

GATGTTCGTGCAGCAATGCTGCTGCGTGCAAATAGCCACATGCGTGGTGCAAGCGGTAT

TCGTCTGGAACTGATTAAACGCATGGAAATCTTTCTGAATGCCGGTGTTACCCCGTATGT

TTATGAATTTGGTAGCATTGGTGCCAGCGGTGATCTGGTTCCGCTGAGCTATATTACCGG
```

-continued

```
TAGCCTGATTGGCCTGGACCCGAGCTTTAAAGTTGATTTTAATGGCAAAGAAATGGACG

CACCGACCGCACTGCGTCAGCTGAATCTGAGTCCGCTGACCCTGCAGCCGAAAGAAGGT

CTGGCAATGATGAATGGCACCAGCGTTATGACCGGTATTGCAGCAAATTGTGTTTATGAT

ACCCAGATTCTGACCGCAATTGCAATGGGTGTTCATGCACTGGATATTCAGGCACTGAAT

GGTACAAATCAGAGCTTTCATCCGTTTATCCATAACAGCAAACCGCATCCGGGTCAGCTG

TGGGCAGCAGATCAGATGATTAGCCTGCTGGCCGGTAGCCAGCTGGTTCGTGATGAACT

GGATGGTAAACATGATTATATGGATGGTGAACTGATCCAGGATCGTTATAGCCTGCGTTG

TCTGCCGCAGTATCTGGGTCCGATTGTTGATGGTATTAGCCAGATTGCCAAACAAATCGA

AATTGAGATTAACAGCGTTACCGATAACCCGCTGATTGATGTTGATAATCAGGCAAGCT

ATCATGGTGGTAATTTTCTGGGTCAGTATGTTGGTATGGGTATGGATCATCTGCGCTATT

ATATCGGTCTGCTGGCAAAACATCTGGATGTTCAGATTGCACTGCTGGCATCACCGGAAT

TTAGCAATGGTCTGCCTCCGAGTCTGGTGGGTAATCGTGAACGTAAAGTTAATATGGGTC

TGAAAGGTCTGCAGATTTGCGGTAATAGCATTATGCCGCTGCTGACCTTTTATGGTAATA

GTATTGCAGATCGTTTTCCGACCCATGCCGAACAGTTTAACCAGAATATTAACAGCCAGG

GTTATACCAGCGCAACCCTGGCACGTCGTAGCGTTGATATTTTTCAGAATTATGTTGCCA

TTGCCCTGATGTTTGGTGTTCAGGCAGTTGATCTGCGTACCTACAAAAAAACCGGTCATT

ATGATGCACGTGCCCAGCTGTCACCGGCAACCGAACGTCTGTATAGCGCAGTTCGTCATG

TTGTTGGTAAAAAACCGAGCTCAGATCGTCCGTATATTTGGAATGATAATGAACAGGGT

CTGGATGAACATATTGCACGTATTAGTGCAGATATTGCAGCCGGTGGTGTTATTGTTCAG

GCCGTTCAGGACATTCTGCCGCCGCTGCAT
```

Polypeptide Sequence of AvPAL Variant No. 1084 (SEQ ID NO: 24):

(SEQ ID NO: 24)

```
MKTLSQAQSKTSSQQFSHTGNSSANVIIGNQKLTINDVVRVARNGTAVSLTNNKDILQRI

QASCDYINNAVEKGEPIYGVTSGFGGMANVVISREQASELQTNLVWFLKTGAGNKLPLADV

RAAMLLRANSHMRGASGIRLELIKRMEIFLNAGVTPYVYEFGSIGASGDLVPLSYITGSLIGLD

PSFKVDFNGKEMDAPTALRQLNLSPLTLQPKEGLAMMNGTSVMTGIAANCVYDTQILTAIA

MGVHALDIQALNGTNQSFHPFIHNSKPHPGQLWAADQMISLLAGSQLVRDELDGKHDYMD

GELIQDRYSLRCLPQYLGPIVDGISQIAKQIEIEINSVTDNPLIDVDNQASYHGGNFLGQYVGM

GMDHLRYYIGLLAKHLDVQIALLASPEFSNGLPPSLVGNRERKVNMGLKGLQICGNSIMPLL

TFYGNSIADRFPTHAEQFNQNINSQGYTSATLARRSVDIFQNYVAIALMFGVQAVDLRTYKK

TGHYDARAQLSPATERLYSAVRHVVGKKPSSDRPYIVVNDNEQGLDE

HIARISADIAAGGVIVQAVQDILPPLH
```

Polynucleotide Sequence of AvPAL Variant No. 967 (SEQ ID NO: 25):

(SEQ ID NO: 25)

```
ATGAAAACCCTGAGTCAGGCACAGAGCAAAACCAGCAGCCAGCAGTTTAGCTTTACCGG

CAATAGCAGCGCAAATGTGATTATTGGTAATCAGAAACTGACCATCAATGATGTTGCGC

GTGTTGCCCGTAATGGCACCCTGGTTAGCCTGACCAATAATACCGATATTCTGCAGGGTA

TTCAGGCCAGCTGTGATTATATCAATAATGCAGTTGAAAGCGGTGAACCGATTTATGGTG

TTACCAGCGGTTTTGGTGGTATGGCAAATGTTGTAATTAGCCGTGAACAGGCAAGCGAAC

TGCAGACCAATCTGGTTTGGTTTCTGAAAACCGGTGCAGGTAATAAACTGCCGCTGGCAG

ATGTTCGTGCAGCAATGCTGCTGCGTGCAAATAGCCACATGCGTGGTGCAAGCGGTATTC

GTCTGGAACTGATTAAACGCGCGGAAATCTTTCTGAATGCCGGTGTTACCCCGTATGTTT

ATGAATTTGGTAGCATTGGTGCCAGCGGTGATCTGGTTCCGCTGAGCTATATTACCGGTA
```

-continued

```
GCCTGATTGGCCTGGACCCGAGCTTTAAAGTTGATTTTAATGGCAAAGAAATGGACGCAC

CGACCGCACTGCGTCAGCTGAATCTGAGTCCGCTGACCCTGCTGCCGAAAGAAGGTCTG

GCAATGATGAATGGCACCAGCGTTATGACCGGTATTGCAGCAAATTGTGTTTATGATACC

CAGATTCTGACCGCAATTGCAATGGGTGTTCATGCACTGGATATTCAGGCACTGAATGGT

ACAAATCAGAGCTTTCATCCGTTTATCCATAACAGCAAACCGCATCCGGGTCAGCTGTGG

GCAGCAGATCAGATGATTAGCCTGCTGGCCGGTAGCCAGCTGGTTCGTGATGAACTGGA

TGGTAAACATGATTATCGTGATGGTGAACTGATCCAGGATCGTTATAGCCTGCGTTGTCT

GCCGCAGTATCTGGGTCCGATTGTTGATGGTATTAGCCAGATTGCCAAACAAATCGAAAT

TGAGATTAACAGCGTTACCGATAACCCGCTGATTGATGTTGATAATCAGGCAAGCTATCA

TGGTGGTAATTTTCTGGGTCAGTATGTTGGTATGGGTATGGATCATCTGCGCTATTATATC

GGTGGCCTGGCAAAACATCTGGATGTTCAGATTGCACTGCTGGCATCACCGGAATTTAGC

AATGGTCTGCCTCCGAGTCTGGTGGGTAATCGTGAACGTAAAGTTAATATGGGTCTGAAA

GGTCTGCAGATTTGCGGTAATAGCATTATGCCGCTGCTGACCTTTTATGGTAATAGTATT

GCAGATCGTTTTCCGACCCATGCCGAACAGTTTAACCAGAATATTAACAGCCAGGGTTAT

ACCAGCGCAACCCTGGCACGTCGTAGCGTTGATATTGGCCAGAATTATGTTGCCATTGCC

CTGATGTTTGGTGTTCAGGCAGTTGATCTGCGTACCTACAAAAAAACCGGTCATTATGAT

GCACGTGCCCAGCTGTCACCGGCAACCGAACGTCTGTATAGCGCAGTTCGTCATGTTGTT

GGTCAGAAACCGAGCTCAGATCGTCCGTATATTTGGAATGATAATGAACAGGGTCTGGA

TGAACATATTGCACGTATTAGTGCAGATATTGCAGCCGGTGGTGTTATTGTTCAGGCCGT

TCAGGACATTCTGCCGAACCTGCAT
```

Polypeptide Sequence of Variant No. 967 (SEQ ID NO: 26):

(SEQ ID NO: 26)

```
MKTLSQAQSKTSSQQFSFTGNSSANVIIGNQKLTINDVARVARNGTLVSLTNNTDILQGIQAS

CDYINNAVESGEPIYGVTSGFGGMANVVISREQASELQTNLVWFLKTGAGNKLPLADVRAA

MLLRANSHMRGASGIRLELIKRAEIFLNAGVTPYVYEFGSIGASGDLVPLSYITGSLIGLDPSFK

VDFNGKEMDAPTALRQLNLSPLTLLPKEGLAMMNGTSVMTGIAANCVYDTQILTAIAMGVH

ALDIQALNGTNQSFHPFIHNSKPHPGQLWAADQMISLLAGSQLVRDELDGKHDYRDGELIQD

RYSLRCLPQYLGPIVDGISQIAKQIEIEINSVTDNPLIDVDNQASYHGGNFLGQYVGMGMDHL

RYYIGGLAKHLDVQIALLASPEFSNGLPPSLVGNRERKVNMGLKGLQICGNSIMPLLTFYGNS

IADRFPTHAEQFNQNINSQGYTSATLARRSVDIGQNYVAIALMFGVQAVDLRTYKKTGHYDA

RAQLSPATERLYSAVRHVVGQKPSSDRPYIVVNDNEQGLDEHIARISADIAAGGVIVQAVQDILPNLH
```

Expression vector pCK100900i:

(SEQ ID NO: 27)

```
TGGCCACCATCACCATCACCATTAGGGAAGAGCAGATGGGCAAGCTTGACCTGTGAAGT

GAAAAATGGCGCACATTGTGCGACATTTTTTTTGAATTCTACGTAAAAAGCAGCCGATA

CATCGGCTGCTTTTTTTTTGNNNGAGGTTCCAACTTGTGGTATAATGAAATAAGATCACT

CCCGGAGCGTATTTTTTGAGTTATCGAGATTTTCAGGAGCTAAGGAGGAACTAAAATGGA

GAAAAAAATCACTGGATATACCACCGTTGATATATCCCAATGGCATCGTAAAGAACATTT

TGAGGCATTTCAGTCAGTTGCTCAATGTACCTATAACCAGACCGTTCAGCTGGATATTAC

GGCCTTTTTAAAGACCGTAAAGAAAAATAAGCACAAGTTTTATCCGGCCTTTATTCACAT

TCTTGCCCGCCTGATGAATGCTCATCCGGAGTTCCGTATGGCAATGAAAGACGGTGAGCT

GGTGATATGGGATAGTGTTCACCCTTGTTACACCGTTTTCCATGAGCAAACTGAAACGTT
```

-continued

```
TTCATCGCTCTGGAGTGAATACCACGACGATTCCGGCAGTTTCTACACATATATTCGCA
AGATGTGGCGTGTTACGGTGAAAACCTGGCCTATTTCCCTAAAGGGTTTATTGAGAATAT
GTTTTTCGTCTCAGCCAATCCCTGGGTGAGTTTCACCAGTTTTGATTTAAACGTGGCCAAT
ATGGACAACTTCTTCGCCCCCGTTTTCACCATGGGCAAATATTATACGCAAGGCGACAAG
GTGCTGATGCCGCTGGCGATTCAGGTTCATCATGCCGTCTGTGATGGCTTCCATGTCGGC
AGAATGCTTAATGAATTACAACAGTACTGCGATGAGTGGCAGGGCGGGGCGTAACTGCA
GGAGCTCAAACAGCAGCCTGTATTCAGGCTGCTTTTTTCGTTTTGGTCTGCGCGTAATCTC
TTGCTCTGAAAACGAAAAAACCGCCTTGCAGGGCGGTTTTTCGAAGGTTCTCTGAGCTAC
CAACTCTTTGAACCGAGGTAACTGGCTTGGAGGAGCGCAGTCACCAAAACTTGTCCTTTC
AGTTTAGCCTTAACCGGCGCATGACTTCAAGACTAACTCCTCTAAATCAATTACCAGTGG
CTGCTGCCAGTGGTGCTTTTGCATGTCTTTCCGGGTTGGACTCAAGACGATAGTTACCGG
ATAAGGCGCAGCGGTCGGACTGAACGGGGGGTTCGTGCATACAGTCCAGCTTGGAGCGA
ACTGCCTACCCGGAACTGAGTGTCAGGCGTGGAATGAGACAAACGCGGCCATAACAGCG
GAATGACACCGGTAAACCGAAAGGCAGGAACAGGAGAGCGCACGAGGGAGCCGCCAGG
GGGAAACGCCTGGTATCTTTATAGTCCTGTCGGGTTTCGCCACCACTGATTTGAGCGTCA
GATTTCGTGATGCTTGTCAGGGGGCGGAGCCTATGGAAAAACGGCTTTGCCGCGGCCCT
CTCACTTCCCTGTTAAGTATCTTCCTGGCATCTTCCAGGAAATCTCCGCCCCGTTCGTAAG
CCATTTCCGCTCGCCGCAGTCGAACGACCGAGCGTAGCGAGTCAGTGAGCGAGGAAGCG
GAATATATCCTGTATCACATATTCTGCTGACGCACCGGTGCAGCCTTTTTTCTCCTGCCAC
ATGAAGCACTTCACTGACACCCTCATCAGTGAACCACCGCTGGTAGCGGTGGTTTTTTA
GGCCTATGGCCTTTTTTTTTNTGNNAAACCTTTCGCGGTATGGNATNANAGCGCCCGGA
AGAGAGTCAATTAAGAGGGTGGTGAATGTGAAACCAGTAACGTTATACGATGTCGCAGA
GTATGCCGGTGTCTCTTATCAGACCGTTTCCCGCGTGGTGAACCAGGCCAGCCACGTTTC
TGCGAAAACGCGGGAAAAAGTGGAAGCGGCGATGGCGGAGCTGAATTACATTCCCAACC
GCGTGGCACAACAACTGGCGGGCAAACAGTCGTTGCTGATTGGCGTTGCCACCTCCAGTC
TGGCCCTGCACGCGCCGTCGCAAATTGTCGCGGCGATTAAATCTCGCGCCGATCAACTGG
GTGCCAGCGTGGTGGTGTCGATGGTAGAACGAAGCGGCGTCGAAGCCTGTAAAGCGGCG
GTGCACAATCTTCTCGCGCAACGCGTCAGTGGGCTGATCATTAACTATCCGCTGGATGAC
CAGGATGCCATTGCTGTGGAAGCTGCCTGCACTAATGTTCCGGCGTTATTTCTTGATGTCT
CTGACCAGACACCCATCAACAGTATTATTTTCTCCCATGAAGACGGTACGCGACTGGGCG
TGGAGCATCTGGTCGCATTGGGTCACCAGCAAATCGCGCTGTTAGCGGGCCCATTAAGTT
CTGTCTCGGCGCGTCTGCGTCTGGCTGGCTGGCATAAATATCTCACTCGCAATCAAATTC
AGCCGATAGCGGAACGGGAAGGCGACTGGAGTGCCATGTCCGGTTTTCAACAAACCATG
CAAATGCTGAATGAGGGCATCGTTCCCACTGCGATGCTGGTTGCCAACGATCAGATGGC
GCTGGGCGCAATGCGCGCCATTACCGAGTCCGGGCTGCGCGTTGGTGCGGACATCTCGGT
AGTGGGATACGACGATACCGAAGACAGCTCATGTTATATCCCGCCGTTAACCACCATCA
AACAGGATTTTCGCCTGCTGGGGCAAACCAGCGTGGACCGCTTGCTGCAACTCTCTCAGG
GCCAGGCGGTGAAGGGCAATCAGCTGTTGCCCGTCTCACTGGTGAAAAGAAAAACCACC
CTGGCGCCCAATACGCAAACCGCCTCTCCCCGCGCGTTGGCCGATTCATTAATGCAGCTG
GCACGACAGGTTTCCCGACTGGAAAGCGGGCAGTGAGCGGTACCCGATAAAAGCGGCTT
CCTGACAGGAGGCCGTTTTGTTTCTCGAGTTAATTAAGGCAGTGAGCGCAACGCAATTAA
```

-continued

```
TGTGAGTTAGCTCACTCATTAGGCACCCCAGGCTTTACACTTTATGCTTCCGGCTCGTATG
TTGTGTGGAATTGTGAGCGGATAACAATTTCACACAGGAAACAGCTATGACCATGATTAC
GGATTCACTGGCCGTCGTTTTACAATCTAGAGGCCAGCCTGGCCATAAGGAGATATACAT
ATGGGCCATCATCATCATCATCATCATCATCATCACAGCAGCGGCCATATCGAAGGTCGT
CATATGAAAACCCTGAGCCAGGCACAGAGCAAAACCAGCAGCCAGCAGTTTAGCTTTAC
CGGCAATAGCAGCGCAAATGTGATTATTGGTAATCAGAAACTGACCATCAATGATGTTG
CACGTGTTGCCCGTAATGGCACCCTGGTTAGCCTGACCAATAATACCGATATTCTGCAGG
GTATTCAGGCCAGCTGTGATTATATCAATAATGCAGTTGAAAGCGGTGAACCGATTTATG
GTGTTACCAGCGGTTTTGGTGGTATGGCAAATGTTGCAATTAGCCGTGAACAGGCAAGCG
AACTGCAGACCAATCTGGTTTGGTTTCTGAAAACCGGTGCAGGTAATAAACTGCCGCTGG
CAGATGTTCGTGCAGCAATGCTGCTGCGTGCAAATAGCCACATGCGTGGTGCAAGCGGT
ATTCGTCTGGAACTGATTAAACGCATGGAAATCTTTCTGAATGCCGGTGTTACCCCGTAT
GTTTATGAATTTGGTAGCATTGGTGCCAGCGGTGATCTGGTTCCGCTGAGCTATATTACC
GGTAGCCTGATTGGCCTGGACCCCGAGCTTTAAAGTTGATTTTAATGGCAAAGAAATGGAC
GCACCGACCGCACTGCGTCAGCTGAATCTGAGTCCGCTGACCCTGCTGCCGAAAGAAGG
TCTGGCAATGATGAATGGCACCAGCGTTATGACCGGTATTGCAGCAAATTGTGTTTATGA
TACCCAGATTCTGACCGCAATTGCAATGGGTGTTCATGCACTGGATATTCAGGCACTGAA
TGGTACAAATCAGAGCTTTCATCCGTTTATCCATAACAGCAAACCGCATCCGGGTCAGCT
GTGGGCAGCAGATCAGATGATTAGCCTGCTGGCCAATAGCCAGCTGGTTCGTGATGAAC
TGGATGGTAAACATGATTATCGTGATCATGAACTGATCCAGGATCGTTATAGCCTGCGTT
GTCTGCCGCAGTATCTGGGTCCGATTGTTGATGGTATTAGCCAGATTGCCAAACAAATCG
AAATTGAGATTAACAGCGTTACCGATAACCCGCTGATTGATGTTGATAATCAGGCAAGCT
ATCATGGTGGTAATTTTCTGGGTCAGTATGTTGGTATGGGTATGGATCATCTGCGCTATTA
TATCGGTCTGCTGGCAAAACATCTGGATGTTCAGATTGCACTGCTGGCATCACCGGAATT
TAGCAATGGTCTGCCTCCGAGTCTGCTGGGTAATCGTGAACGTAAAGTTAATATGGGTCT
GAAAGGTCTGCAGATTTGCGGTAATAGCATTATGCCGCTGCTGACCTTTTATGGTAATAG
TATTGCAGATCGTTTTCCGACCCATGCCGAACAGTTTAACCAGAATATTAACAGCCAGGG
TTATACCAGCGCAACCCTGGCACGTCGTAGCGTTGATATTTTTCAGAATTATGTTGCCATT
GCCCTGATGTTTGGTGTTCAGGCAGTTGATCTGCGTACCTACAAAAAAACCGGTCATTAT
GATGCACGTGCCTGTCTGTCACCGGCAACCGAACGTCTGTATAGCGCAGTTCGTCATGTT
GTTGGTCAGAAACCGACCTCAGATCGTCCGTATATTTGGAATGATAATGAACAGGGTCTG
GATGAACATATTGCACGTATTAGTGCAGATATTGCAGCCGGTGGTGTTATTGTTCAGGCC
GTTCAGGACATTCTGCCGTGTCTGCATTAAGGCCAAAC
```

Example 1

PAL Gene Acquisition and Construction of Expression Vectors

*Anabaena variabilis* phenylalanine ammonia lyase (AvPAL) plasmid DNA was obtained and a synthetic gene encoding AvPAL was codon optimized for expression in *E. coli* and cloned into the *E. coli* expression vector pET16b to provide pET16b-AvPAL (SEQ ID NO:1). The AvPAL open reading frame (SEQ ID NO:2) was amplified by PCR using the oligonucleotides: PAL-pCK-F and PAL-pCK-R and sub-cloned into the expression vector pCK100900i (SEQ ID NO: 27).

| Primer | Sequence 5' to 3' | SEQ ID NO: |
|---|---|---|
| PAL-pCK-F | CTAGAGGCCAGCCTGGCCATAAGGAGAT ATACATATGAAAACCCTGAGCCAGGCAC | SEQ ID NO: 28 |

-continued

| Primer | Sequence 5' to 3' | SEQ ID NO: |
|---|---|---|
| PAL-pCK-R | GATGGTGATGGTGGCCAGTTTGGCCTTA ATGCAGACACGGCAGAATG | SEQ ID NO: 29 |

This plasmid construct was transformed into an *E. coli* strain derived from W3110. Directed evolution techniques generally known by those skilled in the art were used to generate libraries of gene variants from this plasmid construct (See e.g., U.S. Pat. No. 8,383,346 and WO2010/144103).

Example 2

High-Throughput (HTP) Growth and Assays

In this Example, methods used for HTP growth and various assays used to test the variant PALs are described.
High-Throughput (HTP) Growth of PAL and PAL Variants Transformed *E. coli* cells were selected by plating onto LB agar plates containing 1% glucose and 30 µg/ml chloramphenicol. After overnight incubation at 37° C., colonies were placed into NUNC™ (Thermo-Scientific) the wells of 96-well shallow flat bottom plates filled with 180 µl/well LB supplemented with 1% glucose and 30 µg/ml chloramphenicol. The cultures were allowed to grow overnight for 18-20 hours in a shaker (200 rpm, 30° C., and 85% relative humidity; Kuhner). Overnight growth samples (20 µL) were transferred into Costar 96-well deep plates filled with 3804 of Terrific Broth supplemented with 30 µg/ml chloramphenicol. The plates were incubated for 135 minutes in a shaker (250 rpm, 30° C., and 85% relative humidity; Kuhner). The cells were then induced with 40 µL of 10 mM IPTG in sterile water and incubated overnight for 20-24 hours in a shaker (250 rpm, 30° C., and 85% relative humidity; Kuhner). Two replicate cultures were combined, the cells were pelleted (4000 rpm×20 min), the supernatants were discarded, and the cells were frozen at −80° C. prior to analysis.
Lysis of HTP Pellets First, 500 µL of lysis buffer (20 mM Tris pH 7.5, 1 mM MgSO$_4$, 1 mg/ml lysozyme, and 0.5 mg/ml polymyxin B sulfate) were added to the cell pellets. The mixture was agitated for 1.5 h at room temperature, and pelleted (4000 rpm×5 min) prior to use of the clarified lysates in the various HTP assays described herein. Analysis of these lysates by SDS-PAGE revealed the presence of an overexpressed protein at an apparent MW of ~60 kDa, consistent with the expected MW of PAL.
Analysis of Clarified Lysates PAL variant activity was determined by measuring the formation of cinnamic acid as determined by the change in absorbance at 290 nm over time. For this assay, 100 µL of either 200 mM Tris/50 mM phenylalanine, pH 7.5, or 200 mM sodium phosphate/50 mM phenylalanine pH 7.0, 80 µL of water, and 20 µL of clarified lysate were added to the wells of a poly-acrylate 96-well plate (Costar #3635, Corning). The reactions were mixed briefly and the activity was determined by tracking the absorbance at 290 nm over time (every 12-20 s over 5-20 min) using a SpectraMax® Plus$^{384}$ or a SpectraMax® 190 (Molecular Devices) absorbance microplate reader.
HTP-Analysis of Clarified Lysates Pretreated with Protease PAL variants were challenged with chymotrypsin and trypsin to simulate the environment of the lower intestine. First, 30 µL of protease mix (0.01-100 mg/ml chymotrypsin (C4129 Sigma Aldrich), 0.01-100 mg/ml trypsin (T7409 Sigma Aldrich), 1 mM CaCl$_2$, and 1 mM HCl), 0-30 µL of 20 mM sodium taurocholate in 500 mM sodium phosphate pH 7.0, and 90-120 µL of clarified lysate were added to the wells of a 96-well round bottom plate (Costar #3798, Corning). The plates were sealed and incubated at 37° C., 400 rpm, 1" throw for 1 h prior to analysis. For the assay, 100 µL of either 200 mM Tris/50 mM phenylalanine pH 7.5 or 200 mM sodium phosphate/50 mM phenylalanine pH 7.0 and 100 µL of the protease treated lysate were added to the wells of a poly-acrylate 96-well plate (Costar #3635, Corning). The reactions were mixed briefly and the activity was determined by tracking the absorbance at 290 nm over time (every 12-20 s over 5-20 min) using a SpectraMax® Plus$^{384}$ or a SpectraMax® 190 (Molecular Devices) absorbance microplate reader. The results are provided in the following Tables.
HTP-Analysis of Clarified Lysates Pretreated with Acid In this assay, PAL variants were challenged under acidic conditions, in order to simulate the environment of the stomach. First, 20 µL of 1M sodium citrate (pH 3.7-4.5) and 30 µL of water or 50 µL of 400 mM sodium citrate pH 3.7-4.8, and 50 uL of clarified lysate were added to the wells of a 96-well round bottom plate (Costar #3798, Corning). The plate was sealed and incubated at 37° C., 400 rpm, 1" throw for 1 h prior to analysis. For the assay, 100 µL of either 200 mM Tris, 50 mM phenylalanine pH 7.5 and 80 µL 1M Tris pH 7.5 or 200 mM sodium phosphate/50 mM phenylalanine pH 7.0 and 80 µL of 1.0 M sodium phosphate pH7.0, and 20 µL of the acid-treated lysate were added to the wells of a poly-acrylate 96-well plate (Costar #3635, Corning). The reactions were mixed briefly, and the activity was determined by tracking the absorbance at 290 nm over time (every 12-20 s over 5-20 min) using a SpectraMax® Plus$^{384}$ or a SpectraMax® 190 (Molecular Devices) absorbance microplate reader. The results are provided in the following Tables.
HTP Analysis of Clarified Lysates Pretreated with Pepsin In additional assays, PAL variants are challenged with acidic conditions and pepsin to further test the variants under conditions that mimic the gastric environment. First, 50 µL of 0.01-100 mg/ml pepsin in 400 mM sodium citrate pH 1.5-4, and 50 µL of clarified lysate are added to the wells of a 96-well round bottom plate (Costar #3798, Corning). The plate is sealed and incubated at 37° C., 400 rpm, 1" throw for 1-12 h prior to analysis. For the assay, 100 µL of either 200 mM Tris/50 mM phenylalanine pH 7.5 and 80 µL 1M Tris pH 7.5 or 200 mM sodium phosphate/50 mM phenylalanine pH 7.0, and 20 µL of acid-treated lysate are added to the wells of a poly-acrylate 96-well plate (Costar #3635, Corning). The reactions are mixed briefly, and the activity is determined by tracking the absorbance at 290 nm over time (every 12-20 s over 5-20 min) using a SpectraMax® Plus$^{384}$ or a SpectraMax® 190 (Molecular Devices) absorbance microplate reader.

TABLE 2-1

Relative Activity of PAL Variants When Unchallenged (U-C), Protease-Challenged (P-C), and Acid-Challenged (A-C).

| Variant # | U-C | P-C | A-C | Amino Acid Differences Relative to SEQ ID NO: 4 |
|---|---|---|---|---|
| 1 | + | + | + | A39V/A91V/Y158H/S180A/N290G/A394V/S399N/N474Q/K522Y/T524S |
| 2 | + | + | ++ | A39V/A91V/Y158H/A256G/A394V/P404A/N474Q |
| 3 | + | ++ | ++ | A39V/A91V/S180A/A394V/K522F/T524S |
| 4 | + | + | ++ | A39V/A91V/Y158H/T243I/A256G/S399N/P404A/L407V/N474Q |
| 5 | + | + | ++ | E308Q |
| 6 | + | ++ | + | N400K |
| 7 | + | + | + | L364Q |
| 8 | + | + | ++ | A256G/N290G/P404A/L407V/N474Q/K522F |
| 9 | + | + | ++ | Y158H/S180A/A394V/T463N/N474Q/T524S |
| 10 | + | + | ++ | A39V/A91V/Y158H/S180A/K195E/A256G/S399N/L407V/Y459F/T463N/K522N/T524S |
| 11 | + | + | ++ | A39V/A91V/Y158H/S180A/K195E/A256G/N290G/S399N/Y459F/T463N |
| 12 | + | ++ | ++ | A39V/A91V/Y158H/S180A/K195E/T243I/A394V |
| 13 | + | ++ | ++ | A39V/A91V/Y158H/K195E/T243I/A256G/A394V/S399N/N474Q/K522Y/T524S |
| 14 | + | ++ | ++ | A39V/A91V/Y158H/S180A/K195E/I245L/S399N/L407V/Y459F/T463N/N474Q/T524S |
| 15 | + | ++ | + | H307M |
| 16 | + | + | ++ | A39V/A91V/Y158H/S180A/T243L/A394V/S399N/T463N/K522F |
| 17 | + | + | ++ | A91V/N474Q |
| 18 | ++ | + | ++ | S180A/K195E |
| 19 | ++ | + | ++ | A91V/Y158H/T243I/A256G/N290G/S399N/L407V/Y459F/T463N/N474Q/K522N/T524S |
| 20 | ++ | ++ | ++ | A39V/Y158H/S180A/S399N |
| 21 | ++ | ++ | ++ | A91V/N270K |
| 22 | ++ | +++ | ++ | H307G |
| 23 | ++ | ++ | + | N453G |
| 24 | ++ | ++ | ++ | H307Q |
| 25 | ++ | ++ | + | L257W |
| 26 | ++ | + | +++ | A91V/Y158H/I245L/A256G/S399N/Y459F/T463N/K522Y/T524S |
| 27 | ++ | ++ | + | F443H |
| 28 | ++ | ++ | ++ | A91V/Y158H/S180A |
| 29 | ++ | ++ | + | A91Y/Y158H/K195E/S399N |
| 30 | ++ | ++ | +++ | A39V/A91Y/A256G/N290G/A394V/S399N/P404A/L407V/K522Y/T524S |
| 31 | ++ | ++ | + | L257A |
| 32 | ++ | + | +++ | Y158H/K195E/T243L/A256G/A394V/S399N/L407V/N474Q/K522F/T524S |
| 33 | ++ | ++ | | L349M |
| 34 | +++ | +++ | + | I326F |
| 35 | +++ | +++ | +++ | T460G/P528L |

1. Relative activity was calculated as activity of the variant/activity of SEQ ID NO: 4 (encoded by SEQ ID NO: 3).
2. Variant # 22 has the polynucleotide sequence of SEQ ID NO: 7 and polypeptide sequence of SEQ ID NO: 8, and Variant # 30 has polynucleotide sequence of SEQ ID NO: 5 and polypeptide sequence of SEQ ID NO: 6.
3. + = 0.1 to 1.0 relative activity over wild-type AvPAL;
++ = >1.0 to 2.0 relative activity over wild-type AvPAL; and
+++ = >2.0 relative activity over wild-type AvPAL.

TABLE 2-2

Relative Activity of PAL Variants Unchallenged (U-C), Protease-Challenged (P-C), and Acid-Challenged (A-C).

| Variant # | U-C | P-C | A-C | Amino Acid Differences-Relative to Wild-Type AvPAL (SEQ ID NO: 4) |
|---|---|---|---|---|
| 36 | ++ | +++ | ++ | A39V/A91V/N290G/H307G/L407V/T524S |
| 37 | ++ | +++ | ++ | A39V/A91V/N290G/H307G/L407V |
| 38 | + | ++ | + | A39V/A91V/A256G/N290G/H307G/S399N/P404A/L407V/K522Y/T524S |
| 39 | ++ | + | ++ | A39V/A91V/A256G/N290G/S399N/P404A/L407V/K522Y |

TABLE 2-2-continued

Relative Activity of PAL Variants Unchallenged (U-C), Protease-Challenged (P-C), and Acid-Challenged (A-C).

| Variant # | U-C | P-C | A-C | Amino Acid Differences-Relative to Wild-Type AvPAL (SEQ ID NO: 4) |
|---|---|---|---|---|
| 40 | + | ++ | + | A39V/A256G/N290G/H307G/P404A/L407V |
| 41 | + | ++ | + | A39V/A91V/A256G/N290G/H307G/P404A/L407V/T524S |

1. Relative activity was calculated as activity of the variant/activity of Variant No. 30.
2. Variant # 36 has polynucleotide sequence of SEQ ID NO: 9 and polypeptide sequence of SEQ ID NO: 10.
3. + = >1.0 to 3.0 relative activity over Variant 30;
++ = >3.0 to 10 relative activity over Variant 30; and
+++ = >10 to 35 relative activity over Variant 30.

TABLE 2-3

Relative Activity of PAL Variants Unchallenged (U-C), Protease-Challenged (P-C), and Acid-Challenged (A-C).

| Variant # | U-C | A-C | P-C | Mutations (Relative to Variant No. 36) |
|---|---|---|---|---|
| 42 | + | + | + | T54K/G59R/S73K/R305M/C503Q/Q521K/C565P |
| 43 | + | +++ | ++ | T54K/G59R/R305M/C503Q/Q521K/C565N |
| 44 | ++ | +++ | ++ | G59R/C503Q |
| 45 | ++ | +++ | ++ | K32P/G59R/S73K/Q240W/C503Q/C565N |
| 46 | + | + | + | K32P/G59R/S73K/Q240W/C565P |
| 47 | + | +++ | ++ | K32P/T54K/S73K/R305M/C503Q/Q521K/C565N |
| 48 | +++ | +++ | ++ | Y304H/D353A |
| 49 | ++ | +++ | +++ | S73K/D353A |
| 50 | + | + | ++ | A112C/S546R |
| 51 | ++ | + | ++ | S73K/Q240W/Y304H |
| 52 | + | + | ++ | R134Q/Q240W/Y304H/D353A/E509L |

1. Relative activity was calculated as activity of variant/activity of Variant No 36.
2. Variant # 42 has the polynucleotide sequence of SEQ ID NO: 11 and a polypeptide sequence of SEQ ID NO: 12. Variant # 43 has the polynucleotide sequence of SEQ ID NO: 13 and a polypeptide sequence of SEQ ID NO: 14.
3. + = >0.5 to 1.5 relative activity over Variant 36;
++ = >1.5 to 3 relative activity over Variant 36; and
+++ = >3 to 10 relative activity over Variant 36.

TABLE 2-4

Relative Activity of PAL Variants Unchallenged (U-C), Protease-Challenged (P-C), and Acid-Challenged (A-C).

| Variant # | U-C | P-C | A-C | Mutations (Relative to Variant #30) |
|---|---|---|---|---|
| 53 | + | + | + | D303R |
| 54 | + | + | ++ | E308A |
| 55 | + | + | + | E308D |
| 56 | ++ | ++ | + | G256A |
| 57 | + | ++ | + | H307A |
| 58 | + | +++ | + | H307D |
| 59 | + | ++ | + | H307E |
| 60 | + | ++ | + | H307F |
| 61 | + | +++ | + | H307G |
| 62 | + | + | + | H307I |
| 63 | + | + | + | H307L |
| 64 | ++ | +++ | ++ | H307M |
| 65 | + | ++ | + | H307N |
| 66 | ++ | ++ | ++ | H307R |
| 67 | + | + | + | H307Y |
| 68 | + | +++ | + | R305L |
| 69 | + | +++ | + | R305M |
| 70 | + | +++ | + | R305Q |
| 71 | ++ | ++ | + | V91A/G256A |
| 72 | + | ++ | + | Y304H |
| 73 | + | + | + | Y304W |
| 74 | + | + | + | C503K |
| 75 | + | + | + | C503Q |
| 76 | + | + | + | C565A |
| 77 | + | + | + | C565G |
| 78 | + | + | + | C565I |
| 79 | + | + | + | C565K |
| 80 | + | + | + | C565L |
| 81 | + | ++ | + | C565N |
| 82 | + | + | + | C565P |
| 83 | + | + | + | C565T |

1. Relative activity was calculated as activity of variant/activity of Variant No. 30 (Variants 53-73) or SEQ ID NO: 4 (encoded by SEQ ID NO: 3) (Variants 74-83.)
2. + = >0.5 to 1.5 relative activity over Variant 30;
++ = >1.5 to 3 relative activity over Variant 30; and
+++ = >3 to 10 relative activity over Variant 30.

TABLE 2-5

Relative Activity of PAL Variants Unchallenged (U-C), Protease-Challenged (P-C), and Acid-Challenged (A-C).

| Variant # | U-C | P-C | A-C | Mutations Relative to Variant 42 |
|---|---|---|---|---|
| 42 | + | + | + | |
| 1011 | + | + | + | R59G/R134Q/Q240R/K521Q/P564L |
| 1012 | + | + | ++ | R59G/P564M |
| 1013 | + | + | + | R59G/Q240W/E509L/K521Q/P564M |
| 1014 | ++ | ++ | + | Q240W/Y304H/D353N/E509L/K521S/P564L |
| 1015 | + | ++ | + | R59G/R134Q/Q240R/K521Q/P565N |
| 1016 | + | +++ | + | Y304H/D353A/E509L |
| 1017 | + | ++ | + | R59G/R134Q/Y304H/D353N/K521Q |
| 1018 | + | +++ | + | R59G/R134Q/Q240R/K521S |
| 1019 | + | + | + | R134Q/Y304H/D353A/K521S/P565N |
| 1020 | + | + | + | R59G/R134Q/Q240R/Y304H/D353A/K521Q/P564M |
| 1021 | ++ | +++ | ++ | Q240W/D353A/E509L/K521Q |
| 1022 | + | ++ | + | R134Q/Q240W/E509L/K521S |
| 1023 | ++ | ++ | ++ | R134Q/Q240R/D353A/K521Q/P564G |
| 1024 | + | + | + | R134Q/K521Q |
| 1025 | + | +++ | + | K521Q |
| 1026 | + | +++ | + | R134Q/D353A/K521S/P564M |
| 1027 | + | +++ | + | R59G/R134Q/Q240W/D353A |
| 1028 | ++ | ++ | + | R59G/K521S |
| 1029 | + | ++ | + | R59G/D353A |
| 1030 | + | + | + | Q240R/D353A/K521S |
| 1031 | + | + | + | R59G/D353A/E509L/P564L |
| 1032 | + | + | + | R59G/D353A/K521Q |
| 1033 | + | + | + | R59G/R134Q/D353A/E509L/K521Q |
| 1034 | + | + | + | Q240R/Y304H/E509L |
| 1035 | + | + | + | R59G/Q240R/D353A/E509L |
| 1036 | + | + | + | R59G/R134Q/E509L |
| 1037 | + | + | + | Q240W/Y304H/E509L/K521S |
| 1038 | + | + | + | Q240W/D353A/E509L/K521S/P564L/P565N |
| 1039 | + | + | + | R59G/Q240R/D353A/P564M/P565N |
| 1040 | + | + | + | R134Q/D353A/K521S |
| 1041 | + | + | + | R134Q/Q240W/Y304H/D353A/P564L |
| 1042 | + | + | + | Q240R/E509L/P565N |
| 1043 | + | + | + | Q240R/K521S/P564M/P565N |
| 1044 | + | + | + | R134Q/D353A/P564L |
| 1045 | + | + | + | R59G/R134Q |
| 1046 | + | + | + | R59G/Q240R |
| 1047 | + | + | + | Y304H/E509L |
| 1048 | + | + | + | R134Q/Q240R/D353A/E509L/K521Q/P564L |
| 1049 | + | + | + | Q240W/E509L/P564L/P565N |
| 1050 | + | + | + | R59G/E509L/P564L |
| 1051 | + | + | + | R134Q/D353A/E509L/P564L |
| 1052 | + | + | + | R59G/D353A/P565N |
| 1053 | + | + | + | Q240R/E509L |
| 1054 | + | + | + | Q240R |
| 1055 | + | + | + | D353A/K521Q |
| 1056 | + | + | + | Q240W/D353A/E509L |
| 1057 | + | + | + | F18H/L47A/L214Q/E540D |
| 1058 | + | + | + | F18H/L47A/L214Q/E308K/F450Y/S546R |
| 1059 | + | + | + | F18H/L47A/F450Y/P528L/S546R |
| 1060 | + | + | + | L214Q/E308Q/T460G |
| 1061 | + | + | + | F18H/F450Y/E540D |
| 1062 | + | + | + | P528L/S546R |
| 1063 | + | + | + | F18H/L214Q/F450Y |
| 1064 | + | + | + | E308Q/F450Y/R467G |
| 1065 | + | + | + | F18H/E540D |
| 1066 | + | + | + | L47A/L214Q/S546R |
| 1067 | + | + | + | F18H/L214Q/E308Q |
| 1068 | + | + | + | L47A/L214Q/E308Q |
| 1069 | + | + | + | F18H/L47E/L214Q/R467G/E540D/S546R |
| 1070 | + | + | + | L47A/F450Y |
| 1071 | + | + | + | L47A/L214Q |
| 1072 | + | + | + | F18H/L47A/L214Q/S546R |
| 1073 | + | + | + | F18H/L214Q |
| 1074 | + | + | + | L214Q/F450Y/P528L |
| 1075 | + | + | + | F18H/L214Q/E308Q/F450Y/R467G |
| 1076 | + | + | + | L47A/L214Q/E540D |
| 1077 | + | + | + | L214Q/E540D |
| 1078 | + | + | + | F18H/L47A/E308Q/S546R |
| 1079 | + | + | + | F18H |
| 1080 | + | + | + | F18H/L47A/F450Y/S546R |
| 1081 | + | + | + | F18H/L47A/L214Q/F450Y |
| 1082 | + | + | + | F18H/L47A |
| 1083 | + | + | + | L47A |
| 1084 | + | + | + | F18H/L47A/L214Q |

TABLE 2-5-continued

Relative Activity of PAL Variants Unchallenged (U-C),
Protease-Challenged (P-C), and Acid-Challenged (A-C).

| Variant # | U-C | P-C | A-C | Mutations Relative to Variant 42 |
|---|---|---|---|---|
| 1085 | + | + | + | L214Q/S546R |
| 1086 | + | + | + | F18H/L214Q/R467G/S546R |
| 1087 | + | + | + | F18H/L47A/L214Q/E308Q |
| 1088 | + | + | + | F18H/L214Q/T460G |
| 1089 | + | + | + | F18H/L47A/F450Y |
| 1090 | + | + | + | F18H/L214Q/E540D |

1. Relative activity was calculated as activity of variant/activity of Variant No. 42
2. − = < 0.5 relative activity over Variant 42; + = > 0.5 to 1.5 relative activity over Variant No. 42; and ++ = > 1.5 to 3 relative activity over Variant No.42.

Example 3

Assays to Determine Protein Aggregation of PAL Variants

The propensity of the PAL variants to aggregate is determined using the ProteoStat® Protein Aggregation Assay kit (Enzo), according to the manufacturer's instructions. Briefly, purified PAL at 0-100 µM is mixed with ProteoStat® detection reagent (1:2000) and analyzed via flow cytometry. Samples are assessed for fluorescence, consistent with the ProteoStat® Aggregation Standards, as known in the art (See e.g., Bershtein et al., Mol. Cell, 133-144 [2013]).

Example 4

Lyophilized Lysates from Shake Flask (SF) Cultures

Selected HTP cultures grown as described above were plated onto LB-agar plates with 1% glucose and 30 µg/ml chloramphenicol and grown overnight at 37° C. A single colony from each culture was transferred to 50 ml of LB with 1% glucose and 30 µg/ml chloramphenicol. The cultures were grown for 18 h at 30° C., 250 rpm, and subcultured at a dilution of approximately 1:10 into 250 ml of Terrific Broth with 30 µg/ml of chloramphenicol, to a final OD600 of 0.2. The cultures were incubated for 135 minutes at 30° C., 250 rpm, to an OD600 of 0.6 and induced with 1 mM of IPTG. The induced cultures were incubated for 20 h at 30° C., 250 rpm. Following this incubation period, the cultures were centrifuged 4000 rpm×10 min. The supernatant was discarded, and the pellets were resuspended in 30 ml of 50 mM sodium phosphate pH 7.5. The cells were pelleted (4000 rpm×10 min), resuspended in 12 ml of 50 mM sodium phosphate pH 7.5, and lysed using a One Shot Cell Disruption system (Constant Systems) at 17,000 psi. Lysate was pelleted (10,000 rpm×30 min) and the supernatant was frozen and lyophilized to generate an enzyme-containing powder.

Purification of PAL From Shake Flask Cultures

PAL Variant No. 42 was grown in shake flask cultures to saturation, as described above. Saturated cultures were pelleted by centrifugation (4000 rpm×20 min) and the cell pellets were stored at −80° C. prior to purification. The cell pellets were thawed at room temperature and resuspended in 25 mM Tris, pH 8 with 130 mM NaCl at 5 mL of buffer/g of cells. The sample slurry was lysed using a microfluidizer with a pressure setting of 110 psi. The resulting lysate was clarified by centrifugation at 10,000 rpm for 1 hour, followed by filtration through a 0.2 µm PES filter (Millipore).

After filtration, the resulting lysate was heated at 70-85° C. for 1.5-2 hours in the presence or absence of 10 mM Phe. The lysate was removed from the heat and clarified by centrifugation at 10,000 rpm at 4° C. for 1 hour. The supernatant containing soluble PAL was then filtered through a 0.2 µm PES filter prior to loading onto a chromatography column.

The heat-treated, filtered lysate, containing 80-100 mg of total protein, was diluted two-fold using 25 mM Tris, pH 8 with 1.2 M ammonium sulfate. The sample was loaded on to a HiPrep 16/10 Phenyl FF (hi sub) column (GE Healthcare) pre-equilibrated with the 25 mM Tris, pH 8 with 0.6M ammonium sulfate. Following sample loading, the column was washed with three column volumes of the same buffer, followed by a linear gradient of 0.6 M-0 M ammonium sulfate in 25 mM Tris, pH 8 for one column volume. Tightly-bound PAL was eluted off the column using an isocratic elution with 25 mM Tris, pH 8 for three column volumes. Fractions containing active and pure PAL were pooled.

The purified PAL from the phenyl column was buffer-exchanged into 0.5 M Tris, pH 8.5 and concentrated. The concentrated PAL was analyzed by SDS-PAGE and found to be present in a band at ~60 kDa. The purified PAL samples were filtered using a 0.45 µm PES filter and were stored at −80° C. until ready for use.

Example 5

Characterization of Purified PAL and PAL Variants

Figure 2A:
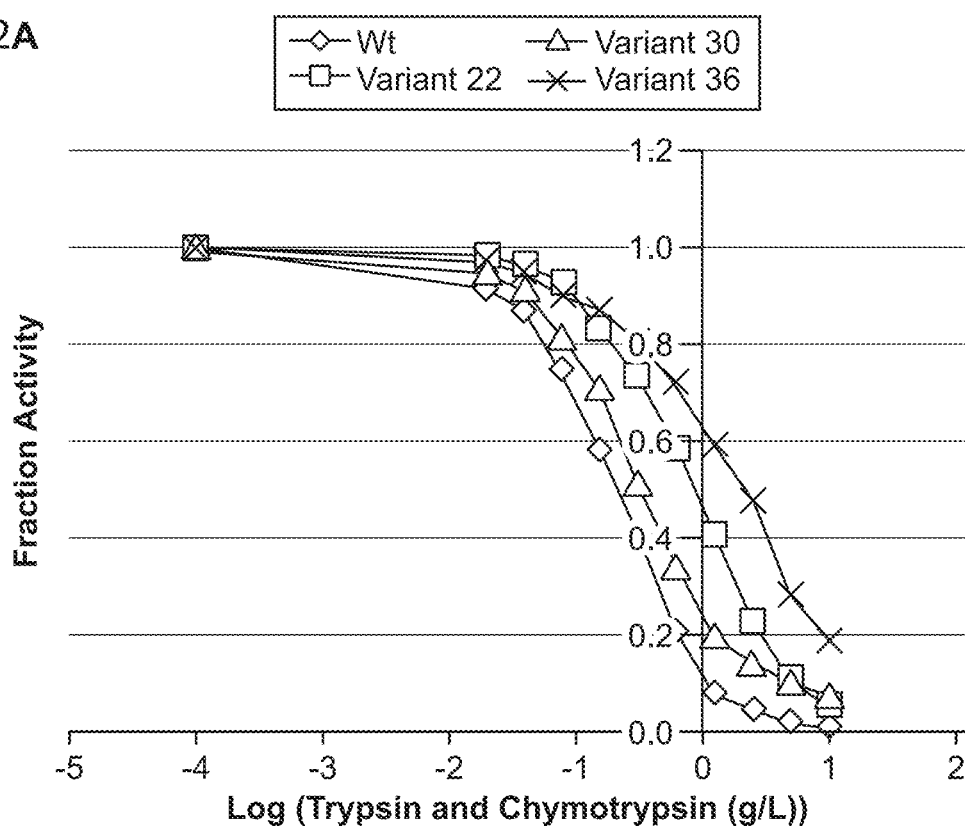
FIG. 2A shows the reduced sensitivity to proteolysis (expressed as chymotrypsin and trypsin tolerance) as compared to wild-type AvPAL tested at pH 7.0 for Variant No. 22 (SEQ ID NO:8), Variant No. 30 (SEQ ID NO:6) and Variant No. 36 (SEQ ID NO:10) as further described in Example 4.
Figure 2B:
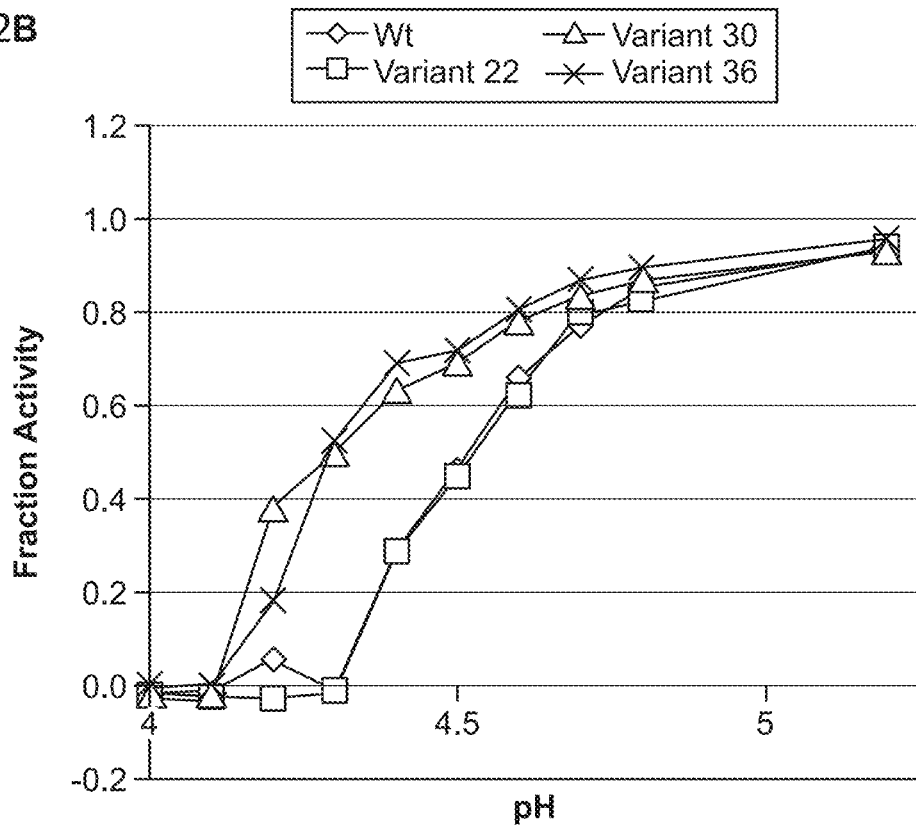
FIG. 2B provides a graph showing an increased tolerance to acidic pH as compared to wild-type AvPAL tested at pH 4.0 to 5.2, for Variant Nos. 22, 30 and 36 as further described in Example 4.

In this Example, assays conducted to characterize wild-type and variant PALs are described.
Tolerance to Acidic pH:

Lyophilized powders containing PAL variants were dissolved at 2 g/L in 20 mM sodium phosphate pH 7.0. Then, 50 µL of the enzyme solutions were mixed with 50 µL of 400 mM citric acid (pH 4.0-5.2) or 100 mM sodium phosphate and reactions were incubated at 37° C. for 1 h at 400 rpm (1" throw). Then, 20 µL of the solution were briefly mixed with 80 µL of 1M sodium phosphate pH 7.0 and 100 µL of 200 mM Tris/50 mM phenylalanine pH 7.5. The enzymatic activity under acidic conditions was determined by tracking the absorbance at 290 nm over time (every 12-20 s over 5-20 min) using a SpectraMax® Plus$^{384}$ or a SpectraMax® 190 (Molecular Devices) absorbance microplate reader. The results are shown FIG. 2. As indicated in FIG. 2, Variant Nos. 30 and 36 maintained more activity after being incubated at pHs approximately 4 to 4.8, compared to the wild-type PAL.

Figure 3:
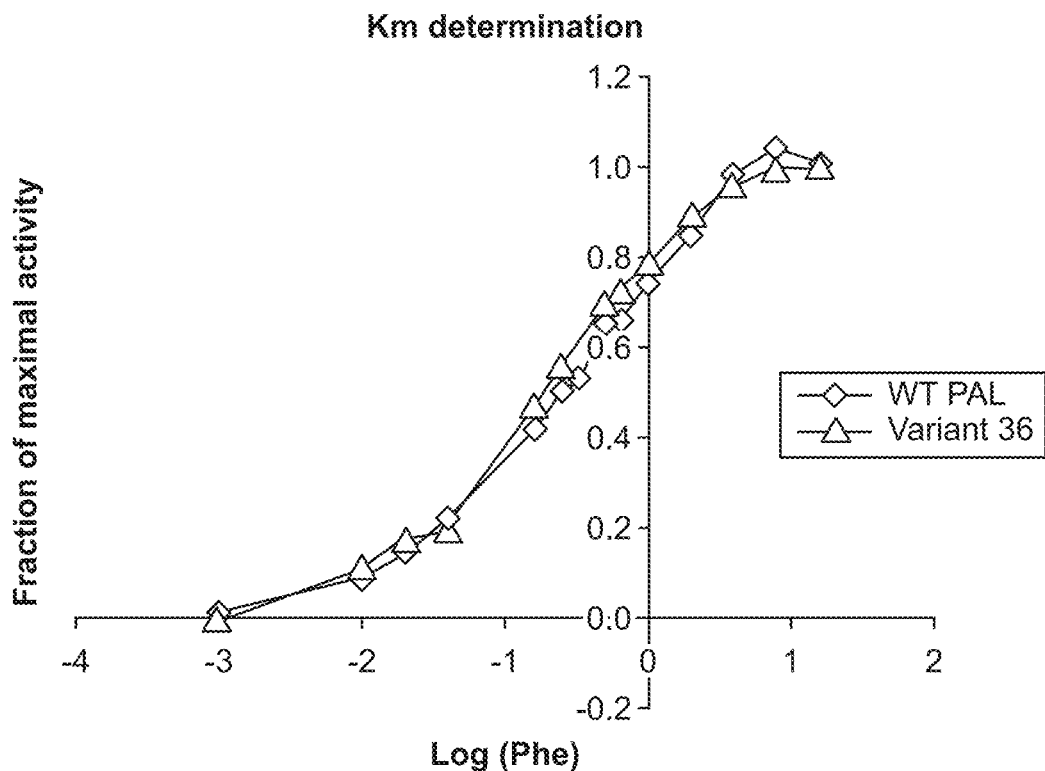
FIG. 3 provides $K_M$ results for wild-type PAL and Variant No. 36.

Determination of $K_M$:

To evaluate whether the mutations in the variant PALs had altered the affinity of the PAL variants for phenylalanine, the Michaelis constant for the wild-type enzyme and Variant 36 were determined. First, 100 μL of 15 μg/ml PAL in 100 mM Tris pH 8.0, and 100 μL of 0-32 mM phenylalanine in 100 mM Tris, pH 8.0, were added to the wells of a poly-acrylate 96-well plate (Costar #3625, Corning). The reaction was mixed briefly and initial rates were determined by tracking the absorbance at 290 nm over time (every 12-20 s over 5-20 min) using a SpectraMax® Plus[384] or a SpectraMax® 190 (Molecular Devices) absorbance microplate reader. The $K_M$ for each tested PAL variant was determined by fitting the data to a Lineweaver-Burke plot, as known in the art. The results are shown in FIG. 3. As shown, the $K_M$ was 74 μM for the wild-type enzyme and 60 μM for Variant 36.

Figure 4:
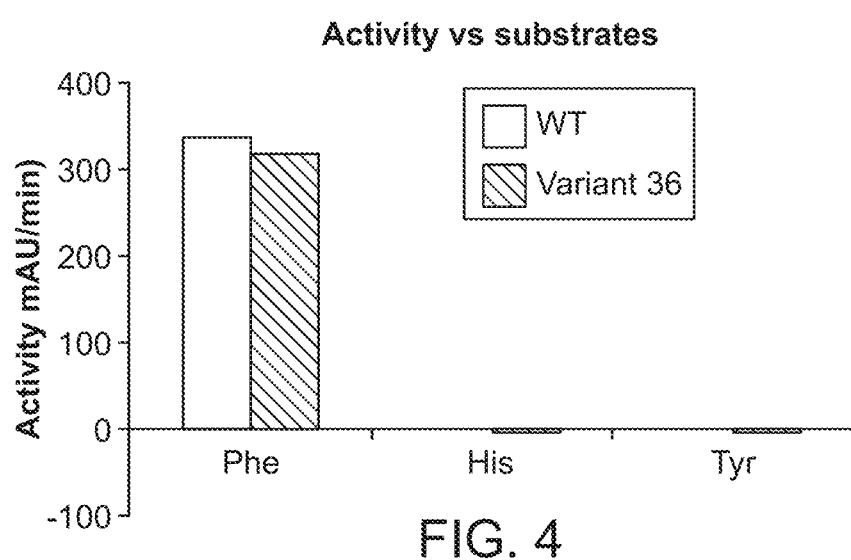
FIG. 4 provides data showing the amino acid specificity of wild-type PAL and Variant No. 36.

Amino Acid Specificity:

Some phenylalanine ammonia lyases demonstrate activity against tyrosine and/or histidine in addition to phenylalanine. To evaluate if the mutations present in the PAL variants had altered the specificity of the PAL variants for phenylalanine, the activities of wild-type enzyme and Variant 36 on these three amino acids were assessed. First, 100 μL of 5 g/L of PAL-containing lyophilized powder in 10 mM sodium phosphate pH 7.0, and 100 μL of 50 mM phenylalanine or histidine or 2.5 mM tyrosine in 200 mM sodium phosphate pH 7.5 were added to the wells of a poly-acrylate 96-well plate (Costar #3635, Corning). The solutions were mixed briefly and initial rates were determined by tracking the absorbance at 290 nm over time (every 12-20 s over 5-20 min) using a SpectraMax® Plus[384] or a SpectraMax® 190 (Molecular Devices) absorbance microplate reader. The results are shown in FIG. 4. As indicated, no detectable activity was observed for either the WT enzyme or Variant No. 36 with either histidine or tyrosine, indicating that these enzymes are specific for phenylalanine.

Resistance to Porcine and Bovine Proteases:

PAL variant samples prepared as described in Example 4, were dissolved at 2 g/L in 100 mM sodium phosphate pH 7.0. Porcine trypsin and bovine chymotrypsin (100 mg each) were dissolved in 2 ml of 100 mM sodium phosphate pH 7.0, and serially diluted 2-fold eleven times in 100 mM sodium phosphate. Then, 80 μL of the PAL variant enzyme solutions were mixed with 20 μL of the trypsin and chymotrypsin solution. The reaction mixtures were incubated at 37° C. for 1 h at 400 rpm (1" throw). Then, 20 μL of the reaction was mixed with 80 μL of water and 100 μL of 100 mM sodium phosphate, 50 mM phenylalanine pH 7.0. Each solution was mixed briefly, and the activity was determined by tracking the absorbance at 290 nm over time (every 12-20 s over 5-20 min) using a SpectraMax® Plus[384] or a SpectraMax® 190 (Molecular Devices) absorbance microplate reader. The results are shown in FIG. 2. As indicated in this Figure, all of the tested variants showed improved protease resistance, as compared to the wild-type PAL, with Variant No. 36 being the most stable towards proteolysis.

Figure 5:
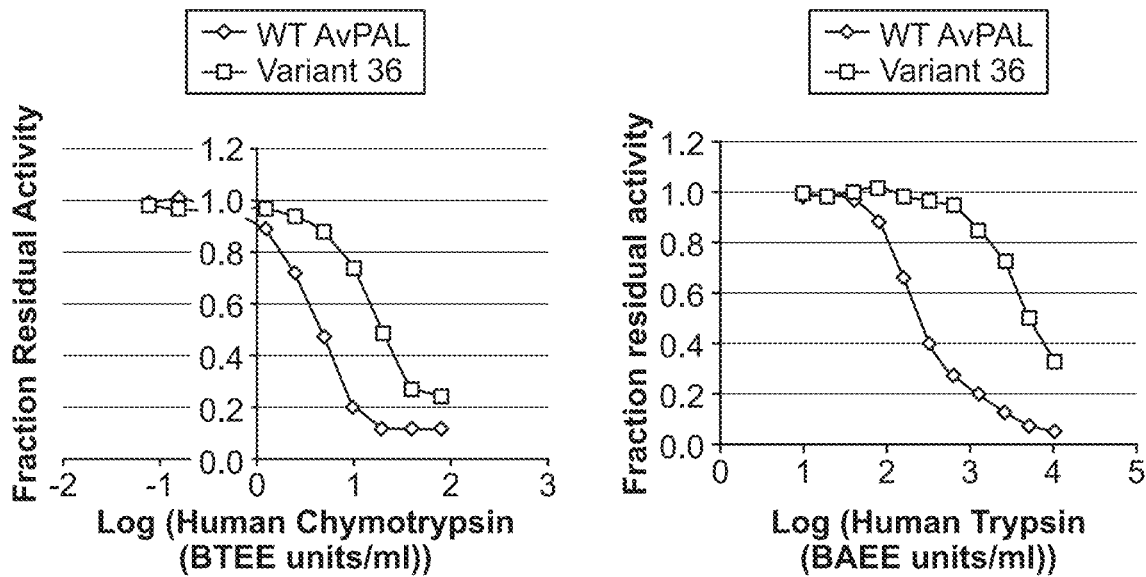
FIG. 5 provides results showing the relative stability of wild-type PAL and Variant No. 36 exposed to human chymotrypsin and trypsin.

Resistance to Human Proteases:

As described above, some evolved PAL variants were screened against porcine trypsin and bovine chymotrypsin to assess their resistance to proteolysis by enzymes present in the gastrointestinal tract. Some of the evolved PAL variants were also tested using human enzymes, to confirm that they are resistant to the human homologues of the porcine or bovine enzymes. In these assays, lyophilized powders of WT PAL and Variant No. 36 (2.4 g/L in 100 mM sodium phosphate, pH 7.0) were incubated with human chymotrypsin (Athens Research) 0-80 BTEE units/ml or human trypsin (ProSpec) (0-10,000 BAEE units/ml) at 37° C. for 2 h. Then, 100 μL of the mixtures were added to the wells of a poly-acrylate 96-well plate (Costar #3635, Corning), followed by the addition of 100 μL of 50 mM phenylalanine, 200 mM sodium phosphate pH 7.0. The solution was mixed briefly and initial rates were determined by tracking the absorbance at 290 nm over time (every 12-20 s over 5-20 min) using a SpectraMax® Plus[384] or a SpectraMax® 190 (Molecular Devices) absorbance microplate reader. The results are shown in FIG. 5. As shown in FIG. 5, Variant No. 36 was more stable than the wild type PAL enzyme.

Figure 6:
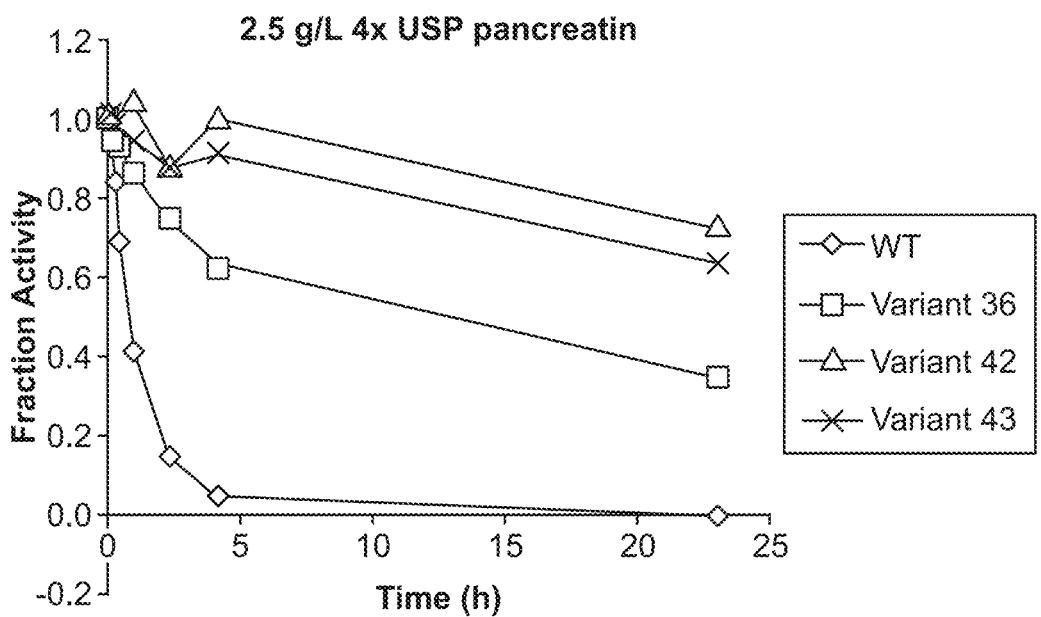
FIG. 6 provides results showing the relative stability of wild-type PAL, and Variant Nos. 36, 42, and 43 exposed to porcine pancreatic extract.

Resistance to Crude Pancreatic Extract:

The evolved PAL variants were also tested to determine their resistance to pancreatic enzymes. Lyophilized powders of WT PAL, Variant No. 36, Variant No. 42, and Variant No. 43 lyophilized powders (prepared as described in Example 4; 12 g/L in 50 mM potassium phosphate pH 6.8) were mixed 1:1 with porcine pancreatin (4× Sigma-Aldrich, St. Louis, Mo.), and incubated at 37° C. with shaking (400 rpm, 1" throw) for up to 23 h. At the indicated time points, a 10 μL aliquot of the reactions was added to 190 μL of 50 mM phenylalanine, 190 mM sodium phosphate pH 7.0, in the wells of a poly-acrylate 96-well plate (Costar #3635, Corning). The reaction was mixed briefly and initial rates were determined by tracking the absorbance at 290 nm over time (every 12-20 s over 5-20 min) using a SpectraMax® Plus[384] or a SpectraMax® 190 (Molecular Devices) absorbance microplate reader. The results are shown in FIG. 6. As shown in FIG. 6, Variant No. 36, Variant No. 42, and Variant No. 43 all showed significant stability under these assay conditions, as compared to the wild-type PAL enzyme.

Figures 7, 8:
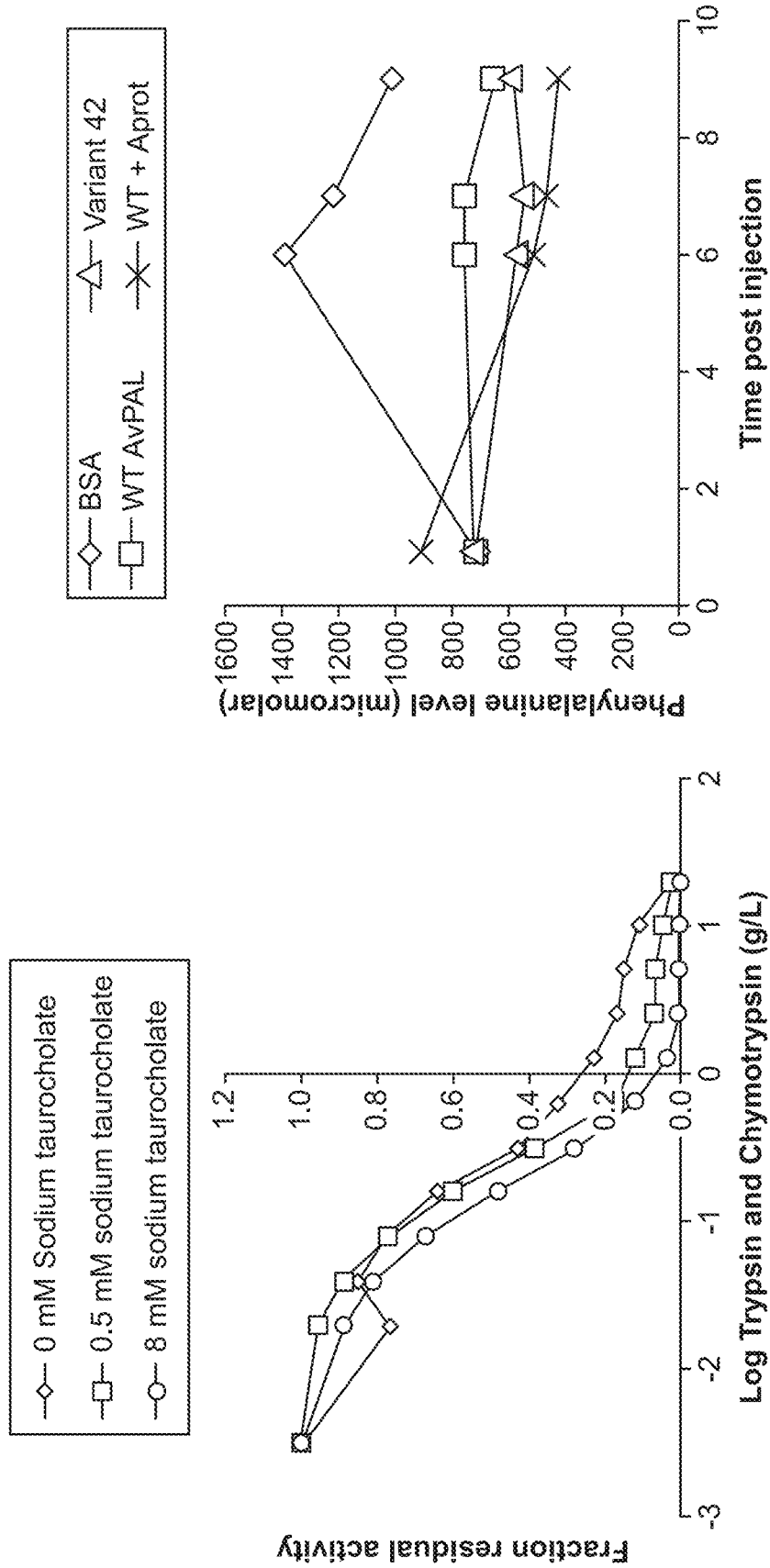
FIG. 7 provides results showing the effect of varying concentrations of sodium taurocholate on the susceptibility of Variant 36 to proteolysis.
FIG. 8 provides results showing serum phenylalanine levels in mice treated with inactive protein (BSA), wild-type PAL, wild-type PAL in combination with aprotinin, or Variant 42.

Impact of Intestinal Detergents:

The evolved PAL variants were also tested for their susceptibility to proteolysis in the presence or absence of intestinal bile acids and fatty acids, to assess whether these acids impact their stability. Lyophilized powders containing Variant No. 36 (prepared as described in Example 4) were dissolved at 50 μg/ml in 0-16 mM sodium taurocholate, 100 mM sodium phosphate, pH 7.0. Porcine trypsin and bovine chymotrypsin (80 mg each) were dissolved in 2 ml of 100 mM sodium phosphate pH 7.0, and serially diluted 2-fold eleven times in 100 mM sodium phosphate. For the assay, 50 μL of the PAL solutions were mixed with 50 μL of the protease solution. The mixtures were incubated at 37° C. for 1 h at 400 rpm (1" throw). Then, 50 μL of the mixtures were mixed with 150 μL of 200 mM sodium phosphate, 50 mM phenylalanine pH 7.0. Each reaction was mixed briefly, and the activity was determined by tracking the absorbance at 290 nm over time (every 12-20 s over 5-20 min) using a SpectraMax® Plus[384] or a SpectraMax® 190 (Molecular Devices) absorbance microplate reader. The results are shown in FIG. 7. As shown in this Figure, additional sodium taurocholate increases the susceptibility of Variant No. 36 to proteolysis.

Example 6

Intestinal Stability of Variant PAL

To assess the stability and activity of PAL variants as they transit through an animal gut, mice were gavaged with purified enzyme variants. Healthy C57Bl/6 mice, 10-12 weeks old and weighing 20-26 g, were maintained in a metabolic cage and fasted for 15 h. Water was provided ad libitum. Following the overnight fast, animals were gavaged using a 21-gauge gavage needle with a mixture of 0.3 ml of 0.5 M Tris-HCl pH 8.5, and 8 mg/ml in 0.5 M Tris-HCl pH 8.5, WT PAL (prepared as described in Example 4) or 8 mg/ml in 0.5 M Tris-HCl pH 8.5 Variant No. 42 (prepared as described in Example 4). At 0.5, 2, or 6 h post-gavage, the animals were decapitated, plasma was collected using green-top capillary blood collection tubes (Ram Scientific), and the contents of the stomach, duodenum (~1-8 cm from the stomach), jejunum (~10-18 cm from the stomach), ileum (~8 cm above the cecum), and colon (~5 cm below the cecum) were collected. The weight of these contents was recorded and the contents were stored at −80° C. prior to analysis.

Stomach or intestinal contents were diluted 4× with 100 mM sodium phosphate pH 7.0, mixed briefly, and centrifuged at 14,000 rpm×2 min. The supernatants were transferred to a 350 µL, 0.45 µM, AcroPrep™ Advanced 96-well filter plate (Pall Corp), and particulates were removed via vacuum filtration. The clarified filtrate was assessed for enzymatic activity as described in the previous Examples and for the presence of intact PAL protein by SDS-PAGE. The results indicated that enzymatic activity in the duodenum and jejunum appeared to be higher for the evolved PAL variants, as compared to the wild-type PAL enzyme and negative control.

Example 7

Plasma Phenylalanine Levels

Plasma samples collected from the mice described in Example 6 were evaluated to determine the quantity of phenylalanine present in the bloodstreams of the tested mice. Mouse plasma (50 µL) was combined with 250 µL of acetontrile containing 0.6 mM of dl-phenylalanine (Ring $D_5$) (i.e., an isotopically labeled version of phenylalanine comprising deuterium rather than hydrogen bonded with the aromatic ring carbons; Cambridge Isotope Laboratories). The samples were mixed at RT for 5 min, centrifuged at 3200×g for 10 min at 4° C. and the supernatants were transferred to a plate for sample analysis. For the analysis, 10 µL of each sample was injected into a3200 QTRAP® LC/MS/MS system (AB Sciex) across a DISCOVERY® $C_{18}$ column (150×2.1 mM, 5 µm beads) (Supelco, now Sigma-Aldrich), eluting with 0.1% formic acid in water (A) and acetonitrile (B). Samples were eluted across a 5 min gradient (t=0, 97% A; 3 min, 50% A; 3.5 min, 5% A; 4 min, 97% A; 5 min, 95% A) looking for a transition of 166 to120 for endogenous phenylalanine and 171 to 125 for the isotopically labeled standard. The results indicated that the plasma phenylalanine levels were lower at the 30 minute time-point in samples from mice that were given the evolved PAL variant (i.e., Variant No. 42), as compared to the wild-type PAL enzyme and negative control.

Example 8

Therapeutic Function of Variant PAL

To assess whether PAL variants reduce serum Phe levels in vivo, a mouse model of PKU was used. In these experiments, the PAL proteins were gavaged into affected animals. First, a consistent baseline Phe level was established in the mice by removing Phe from their diets for three days followed by injection of known quantity of Phe-containing solution. Three- to six-month old homozygous PAH enu-2 mice with a C57Bl/6 background (See, McDonald et al., Proc. Natl. Acad. Sci. USA 87:1965-1967 [1990]) were transferred to a phenylalanine-free diet (TD.97152, Harlan) with 0.03 g/L of Phe provided in their drinking water for 72 h. Prior to initiating treatment at time=0 h, mice were injected with 0.15 mg/g of body weight Phe (from a 10 g/L solution of Phe in water). Fifty-five minutes post-injection, approximately 20 µL of blood was collected by tail-vein puncture and spotted onto filter paper. Subsequently, at times 1 h-, 3 h-, and 5 h-post injection the mice were gavaged with 0.3 ml of 50-100 g/L of WT AvPAL, WT AvPAL plus aprotinin, BSA, or Variant No. 42. At 6 h-, 7 h-, and 9 h-post injection, additional blood spots were collected on filter paper. The blood spots were dried and stored at −20° C. prior to LC-MS/MS analysis for Phe and Tyr levels using methods known in the art (See, Chase et al., Clin. Chem., 39:66-71 [1993]).

The results are shown in FIG. 8. As indicated in this Figure, gavage with inactive protein (BSA), led to increased serum Phe levels. In contrast, treatment with proteolytically susceptible WT AvPAL resulted in constant Phe-levels, while the same protein, combined with the protease inhibitor aprotinin resulted in a significant drop in Phe-levels. The results also show that administering the engineered-PAL Variant No. 42 resulted in decreased serum Phe levels in the absence of protease inhibitors.

Example 9

Deimmunization of PAL

In this Example, experiments conducted to identify diversity that would remove T-cell epitopes from PAL are described.
Identification of Deimmunizing Diversity:
To identify amino acids that, when mutated, could remove T-cell epitopes, computational methods were used to identify PAL sequences predicted to elicit a T-cell response. In parallel, experimental searches for allowable, non-deleterious mutations were also conducted, particularly for amino acids that maintain protein activity in an unchallenged assay (e.g., in the assays described in Example 2). Active variants were then analyzed for the effect of the mutations on the predicted immunogenicity.
Computational Identification of Putative T-Cell Epitopes in a Variant AvPAL:
Putative T-cell epitopes in a AvPAL Variant No. 36 were identified using the Immune Epitope Database (IEDB; Immune Epitope Database and Analysis Resource website) tools, as known in the art and proprietary statistical analysis tools (See e.g., iedb.org and Vita et al., Nucl. Acids Res., 38(Database issue):D854-62 [2010]. Epub 2009 Nov. 11]). The AvPAL variant was parsed into all possible 15-mer analysis frames, with each frame overlapping the last by 14 amino acids. The 15-mer analysis frames were evaluated for immunogenic potential by scoring their 9-mer core regions for predicted binding to eight common Class II HLA-DR alleles (DRB1*0101, DRB1*0301, DRB1*0401, DRB1*0701, DRB1*0801, DRB1*1101, DRB1*1301, and DRB1*1501) that collectively cover nearly 95% of the human population (See e.g., Southwood et al., J. Immunol., 160:3363-3373 [1998]), using methods recommended on the IEDB website. Potential T-cell epitope clusters contained within the variant AvPAL (i.e., sub-regions contained within the variant AvPAL which have an unusually high potential for immunogenicity) were identified using statistical analysis tools, as known in the art. The identified T-cell epitope clusters were screened against the IEDB database of known epitopes and the GenBank protein database. These screens identified 10 (ten) putative T-cell epitopes in the variant AvPAL Variant No. 36. These epitopes are referred to as TCE-I, II, III, IV, V, VI, VII, VIII, IX, and X, below.

Design of Deimmunizing Libraries:

First, a combinatorial library containing all neutral, and beneficial mutations identified from the rounds of directed evolution used to create variant AvPALs, at the 10 putative T-cell epitope regions identified as described above was developed. The effects of these mutations on the predicted binding to the eight common Class II HLA-DR alleles were analyzed. Multiple mutations were predicted to remove or reduce TCE-I, II, VI, VII. These mutations were combined into a combinatorial library. Libraries were then designed using saturation mutagenesis to mutagenize every single amino acid within the remaining six T-cell epitopes (i.e., TCE-III, IV, V, VIII, IX, and X). Finally a combinatorial library was created containing beneficial diversity identified from multiple rounds of evolution that targeted TCE-I, III, IV, VIII, and X, along with C503 and C565, two amino acids reported to impact the aggregation state of PAL variants. The best hits from this library were subjected to further saturation mutagenesis targeting TCE-III and VIII and additional targeted mutagenesis at a few positions.

Construction and Screening of Deimmunizing Libraries:

Combinatorial and saturation mutagenesis libraries designed as described above were constructed by methods known in the art, and tested for activity in an unchallenged assay as described in Example 2. Active variants were identified and sequenced. Their activities and mutations with respect to AvPAL Variant No. 36 and numerous AvPAL Variants are provided in Tables 9-1 through 9-7, below.

Identification of Deimmunizing Diversity:

Active variants were analyzed for their levels of immunogenicity by evaluating their binding to the eight common Class II HLA-DR alleles described above. The total immunogenicity score and immunogenic hit count are shown in Tables 9-1 to 9-7. The total immunogenicity score reflects the overall predicted immunogenicity of the variant (i.e., a higher score indicates a higher level of predicted immunogenicity). The immunogenic "hit count" indicates the number of 15-mer analysis frames with an unusually high potential for immunogenicity (i.e., a higher hit count indicates a higher potential for immunogenicity). Mutations with a lower total predicted immunogenicity score and/or an immunogenic hit count less than that of the reference variant were considered to be "deimmunizing mutations." The deimmunizing mutations that were identified as being the best were recombined to generate a number of variants that are active and predicted to be significantly less immunogenic than the starting reference variant AvPAL. In the following Tables, the FIOP results are from the unchallenged assay; for the total immunogenicity score (TIS) and immunogenic hit count (IHC), the results are indicated for the whole PAL protein (Tables 9-1, 9-8, and 9-9) or for the indicated epitope (Tables 9-2 to 9-7).

TABLE 9-1

FIOP, Total Immunogenicity (TIS), and Immunogenic Hit Count (IHC) for Variants Targeting TCE-I, II, VI, and VII
("−" = FIOP < 0.7; "+" = FIOP 0.7 < FIOP < 1.4; "++" = FIOP > 1.4)

| Variant # | Active Mutations (as Compared to Variant No. 36) | FIOP | TIS | IHC |
|---|---|---|---|---|
| Variant 36 | | + | 680 | 52 |
| 100 | I27E/L214E | + | 634 | 51 |
| 101 | V105C/R134Q/Q205T/P266H/L278D | + | 645 | 48 |
| 102 | I27E/L214E/C503Q/A547D | + | 629 | 51 |
| 103 | V105C/Q205T/P210C/L214E/C503Q/A547D | + | 619 | 49 |
| 104 | I27E/A112C/R134Q/Q205T/I285E/C503Q | + | 622 | 45 |
| 105 | V39A/P266H | + | 665 | 45 |
| 106 | I27E/V39A/V105C/R134Q/P210C | + | 607 | 41 |
| 107 | I27E/V39A/V105C/P210C/L214E/P266H/L278D | + | 590 | 42 |
| 108 | V39A/V105C/L214E/P266H/A547D/C565N | + | 613 | 42 |
| 109 | I27E/V39A/A112C/L214E | + | 616 | 42 |
| 110 | I27E/V39A/R134Q/A153G/L214E/P266H/I285E/C503Q/A551D/C565N | + | 572 | 37 |
| 111 | I27E/R134Q/L278D/I285E/A551D/C565N | + | 626 | 48 |
| 112 | I27E/V39A/V105C/A112C/Q205T/P266H/I285E/C503Q/A551D | + | 594 | 39 |
| 113 | I27E/V105C/L214E/P266H/C503Q | + | 614 | 49 |
| 114 | I27E/V39A/R134Q | + | 637 | 44 |
| 115 | C503Q/A547D | + | 675 | 52 |
| 116 | V105C/C503Q | + | 660 | 50 |
| 117 | I27E/R134Q/Q205T/P266H/L278D/A547D | + | 641 | 50 |
| 118 | I27E/V105C/R134Q/P210C/P266H/L278D/I285E/C503Q/A551D/C565N | + | 596 | 45 |
| 119 | I27E/V39A/V105C/R134Q/Q205T/L278D/I285E/C503Q/A547D/A551D/C565N | + | 585 | 38 |
| 120 | V105C/R134Q/L214E/C503Q/A547D/A551D | + | 619 | 48 |
| 121 | I27E/V39A/V105C/L214E/L278D/L309P/C503Q/A547D/A551D | + | 587 | 42 |
| 122 | V105C/L278D/C503Q/A551D | + | 655 | 50 |
| 123 | I27E/V105C/R134Q/P210C/L214E/P266H/L278D/A551D/C565N | ++ | 591 | 48 |
| 124 | I27E/R134Q/L214E/C503Q/A547D | ++ | 620 | 50 |
| 125 | R134Q/P210C/L214E/L278D/C503Q/A547D/C565N | + | 630 | 50 |
| 126 | I27E/V39A/V105C/Q205T/P210C/L214E/L278D/A547D | + | 585 | 42 |
| 127 | V39A/Q205T/L278D/A547D/A551D | + | 654 | 44 |
| 128 | V105C/R134Q/L214E/P266H/I285E/C503Q/A551D/C565N | + | 598 | 45 |
| 129 | I27E/V105C/L214E/A547D/A551D/C565N | + | 609 | 49 |
| 130 | I27E/V39A/V105C/Q205T/L278D/C503Q/A547D | + | 615 | 42 |
| 131 | I27E/V39A/V105C/R134Q/L214E/I285E/C503Q/A547D/A551D | + | 564 | 38 |
| 132 | C503Q/A547D/A551D/C565N | + | 675 | 52 |
| 133 | V105C/R134Q/L214E/C503Q/A547D | + | 619 | 48 |
| 134 | I27E/V105C/Q205T/C503Q/A547D/A551D/C565N | + | 630 | 49 |
| 135 | I27E/V39A | + | 646 | 45 |
| 136 | I27E/V39A/V105C/L214E/P266H/C503Q/A547D/C565N | + | 594 | 42 |

TABLE 9-1-continued

FIOP, Total Immunogenicity (TIS), and Immunogenic Hit Count (IHC) for Variants Targeting TCE-I, II, VI, and VII
("–" = FIOP < 0.7; "+" = FIOP 0.7 < FIOP < 1.4; "++" = FIOP > 1.4)

| Variant # | Active Mutations (as Compared to Variant No. 36) | FIOP | TIS | IHC |
|---|---|---|---|---|
| 137 | A112C/R134Q/L214E/C503Q/A547D/A551D/C565N | + | 636 | 48 |
| 138 | I27E/A112C/R134Q/A153R/L214E/P266H/C503Q | + | 619 | 47 |
| 139 | C503Q/A551D | + | 675 | 52 |
| 140 | I27E/V39A/V105C/R134Q/L278D/C503Q/C565N | + | 617 | 42 |
| 141 | R134Q/Q205T/L214E/I285E/C503Q/A551D/C565N | + | 613 | 47 |
| 142 | V105C/L214E/I285E/A547D/C565N | + | 607 | 46 |
| 143 | I27E/V39A/R43L/L214E/A547D | + | 625 | 45 |
| 144 | I27E/V39A/P210C/L214E/I285E/C503Q/A551D | + | 584 | 41 |
| 145 | I27E/R134Q/L214E/C503Q/A547D/A551D | + | 620 | 50 |
| 146 | V39A/V105C/A153R/P266H/A547D/A551D | + | 637 | 42 |
| 147 | V39A/C503Q | + | 665 | 45 |
| 148 | I27E/V39A/V105C/P210C/I285E/C503Q/A547D/A551D/C565N | + | 590 | 39 |
| 149 | R134Q/L214E/L278D/C503Q/A551D | + | 639 | 50 |
| 150 | I27E/V39A/R134Q/C503Q/A547D | + | 632 | 44 |
| 151 | A153R | + | 677 | 51 |
| 152 | I27E/V39A/V105C/A112C/R134Q/L214E/L278D/C503Q/A547D/C565N | + | 585 | 41 |
| 153 | C503Q/A547D/C565N | + | 675 | 52 |
| 154 | I27E/V39A/L214E/P266H/L278D/C503Q/A547D/A551D/C565N | + | 614 | 44 |
| 155 | L278D/A547D | + | 675 | 52 |
| 156 | V39A/G45S/L278D/C503Q/A551D | + | 667 | 45 |
| 157 | V39A/A153R/C503Q/A547D | + | 657 | 44 |
| 158 | R134Q/P210C/L214E/C503Q/A547D/A551D | + | 630 | 50 |
| 159 | I27E/A547D/C565N | + | 656 | 52 |
| 160 | V39A/R134Q/P210C/L214E/A547D/C565N | + | 615 | 43 |
| 161 | I27E/V39A/P210C/P266H/I285E/C503Q/A547D | + | 610 | 41 |
| 162 | I27E/V39A/R134Q/L278D/C503Q/A547D | + | 632 | 44 |
| 163 | I27E/V105C/R134Q/Q205T/P210C/C503Q | + | 622 | 48 |
| 164 | I27E/V105C/R134Q/L214E/L278D/C503Q/A547D | + | 600 | 48 |
| 165 | I27E/V105C/C503Q/A547D/C565N | + | 636 | 50 |
| 166 | I27E/L214E/C503Q | + | 634 | 51 |
| 167 | V105C/L214E/L278D/C503Q/A547D/A551D | + | 628 | 49 |
| 168 | I27E/V105C/Q205T/L214E/P266H | + | 609 | 49 |
| 169 | V39A/A112C/R134Q/L214E/C503Q/A547D/A551D | + | 621 | 41 |
| 170 | I27E/R134Q/L214E/C503Q/C565N | + | 625 | 50 |
| 171 | I27E/V39A/R134Q/A153R/Q205T/L214E/P266H/C503Q | + | 602 | 42 |
| 172 | I27E/V39A/L214E/C503Q/A551D | + | 614 | 44 |
| 173 | V39A/V105C/Q205T/A551D | + | 634 | 42 |
| 174 | I27E/V39A/Q205T/C503Q/A547D/C565N | + | 635 | 44 |
| 176 | I27E/V39A/V105C/R134Q/P210C/L214E/C503Q/A551D/C565N | + | 576 | 41 |
| 177 | V39A/P275R/L278D/C503Q/A551D | + | 667 | 45 |
| 178 | I27E/V39A/V105C/Q205T/P210C/L278D/A547D | + | 611 | 42 |
| 179 | V105C/A153R/Q205T/L214E/P266H/C503Q/A547D | + | 620 | 48 |
| 180 | V105C/A112C/R134Q/Q205T/L214E/Y492H/C503Q/A547D | + | 614 | 48 |
| 181 | I27E/P210C/L278D/C503Q | + | 651 | 51 |
| 182 | I27E/P210C/C503Q | + | 651 | 51 |
| 183 | I27E/V39A/R134Q/A153R/L214E/C503Q/A547D | + | 602 | 42 |
| 184 | I27E/P266H/A547D/A551D | + | 656 | 52 |
| 185 | V105C/L214E/I285E/C503Q/A547D/A551D/C565N | + | 607 | 46 |
| 186 | I27E/V105C/P266H/I285E/C503Q/A547D/C565N | + | 615 | 47 |
| 187 | Q205T/L278D/I285E/A547D/A551D | + | 648 | 48 |
| 188 | V39A/V105C/Q205T/C503Q | + | 639 | 42 |
| 189 | I27E/V39A/Q205T/P266H/I285E/A547D/A551D/C565N | + | 614 | 41 |
| 190 | V105C/L214E/I285E | + | 612 | 46 |
| 191 | V105C/R134Q/C503Q/A547D/C565N | + | 646 | 49 |
| 192 | I27E/V39A/V105C/R134Q/C503Q/A551D | + | 612 | 42 |
| 193 | I27E/R134Q/Q205T/I285E/C503Q/A551D | + | 620 | 47 |
| 194 | I27E/V39A/A112C/Q205T/L278D/I285E | + | 616 | 39 |
| 195 | I27E/V39A/A112C/Q205T/L214E/P266H/C503Q/A551D/C565N | + | 606 | 42 |
| 196 | I27E/V39A/L278D/A547D | + | 641 | 45 |
| 197 | I27E/V39A/V105C/R134Q/Q205T/L214E/A551D/C565N | + | 580 | 41 |
| 198 | I27E/G45D/Q205T/P266H/C565N | + | 656 | 51 |
| 199 | I27E/V39A/A112C/L214E/L278D/C503Q/A547D/A551D | + | 611 | 42 |
| 200 | I27E/Q205T | + | 655 | 51 |
| 201 | I27E/A112C/R134Q/Q205T/L278D/C503Q | + | 643 | 48 |
| 202 | C565N | + | 680 | 52 |
| 203 | I27E/V39A/V105C/R134Q/Q205T/P210C/L278D/C503Q/A547D | + | 602 | 41 |
| 204 | V105C/L214E/P266H/L278D/A547D | + | 628 | 49 |
| 205 | V105C/R134Q/A153R/Q205T/L214E/C503Q | + | 616 | 47 |
| 206 | V105C/R134Q/C503Q | + | 651 | 49 |
| 207 | I27E/V39A/Q205T/L278D/C503Q/C565N | + | 640 | 44 |
| 208 | I27E/V39A/V105C/S131N/R134Q/Q205T/L214E/C503Q/A547D/C565N | + | 579 | 41 |
| 209 | Q205T/L214E/I285E/C503Q/A551D | + | 622 | 48 |
| 210 | I27E/L214E/L278D/C503Q | + | 634 | 51 |

TABLE 9-1-continued

FIOP, Total Immunogenicity (TIS), and Immunogenic Hit
Count (IHC) for Variants Targeting TCE-I, II, VI, and VII
("−" = FIOP < 0.7; "+" = FIOP 0.7 < FIOP < 1.4; "++" = FIOP > 1.4)

| Variant # | Active Mutations (as Compared to Variant No.

TABLE 9-1-continued

FIOP, Total Immunogenicity (TIS), and Immunogenic Hit Count (IHC) for Variants Targeting TCE-I, II, VI, and VII
("–" = FIOP < 0.7; "+" = FIOP 0.7 < FIOP < 1.4; "++" = FIOP > 1.4)

| Variant # | Active Mutations (as Compared to Variant No. 36) | FIOP | TIS | IHC |
|---|---|---|---|---|
| 284 | I27E/V105C/Q205T | + | 635 | 49 |
| 285 | I27E/Q205T/P266H/L278D/I285E/A551D/C565N | + | 629 | 48 |
| 286 | I27E/R134Q/L214E/C503Q | + | 625 | 50 |
| 287 | V105C/Q205T/L214E/C503Q/A547D/A551D/C565N | + | 623 | 49 |
| 288 | V39A/V105C/L214E/I285E/C503Q/A551D/C565N | + | 592 | 39 |
| 289 | I27E/V39A/V105C/L278D/C503Q/A547D/C565N | + | 621 | 43 |
| 290 | I27E/V39A/V105C/R134Q/I285E/A547D/A551D | + | 591 | 39 |
| 291 | I27E/V39A/A112C/R134Q/L214E/P266H/A551D | + | 602 | 41 |
| 292 | I27E/L278D/C503Q/A551D | + | 656 | 52 |
| 293 | I27E/V39A/R134Q/A153R/A547D | + | 629 | 43 |
| 294 | P266H/C565N | + | 680 | 52 |
| 295 | I27E/V105C/I285E/C503Q/A547D/A551D/C565N | + | 615 | 47 |
| 296 | I27E/V39A/L278D | + | 646 | 45 |
| 297 | P210C/L214E/P266H | + | 644 | 51 |
| 298 | I27E/V39A/R134Q/P210C/L214E/C503Q | + | 601 | 43 |
| 299 | I27E/V39A/R43L/V105C/A153R/L214E/P266H/L278D/C503Q | + | 607 | 42 |
| 300 | I27E/V105C/Q205T/L214E/L278D/I285E/C503Q/A547D/A551D/C565N | + | 583 | 46 |
| 301 | I27E/V39A/V105C/C503Q/A547D/A551D/C565N | + | 621 | 43 |
| 302 | I27E/V105C/L214E/I285E/A551D/C565N | + | 588 | 46 |
| 303 | I27E/P210C/A551D | + | 646 | 51 |
| 304 | I27E/V39A/V105C/Q205T/L214E/L278D/C503Q/A547D | + | 589 | 42 |
| 305 | I27E/V105C/L278D/A547D | + | 636 | 50 |
| 306 | C503Q | + | 680 | 52 |
| 307 | I27E/V39A/V105C/R134Q/L214E/L278D/A547D/A551D | + | 585 | 41 |
| 308 | I27E/R134Q | + | 652 | 51 |
| 309 | V39A/R134Q | + | 656 | 44 |
| 310 | I27E/V39A/V105C/A112C/Q205T/P210C/P266H/C503Q/A547D | + | 611 | 42 |
| 311 | V39A/A112C/A153R/Q205T/L278D/C503Q/A547D | + | 648 | 41 |
| 312 | I27E/V105C/P266H | + | 641 | 50 |
| 313 | I27E/V39A/V105C/R134Q/P210C/L214E | + | 581 | 41 |
| 314 | I27E/V39A/V105C/R134Q/L278D/A551D | + | 612 | 42 |
| 315 | I27E/V39A/V105C/A112C/R134Q/A153R/Q205T/L214E/P266H/L278D/C503Q/A551D | + | 577 | 40 |
| 316 | I27E/V105C/R134Q/A153R/I285E/A547D | + | 603 | 45 |
| 317 | I27E/V39A/A112C/A547D | + | 638 | 43 |
| 318 | I27E/V39A/R134Q/A153R/L214E/P266H/L278D/C503Q/A547D/C565N | + | 602 | 42 |
| 319 | I27E/V105C/Q205T/P266H/C503Q | + | 635 | 49 |
| 320 | I27E/V39A/V105C/R134Q/L278D/I285E/C503Q | + | 596 | 39 |
| 321 | C503Q/A551D/C565N | + | 675 | 52 |
| 322 | I27E/V39A/A112C/R134Q/Q205T/P210C/L214E/A551D/C565N | + | 593 | 41 |
| 323 | R134Q/C503Q/A547D/A551D | + | 666 | 51 |
| 324 | I27E/A112C/Q205T/P266H/L278D/I285E/C503Q | + | 631 | 46 |
| 325 | P266H/L278D/C503Q | + | 680 | 52 |
| 326 | I27E/V39A/Q205T/P266H/A551D | + | 635 | 44 |
| 327 | Q205T/L214E/I285E/C503Q/C565N | + | 627 | 48 |
| 328 | I27E/V105C/R134Q/Q205T/L214E/P266H/L278D/C503Q/C565N | + | 600 | 48 |
| 329 | I27E/V39A/V105C/R134Q/P266H/C503Q | + | 617 | 42 |
| 330 | I27E/V39A/V105C/R134Q/P210C/L214E/I285E/A547D | + | 555 | 38 |
| 331 | I27E/V39A/V105C/Q205T/P210C/L278D/C503Q | + | 616 | 42 |
| 332 | I27E/V39A/R134Q/A547D/C565N | + | 632 | 44 |
| 333 | V105C/A547D/A551D | + | 655 | 50 |
| 334 | I27E/V105C/R134Q/A153R/P210C/L214E/C503Q/A547D | + | 588 | 47 |
| 335 | I27E/P210C/L214E/C503Q/A547D | ++ | 620 | 51 |
| 336 | I27E/V105C/C503Q/A547D/A551D/C565N | + | 636 | 50 |
| 337 | I27E/V105C/R134Q/L214E/L278D/C503Q/A547D/A551D/C565N | + | 600 | 48 |
| 338 | I27E/V39A/V105C/A153R/Q205T/L278D/C503Q/A547D/A551D | + | 612 | 41 |
| 339 | I27E/V39A/V105C/A112C/L214E/I285E/C503Q/A547D | + | 573 | 39 |
| 340 | L214E/A547D | + | 648 | 51 |
| 341 | V105C/Q205T/L214E/L278D | + | 628 | 49 |
| 342 | I27E/V39A/Q205T/L214E/C503Q/C565N | + | 614 | 44 |
| 343 | I27E/P210C | + | 651 | 51 |
| 344 | V105C/Q205T/C503Q/A551D | + | 649 | 49 |
| 345 | I27E/V39A/A112C/R134Q/P266H/I285E | + | 613 | 39 |
| 346 | V39A/P210C/L214E/L278D/I285E/C503Q/A551D | + | 603 | 41 |
| 347 | I27E/Q205T/L214E/C503Q/A547D/C565N | + | 624 | 51 |
| 348 | I27E/V39A/L214E/L278D/C503Q/A547D/C565N | + | 614 | 44 |
| 349 | I27E/P210C/C503Q/C565N | + | 651 | 51 |
| 350 | I27E/L278D/C503Q/A551D/C565N | + | 656 | 52 |
| 351 | R134Q/L214E/L278D/C503Q | + | 644 | 50 |
| 352 | I27E/A153R/L214E/L278D/I285E/A551D/C565N | + | 605 | 47 |
| 353 | I27E/V105C/L214E/A551D/C565N | + | 609 | 49 |
| 354 | V39A/R134Q/Q205T/L214E/C503Q/C565N | + | 624 | 43 |

TABLE 9-2

FIOP, Total Immunogenicity (TIS), and Immunogenic Hit Count (IHC) for Variants Targeting TCE-III
("−" = FIOP < 0.7; "+" = FIOP 0.7 < FIOP < 1.4; "++" = FIOP > 1.4)

| Variant # | Active Mutations (as Compared to Variant No. 36) | FIOPC | TIS | IHC |
|---|---|---|---|---|
| Variant 36 |  | + | 71 | 7 |
| 400 | V80I/R134C/P564Q | + | 60 | 5 |
| 401 | V121C | + | 44 | 6 |
| 402 | R134L | + | 78 | 7 |
| 403 | A124G | + | 58 | 7 |
| 404 | R134W | + | 63 | 5 |
| 405 | L126M | + | 56 | 5 |
| 406 | N130C/M370I | + | 62 | 6 |
| 407 | N130Q | + |

TABLE 9-5-continued

FIOP, Total Immunogenicity (TIS), and Immunogenic Hit Count (IHC) for Variants Targeting TCE-VIII.
("−" = FIOP < 0.7; "+" = FIOP 0.7 < FIOP < 1.4; "++" = FIOP > 1.4)

| Variant # | Active Mutations (as Compared to Variant No. 36) | FIOPC | TIS | IHC |
|---|---|---|---|---|
| 701 | A112S/M370A/A507E | + | 71 | 10 |
| 702 | Q240K/H374R | + | 83 | 10 |
| 703 | S461G | + | 83 | 10 |
| 704 | H374D | + | 83 | 10 |
| 705 | M372A | + | 74 | 10 |
| 706 | L349M | + | 83 | 10 |
| 707 | Y378S | + | 74 | 7 |
| 708 | G371H | + | 91 | 11 |
| 709 | Y377N | + | 82 | 10 |
| 710 | I379N | + | 80 | 8 |
| 711 | D191Y/H385N | + | 81 | 10 |
| 712 | I379L | + | 83 | 10 |
| 713 | R43S/H374R | + | 83 | 10 |
| 714 | Q355K/H374S | + | 83 | 10 |
| 715 | P275T/H374R | + | 83 | 10 |
| 716 | H374Q/P396Q | + | 99 | 14 |
| 717 | H385N | + | 81 | 10 |
| 718 | Y378L | + | 78 | 9 |
| 719 | I379C | + | 70 | 7 |
| 720 | M370G | + | 64 | 10 |
| 721 | M372V | + | 76 | 10 |
| 722 | K384R | + | 87 | 10 |
| 723 | A383V | + | 88 | 13 |
| 724 | M147I/H374S | + | 83 | 10 |
| 725 | Y378F/P404Q | + | 85 | 10 |
| 726 | H374S | + | 83 | 10 |
| 727 | Y378E | + | 55 | 2 |
| 728 | H374R/G417C | + | 83 | 10 |
| 729 | L418M | + | 83 | 10 |
| 730 | S525L | + | 83 | 10 |
| 731 | Y378D | + | 60 | 4 |
| 732 | A383S | + | 88 | 10 |
| 733 | D387S | + | 96 | 11 |
| 734 | L382H | + | 78 | 10 |
| 735 | L382C | + | 76 | 8 |
| 736 | G371Q | + | 84 | 10 |
| 737 | H374L | + | 85 | 11 |
| 738 | Y378C | + | 58 | 5 |
| 739 | H374A | + | 83 | 10 |
| 740 | L375M | + | 77 | 10 |
| 741 | H385C | + | 74 | 8 |
| 742 | A334S/H374V | + | 85 | 11 |
| 743 | H374R | + | 83 | 10 |
| 744 | H385M/P403H | + | 83 | 11 |
| 745 | Y378I | + | 83 | 10 |
| 746 | Y377I | + | 86 | 10 |
| 747 | H385G | + | 74 | 7 |
| 748 | H385S/P403H | + | 79 | 9 |
| 749 | H374N | + | 83 | 10 |
| 750 | S187R/L381V | + | 78 | 7 |
| 751 | L382S | + | 77 | 9 |
| 752 | Y377C | + | 75 | 7 |
| 753 | L381V | + | 78 | 7 |
| 754 | G371S | + | 88 | 10 |
| 755 | A256S/L381N | + | 70 | 6 |
| 756 | I379M | + | 80 | 10 |
| 757 | R43S/H374K | + | 83 | 10 |
| 758 | I379H | + | 76 | 7 |
| 759 | M370S | + | 64 | 10 |
| 760 | P275Q/M370S | + | 64 | 10 |
| 761 | G425V | + | 83 | 10 |
| 762 | A447S | + | 83 | 10 |
| 763 | L382M | + | 80 | 10 |
| 764 | G371N | + | 84 | 10 |
| 765 | L381M/Q560K | + | 79 | 10 |
| 767 | L382I | + | 77 | 8 |
| 768 | H374G | + | 83 | 10 |
| 769 | M370I | + | 76 | 10 |
| 770 | Q332K/Y377M | + | 86 | 10 |
| 771 | Y378N | + | 64 | 5 |
| 772 | L375I | + | 83 | 10 |
| 773 | H374T | + | 83 | 10 |
| 774 | L381G | + | 60 | 4 |

TABLE 9-6

FIOP, Total Immunogenicity (TIS), and Immunogenic Hit Count (IHC) for Variants Targeting TCE-IX.
("−" = FIOP < 0.7; "+" = FIOP 0.7 < FIOP < 1.4; "++" = FIOP > 1.4)

| Variant No. | Active Mutations (as Compared to Variant No. 36) | FIOPC | TIS | IHC |
|---|---|---|---|---|
| Variant 36 | | + | 45 | 4 |
| 800 | I439V | + | 49 | 4 |
| 801 | I439C | + | 39 | 1 |
| 802 | S438F | + | 50 | 4 |
| 803 | T433S | + | 44 | 0 |
| 804 | T433A | + | 35 | 0 |
| 805 | Y435Q/H446N | + | 43 | 2 |
| 806 | L431V | + | 28 | 0 |
| 807 | N437Q | + | 40 | 0 |
| 808 | L213M/S438L | + | 46 | 4 |
| 809 | L432C | + | 39 | 2 |
| 810 | L432V | + | 47 | 4 |
| 811 | T433L | + | 50 | 4 |
| 812 | L431P | + | 18 | 0 |
| 813 | I439F | + | 47 | 4 |
| 814 | S286R/Y435T | + | 53 | 4 |
| 815 | S98I | + | 45 | 4 |
| 816 | S438R | + | 48 | 4 |
| 817 | S331I | + | 45 | 4 |
| 818 | S438M | + | 44 | 4 |
| 819 | Q240K/T433Y | + | 41 | 0 |
| 820 | T433I | + | 46 | 3 |
| 821 | T433N | + | 38 | 0 |
| 822 | L431S | + | 27 | 0 |
| 823 | N437G | + | 38 | 0 |
| 824 | L431E | + | 26 | 0 |
| 825 | L431C | + | 25 | 0 |
| 826 | G436T | + | 45 | 0 |
| 827 | G436D | + | 42 | 1 |
| 828 | T433V | + | 59 | 7 |
| 829 | N437T/L538M | + | 52 | 4 |
| 830 | A289S/L431E | + | 26 | 0 |
| 831 | T433Q | + | 37 | 0 |
| 832 | I439L | + | 46 | 4 |
| 833 | F434C | + | 34 | 0 |
| 834 | T433P | + | 35 | 0 |
| 835 | A24S/F434M | + | 69 | 8 |
| 836 | L431G | + | 18 | 0 |
| 837 | S438C | + | 45 | 1 |
| 838 | T433W | + | 33 | 0 |
| 839 | Y435L | + | 57 | 5 |
| 840 | A62S/T433N | + | 38 | 0 |
| 841 | N437E | + | 46 | 3 |
| 842 | A477S | + | 45 | 4 |
| 843 | G436M | + | 87 | 11 |
| 844 | T433R | + | 70 | 10 |
| 845 | S438T | + | 46 | 4 |

TABLE 9-7

FIOP, Total Immunogenicity (TIS), and Immunogenic Hit Count (IHC) for Variants Targeting TCE-X.
("−" = FIOP < 0.7; "+" = FIOP 0.7 < FIOP < 1.4; "++" = FIOP > 1.4)

| Variant # | Active Mutations (as Compared to Variant No. 36) | FIOPC | TIS | IHC |
|---|---|---|---|---|
| Variant 36 |  | + | 47 | 7 |
| 900 | I471V | + | 45 | 7 |
| 901 | F472G | + | 16 | 0 |
| 902 | G483S | + | 60 | 9 |
| 903 | G483A/S524I | + | 64 | 10 |
| 904 | Y475C | + | 20 | 0 |
| 905 | I478N | + | 44 | 6 |
| 906 | V476I | + | 30 | 2 |
| 907 | N474D/R490H | + | 29 | 3 |
| 908 | P275Q | + | 47 | 7 |
| 909 | Q473K | + | 55 | 7 |
| 910 | G483H | + | 58 | 8 |
| 911 | Q473H/A507S | + | 52 | 7 |
| 912 | N474H | + | 49 | 7 |
| 913 | Y475F | + | 58 | 7 |
| 914 | I478S | + | 46 | 6 |
| 915 | Q473M | + | 69 | 9 |
| 916 | V476C | + | 23 | 0 |
| 917 | L104M/V476L | + | 36 | 3 |
| 918 | A119E/G365A | + | 47 | 7 |
| 919 | N474W | + | 51 | 7 |
| 920 | I471K | + | 29 | 2 |
| 921 | Q292H/A479G | + | 35 | 2 |
| 922 | G276V | + | 47 | 7 |
| 923 | I471N | + | 26 | 1 |
| 924 | A479S | + | 53 | 7 |
| 925 | A558S | + | 47 | 7 |
| 926 | Q473S | + | 56 | 8 |
| 927 | Q473R | + | 62 | 8 |
| 928 | Y475Q | + | 33 | 5 |
| 929 | I471G | + | 32 | 3 |
| 930 | A479G | + | 35 | 2 |
| 931 | A70S/N474E | + | 32 | 3 |
| 932 | I471F | + | 48 | 7 |
| 933 | Q58R/Y475H | + | 32 | 5 |
| 934 | F482L | + | 56 | 9 |
| 935 | V476L | + | 36 | 3 |
| 936 | A24E | + | 47 | 7 |
| 937 | N474R | + | 55 | 7 |
| 938 | G483C | + | 49 | 6 |
| 939 | Q473H | + | 52 | 7 |
| 940 | I471M | + | 46 | 7 |
| 941 | I471R | + | 31 | 2 |
| 942 | P404T/A477V | + | 47 | 6 |
| 943 | G483R/G537C | + | 78 | 13 |
| 944 | F482C | + | 45 | 6 |
| 945 | Q355H/I478C | + | 31 | 1 |
| 946 | L206M | + | 47 | 7 |
| 947 | N474A | + | 48 | 7 |
| 948 | Y475L | + | 60 | 7 |
| 949 | I471W | + | 34 | 4 |

TABLE 9-8

FIOP, Total Immunogenicity (TIS), and Immunogenic Hit Count (IHC) for Variants Targeting TCE-I, III, IV, VIII, and X
("−" = FIOP < 0.7; "+" = FIOP 0.7 < FIOP < 1.4; "++" = FIOP > 1.4)

| Variant # | Active Mutations (as Compared to Variant No. 36) | FIOP | TIS | IHC |
|---|---|---|---|---|
| Variant 36 |  | + |  |  |
| 950 | F472G/C503Q/C565N | + | 651 | 45 |
| 951 | L381G/F472GC503Q/C565N | + | 628 | 39 |
| 952 | M133R/C503Q | + | 663 | 48 |
| 953 | M133R/L381G/C565N | + | 640 | 42 |
| 954 | V39A/C503Q/C565N | + | 667 | 45 |
| 955 | V39A/F472G/C503Q/C565N | + | 636 | 38 |
| 956 | V39A/G248C/L381G/F472G/C503Q/C565N | + | 613 | 32 |
| 957 | V39A/K115E/M133R/C565N | ++ | 646 | 39 |
| 958 | V39A/L381G | + | 644 | 39 |
| 959 | V39A/M133R/C503Q | + | 648 | 41 |
| 960 | V39A/M133R/C503Q/C565N | + | 648 | 41 |
| 961 | V39A/M133R/F472G/C503Q/C565N | + | 617 | 34 |
| 962 | V39A/M133R/F472G/C565N | + | 617 | 34 |
| 963 | V39A/M147A/C565N | + | 641 | 35 |
| 964 | V39A/M147A/F472G/C503Q/C565N | + | 610 | 28 |
| 965 | V39A/M147A/F472G/C565N | + | 610 | 28 |
| 966 | V39A/M147A/L381G/C503Q/C565N | + | 618 | 29 |
| 967 | V39A/M147A/L381G/F472G/C503Q/C565N | + | 587 | 22 |
| 968 | V39A/M147A/Y378E/C503Q/C565N | + | 613 | 27 |
| 969 | V39A/M147A/Y378E/C565N | + | 613 | 27 |
| 970 | V39A/Y378E/C503Q/C565N | + | 639 | 37 |
| 971 | V39A/Y378E/C565N | + | 639 | 37 |
| 972 | Y378D/C503Q | + | 659 | 46 |
| 973 | Y378E/F472G/C503Q/C565N | + | 623 | 37 |

TABLE 9-9

FIOP, Total Immunogenicity (TIS), and Immunogenic Hit Count (IHC) for Variants Targeting TCE-III and VIII
("−" = FIOP < 0.7; "+" = FIOP 0.7 < FIOP < 1.4; "++" = FIOP > 1.4)

| Variant # | Active Mutations (as Compared to Variant No. 967) | FIOP | TIS | IHC |
|---|---|---|---|---|
| Variant 967 |  | + |  |  |
| 974 | A129I | − | 598 | 26 |
| 975 | A129V | − | 595 | 24 |
| 976 | A136K | ++ | 595 | 22 |
| 977 | A24E/G381L | + | 604 | 28 |
| 978 | A289S | + | 590 | 23 |
| 979 | A383C | + | 577 | 18 |
| 980 | A383M | ++ | 602 | 28 |
| 981 | G381A | ++ | 598 | 24 |
| 982 | G381C | − | 580 | 22 |
| 983 | G381F | + | 601 | 25 |
| 984 | G381I | ++ | 610 | 27 |
| 985 | G381L | ++ | 610 | 28 |
| 986 | G381M | + | 606 | 28 |
| 987 | G381N | + | 597 | 24 |
| 988 | G381Q | + | 590 | 23 |
| 989 | G381S | + | 601 | 24 |
| 990 | G381T | + | 590 | 23 |
| 991 | H132L | − | 603 | 25 |
| 992 | H132S | − | 592 | 23 |
| 993 | H374G | + | 587 | 22 |
| 994 | H374M | + | 589 | 23 |
| 995 | H374Q | − | 587 | 22 |
| 996 | L127V | − | 576 | 22 |
| 997 | L431M | + | 591 | 22 |
| 998 | L563M | − | 587 | 22 |
| 999 | M372L | − | 580 | 22 |
| 1000 | R134C | − | 576 | 20 |
| 1001 | R134F | + | 588 | 21 |
| 1002 | R134H | + | 579 | 21 |
| 1003 | R134K | − | 585 | 21 |
| 1004 | S131C | − | 579 | 21 |
| 1005 | S131T | + | 580 | 21 |
| 1006 | V388C | + | 577 | 21 |
| 1007 | V388T | + | 578 | 21 |
| 1008 | R134H/V388T | + | 570 | 20 |
| 1009 | R134H/Y378E/G381L | + | 574 | 19 |
| 1010 | R134H/Y378E/G381L/V388T | + | 566 | 19 |

In Vitro Testing of Deimmunized PAL Variants:

The deimmunized PAL variants are tested in a dendritic T-cell assay to empirically test their capacity to elicit a T-cell response. Peripheral blood mononuclear cells (PBMCs) are isolated from a human donor using standard techniques. These cells are used as a source of monocytes that are cultured in defined media to generate immature dendritic cells. These immature dendritic cells (DCs) are loaded with deimmunized PAL variants, and are then induced into a more mature phenotype by further culturing in defined media to provide antigen-primed DCs. CD8+ T cell-depleted donor PBMCs obtained from the same donor samples as the DCs are labeled with CFSE, then cultured with the antigen-primed DCs for 7 days, after which octuplicates are tested. Each DC-T cell culture includes a set of untreated controls (i.e., negative controls). The assay also incorporates reference antigen controls (i.e., positive controls), comprising two potent whole protein antigens. Assays utilizing cells isolated from 50 human donors with diverse Major Histocompatibility Complex Class II alleles provide a statistically relevant assessment of the PAL variants' capacity to elicit a T-cell response.

While the invention has been described with reference to the specific embodiments, various changes can be made and equivalents can be substituted to adapt to a particular situation, material, composition of matter, process, process step or steps, thereby achieving benefits of the invention without departing from the scope of what is claimed.

For all purposes in the United States of America, each and every publication and patent document cited in this disclosure is incorporated herein by reference as if each such publication or document was specifically and individually indicated to be incorporated herein by reference. Citation of publications and patent documents is not intended as an indication that any such document is pertinent prior art, nor does it constitute an admission as to its contents or date.

What is claimed is:

1. An engineered polypeptide comprising an amino acid sequence with at least 90% sequence identity to reference sequence SEQ ID NO: 24, wherein said amino acid sequence comprises an R134Q substitution.

2. The engineered polypeptide of claim 1, wherein said engineered polypeptide further comprises at least one additional substitution at a position in SEQ ID NO:24, and wherein said positions are numbered with reference to SEQ ID NO:24.

3. The engineered polypeptide of claim 1, wherein said engineered polypeptide exhibits at least one improved property selected from enhanced catalytic activity, reduced sensitivity to proteolysis, increased tolerance to acidic pH, as compared to the reference sequence SEQ ID NO:24.

4. The engineered polypeptide of claim 1 wherein the engineered polypeptide further comprises at least one amino acid residue differences as compared to SEQ ID NO:24, wherein the amino acid residue differences are at one or more amino acid positions selected from 20, 24, 27, 39, 43, 45, 47, 54, 58, 59, 62, 70, 73, 80, 82, 91, 94, 98, 104, 105, 110, 112, 115, 117, 118, 119, 121, 123, 124, 125, 126, 127, 128, 129, 130, 131, 133, 135, 139, 140, 141, 142, 143, 144, 145, 146, 147, 149, 150, 151, 153, 154, 156, 157, 158, 159, 172, 174, 175, 176, 177, 178, 180, 187, 191, 195, 199, 205, 206, 210, 212, 213, 214, 232, 240, 243, 245, 247, 248, 250, 256, 257, 266, 270, 275, 278, 279, 285, 286, 289, 290, 292, 304, 305, 307, 308, 309, 319, 321, 326, 331, 332, 334, 349, 355, 364, 365, 369, 370, 371, 372, 374, 375, 377, 378, 379, 381, 382, 383, 384, 385, 387, 389, 394, 396, 399, 400, 403, 404, 407, 417, 418, 425, 431, 432, 433, 434, 435, 436, 437, 438, 439, 443, 446, 447, 453, 456, 459, 460, 461, 463, 471, 472, 473, 474, 475, 476, 477, 478, 479, 482, 483, 503, 507, 521, 522, 524, 525, 528, 538, 546, 547, 551, 558, 560, 564, 565, and/or any combinations thereof, wherein the amino acid positions are numbered with reference to SEQ ID NO:24.

5. The engineered polynucleotide encoding an engineered polypeptide of claim 4, wherein the further amino acid residue difference as compared to SEQ ID NO:24 is selected from one or more of the following substitutions 112C, 158H, 180A, 195E, 240R/W, 243I/L, 245L, 256G, 257W/A, 270K, 304H, 307Q/M, 308Q, 326F, 349M, 364Q, 394V, 399N, 400K, 404A, 443H, 453G, 459F, 460G, 463N, 474Q, 521S, 522Y/F/N, 528L, 546R, and 564 G/L/M, when optimally aligned with the polypeptide of SEQ ID NO:24.

6. The engineered polypeptide of claim 3, wherein the improved property is selected from reduced sensitivity to proteolysis and/or increased tolerance to acidic pH.

7. The engineered polypeptide of claim 6, wherein the engineered polypeptide is resistant to proteolysis by at least one digestive tract enzyme, wherein said engineered polypeptide is resistant to proteolysis by chymotrypsin, trypsin, carboxypeptidases, and/or elastases.

8. The engineered polypeptide of claim 1, wherein said engineered polypeptide is deimmunized.

9. The engineered polypeptide of claim 1, wherein said engineered polypeptide has phenylalanine ammonia lyase activity.

10. The engineered polypeptide of claim 1, wherein said polypeptide is purified.

11. A polynucleotide sequence encoding at least one engineered polypeptide of claim 1.

12. The polynucleotide sequence of claim 11, wherein said polynucleotide sequence is operably linked to a control sequence.

13. The polynucleotide sequence of claim 11, wherein said polynucleotide sequence is codon-optimized.

14. An expression vector comprising at least one polynucleotide sequence of claim 11, and at least one control sequence.

15. The expression vector of claim 14, wherein said control sequence is a promoter.

16. A host cell transformed with at least expression vector of claim 15.

17. A method of producing an engineered polypeptide in a host cell comprising culturing a host cell comprising at least one expression vector of claim 14, under suitable culture conditions, such that at least one engineered phenylalanine ammonia lyase (PAL) polypeptide is produced.

18. The method of claim 17, further comprising recovering at least one engineered polypeptide from the culture and/or host cells.

19. The method of claim 18, further comprising the step of purifying said at least one engineered polypeptide.

20. A composition comprising at least one engineered polypeptide of claim 1.

21. The composition of claim 20, wherein said composition is a pharmaceutical composition.

22. The composition of claim 21, wherein said composition is suitable for the treatment of phenylketonuria.

23. The pharmaceutical composition of claim 21, wherein said composition is suitable for oral administration to a human.

24. The pharmaceutical composition of claim 23, wherein said composition is in the form of a pill, tablet, capsule, gelcap, liquid, or emulsion.

25. The pharmaceutical composition of claim 24, wherein said pill, tablet, capsule, or gelcap further comprises an enteric coating.

26. The pharmaceutical composition of claim 21, wherein said composition is suitable for parenteral injection into a human.

27. The pharmaceutical composition of claim 21, wherein said composition is coadministered with at least one additional therapeutically effective compound.

28. A method for treating and/or preventing the symptoms of phenylketonuria in a subject, comprising providing a subject having phenylketonuria and the pharmaceutical composition of claim 21, and providing said pharmaceutical composition to said subject.

29. The method of claim 28, wherein said symptoms of phenylketonuria are ameliorated.

30. The method of claim 29, wherein said subject is able to eat a diet that is less restricted in its methionine, phenylalanine and/or tyrosine content than diets required by subjects who have not been provided at least one pharmaceutical composition comprising at least one engineered polypeptide having phenylalanine ammonia lyase (PAL) activity.

31. The method of claim 30, wherein said subject is an infant, child, young adult or adult human.

* * * * *

SEQUENCE LISTING

```
<160> NUMBER OF SEQ ID NOS: 33

<210> SEQ ID NO 1
<211> LENGTH: 7407
<212> TYPE: DNA
<213> ORGANISM: Artificial Sequence
<220> FEATURE:
<223> OTHER INFORMATION: Synthetic polynucleotide

<400> SEQUENCE: 1
tctcatgttt gacagcttat catcgataag ctttaatgcg gtagtttatc acagttaaat     60
tgctaacgca gtcaggcacc gtgtatgaaa tctaacaatg cgctcatcgt catcctcggc    120
accgtcaccc tggatgctgt aggcataggc ttggttatgc cggtactgcc gggcctcttg    180
cgggatatcc ggatatagtt cctcctttca gcaaaaaacc cctcaagacc cgtttagagg    240
ccccaagggg ttatgctagt tattgctcag cggtggcagc agccaactca gcttcctttc    300
gggctttgtt agcagccgga tccttaatgc agacacggca gaatgtcctg aacggcctga    360
acaataacac caccggctgc aatatctgca ctaatacgtg caatatgttc atccagaccc    420
tgttcattat cattccaaat atacggacga tctgaggtcg gtttctgacc aacaacatga    480
cgaactgcgc tatacagacg ttcggttgcc ggtgacagac aggcacgtgc atcataatga    540
ccggtttttt tgtaggtacg cagatcaact gcctgaacac caaacatcag ggcaatggca    600
acataattct gaaaaatatc aacgctacga cgtgccaggg ttgcgctggt ataaccctgg    660
ctgttaatat tctggttaaa ctgttcggca tgggtcggaa aacgatctgc aatactatta    720
ccataaaagg tcagcagcgg cataatgcta ttaccgcaaa tctgcagacc tttcagaccc    780
atattaactt tacgttcacg attacccagc agactcggag gcagaccatt gctaaattcc    840
ggtgatgcca gcagtgcaat ctgaacatcc agatgttttg ccagcagacc gatataatag    900
cgcagatgat ccatacccat accaacatac tgacccagaa aattaccacc atgatagctt    960
gcctgattat caacatcaat cagcgggtta tcggtaacgc tgttaatctc aatttcgatt   1020
tgtttggcaa tctggctaat accatcaaca atcggaccca gatactgcgg cagacaacgc   1080
aggctataac gatcctggat cagttcatga tcacgataat catgtttacc atccagttca   1140
tcacgaacca gctggctatt ggccagcagg ctaatcatct gatctgctgc ccacagctga   1200
cccggatgcg gtttgctgtt atggataaac ggatgaaagc tctgatttgt accattcagt   1260
gcctgaatat ccagtgcatg aacacccatt gcaattgcgg tcagaatctg ggtatcataa   1320
acacaatttg ctgcaatacc ggtcataacg ctggtgccat tcatcattgc cagaccttct   1380
```

```
ttcggcagca gggtcagcgg actcagattc agctgacgca gtgcggtcgg tgcgtccatt    1440
tctttgccat taaaatcaac tttaaagctc gggtccaggc caatcaggct accggtaata    1500
tagctcagcg gaaccagatc accgctggca ccaatgctac caaattcata aacatacggg    1560
gtaacaccgg cattcagaaa gatttccatg cgtttaatca gttccagacg aataccgctt    1620
gcaccacgca tgtggctatt tgcacgcagc agcattgctg cacgaacatc tgccagcggc    1680
agtttattac ctgcaccggt tttcagaaac caaaccagat tggtctgcag ttcgcttgcc    1740
tgttcacggc taattgcaac atttgccata ccaccaaaac cgctggtaac accataaatc    1800
ggttcaccgc tttcaactgc attattgata taatcacagc tggcctgaat accctgcaga    1860
atatcggtat tattggtcag gctaaccagg gtgccattac gggcaacacg tgcaacatca    1920
ttgatggtca gttctgatt accaataatc acatttgcgc tgctattgcc ggtaaagcta    1980
aactgctggc tgctggtttt gctctgtgcc tggctcaggg ttttcatatg acgaccttcg    2040
atatggccgc tgctgtgatg atgatgatga tgatgatgat gatggcccat ggtatatctc    2100
cttcttaaag ttaaacaaaa ttatttctag aggggaattg ttatccgctc acaattcccc    2160
tatagtgagt cgtattaatt tcgcgggatc gagatctcga tcctctacgc cggacgcatc    2220
gtggccggca tcaccggcgc cacaggtgcg gttgctggcg cctatatcgc cgacatcacc    2280 gatgggggaag atcgggctcg ccacttcggg ctcatgagcg cttgtttcgg cgtgggtatg    2340
gtggcaggcc ccgtggccgg gggactgttg ggcgccatct ccttgcatgc accattcctt    2400
gcggcggcgg tgctcaacgg cctcaaccta ctactgggct gcttcctaat gcaggagtcg    2460
cataagggag agcgtcgaga tcccggacac catcgaatgg cgcaaaacct ttcgcggtat    2520
ggcatgatag cgcccggaag agagtcaatt cagggtggtg aatgtgaaac cagtaacgtt    2580
atacgatgtc gcagagtatg ccggtgtctc ttatcagacc gtttcccgcg tggtgaacca    2640
ggccagccac gtttctgcga aaacgcggga aaaagtggaa gcggcgatgg cggagctgaa    2700
ttacattccc aaccgcgtgg cacaacaact ggcgggcaaa cagtcgttgc tgattggcgt    2760
tgccacctcc agtctggccc tgcacgcgcc gtcgcaaatt gtcgcggcga ttaaatctcg    2820
cgccgatcaa ctgggtgcca gcgtggtggt gtcgatggta gaacgaagcg gcgtcgaagc    2880
ctgtaaagcg gcggtgcaca atcttctcgc gcaacgcgtc agtgggctga tcattaacta    2940
tccgctggat gaccaggatg ccattgctgt ggaagctgcc tgcactaatg ttccggcgtt    3000
atttcttgat gtctctgacc agacacccat caacagtatt attttctccc atgaagacgg    3060
tacgcgactg ggcgtggagc atctggtcgc attgggtcac cagcaaatcg cgctgttagc    3120
gggcccatta agttctgtct cggcgcgtct gcgtctggct ggctggcata aatatctcac    3180
tcgcaatcaa attcagccga tagcggaacg ggaaggcgca tggagtgcca tgtccggttt    3240
tcaacaaacc atgcaaatgc tgaatgaggg catcgttccc actgcgatgc tggttgccaa    3300
cgatcagatg gcgctgggcg caatgcgcgc cattaccgag tccgggctgc gcgttggtgc    3360
ggatatctcg gtagtgggat acgacgatac cgaagacagc tcatgttata tcccgccgtt    3420
aaccaccatc aaacaggatt ttcgcctgct ggggcaaacc agcgtggacc gcttgctgca    3480
actctctcag ggccaggcgg tgaagggcaa tcagctgttg cccgtctcac tggtgaaaag    3540
aaaaaccacc ctggcgccca atacgcaaac cgcctctccc cgcgcgttgg ccgattcatt    3600
aatgcagctg gcacgacagg tttcccgact ggaaagcggg cagtgagcgc aacgcaatta    3660
atgtaagtta gctcactcat taggcaccgg gatctcgacc gatgcccttg agagccttca    3720
```

```
acccagtcag ctccttccgg tgggcgcggg gcatgactat cgtcgccgca cttatgactg   3780
tcttctttat catgcaactc gtaggacagg tgccggcagc gctctgggtc attttcggcg   3840
aggaccgctt tcgctggagc gcgacgatga tcggcctgtc gcttgcggta ttcggaatct   3900
tgcacgccct cgctcaagcc ttcgtcactg gtcccgccac caaacgtttc ggcgagaagc   3960
aggccattat cgccggcatg gcggccgacg cgctgggcta cgtcttgctg gcgttcgcga   4020
cgcgaggctg gatggccttc cccattatga ttcttctcgc ttccggcggc atcgggatgc   4080
ccgcgttgca ggccatgctg tccaggcagg tagatgacga ccatcaggga cagcttcaag   4140
gatcgctcgc ggctcttacc agcctaactt cgatcactgg accgctgatc gtcacggcga   4200
tttatgccgc ctcggcgagc acatggaacg ggttggcatg gattgtaggc gccgccctat   4260
accttgtctg cctccccgcg ttgcgtcgcg gtgcatggag ccgggccacc tcgacctgaa   4320
tggaagccgg cggcacctcg ctaacggatt caccactcca agaattggag ccaatcaatt   4380
cttgcggaga actgtgaatg cgcaaaccaa cccttggcag aacatatcca tcgcgtccgc   4440
catctccagc agccgcacgc ggcgcatctc gggcagcgtt gggtcctggc cacgggtgcg   4500
catgatcgtg ctcctgtcgt tgaggacccg gctaggctgg cggggttgcc ttactggtta   4560
gcagaatgaa tcaccgatac gcgagcgaac gtgaagcgac tgctgctgca aaacgtctgc   4620
gacctgagca caacatgaa tggtcttcgg tttccgtgtt tcgtaaagtc tggaaacgcg   4680
gaagtcagcg ccctgcacca ttatgttccg gatctgcatc gcaggatgct gctggctacc   4740
ctgtggaaca cctacatctg tattaacgaa gcgctggcat tgaccctgag tgattttct   4800
ctggtcccgc cgcatccata ccgccagttg tttaccctca caacgttcca gtaaccgggc   4860
atgttcatca tcagtaaccc gtatcgtgag catcctctct cgtttcatcg gtatcattac   4920
ccccatgaac agaaatcccc cttacacgga ggcatcagtg accaaacagg aaaaaaccgc   4980
ccttaacatg gcccgcttta tcagaagcca gacattaacg cttctggaga aactcaacga   5040
gctggacgcg gatgaacagg cagacatctg tgaatcgctt cacgaccacg ctgatgagct   5100
ttaccgcagc tgcctcgcgc gtttcggtga tgacggtgaa aacctctgac acatgcagct   5160
cccggagacg gtcacagctt gtctgtaagc ggatgccggg agcagacaag cccgtcaggg   5220
cgcgtcagcg ggtgttggcg ggtgtcgggg cgcagccatg acccagtcac gtagcgatag   5280
cggagtgtat actggcttaa ctatgcggca tcagagcaga ttgtactgag agtgcaccat   5340
atatgcggtg tgaaataccg cacagatgcg taaggagaaa ataccgcatc aggcgctctt   5400
ccgcttcctc gctcactgac tcgctgcgct cggtcgttcg gctgcggcga gcggtatcag   5460
ctcactcaaa ggcggtaata cggttatcca cagaatcagg ggataacgca ggaaagaaca   5520
tgtgagcaaa aggccagcaa aaggccagga accgtaaaaa ggccgcgttg ctggcgtttt   5580
tccataggct ccgcccccct gacgagcatc acaaaaatcg acgctcaagt cagaggtggc   5640
gaaacccgac aggactataa agataccagg cgtttccccc tggaagctcc ctcgtgcgct   5700
ctcctgttcc gaccctgccg cttaccggat acctgtccgc ctttctccct tcgggaagcg   5760
tggcgctttc tcatagctca cgctgtaggt atctcagttc ggtgtaggtc gttcgctcca   5820
agctgggctg tgtgcacgaa ccccccgttc agcccgaccg ctgcgcctta tccggtaact   5880
atcgtcttga gtccaacccg gtaagacacg acttatcgcc actggcagca gccactggta   5940
acaggattag cagagcgagg tatgtaggcg gtgctacaga gttcttgaag tggtggccta   6000
actacgcta cactagaagg acagtatttg gtatctgcgc tctgctgaag ccagttacct   6060
tcggaaaaag agttggtagc tcttgatccg gcaaacaaac caccgctggt agcggtggtt   6120
```

```
ttttttgtttg caagcagcag attacgcgca gaaaaaaagg atctcaagaa gatcctttga    6180
tcttttctac ggggtctgac gctcagtgga acgaaaactc acgttaaggg attttggtca    6240
tgagattatc aaaaaggatc ttcacctaga tccttttaaa ttaaaaatga agttttaaat    6300
caatctaaag tatatatgag taaacttggt ctgacagtta ccaatgctta atcagtgagg    6360
cacctatctc agcgatctgt ctatttcgtt catccatagt tgcctgactc cccgtcgtgt    6420
agataactac gatacgggag ggcttaccat ctggccccag tgctgcaatg ataccgcgag    6480
acccacgctc accggctcca gatttatcag caataaacca gccagccgga agggccgagc    6540
gcagaagtgg tcctgcaact ttatccgcct ccatccagtc tattaattgt tgccgggaag    6600
ctagagtaag tagttcgcca gttaatagtt tgcgcaacgt tgttgccatt gctgcaggca    6660
tcgtggtgtc acgctcgtcg tttggtatgg cttcattcag ctccggttcc caacgatcaa    6720
ggcgagttac atgatccccc atgttgtgca aaaaagcggt tagctccttc ggtcctccga    6780
tcgttgtcag aagtaagttg gccgcagtgt tatcactcat ggttatggca gcactgcata    6840
attctcttac tgtcatgcca tccgtaagat gcttttctgt gactggtgag tactcaacca    6900
agtcattctg agaatagtgt atgcggcgac cgagttgctc ttgcccggcg tcaacacggg    6960
ataataccgc gccacatagc agaactttaa aagtgctcat cattggaaaa cgttcttcgg    7020
ggcgaaaact ctcaaggatc ttaccgctgt tgagatccag ttcgatgtaa cccactcgtg    7080
cacccaactg atcttcagca tcttttactt tcaccagcgt ttctgggtga gcaaaaacag    7140
gaaggcaaaa tgccgcaaaa aagggaataa gggcgacacg gaaatgttga atactcatac    7200
tcttcctttt tcaatattat tgaagcattt atcagggtta ttgtctcatg agcggataca    7260
tatttgaatg tatttagaaa aataaacaaa taggggttcc gcgcacattt ccccgaaaag    7320
tgccacctga cgtctaagaa accattatta tcatgacatt aacctataaa aataggcgta    7380
tcacgaggcc ctttcgtctt caagaat                                        7407
```

<210> SEQ ID NO 2
<211> LENGTH: 1701
<212> TYPE: DNA
<213> ORGANISM: Artificial Sequence
<220> FEATURE:
<223> OTHER INFORMATION: Synthetic polynucleotide

<400> SEQUENCE: 2

```
atgaaaaccc tgagccaggc acagagcaaa accagcagcc agcagtttag ctttaccggc      60
aatagcagcg caaatgtgat tattggtaat cagaaactga ccatcaatga tgttgcacgt     120
gttgcccgta atggcaccct ggttagcctg accaataata ccgatattct gcagggtatt     180
caggccagct gtgattatat caataatgca gttgaaagcg tgaaccgat ttatggtgtt      240 accagcggtt ttggtggtat ggcaaatgtt gcaattagcc gtgaacaggc aagcgaactg     300
cagaccaatc tggtttggtt tctgaaaacc ggtgcaggta taaaactgcc gctggcagat     360
gttcgtgcag caatgctgct gcgtgcaaat agccacatgc gtggtgcaag cggtattcgt     420
ctggaactga ttaaacgcat ggaaatcttt ctgaatgccg tgttaccccc gtatgtttat     480
gaatttggta gcattggtgc cagcggtgat ctggttccgc tgagctatat taccggtagc     540
ctgattggcc tggaccccgag ctttaaagtt gattttaatg caaagaaat ggacgcaccg     600 accgcactgc gtcagctgaa tctgagtccg ctgaccctgc tgccgaaaga aggtctggca     660
atgatgaatg gcaccagcgt tatgaccggt attgcagcaa attgtgttta tgatacccag     720
```

```
attctgaccg caattgcaat gggtgttcat gcactggata ttcaggcact gaatggtaca      780
aatcagagct ttcatccgtt tatccataac agcaaaccgc atccgggtca gctgtgggca      840
gcagatcaga tgattagcct gctggccaat agccagctgg ttcgtgatga actggatggt      900
aaacatgatt atcgtgatca tgaactgatc caggatcgtt atagcctgcg ttgtctgccg      960
cagtatctgg gtccgattgt tgatggtatt agccagattg ccaaacaaat cgaaattgag     1020
attaacagcg ttaccgataa cccgctgatt gatgttgata tcaggcaag ctatcatggt     1080 ggtaattttc tgggtcagta tgttggtatg ggtatggatc atctgcgcta ttatatcggt     1140
ctgctggcaa acatctgga tgttcagatt gcactgctgg catcaccgga atttagcaat     1200
ggtctgcctc cgagtctgct gggtaatcgt gaacgtaaag ttaatatggg tctgaaaggt     1260
ctgcagattt gcggtaatag cattatgccg ctgctgacct tttatggtaa tagtattgca     1320
gatcgttttc cgacccatgc cgaacagttt aaccagaata ttaacagcca gggttatacc     1380
agcgcaaccc tggcacgtcg tagcgttgat attttcaga attatgttgc cattgccctg     1440
atgtttggtg ttcaggcagt tgatctgcgt acctacaaaa aaccggtca ttatgatgca     1500 cgtgcctgtc tgtcaccggc aaccgaacgt ctgtatagcg cagttcgtca tgttgttggt     1560
cagaaaccga cctcagatcg tccgtatatt tggaatgata tgaacaggg tctggatgaa     1620 catattgcac gtattagtgc agatattgca gccggtggtg ttattgttca ggccgttcag     1680
gacattctgc cgtgtctgca t                                               1701

<210> SEQ ID NO 3
<211> LENGTH: 1701
<212> TYPE: DNA
<213> ORGANISM: Anabaena variabilis

<400> SEQUENCE: 3
atgaaaaccc tgagccaggc acagagcaaa accagcagcc agcagtttag ctttaccggc       60
aatagcagcg caaatgtgat tattggtaat cagaaactga ccatcaatga tgttgcacgt      120
gttgcccgta atggcaccct ggttagcctg accaataata ccgatattct gcagggtatt      180
caggccagct gtgattatat caataatgca gttgaaagcg gtgaaccgat ttatggtgtt      240
accagcggtt ttggtggtat ggcaaatgtt gcaattagcc gtgaacaggc aagcgaactg      300
cagaccaatc tggtttggtt tctgaaaacc ggtgcaggta taaaactgcc gctggcagat      360
gttcgtgcag caatgctgct gcgtgcaaat agccacatgc gtggtgcaag cggtattcgt      420
ctggaactga ttaaacgcat ggaaatcttt ctgaatgccg tgttaccccg tatgtttat      480 gaatttggta gcattggtgc cagcggtgat ctggttccgc tgagctatat taccggtagc      540
ctgattggcc tggaccccgag ctttaaagtt gattttaatg gcaaagaaat ggacgcaccg      600
accgcactgc gtcagctgaa tctgagtccg ctgacccctgc tgccgaaaga aggtctggca      660
atgatgaatg gcaccagcgt tatgaccggt attgcagcaa attgtgttta tgatacccag      720
attctgaccg caattgcaat gggtgttcat gcactggata ttcaggcact gaatggtaca      780
aatcagagct ttcatccgtt tatccataac agcaaaccgc atccgggtca gctgtgggca      840
gcagatcaga tgattagcct gctggccaat agccagctgg ttcgtgatga actggatggt      900
aaacatgatt atcgtgatca tgaactgatc caggatcgtt atagcctgcg ttgtctgccg      960
cagtatctgg gtccgattgt tgatggtatt agccagattg ccaaacaaat cgaaattgag     1020
attaacagcg ttaccgataa cccgctgatt gatgttgata tcaggcaag ctatcatggt     1080 ggtaattttc tgggtcagta tgttggtatg ggtatggatc atctgcgcta ttatatcggt     1140
```

```
ctgctggcaa aacatctgga tgttcagatt gcactgctgg catcaccgga atttagcaat    1200
ggtctgcctc cgagtctgct gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacagttt aaccagaata ttaacagcca gggttatacc    1380
agcgcaaccc tggcacgtcg tagcgttgat atttttcaga attatgttgc cattgccctg    1440
atgtttggtg ttcaggcagt tgatctgcgt acctacaaaa aaaccggtca ttatgatgca    1500
cgtgcctgtc tgtcaccggc aaccgaacgt ctgtatagcg cagttcgtca tgttgttggt    1560
cagaaaccga cctcagatcg tccgtatatt tggaatgata tgaacaggg tctggatgaa    1620 catattgcac gtattagtgc agatattgca gccggtggtg ttattgttca ggccgttcag    1680
gacattctgc cgtgtctgca t                                              1701
```

<210> SEQ ID NO 4
<211> LENGTH: 567
<212> TYPE: PRT
<213> ORGANISM: Anabaena variabilis

<400> SEQUENCE: 4

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270
```

```
Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 5
<211> LENGTH: 1701
<212> TYPE: DNA
<213> ORGANISM: Artificial Sequence
<220> FEATURE:
<223> OTHER INFORMATION: Synthetic polynucleotide

<400> SEQUENCE: 5
atgaaaaccc tgagtcaggc acagagcaaa accagcagcc agcagtttag ctttaccggc      60
aatagcagcg caaatgtgat tattggtaat cagaaactga ccatcaatga tgttgtacgt    120
gttgcccgta atggcaccct ggttagcctg accaataata ccgatattct gcagggtatt    180
caggccagct gtgattatat caataatgca gttgaaagcg gtgaaccgat ttatggtgtt    240
accagcggtt ttggtggtat ggcaaatgtt gtaattagcc gtaacaggc aagcgaactg    300 cagaccaatc tggtttggtt tctgaaaacc ggtgcaggta taaaactgcc gctggcagat    360
```

```
gttcgtgcag caatgctgct gcgtgcaaat agccacatgc gtggtgcaag cggtattcgt    420
ctggaactga ttaaacgcat ggaaatcttt ctgaatgccg tgttacccc gtatgtttat     480 gaatttggta gcattggtgc cagcggtgat ctggttccgc tgagctatat taccggtagc    540
ctgattggcc tggaccccgag ctttaaagtt gattttaatg caaagaaat ggacgcaccg    600 accgcactgc gtcagctgaa tctgagtccg ctgaccctgc tgccgaaaga aggtctggca    660
atgatgaatg gcaccagcgt tatgaccggt attgcagcaa attgtgttta tgataccag    720 attctgaccg caattgcaat gggtgttcat gcactggata ttcagggact gaatggtaca    780
aatcagagct ttcatccgtt tatccataac agcaaaccgc atccgggtca gctgtgggca    840
gcagatcaga tgattagcct gctggccggt agccagctgg ttcgtgatga actggatggt    900
aaacatgatt atcgtgatca tgaactgatc caggatcgtt atagcctgcg ttgtctgccg    960
cagtatctgg gtccgattgt tgatggtatt agccagattg ccaaacaaat cgaaattgag   1020
attaacagcg ttaccgataa cccgctgatt gatgttgata tcaggcaag ctatcatggt    1080 ggtaattttc tgggtcagta tgttggtatg gtatggatc atctgcgcta ttatatcggt    1140
ctgctggcaa acatctggca tgttcagatt gcactgctgg tatcaccgga atttaacaat    1200
ggtctgcctg cgagtctggt gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacagttt aaccagaata ttaacagcca gggttatacc    1380
agcgcaaccc tggcacgtcg tagcgttgat atttttcaga attatgttgc cattgccctg    1440
atgtttggtg ttcaggcagt tgatctgcgt acctacaaaa aaaccggtca ttatgatgca    1500
cgtgcctgtc tgtcaccggc aaccgaacgt ctgtatagcg cagttcgtca tgttgttggt    1560
cagtatccga gctcagatcg tccgtatatt tggaatgata atgaacaggg tctggatgaa    1620
catattgcac gtattagtgc agatattgca gccggtggtg ttattgttca ggccgttcag    1680
gacattctgc cgtgtctgca t                                               1701
```

<210> SEQ ID NO 6
<211> LENGTH: 567
<212> TYPE: PRT
<213> ORGANISM: Artificial Sequence
<220> FEATURE:
<223> OTHER INFORMATION: Synthetic polypeptide

<400> SEQUENCE: 6

```
Met Lys Thr Leu Ser Gln Ala Gln Ser Lys Thr Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Val Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
```

```
            115                 120                 125
Ala Asn Ser His Met Arg Gly Ala Ser Gly Ile Arg Leu Glu Leu Ile
130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
                180                 185                 190

Asn Gly Lys Glu Met Asp Ala Pro Thr Ala Leu Arg Gln Leu Asn Leu
                195                 200                 205

Ser Pro Leu Thr Leu Leu Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Gly
                245                 250                 255

Leu Asn Gly Thr Asn Gln Ser Phe His Pro Phe Ile His Asn Ser Lys
                260                 265                 270

Pro His Pro Gly Gln Leu Trp Ala Ala Asp Gln Met Ile Ser Leu Leu
                275                 280                 285

Ala Gly Ser Gln Leu Val Arg Asp Glu Leu Asp Gly Lys His Asp Tyr
290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
                340                 345                 350

Asp Asn Gln Ala Ser Tyr His Gly Gly Asn Phe Leu Gly Gln Tyr Val
                355                 360                 365

Gly Met Gly Met Asp His Leu Arg Tyr Tyr Ile Gly Leu Leu Ala Lys
370                 375                 380

His Leu Asp Val Gln Ile Ala Leu Leu Val Ser Pro Glu Phe Asn Asn
385                 390                 395                 400

Gly Leu Pro Ala Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
                420                 425                 430

Thr Phe Tyr Gly Asn Ser Ile Ala Asp Arg Phe Pro Thr His Ala Glu
                435                 440                 445

Gln Phe Asn Gln Asn Ile Asn Ser Gln Gly Tyr Thr Ser Ala Thr Leu
                450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
                500                 505                 510

Ser Ala Val Arg His Val Val Gly Gln Tyr Pro Ser Ser Asp Arg Pro
                515                 520                 525

Tyr Ile Trp Asn Asp Asn Glu Gln Gly Leu Asp Glu His Ile Ala Arg
                530                 535                 540
```

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 7
<211> LENGTH: 1701
<212> TYPE: DNA
<213> ORGANISM: Artificial Sequence
<220> FEATURE:
<223> OTHER INFORMATION: Synthetic polynucleotide

<400> SEQUENCE: 7

```
atgaaaaccc tgagccaggc acagagcaaa accagcagcc agcagtttag ctttaccggc      60
aatagcagcg caaatgtgat tattggtaat cagaaactga ccatcaatga tgttgcacgt     120
gttgcccgta atggcaccct ggttagcctg accaataata ccgatattct gcagggtatt     180
caggccagct gtgattatat caataatgca gttgaaagcg gtgaaccgat ttatggtgtt     240
accagcggtt ttggtggtat ggcaaatgtt gcaattagcc gtgaacaggc aagcgaactg     300
cagaccaatc tggtttggtt tctgaaaacc ggtgcaggta taaactgcc gctggcagat     360
gttcgtgcag caatgctgct gcgtgcaaat agccacatgc gtggtgcaag cggtattcgt     420
ctggaactga ttaaacgcat ggaaatcttt ctgaatgccg tgttacccc gtatgtttat     480
gaatttggta gcattggtgc cagcggtgat ctggttccgc tgagctatat accggtagc     540
ctgattggcc tggacccgag ctttaaagtt gattttaatg caaagaaat ggacgcaccg     600
accgcactgc gtcagctgaa tctgagtccg ctgaccctgc tgccgaaaga aggtctggca     660
atgatgaatg caccagcgt tatgaccggt attgcagcaa attgtgttta tgatacccag     720
attctgaccg caattgcaat gggtgttcat gcactggata ttcaggcact gaatggtaca     780
aatcagagct tcatccgtt tatccataac agcaaaccgc atccgggtca gctgtgggca     840
gcagatcaga tgattagcct gctggccaat agccagctgg ttcgtgatga actggatggt     900
aaacatgatt atcgtgatgg tgaactgatc aggatcgtt atagcctgcg ttgtctgccg     960
cagtatctgg gtccgattgt tgatggtatt agccagattg ccaaacaaat cgaaattgag    1020
attaacagcg ttaccgataa cccgctgatt gatgttgata tcaggcaag ctatcatggt    1080
ggtaattttc tgggtcagta tgttggtatg gtatggatc atctgcgcta ttatatcggt    1140
ctgctggcaa acatctggga tgttcagatt gcactgctgg catcaccgga atttagcaat    1200
ggtctgcctc cgagtctgct gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacagttt aaccagaata ttaacagcca gggttatacc    1380
agcgcaaccc tggcacgtcg tagcgttgat attttttcaga attatgttgc cattgccctg    1440
atgtttggtg ttcaggcagt tgatctgcgt acctacaaaa aaaccggtca ttatgatgca    1500
cgtgcctgtc tgtcaccggc aaccgaacgt ctgtatagcg cagttcgtca tgttgttggt    1560
cagaaaccga cctcagatcg tccgtatatt tggaatgata tgaacaggg tctggatgaa    1620
catattgcac gtattagtgc agatattgca gccggtggtg ttattgttca ggccgttcag    1680
gacattctgc cgtgtctgca t                                              1701
```

<210> SEQ ID NO 8
<211> LENGTH: 567
<212> TYPE: PRT

<213> ORGANISM: Artificial Sequence
<220> FEATURE:
<223> OTHER INFORMATION: Synthetic polypeptide

<400> SEQUENCE: 8

```
Met Lys Thr Leu Ser Gln Ala Gln Ser Lys Thr Ser Ser Gln Phe
1               5                   10                  15

Ser Phe Thr Gly Asn Ser Ala Asn Val Ile Ile Gly Asn Gln Lys
                20                  25                  30

Leu Thr Ile Asn Asp Val Ala Arg Val Ala Arg Asn Gly Thr Leu Val
            35                  40                  45

Ser Leu Thr Asn Asn Thr Asp Ile Leu Gln Gly Ile Gln Ala Ser Cys
50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
                100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
                180                 185                 190

Asn Gly Lys Glu Met Asp Ala Pro Thr Ala Leu Arg Gln Leu Asn Leu
            195                 200                 205

Ser Pro Leu Thr Leu Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
                260                 265                 270

Pro His Pro Gly Gln Leu Trp Ala Ala Asp Gln Met Ile Ser Leu Leu
            275                 280                 285

Ala Asn Ser Gln Leu Val Arg Asp Glu Leu Asp Gly Lys His Asp Tyr
290                 295                 300

Arg Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
                340                 345                 350

Asp Asn Gln Ala Ser Tyr His Gly Gly Asn Phe Leu Gly Gln Tyr Val
            355                 360                 365

Gly Met Gly Met Asp His Leu Arg Tyr Tyr Ile Gly Leu Leu Ala Lys
370                 375                 380

His Leu Asp Val Gln Ile Ala Leu Leu Ala Ser Pro Glu Phe Ser Asn
```

```
                385                 390                 395                 400
            Gly Leu Pro Pro Ser Leu Leu Gly Asn Arg Glu Arg Lys Val Asn Met
                            405                 410                 415
            Gly Leu Lys Gly Leu Gln Ile Cys Gly Asn Ser Ile Met Pro Leu Leu
                        420                 425                 430
            Thr Phe Tyr Gly Asn Ser Ile Ala Asp Arg Phe Pro Thr His Ala Glu
                    435                 440                 445
            Gln Phe Asn Gln Asn Ile Asn Ser Gln Gly Tyr Thr Ser Ala Thr Leu
                450                 455                 460
            Ala Arg Arg Ser Val Asp Ile Phe Gln Asn Tyr Val Ala Ile Ala Leu
            465                 470                 475                 480
            Met Phe Gly Val Gln Ala Val Asp Leu Arg Thr Tyr Lys Lys Thr Gly
                            485                 490                 495
            His Tyr Asp Ala Arg Ala Cys Leu Ser Pro Ala Thr Glu Arg Leu Tyr
                        500                 505                 510
            Ser Ala Val Arg His Val Val Gly Gln Lys Pro Thr Ser Asp Arg Pro
                    515                 520                 525
            Tyr Ile Trp Asn Asp Asn Glu Gln Gly Leu Asp Glu His Ile Ala Arg
                530                 535                 540
            Ile Ser Ala Asp Ile Ala Ala Gly Gly Val Ile Val Gln Ala Val Gln
            545                 550                 555                 560
            Asp Ile Leu Pro Cys Leu His
                            565

<210> SEQ ID NO 9
<211> LENGTH: 1701
<212> TYPE: DNA
<213> ORGANISM: Artificial Sequence
<220> FEATURE:
<223> OTHER INFORMATION: Synthetic polynucleotide

<400> SEQUENCE: 9
atgaaaaccc tgagtcaggc acagagcaaa accagcagcc agcagtttag ctttaccggc      60
aatagcagcg caaatgtgat tattggtaat cagaaactga ccatcaatga tgttgtacgt     120
gttgcccgta atggcaccct ggttagcctg accaataata ccgatattct gcagggtatt     180
caggccagct gtgattatat caataatgca gttgaaagcg tgaaccgat ttatggtgtt      240 accagcggtt ttggtggtat ggcaaatgtt gtaattagcc gtgaacaggc aagcgaactg     300
cagaccaatc tggtttggtt tctgaaaacc ggtgcaggta taaactgcc gctggcagat     360 gttcgtgcag caatgctgct gcgtgcaaat agccacatgc gtggtgcaag cggtattcgt     420
ctggaactga ttaaacgcat ggaaatcttt ctgaatgccg gtgttacccc gtatgtttat     480
gaatttggta gcattggtgc cagcggtgat ctggttccgc tgagctatat taccggtagc     540
ctgattggcc tggacccgag ctttaaagtt gattttaatg caaagaaat ggacgcaccg     600 accgcactgc gtcagctgaa tctgagtccg ctgaccctgc tgccgaaaga aggtctggca     660
atgatgaatg gcaccagcgt tatgaccggt attgcagcaa attgtgttta tgatacccag     720
attctgaccg caattgcaat gggtgttcat gcactggata ttcaggcact gaatggtaca     780
aatcagagct tcatccgtt tatccataac agcaaaccgc atccgggtca gctgtgggca     840
gcagatcaga tgattagcct gctggccggt agccagctgg ttcgtgatga actggatggt     900
aaacatgatt atcgtgatgg tgaactgatc caggatcgtt atagcctgcg ttgtctgccg     960
cagtatctgg gtccgattgt tgatggtatt agccagattg ccaaacaaat cgaaattgag    1020
```

```
attaacagcg ttaccgataa cccgctgatt gatgttgata atcaggcaag ctatcatggt    1080 ggtaatttc  tgggtcagta tgttggtatg ggtatggatc atctgcgcta ttatatcggt    1140
ctgctggcaa aacatctgga tgttcagatt gcactgctgg catcaccgga atttagcaat    1200
ggtctgcctc cgagtctggt gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacagttt aaccagaata ttaacagcca gggttatacc    1380
agcgcaaccc tggcacgtcg tagcgttgat attttcaga  attatgttgc cattgccctg    1440
atgtttggtg ttcaggcagt tgatctgcgt acctacaaaa aaaccggtca ttatgatgca    1500
cgtgcctgtc tgtcaccggc aaccgaacgt ctgtatagcg cagttcgtca tgttgttggt    1560
cagaaaccga gctcagatcg tccgtatatt tggaatgata atgaacaggg tctggatgaa    1620
catattgcac gtattagtgc agatattgca gccggtggtg ttattgttca ggccgttcag    1680
gacattctgc cgtgtctgca t                                              1701
```

<210> SEQ ID NO 10
<211> LENGTH: 567
<212> TYPE: PRT
<213> ORGANISM: Artificial Sequence
<220> FEATURE:
<223> OTHER INFORMATION: Synthetic polypeptide

<400> SEQUENCE: 10

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Val Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240
```

```
Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Gly Ser Gln Leu Val Arg Asp Glu Leu Asp Gly Lys His Asp Tyr
    290                 295                 300

Arg Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Ser Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 11
<211> LENGTH: 1701
<212> TYPE: DNA
<213> ORGANISM: Artificial Sequence
<220> FEATURE:
<223> OTHER INFORMATION: Synthetic polynucleotide

<400> SEQUENCE: 11
atgaaaaccc tgagtcaggc acagagcaaa accagcagcc agcagtttag ctttaccggc      60
aatagcagcg caaatgtgat tattggtaat cagaaactga ccatcaatga tgttgtacgt     120
gttgcccgta atggcaccct ggttagcctg accaataata aagatattct gcagcgtatt     180
```

| | |
|---|---|
| caggccagct gtgattatat caataatgca gttgaaaaag gtgaaccgat ttatggtgtt | 240 |
| accagcggtt ttggtggtat ggcaaatgtt gtaattagcc gtgaacaggc aagcgaactg | 300 |
| cagaccaatc tggtttggtt tctgaaaacc ggtgcaggta ataaactgcc gctggcagat | 360 |
| gttcgtgcag caatgctgct gcgtgcaaat agccacatgc gtggtgcaag cggtattcgt | 420 |
| ctggaactga ttaaacgcat ggaaatcttt ctgaatgccg gtgttacccc gtatgtttat | 480 |
| gaatttggta gcattggtgc cagcggtgat ctggttccgc tgagctatat taccggtagc | 540 |
| ctgattggcc tggacccgag ctttaaagtt gattttaatg caagaaaat ggacgcaccg | 600 |
| accgcactgc gtcagctgaa tctgagtccg ctgaccctgc tgccgaaaga aggtctggca | 660 |
| atgatgaatg gcaccagcgt tatgaccggt attgcagcaa attgtgttta tgatacccag | 720 |
| attctgaccg caattgcaat gggtgttcat gcactggata ttcaggcact gaatggtaca | 780 |
| aatcagagct ttcatccgtt tatccataac agcaaaccgc atccgggtca gctgtgggca | 840 |
| gcagatcaga tgattagcct gctggccggt agccagctgg ttcgtgatga actggatggt | 900 |
| aaacatgatt atatggatgg tgaactgatc caggatcgtt atagcctgcg ttgtctgccg | 960 |
| cagtatctgg gtccgattgt tgatggtatt agccagattg ccaaacaaat cgaaattgag | 1020 |
| attaacagcg ttaccgataa cccgctgatt gatgttgata tcaggcaag ctatcatggt | 1080 |
| ggtaattttc tgggtcagta tgttggtatg ggtatggatc atctgcgcta ttatatcggt | 1140 |
| ctgctggcaa acatctggga tgttcagatt gcactgctgg catcaccgga atttagcaat | 1200 |
| ggtctgcctc cgagtctggt gggtaatcgt gaacgtaaag ttaatatggg tctgaaaggt | 1260 |
| ctgcagattt gcgtaatag cattatgccg ctgctgacct tttatggtaa tagtattgca | 1320 |
| gatcgttttc cgacccatgc cgaacagttt aaccagaata ttaacagcca gggttatacc | 1380 |
| agcgcaaccc tggcacgtcg tagcgttgat atttttcaga attatgttgc cattgccctg | 1440 |
| atgtttggtg ttcaggcagt tgatctgcgt acctacaaaa aaaccggtca ttatgatgca | 1500 |
| cgtgcccagc tgtcaccggc aaccgaacgt ctgtatagcg cagttcgtca tgttgttggt | 1560 |
| aaaaaaccga gctcagatcg tccgtatatt tggaatgata atgaacaggg tctggatgaa | 1620 |
| catattgcac gtattagtgc agatattgca gccggtggtg ttattgttca ggccgttcag | 1680 |
| gacattctgc cgccgctgca t | 1701 |

<210> SEQ ID NO 12
<211> LENGTH: 567
<212> TYPE: PRT
<213> ORGANISM: Artificial Sequence
<220> FEATURE:
<223> OTHER INFORMATION: Synthetic polypeptide

<400> SEQUENCE: 12

```
Met Lys Thr Leu Ser Gln Ala Gln Ser Lys Thr Ser Gln Gln Phe
1               5                  10                  15

Ser Phe Thr Gly Asn Ser Ser Ala Asn Val Ile Ile Gly Asn Gln Lys
            20                  25                  30

Leu Thr Ile Asn Asp Val Val Arg Val Ala Arg Asn Gly Thr Leu Val
        35                  40                  45

Ser Leu Thr Asn Asn Lys Asp Ile Leu Gln Arg Ile Gln Ala Ser Cys
    50                  55                  60

Asp Tyr Ile Asn Asn Ala Val Glu Lys Gly Glu Pro Ile Tyr Gly Val
65                  70                  75                  80

Thr Ser Gly Phe Gly Gly Met Ala Asn Val Val Ile Ser Arg Glu Gln
                85                  90                  95
```

```
Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Gly Ser Gln Leu Val Arg Asp Glu Leu Asp Gly Lys His Asp Tyr
290                 295                 300

Met Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Gln Leu Ser Pro Ala Thr Glu Arg Leu Tyr
            500                 505                 510
```

```
Ser Ala Val Arg His Val Val Gly Lys Lys Pro Ser Ser Asp Arg Pro
    515                 520                 525

Tyr Ile Trp Asn Asp Asn Glu Gln Gly Leu Asp Glu His Ile Ala Arg
530                 535                 540

Ile Ser Ala Asp Ile Ala Ala Gly Gly Val Ile Val Gln Ala Val Gln
545                 550                 555                 560

Asp Ile Leu Pro Pro Leu His
                565

<210> SEQ ID NO 13
<211> LENGTH: 1701
<212> TYPE: DNA
<213> ORGANISM: Artificial Sequence
<220> FEATURE:
<223> OTHER INFORMATION: Synthetic polynucleotide

<400> SEQUENCE: 13 atgaaaccc tgagtcaggc acagagcaaa accagcagcc agcagtttag ctttaccggc     60
aatagcagcg caaatgtgat tattggtaat cagaaactga ccatcaatga tgttgtacgt    120
gttgcccgta atggcaccct ggttagcctg accaataata agatattct gcagcgtatt    180 caggccagct gtgattatat caataatgca gttgaaagcg gtgaaccgat ttatggtgtt    240
accagcggtt tggtggtat ggcaaatgtt gtaattagcc gtgaacaggc aagcgaactg    300
cagaccaatc tggttttggtt tctgaaaacc ggtgcaggta taaactgcc gctggcagat    360 gttcgtgcag caatgctgct gcgtgcaaat agccacatgc gtggtgcaag cggtattcgt    420
ctggaactga ttaaacgcat ggaaatcttt ctgaatgccg tgttacccc gtatgtttat    480 gaatttggta gcattggtgc cagcggtgat ctggttccgc tgagctatat taccggtagc    540
ctgattggcc tggaccccgag ctttaaagtt gattttaatg caaagaaat ggacgcaccg    600 accgcactgc gtcagctgaa tctgagtccg ctgaccctgc tgccgaaaga aggtctggca    660
atgatgaatg caccagcgt tatgaccggt attgcagcaa attgtgttta tgatacccag    720
attctgaccg caattgcaat gggtgttcat gcactggata ttcaggcact gaatggtaca    780
aatcagagct tcatccgtt tatccataac agcaaaccgc atccgggtca gctgtgggca    840
gcagatcaga tgattagcct gctggccggt agccagctgg ttcgtgatga actggatggt    900
aaacatgatt atatggatgg tgaactgatc caggatcgtt atagcctgcg ttgtctgccg    960
cagtatctgg gtccgattgt tgatggtatt agccagattg ccaaacaaat cgaaattgag  1020
attaacagcg ttaccgataa cccgctgatt gatgttgata tcaggcaag ctatcatggt  1080 ggtaattttc tgggtcagta tgttggtatg ggtatggatc atctgcgcta ttatatcggt  1140
ctgctggcaa acatctgga tgttcagatt gcactgctgg catcaccgga atttagcaat  1200
ggtctgcctc cgagtctggt gggtaatcgt gaacgtaaag ttaatatggg tctgaaaggt  1260
ctgcagattt gcggtaatag cattatgccg ctgctgacct tttatggtaa tagtattgca  1320
gatcgttttc cgacccatgc cgaacagttt aaccagaata ttaacagcca gggttatacc  1380
agcgcaaccc tggcacgtcg tagcgttgat attttttcaga attatgttgc cattgccctg  1440
atgtttggtg ttcaggcagt tgatctgcgc acctacaaaa aaaccggtca ttatgatgca  1500
cgtgcccagc tgtcaccggc aaccgaacgt ctgtatagcg cagttcgtca tgttgttggt  1560
aaaaaaccga gctcagatcg tccgtatatt tggaatgata tgaacaggg tctggatgaa  1620 catattgcac gtattagtgc agatattgca gccggtggtg ttattgttca ggccgttcag  1680
gacattctgc cgaacctgca t                                              1701
```

<210> SEQ ID NO 14
<211> LENGTH: 567
<212> TYPE: PRT
<213> ORGANISM: Artificial Sequence
<220> FEATURE:
<223> OTHER INFORMATION: Synthetic polypeptide

<400> SEQUENCE: 14

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Val Arg Val Ala Arg Asn Gly Thr Leu Val
        35                  40                  45

Ser Leu Thr Asn Asn Lys Asp Ile Leu Gln Arg Ile Gln Ala Ser Cys
    50                  55                  60

Asp Tyr Ile Asn Ala Val Glu Ser Gly Glu Pro Ile Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Gly Ser Gln Leu Val Arg Asp Glu Leu Asp Gly Lys His Asp Tyr
    290                 295                 300

Met Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365
```

```
Gly Met Gly Met Asp His Leu Arg Tyr Tyr Ile Gly Leu Leu Ala Lys
        370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Gln Leu Ser Pro Ala Thr Glu Arg Leu Tyr
            500                 505                 510

Ser Ala Val Arg His Val Val Gly Lys Lys Pro Ser Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Val Gln Ala Val Gln
545                 550                 555                 560

Asp Ile Leu Pro Asn Leu His
                565
```

<210> SEQ ID NO 15
<211> LENGTH: 1701
<212> TYPE: DNA
<213> ORGANISM: Artificial Sequence
<220> FEATURE:
<223> OTHER INFORMATION: Synthetic polynucleotide

<400> SEQUENCE: 15

```
atgaaaaccc tgagtcaggc acagagcaaa accagcagcc agcagtttag ctttaccggc     60
aatagcagcg caaatgtgat tattggtaat cagaaactga ccatcaatga tgttgcgcgt    120
gttgcccgta atggcaccct ggttagcctg accaataata ccgatattct gcagggtatt    180
caggccagct gtgattatat caataatgca gttgaaagcg tgaaccgat ttatggtgtt     240
accagcggtt ttggtggtat ggcaaatgtt gtaattagcc gtgaacaggc aagcgaactg    300
cagaccaatc tggtttggtt tctgaaaacc ggtgcaggta taaaactgcc gctggcagat    360
gttcgtgcag caatgctgct gcgtgcaaat agccacatgc atggtgcaag cggtattcgt    420
ctggaactga ttaaacgcgc ggaaatcttt ctgaatgccg tgttacccc gtatgtttat    480
gaatttggta gcattggtgc cagcggtgat ctggttccgc tgagctatat taccggtagc    540
ctgattggcc tggacccgag ctttaaagtt gattttaatg caaagaaat ggacgcaccg    600
accgcactgc gtcagctgaa tctgagtccg ctgaccctgc tgccgaaaga aggtctggca    660
atgatgaatg caccagcgt tatgaccggt attgcagcaa ttgtgttta tgatacccag    720
attctgaccg caattgcaat gggtgttcat gcactggata ttcaggcact gaatggtaca    780
aatcagagct tcatccgtt tatccataac agcaaaccgc atccgggtca gctgtgggca    840
gcagatcaga tgattagcct gctggccggt agccagctgg ttcgtgatga actggatggt    900
```

```
aaacatgatt atcgtgatgg tgaactgatc caggatcgtt atagcctgcg ttgtctgccg    960
cagtatctgg gtccgattgt tgatggtatt agccagattg ccaaacaaat cgaaattgag   1020
attaacagcg ttaccgataa cccgctgatt gatgttgata tcaggcaag ctatcatggt   1080 ggtaattttc tgggtcagta tgttggtatg ggtatggatc atctgcgcta ttatatcggt   1140
ggcctggcaa aacatctgga tgttcagatt gcactgctgg catcaccgga atttagcaat   1200
ggtctgcctc cgagtctggt gggtaatcgt gaacgtaaag ttaatatggg tctgaaaggt   1260
ctgcagattt gcggtaatag cattatgccg ctgctgacct tttatggtaa tagtattgca   1320
gatcgttttc cgacccatgc cgaacagttt aaccagaata ttaacagcca gggttatacc   1380
agcgcaaccc tggcacgtcg tagcgttgat attggccaga attatgttgc cattgccctg   1440
atgtttggtg ttcaggcagt tgatctgcgt acctacaaaa aaaccggtca ttatgatgca   1500
cgtgcccagc tgtcaccggc aaccgaacgt ctgtatagcg cagttcgtca tgttgttggt   1560
cagaaaccga gctcagatcg tccgtatatt tggaatgata tgaacaggg tctggatgaa   1620 catattgcac gtattagtgc agatattgca gccggtggtg ttattgttca ggccgttcag   1680
gacattctgc cgaacctgca t                                             1701
```

```
<210> SEQ ID NO 16
<211> LENGTH: 567
<212> TYPE: PRT
<213> ORGANISM: Artificial Sequence
<220> FEATURE:
<223> OTHER INFORMATION: Synthetic polypeptide

<400> SEQUENCE: 16
```

```
Met Lys Thr Leu Ser Gln Ala Gln Ser Lys Thr Ser Gln Gln Phe
1               5                   10                  15

Ser Phe Thr Gly Asn Ser Ser Ala Asn Val Ile Ile Gly Asn Gln Lys
                20                  25                  30

Leu Thr Ile Asn Asp Val Ala Arg Val Ala Arg Asn Gly Thr Leu Val
            35                  40                  45

Ser Leu Thr Asn Asn Thr Asp Ile Leu Gln Gly Ile Gln Ala Ser Cys
50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met His Gly Ala Ser Gly Ile Arg Leu Glu Leu Ile
    130                 135                 140

Lys Arg Ala Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
```

```
                210                 215                 220
Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Gly Ser Gln Leu Val Arg Asp Glu Leu Asp Gly Lys His Asp Tyr
290                 295                 300

Arg Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Gly Leu Ala Lys
370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
450                 455                 460

Ala Arg Arg Ser Val Asp Ile Gly Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Gln Leu Ser Pro Ala Thr Glu Arg Leu Tyr
            500                 505                 510

Ser Ala Val Arg His Val Val Gly Gln Lys Pro Ser Ser Asp Arg Pro
        515                 520                 525

Tyr Ile Trp Asn Asp Asn Glu Gln Gly Leu Asp Glu His Ile Ala Arg
530                 535                 540

Ile Ser Ala Asp Ile Ala Ala Gly Gly Val Ile Val Gln Ala Val Gln
545                 550                 555                 560

Asp Ile Leu Pro Asn Leu His
                565

<210> SEQ ID NO 17
<211> LENGTH: 1701
<212> TYPE: DNA
<213> ORGANISM: Artificial Sequence
<220> FEATURE:
<223> OTHER INFORMATION: Synthetic polynucleotide

<400> SEQUENCE: 17
atgaaaaccc tgagtcaggc acagagcaaa accagcagcc agcagtttag ctttaccggc      60
```

```
aatagcagcg caaatgtgat tattggtaat cagaaactga ccatcaatga tgttgcgcgt    120
gttgcccgta atggcaccct ggttagcctg accaataata ccgatattct gcagggtatt    180
caggccagct gtgattatat caataatgca gttgaaagcg gtgaaccgat ttatggtgtt    240
accagcggtt ttggtggtat ggcaaatgtt gtaattagcc gtgaacaggc aagcgaactg    300
cagaccaatc tggtttggtt tctgaaaacc ggtgcaggta taaactgcc gctggcagat     360 gttcgtgcag caatgctgct gcgtgcaaat agccacatgc atggtgcaag cggtattcgt    420
ctggaactga ttaaacgcgc ggaaatcttt ctgaatgccg tgttacccc gtatgtttat     480 gaatttggta gcattggtgc cagcggtgat ctggttccgc tgagctatat taccggtagc    540
ctgattggcc tggacccgag ctttaaagtt gattttaatg caaagaaat ggacgcaccg     600 accgcactgc gtcagctgaa tctgagtccg ctgaccctgc tgccgaaaga aggtctggca    660
atgatgaatg gcaccagcgt tatgaccggt attgcagcaa attgtgttta tgatacccag    720
attctgaccg caattgcaat gggtgttcat gcactggata ttcaggcact gaatggtaca    780
aatcagagct ttcatccgtt tatccataac agcaaaccgc atccgggtca gctgtgggca    840
gcagatcaga tgattagcct gctggccggt agccagctgg ttcgtgatga actggatggt    900
aaacatgatt atcgtgatgg tgaactgatc caggatcgtt atagcctgcg ttgtctgccg    960
cagtatctgg gtccgattgt tgatggtatt agccagattg ccaaacaaat cgaaattgag    1020
attaacagcg ttaccgataa cccgctgatt gatgttgata tcaggcaag ctatcatggt     1080 ggtaattttc tgggtcagta tgttggtatg ggtatggatc atctgcgcta ttatatcggt    1140
ggcctggcaa aacatctgga tacccagatt gcactgctgg catcaccgga atttagcaat    1200
ggtctgcctc cgagtctggt gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacagttt aaccagaata ttaacagcca gggttatacc    1380
agcgcaaccc tggcacgtcg tagcgttgat attggccaga attatgttgc cattgccctg    1440
atgtttggtg ttcaggcagt tgatctgcgt acctacaaaa aaaccggtca ttatgatgca    1500
cgtgcccagc tgtcaccggc aaccgaacgt ctgtatagcg cagttcgtca tgttgttggt    1560
cagaaaccga gctcagatcg tccgtatatt tggaatgata atgaacaggg tctggatgaa    1620
catattgcac gtattagtgc agatattgca gccggtggtg ttattgttca ggccgttcag    1680
gacattctgc cgaacctgca t                                              1701
```

<210> SEQ ID NO 18
<211> LENGTH: 567
<212> TYPE: PRT
<213> ORGANISM: Artificial Sequence
<220> FEATURE:
<223> OTHER INFORMATION: Synthetic polypeptide

<400> SEQUENCE: 18

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60
```

-continued

```
Asp Tyr Ile Asn Asn Ala Val Glu Ser Gly Glu Pro Ile Tyr Gly Val
 65                  70                  75                  80

Thr Ser Gly Phe Gly Gly Met Ala Asn Val Val Ile Ser Arg Glu Gln
             85                  90                  95

Ala Ser Glu Leu Gln Thr Asn Leu Val Trp Phe Leu Lys Thr Gly Ala
        100                 105                 110

Gly Asn Lys Leu Pro Leu Ala Asp Val Arg Ala Ala Met Leu Leu Arg
        115                 120                 125

Ala Asn Ser His Met His Gly Ala Ser Gly Ile Arg Leu Glu Leu Ile
    130                 135                 140

Lys Arg Ala Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Gly Ser Gln Leu Val Arg Asp Glu Leu Asp Gly Lys His Asp Tyr
    290                 295                 300

Arg Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Gly Leu Ala Lys
    370                 375                 380

His Leu Asp Thr Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Gly Gln Asn Tyr Val Ala Ile Ala Leu
465                 470                 475                 480

Met Phe Gly Val Gln Ala Val Asp Leu Arg Thr Tyr Lys Lys Thr Gly
```

485                 490                 495
His Tyr Asp Ala Arg Ala Gln Leu Ser Pro Ala Thr Glu Arg Leu Tyr
            500                 505                 510

Ser Ala Val Arg His Val Val Gly Gln Lys Pro Ser Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Asn Leu His
            565

<210> SEQ ID NO 19
<211> LENGTH: 1701
<212> TYPE: DNA
<213> ORGANISM: Artificial Sequence
<220> FEATURE:
<223> OTHER INFORMATION: Synthetic polynucleotide

<400> SEQUENCE: 19
atgaaaaccc tgagtcaggc acagagcaaa accagcagcc agcagtttag ctttaccggc      60
aatagcagcg caaatgtgat tattggtaat cagaaactga ccatcaatga tgttgcgcgt     120
gttgcccgta atggcaccct ggttagcctg accaataata ccgatattct gcagggtatt     180
caggccagct gtgattatat caataatgca gttgaaagcg gtgaaccgat ttatggtgtt     240
accagcggtt ttggtggtat ggcaaatgtt gtaattagcc gtgaacaggc aagcgaactg     300
cagaccaatc tggtttggtt tctgaaaacc ggtgcaggta taaaactgcc gctggcagat     360
gttcgtgcag caatgctgct gcgtgcaaat agccacatgc atggtgcaag cggtattcgt     420
ctggaactga ttaaacgcgc ggaaatcttt ctgaatgccg tgttaccccc gtatgtttat     480
gaatttggta gcattggtgc cagcggtgat ctggttccgc tgagctatat taccggtagc     540
ctgattggcc tggacccgag ctttaaagtt gattttaatg caaagaaat ggacgcaccg     600
accgcactgc gtcagctgaa tctgagtccg ctgaccctgc tgccgaaaga aggtctggca     660
atgatgaatg gcaccagcgt tatgaccggt attgcagcaa attgtgttta tgataccccag     720
attctgaccg caattgcaat gggtgttcat gcactggata ttcaggcact gaatggtaca     780
aatcagagct ttcatccgtt tatccataac agcaaaccgc atccgggtca gctgtgggca     840
gcagatcaga tgattagcct gctggccggt agccagctgg ttcgtgatga actggatggt     900
aaacatgatt atcgtgatgg tgaactgatc caggatcgtt atagcctgcg ttgtctgccg     960
cagtatctgg gtccgattgt tgatggtatt agccagattg ccaaacaaat cgaaattgag    1020
attaacagcg ttaccgataa cccgctgatt gatgttgata tcaggcaag ctatcatggt    1080
ggtaattttc tgggtcagta tgttggtatg gtatggatc atctgcgcta tgaaatcggt    1140
ctgctggcaa acatctggga tgttcagatt gcactgctgg catcaccgga atttagcaat    1200
ggtctgcctc cgagtctggt gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacagttt aaccagaata ttaacagcca gggttatacc    1380
agcgcaaccc tggcacgtcg tagcgttgat attggccaga attatgttgc cattgccctg    1440
atgtttggtg ttcaggcagt tgatctgcgc acctacaaaa aaaccggtca ttatgatgca    1500
cgtgcccagc tgtcaccggc aaccgaacgt ctgtatagcg cagttcgtca tgttgttggt    1560

-continued

```
cagaaaccga gctcagatcg tccgtatatt tggaatgata atgaacaggg tctggatgaa    1620
catattgcac gtattagtgc agatattgca gccggtggtg ttattgttca ggccgttcag    1680
gacattctgc cgaacctgca t                                              1701
```

<210> SEQ ID NO 20
<211> LENGTH: 567
<212> TYPE: PRT
<213> ORGANISM: Artificial Sequence
<220> FEATURE:
<223> OTHER INFORMATION: Synthetic polypeptide

<400> SEQUENCE: 20

```
Met Lys Thr Leu Ser Gln Ala Gln Ser Lys Thr Ser Gln Gln Phe
1               5                   10                  15

Ser Phe Thr Gly Asn Ser Ser Ala Asn Val Ile Ile Gly Asn Gln Lys
                20                  25                  30

Leu Thr Ile Asn Asp Val Ala Arg Val Ala Arg Asn Gly Thr Leu Val
            35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp Phe Leu Lys Thr Gly Ala
                100                 105                 110

Gly Asn Lys Leu Pro Leu Ala Asp Val Arg Ala Ala Met Leu Leu Arg
            115                 120                 125

Ala Asn Ser His Met His Gly Ala Ser Gly Ile Arg Leu Glu Leu Ile
    130                 135                 140

Lys Arg Ala Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Gly Ser Gln Leu Val Arg Asp Glu Leu Asp Gly Lys His Asp Tyr
    290                 295                 300

Arg Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335
```

```
Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Glu Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Gly Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Gln Leu Ser Pro Ala Thr Glu Arg Leu Tyr
            500                 505                 510

Ser Ala Val Arg His Val Val Gly Gln Lys Pro Ser Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Asn Leu His
                565
```

<210> SEQ ID NO 21
<211> LENGTH: 1701
<212> TYPE: DNA
<213> ORGANISM: Artificial Sequence
<220> FEATURE:
<223> OTHER INFORMATION: Synthetic polynucleotide

<400> SEQUENCE: 21

```
atgaaaaccc tgagtcaggc acagagcaaa accagcagcc agcagtttag ctttaccggc      60
aatagcagcg caaatgtgat tattggtaat cagaaactga ccatcaatga tgttgcgcgt     120
gttgcccgta atggcaccct ggttagcctg accaataata ccgatattct gcagggtatt     180
caggccagct gtgattatat caataatgca gttgaaagcg tgaaccgat ttatggtgtt      240
accagcggtt ttggtggtat ggcaaatgtt gtaattagcc gtgaacaggc aagcgaactg     300
cagaccaatc tggtttggtt tctgaaaacc ggtgcaggta taaactgcc gctggcagat      360
gttcgtgcag caatgctgct gcgtgcaaat agccacatgc atggtgcaag cggtattcgt     420
ctggaactga ttaaacgcgc ggaaatcttt ctgaatgccg tgttacccc gtatgtttat      480
gaatttggta gcattggtgc cagcggtgat ctggttccgc tgagctatat taccggtagc     540
ctgattggcc tggacccgag ctttaaagtt gattttaatg caaagaaat ggacgcaccg      600
accgcactgc gtcagctgaa tctgagtccg ctgaccctgc tgccgaaaga aggtctggca     660
atgatgaatg gcaccagcgt tatgaccggt attgcagcaa attgtgttta tgatacccag     720
```

-continued

| | |
|---|---|
| attctgaccg caattgcaat gggtgttcat gcactggata ttcaggcact gaatggtaca | 780 |
| aatcagagct ttcatccgtt tatccataac agcaaaccgc atccgggtca gctgtgggca | 840 |
| gcagatcaga tgattagcct gctggccggt agccagctgg ttcgtgatga actggatggt | 900 |
| aaacatgatt atcgtgatgg tgaactgatc caggatcgtt atagcctgcg ttgtctgccg | 960 |
| cagtatctgg gtccgattgt tgatggtatt agccagattg ccaaacaaat cgaaattgag | 1020 |
| attaacagcg ttaccgataa cccgctgatt gatgttgata tcaggcaag ctatcatggt | 1080 |
| ggtaattttc tgggtcagta tgttggtatg ggtatggatc atctgcgcta tgaaatcggt | 1140 |
| ctgctggcaa acatctgga tacccagatt gcactgctgg catcaccgga atttagcaat | 1200 |
| ggtctgcctc cgagtctggt gggtaatcgt gaacgtaaag ttaatatggg tctgaaaggt | 1260 |
| ctgcagattt gcggtaatag cattatgccg ctgctgacct tttatggtaa tagtattgca | 1320 |
| gatcgttttc cgacccatgc cgaacagttt aaccagaata ttaacagcca gggttatacc | 1380 |
| agcgcaaccc tggcacgtcg tagcgttgat attggccaga attatgttgc cattgccctg | 1440 |
| atgtttggtg ttcaggcagt tgatctgcgt acctacaaaa aaaccggtca ttatgatgca | 1500 |
| cgtgcccagc tgtcaccggc aaccgaacgt ctgtatagcg cagttcgtca tgttgttggt | 1560 |
| cagaaaccga gctcagatcg tccgtatatt tggaatgata atgaacaggg tctggatgaa | 1620 |
| catattgcac gtattagtgc agatattgca gccggtggtg ttattgttca ggccgttcag | 1680 |
| gacattctgc gaacctgca t | 1701 |

<210> SEQ ID NO 22
<211> LENGTH: 567
<212> TYPE: PRT
<213> ORGANISM: Artificial Sequence
<220> FEATURE:
<223> OTHER INFORMATION: Synthetic polypeptide

<400> SEQUENCE: 22

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met His Gly Ala Ser Gly Ile Arg Leu Glu Leu Ile
    130                 135                 140

Lys Arg Ala Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
         195                 200                 205

Ser Pro Leu Thr Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Gly Ser Gln Leu Val Arg Asp Glu Leu Asp Gly Lys His Asp Tyr
    290                 295                 300

Arg Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Glu Ile Gly Leu Leu Ala Lys
    370                 375                 380

His Leu Asp Thr Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Gly Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Gln Leu Ser Pro Ala Thr Glu Arg Leu Tyr
            500                 505                 510

Ser Ala Val Arg His Val Val Gly Gln Lys Pro Ser Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Asn Leu His
                565

<210> SEQ ID NO 23
<211> LENGTH: 1701
<212> TYPE: DNA
<213> ORGANISM: Artificial Sequence
<220> FEATURE:

<223> OTHER INFORMATION: Synthetic polynucleotide

<400> SEQUENCE: 23

```
atgaaaaccc tgagtcaggc acagagcaaa accagcagcc agcagtttag ccataccggc    60
aatagcagcg caaatgtgat tattggtaat cagaaactga ccatcaatga tgttgtacgt   120
gttgcccgta atggcaccgc ggttagcctg accaataata agatattct gcagcgtatt    180
caggccagct gtgattatat caataatgca gttgaaaaag gtgaaccgat ttatggtgtt   240
accagcggtt ttggtggtat ggcaaatgtt gtaattagcc gtgaacaggc aagcgaactg   300
cagaccaatc tggtttggtt tctgaaaacc ggtgcaggta taaactgcc gctggcagat    360
gttcgtgcag caatgctgct gcgtgcaaat agccacatgc gtggtgcaag cggtattcgt   420
ctggaactga ttaaacgcat ggaaatcttt ctgaatgccg tgttaccc gtatgtttat     480
gaatttggta gcattggtgc cagcggtgat ctggttccgc tgagctatat taccggtagc   540
ctgattggcc tggaccccgag ctttaaagtt gattttaatg caagaaat ggacgcaccg    600
accgcactgc gtcagctgaa tctgagtccg ctgaccctgc agccgaaaga aggtctggca   660
atgatgaatg caccagcgt tatgaccggt attgcagcaa attgtgttta tgataccag    720
attctgaccg caattgcaat gggtgttcat gcactggata ttcaggcact gaatggtaca   780
aatcagagct ttcatccgtt tatccataac agcaaaccgc atccgggtca gctgtgggca   840
gcagatcaga tgattagcct gctggccggt agccagctgg ttcgtgatga actggatggt   900
aaacatgatt atatggatgg tgaactgatc caggatcgtt atagcctgcg ttgtctgccg   960
cagtatctgg gtccgattgt tgatggtatt agccagattg ccaaacaaat cgaaattgag  1020
attaacagcg ttaccgataa cccgctgatt gatgttgata tcaggcaag ctatcatggt  1080
ggtaattttc tgggtcagta tgttggtatg gtatggatc atctgcgcta ttatatcggt   1140
ctgctggcaa acatctgga tgttcagatt gcactgctgg catcaccgga atttagcaat   1200
ggtctgcctc cgagtctggt gggtaatcgt gaacgtaaag ttaatatggg tctgaaaggt  1260
ctgcagattt gcggtaatag cattatgccg ctgctgacct tttatggtaa tagtattgca  1320
gatcgttttc cgacccatgc cgaacagttt aaccagaata ttaacagcca gggttatacc  1380
agcgcaaccc tggcacgtcg tagcgttgat attttttcaga attatgttgc cattgccctg  1440
atgtttggtg ttcaggcagt tgatctgcgt acctacaaaa aaaccggtca ttatgatgca  1500
cgtgcccagc tgtcaccggc aaccgaacgt ctgtatagcg cagttcgtca tgttgttggt  1560
aaaaaaccga gctcagatcg tccgtatatt tggaatgata tgaacaggg tctggatgaa  1620
catattgcac gtattagtgc agatattgca gccggtggtg ttattgttca ggccgttcag  1680
gacattctgc cgccgctgca t                                            1701
```

<210> SEQ ID NO 24
<211> LENGTH: 567
<212> TYPE: PRT
<213> ORGANISM: Artificial Sequence
<220> FEATURE:
<223> OTHER INFORMATION: Synthetic polypeptide

<400> SEQUENCE: 24

```
Met Lys Thr Leu Ser Gln Ala Gln Ser Lys Thr Ser Ser Gln Gln Phe
1               5                   10                  15

Ser His Thr Gly Asn Ser Ser Ala Asn Val Ile Ile Gly Asn Gln Lys
            20                  25                  30

Leu Thr Ile Asn Asp Val Val Arg Val Ala Arg Asn Gly Thr Ala Val
```

-continued

```
            35                  40                  45
Ser Leu Thr Asn Asn Lys Asp Ile Leu Gln Arg Ile Gln Ala Ser Cys
 50                  55                  60

Asp Tyr Ile Asn Asn Ala Val Glu Lys Gly Glu Pro Ile Tyr Gly Val
 65                  70                  75                  80

Thr Ser Gly Phe Gly Gly Met Ala Asn Val Val Ile Ser Arg Glu Gln
                 85                  90                  95

Ala Ser Glu Leu Gln Thr Asn Leu Val Trp Phe Leu Lys Thr Gly Ala
                100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
                180                 185                 190

Asn Gly Lys Glu Met Asp Ala Pro Thr Ala Leu Arg Gln Leu Asn Leu
            195                 200                 205

Ser Pro Leu Thr Leu Gln Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
                260                 265                 270

Pro His Pro Gly Gln Leu Trp Ala Ala Asp Gln Met Ile Ser Leu Leu
            275                 280                 285

Ala Gly Ser Gln Leu Val Arg Asp Glu Leu Asp Gly Lys His Asp Tyr
290                 295                 300

Met Asp Gly Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
                340                 345                 350

Asp Asn Gln Ala Ser Tyr His Gly Gly Asn Phe Leu Gly Gln Tyr Val
            355                 360                 365

Gly Met Gly Met Asp His Leu Arg Tyr Tyr Ile Gly Leu Leu Ala Lys
370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
            435                 440                 445

Gln Phe Asn Gln Asn Ile Asn Ser Gln Gly Tyr Thr Ser Ala Thr Leu
            450                 455                 460
```

```
Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Gln Leu Ser Pro Ala Thr Glu Arg Leu Tyr
            500                 505                 510

Ser Ala Val Arg His Val Val Gly Lys Lys Pro Ser Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Pro Leu His
                565

<210> SEQ ID NO 25
<211> LENGTH: 1701
<212> TYPE: DNA
<213> ORGANISM: Artificial Sequence
<220> FEATURE:
<223> OTHER INFORMATION: Synthetic polynucleotide

<400> SEQUENCE: 25
atgaaaaccc tgagtcaggc acagagcaaa accagcagcc agcagtttag ctttaccggc      60
aatagcagcg caaatgtgat tattggtaat cagaaactga ccatcaatga tgttgcgcgt     120
gttgcccgta atggcaccct ggttagcctg accaataata ccgatattct gcagggtatt     180
caggccagct gtgattatat caataatgca gttgaaagcg gtgaaccgat ttatggtgtt     240
accagcggtt ttggtggtat ggcaaatgtt gtaattagcc gtgaacaggc aagcgaactg     300
cagaccaatc tggtttggtt tctgaaaacc ggtgcaggta taaaactgcc gctggcagat     360
gttcgtgcag caatgctgct gcgtgcaaat agccacatgc gtggtgcaag cggtattcgt     420
ctggaactga ttaaacgcgc ggaaatcttt ctgaatgccg gtgttacccc gtatgtttat     480
gaatttggta gcattggtgc cagcggtgat ctggttccgc tgagctatat taccggtagc     540
ctgattggcc tggacccgag ctttaaagtt gattttaatg caaagaaat ggacgcaccg     600 accgcactgc gtcagctgaa tctgagtccg ctgaccctgc tgccgaaaga aggtctggca     660
atgatgaatg gcaccagcgt tatgaccggt attgcagcaa attgtgttta tgatacccag     720
attctgaccg caattgcaat gggtgttcat gcactggata ttcaggcact gaatggtaca     780
aatcagagct tcatccgtt tatccataac agcaaaccgc atccgggtca gctgtgggca     840
gcagatcaga tgattagcct gctggccggt agccagctgg ttcgtgatga actggatggt     900
aaacatgatt atcgtgatgg tgaactgatc caggatcgtt atagcctgcg ttgtctgccg     960
cagtatctgg gtccgattgt tgatggtatt agccagattg ccaaacaaat cgaaattgag    1020
attaacagcg ttaccgataa cccgctgatt gatgttgata tcaggcaag ctatcatggt    1080 ggtaattttc tgggtcagta tgttggtatg gtatggatc atctgcgcta ttatatcggt    1140
ggcctggcaa acatctggga tgttcagatt gcactgctgg catcaccgga atttagcaat    1200
ggtctgcctc cgagtctggt gggtaatcgt gaacgtaaag ttaatatggg tctgaaaggt    1260
ctgcagattt gcggtaatag cattatgccg ctgctgacct tttatggtaa tagtattgca    1320
gatcgttttc cgacccatgc cgaacagttt aaccagaata ttaacagcca gggttatacc    1380
agcgcaaccc tggcacgtcg tagcgttgat attggccaga attatgttgc cattgccctg    1440
```

```
atgtttggtg ttcaggcagt tgatctgcgt acctacaaaa aaaccggtca ttatgatgca   1500
cgtgcccagc tgtcaccggc aaccgaacgt ctgtatagcg cagttcgtca tgttgttggt   1560
cagaaaccga gctcagatcg tccgtatatt tggaatgata atgaacaggg tctggatgaa   1620
catattgcac gtattagtgc agatattgca gccggtggtg ttattgttca ggccgttcag   1680
gacattctgc cgaacctgca t                                             1701
```

<210> SEQ ID NO 26
<211> LENGTH: 567
<212> TYPE: PRT
<213> ORGANISM: Artificial Sequence
<220> FEATURE:
<223> OTHER INFORMATION: Synthetic polypeptide

<400> SEQUENCE: 26

```
Met Lys Thr Leu Ser Gln Ala Gln Ser Lys Thr Ser Gln Gln Phe
1               5                   10                  15

Ser Phe Thr Gly Asn Ser Ala Asn Val Ile Ile Gly Asn Gln Lys
                20                  25                  30

Leu Thr Ile Asn Asp Val Ala Arg Val Ala Arg Asn Gly Thr Leu Val
                    35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Val Ile Ser Arg Glu Gln
                85                  90                  95

Ala Ser Glu Leu Gln Thr Asn Leu Val Trp Phe Leu Lys Thr Gly Ala
                100                 105                 110

Gly Asn Lys Leu Pro Leu Ala Asp Val Arg Ala Ala Met Leu Leu Arg
            115                 120                 125

Ala Asn Ser His Met Arg Gly Ala Ser Gly Ile Arg Leu Glu Leu Ile
        130                 135                 140

Lys Arg Ala Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
                180                 185                 190

Asn Gly Lys Glu Met Asp Ala Pro Thr Ala Leu Arg Gln Leu Asn Leu
            195                 200                 205

Ser Pro Leu Thr Leu Pro Lys Glu Gly Leu Ala Met Met Asn Gly
        210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
                260                 265                 270

Pro His Pro Gly Gln Leu Trp Ala Ala Asp Gln Met Ile Ser Leu Leu
            275                 280                 285

Ala Gly Ser Gln Leu Val Arg Asp Glu Leu Asp Gly Lys His Asp Tyr
        290                 295                 300

Arg Asp Gly Glu Leu Ile Gln Asp Arg Tyr Ser Leu Arg Cys Leu Pro
```

```
                305                 310                 315                 320
Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
                340                 345                 350

Asp Asn Gln Ala Ser Tyr His Gly Asn Phe Leu Gly Gln Tyr Val
                355                 360                 365

Gly Met Gly Met Asp His Leu Arg Tyr Tyr Ile Gly Gly Leu Ala Lys
        370                 375                 380

His Leu Asp Val Gln Ile Ala Leu Leu Ala Ser Pro Glu Phe Ser Asn
385                 390                 395                 400

Gly Leu Pro Pro Ser Leu Val Gly Asn Arg Glu Arg Lys Val Asn Met
                405                 410                 415

Gly Leu Lys Gly Leu Gln Ile Cys Gly Asn Ser Ile Met Pro Leu Leu
                420                 425                 430

Thr Phe Tyr Gly Asn Ser Ile Ala Asp Arg Phe Pro Thr His Ala Glu
            435                 440                 445

Gln Phe Asn Gln Asn Ile Asn Ser Gln Gly Tyr Thr Ser Ala Thr Leu
            450                 455                 460

Ala Arg Arg Ser Val Asp Ile Gly Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Gln Leu Ser Pro Ala Thr Glu Arg Leu Tyr
                500                 505                 510

Ser Ala Val Arg His Val Val Gly Gln Lys Pro Ser Ser Asp Arg Pro
            515                 520                 525

Tyr Ile Trp Asn Asp Asn Glu Gln Gly Leu Asp Glu His Ile Ala Arg
            530                 535                 540

Ile Ser Ala Asp Ile Ala Ala Gly Gly Val Ile Val Gln Ala Val Gln
545                 550                 555                 560

Asp Ile Leu Pro Asn Leu His
                565

<210> SEQ ID NO 27
<211> LENGTH: 4945
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (140)..(142)
<223> OTHER INFORMATION: n is a, c, g, or t
<220> FEATURE:
<221> NAME/KEY: misc_feature
<222> LOCATION: (1758)..(1758)
<223> OTHER INFORMATION: n is a, c, g, or t
<220> FEATURE:
<221> NAME/KEY: misc_feature
<222> LOCATION: (1761)..(1762)
<223> OTHER INFORMATION: n is a, c, g, or t
<220> FEATURE:
<221> NAME/KEY: misc_feature
<222> LOCATION: (1781)..(1781)
<223> OTHER INFORMATION: n is a, c, g, or t
<220> FEATURE:
<221> NAME/KEY: misc_feature
<222> LOCATION: (1784)..(1784)
<223> OTHER INFORMATION: n is a, c, g, or t
<220> FEATURE:
<221> NAME/KEY: misc_feature
```

<222> LOCATION: (1786)..(1786)
<223> OTHER INFORMATION: n is a, c, g, or t

<400> SEQUENCE: 27

```
tggccaccat caccatcacc attagggaag agcagatggg caagcttgac ctgtgaagtg      60
aaaaatggcg cacattgtgc gacatttttt tttgaattct acgtaaaaag cagccgatac     120
atcggctgct ttttttttgn nngaggttcc aacttgtggt ataatgaaat aagatcactc     180
cggagcgtat tttttgagtt atcgagattt tcaggagcta aggaggaact aaaatggaga     240
aaaaaatcac tggatatacc accgttgata tatcccaatg gcatcgtaaa gaacattttg     300
aggcatttca gtcagttgct caatgtacct ataaccagac cgttcagctg gatattacgg     360
cctttttaaa gaccgtaaag aaaaataagc acaagtttta tccggccttt attcacattc     420
ttgcccgcct gatgaatgct catccggagt tccgtatggc aatgaaagac ggtgagctgg     480
tgatatggga tagtgttcac ccttgttaca ccgttttcca tgagcaaact gaaacgtttt     540
catcgctctg gagtgaatac cacgacgatt tccggcagtt tctacacata tattcgcaag     600
atgtggcgtg ttacggtgaa aacctggcct atttccctaa agggtttatt gagaatatgt     660
ttttcgtctc agccaatccc tgggtgagtt tcaccagttt tgatttaaac gtggccaata     720
tggacaactt cttcgccccc gttttcacca tgggcaaata ttatacgcaa ggcgacaagg     780
tgctgatgcc gctggcgatt caggttcatc atgccgtctg tgatggcttc catgtcggca     840
gaatgcttaa tgaattacaa cagtactgcg atgagtggca gggcggggcg taactgcagg     900
agctcaaaca gcagcctgta ttcaggctgc tttttttcgtt ttggtctgcg cgtaatctct     960
tgctctgaaa cgaaaaaac cgccttgcag ggcggttttt cgaaggttct ctgagctacc    1020
aactctttga accgaggtaa ctggcttgga ggagcgcagt caccaaaact tgtcctttca    1080
gtttagcctt aaccggcgca tgacttcaag actaactcct ctaaatcaat taccagtggc    1140
tgctgccagt ggtgcttttg catgtctttc cgggttggac tcaagacgat agttaccgga    1200
taaggcgcag cggtcggact gaacgggggg ttcgtgcata cagtccagct tggagcgaac    1260
tgcctacccg gaactgagtg tcaggcgtgg aatgagacaa acgcggccat aacagcggaa    1320
tgacaccggt aaaccgaaag gcaggaacag gagagcgcac gagggagccg ccaggggaa    1380
acgcctggta tctttatagt cctgtcgggt ttcgccacca ctgatttgag cgtcagattt    1440
cgtgatgctt gtcaggggggg cggagcctat ggaaaaacgg ctttgccgcg ccctctcac    1500
ttccctgtta agtatcttcc tggcatcttc caggaaatct ccgccccgtt cgtaagccat    1560
ttccgctcgc cgcagtcgaa cgaccgagcg tagcgagtca gtgagcgagg aagcggaata    1620
tatcctgtat cacatattct gctgacgcac cggtgcagcc ttttttctcc tgccacatga    1680
agcacttcac tgacaccctc atcagtgaac caccgctggt agcggtggtt tttttaggcc    1740
tatggccttt ttttttttntg nnaaacctttt cgcggtatgg natnanagcg cccggaagag    1800
agtcaattaa gagggtggtg aatgtgaaac cagtaacgtt atacgatgtc gcagagtatg    1860
ccggtgtctc ttatcagacc gtttcccgcg tggtgaacca ggccagccac gtttctgcga    1920
aaacgcggga aaaagtggaa gcggcgatgg cggagctgaa ttacattccc aaccgcgtgg    1980
cacaacaact ggcgggcaaa cagtcgttgc tgattggcgt tgccacctcc agtctggccc    2040
tgcacgcgcc gtcgcaaatt gtcgcggcga ttaaatctcg cgccgatcaa ctgggtgcca    2100
gcgtggtggt gtcgatggta gaacgaagcg gcgtcgaagc ctgtaaagcg gcggtgcaca    2160
atcttctcgc gcaacgcgtc agtgggctga tcattaacta tccgctggat gaccaggatg    2220
```

```
ccattgctgt ggaagctgcc tgcactaatg ttccggcgtt atttcttgat gtctctgacc    2280
agacacccat caacagtatt attttctccc atgaagacgg tacgcgactg ggcgtggagc    2340
atctggtcgc attgggtcac cagcaaatcg cgctgttagc gggcccatta agttctgtct    2400
cggcgcgtct gcgtctggct ggctggcata aatatctcac tcgcaatcaa attcagccga    2460
tagcggaacg ggaaggcgac tggagtgcca tgtccggttt tcaacaaacc atgcaaatgc    2520
tgaatgaggg catcgttccc actgcgatgc tggttgccaa cgatcagatg gcgctgggcg    2580
caatgcgcgc cattaccgag tccgggctgc gcgttggtgc ggacatctcg gtagtgggat    2640
acgacgatac cgaagacagc tcatgttata tcccgccgtt aaccaccatc aaacaggatt    2700
ttcgcctgct ggggcaaacc agcgtggacc gcttgctgca actctctcag ggccaggcgg    2760
tgaagggcaa tcagctgttg cccgtctcac tggtgaaaag aaaaaccacc ctggcgccca    2820
atacgcaaac cgcctctccc cgcgcgttgg ccgattcatt aatgcagctg gcacgacagg    2880
tttcccgact ggaaagcggg cagtgagcgg tacccgataa aagcggcttc ctgacaggag    2940
gccgttttgt ttctcgagtt aattaaggca gtgagcgcaa cgcaattaat gtgagttagc    3000
tcactcatta ggcaccccag gctttacact ttatgcttcc ggctcgtatg ttgtgtggaa    3060
ttgtgagcgg ataacaattt cacacaggaa acagctatga ccatgattac ggattcactg    3120
gccgtcgttt tacaatctag aggccagcct ggccataagg agatatacat atgggccatc    3180
atcatcatca tcatcatcat catcacagca gcggccatat cgaaggtcgt catatgaaaa    3240
ccctgagcca ggcacagagc aaaaccagca gccagcagtt tagctttacc ggcaatagca    3300
gcgcaaatgt gattattggt aatcagaaac tgaccatcaa tgatgttgca cgtgttgccc    3360
gtaatggcac cctggttagc ctgaccaata ataccgatat tctgcagggt attcaggcca    3420
gctgtgatta tatcaataat gcagttgaaa gcggtgaacc gatttatggt gttaccagcg    3480
gttttggtgg tatggcaaat gttgcaatta gccgtgaaca ggcaagcgaa ctgcagacca    3540
atctggtttg gttctgaaaa ccggtgcag gtaataaact gccgctggca gatgttcgtg    3600
cagcaatgct gctgcgtgca aatagccaca tgcgtggtgc aagcggtatt cgtctggaac    3660
tgattaaacg catggaaatc tttctgaatg ccggtgttac cccgtatgtt tatgaatttg    3720
gtagcattgg tgccagcggt gatctggttc cgctgagcta tattaccggt agcctgattg    3780
gcctggaccc gagctttaaa gttgatttta atggcaaaga aatggacgca ccgaccgcac    3840
tgcgtcagct gaatctgagt ccgctgaccc tgctgccgaa agaaggtctg gcaatgatga    3900
atggcaccag cgttatgacc ggtattgcag caaattgtgt ttatgatacc cagattctga    3960
ccgcaattgc aatgggtgtt catgcactgg atattcaggc actgaatggt acaaatcaga    4020
gctttcatcc gtttatccat aacagcaaac cgcatccggg tcagctgtgg gcagcagatc    4080
agatgattag cctgctggcc aatagccagc tggttcgtga tgaactggat ggtaaacatg    4140
attatcgtga tcatgaactg atccaggatc gttatagcct gcgttgtctg ccgcagtatc    4200
tgggtccgat tgttgatggt attagccaga ttgccaaaca aatcgaaatt gagattaaca    4260
gcgttaccga taaccegctg attgatgttg ataatcaggc aagctatcat ggtggtaatt    4320
ttctgggtca gtatgttggt atgggtatgg atcatctgcg ctattatatc ggtctgctgg    4380
caaaacatct ggatgttcag attgcactgc tggcatcacc ggaatttagc aatggtctgc    4440
ctccgagtct gctgggtaat cgtgaacgta aagttaatat gggtctgaaa ggtctgcaga    4500
tttgcggtaa tagcattatg ccgctgctga ccttttatgg taatagtatt gcagatcgtt    4560
ttccgacccca tgccgaacag tttaaccaga atattaacag ccagggttat accagcgcaa    4620
```

```
cccctggcacg tcgtagcgtt gatattttc agaattatgt tgccattgcc ctgatgtttg    4680
gtgttcaggc agttgatctg cgtacctaca aaaaaaccgg tcattatgat gcacgtgcct    4740
gtctgtcacc ggcaaccgaa cgtctgtata gcgcagttcg tcatgttgtt ggtcagaaac    4800
cgacctcaga tcgtccgtat atttggaatg ataatgaaca gggtctggat gaacatattg    4860
cacgtattag tgcagatatt gcagccggtg gtgttattgt tcaggccgtt caggacattc    4920
tgccgtgtct gcattaaggc caaac                                          4945
```

<210> SEQ ID NO 28
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 28

```
ctagaggcca gcctggccat aaggagatat acatatgaaa accctgagcc aggcac        56
```

<210> SEQ ID NO 29
<211> LENGTH: 47
<212> TYPE: DNA
<213> ORGANISM: Artificial Sequence
<220> FEATURE:
<223> OTHER INFORMATION: Synthetic polynucleotide

<400> SEQUENCE: 29

```
gatggtgatg gtggccagtt tggccttaat gcagacacgg cagaatg                  47
```

<210> SEQ ID NO 30
<211> LENGTH: 569
<212> TYPE: PRT
<213> ORGANISM: Nostoc punctiforme

<400> SEQUENCE: 30

```
Met Asn Ile Thr Ser Leu Gln Gln Asn Ile Thr Arg Ser Trp Gln Ile
1               5                   10                  15

Pro Phe Thr Asn Ser Ser Asp Ser Ile Val Thr Val Gly Asp Arg Asn
            20                  25                  30

Leu Thr Ile Asp Glu Val Val Asn Val Ala Arg His Gly Thr Gln Val
        35                  40                  45

Arg Leu Thr Asp Asn Ala Asp Val Ile Arg Gly Val Gln Ala Ser Cys
    50                  55                  60

Asp Tyr Ile Asn Asn Ala Val Glu Thr Ala Gln Pro Ile Tyr Gly Val
65                  70                  75                  80

Thr Ser Gly Phe Gly Gly Met Ala Asp Val Val Ile Ser Arg Glu Gln
                85                  90                  95

Ala Ala Glu Leu Gln Thr Asn Leu Ile Trp Phe Leu Lys Ser Gly Ala
            100                 105                 110

Gly Asn Lys Leu Ser Leu Ala Asp Val Arg Ala Ala Met Leu Leu Arg
        115                 120                 125

Ala Asn Ser His Leu Tyr Gly Ala Ser Gly Ile Arg Leu Glu Leu Ile
    130                 135                 140

Gln Arg Ile Glu Thr Phe Leu Asn Ala Gly Val Thr Pro His Val Tyr
145                 150                 155                 160

Glu Phe Gly Ser Ile Gly Ala Ser Gly Asp Leu Val Pro Leu Ser Tyr
                165                 170                 175

Ile Thr Gly Ala Leu Ile Gly Leu Asp Pro Ser Phe Thr Val Asp Phe
```

```
            180                 185                 190
Asp Gly Lys Glu Met Asp Ala Val Thr Ala Leu Ser Arg Leu Gly Leu
            195                 200                 205

Pro Lys Leu Gln Leu Gln Pro Lys Glu Gly Leu Ala Met Met Asn Gly
            210                 215                 220

Thr Ser Val Met Thr Gly Ile Ala Ala Asn Cys Val Tyr Asp Ala Lys
225                 230                 235                 240

Val Leu Leu Ala Leu Thr Met Gly Val His Ala Leu Ala Ile Gln Gly
            245                 250                 255

Leu Tyr Gly Thr Asn Gln Ser Phe His Pro Phe Ile His Gln Cys Lys
            260                 265                 270

Pro His Pro Gly Gln Leu Trp Thr Ala Asp Gln Met Phe Ser Leu Leu
            275                 280                 285

Lys Asp Ser Ser Leu Val Arg Glu Glu Leu Asp Gly Lys His Glu Tyr
            290                 295                 300

Arg Gly Lys Asp Leu Ile Gln Asp Arg Tyr Ser Leu Arg Cys Leu Ala
305                 310                 315                 320

Gln Phe Ile Gly Pro Ile Val Asp Gly Val Ser Glu Ile Thr Lys Gln
            325                 330                 335

Ile Glu Val Glu Met Asn Ser Val Thr Asp Asn Pro Leu Ile Asp Val
            340                 345                 350

Glu Asn Gln Val Ser Tyr His Gly Gly Asn Phe Leu Gly Gln Tyr Val
            355                 360                 365

Gly Val Thr Met Asp Arg Leu Arg Tyr Tyr Ile Gly Leu Leu Ala Lys
            370                 375                 380

His Ile Asp Val Gln Ile Ala Leu Leu Val Ser Pro Glu Phe Ser Asn
385                 390                 395                 400

Gly Leu Pro Pro Ser Leu Val Gly Asn Ser Asp Arg Lys Val Asn Met
            405                 410                 415

Gly Leu Lys Gly Leu Gln Ile Ser Gly Asn Ser Ile Met Pro Leu Leu
            420                 425                 430

Ser Phe Tyr Gly Asn Ser Leu Ala Asp Arg Phe Pro Thr His Ala Glu
            435                 440                 445

Gln Phe Asn Gln Asn Ile Asn Ser Gln Gly Tyr Ile Ser Ala Asn Leu
            450                 455                 460

Thr Arg Arg Ser Val Asp Ile Phe Gln Asn Tyr Met Ala Ile Ala Leu
465                 470                 475                 480

Met Phe Gly Val Gln Ala Val Asp Leu Arg Thr Tyr Lys Met Lys Gly
            485                 490                 495

His Tyr Asp Ala Arg Thr Cys Leu Ser Pro Asn Thr Val Gln Leu Tyr
            500                 505                 510

Thr Ala Val Cys Glu Val Val Gly Lys Pro Leu Thr Ser Val Arg Pro
            515                 520                 525

Tyr Ile Trp Asn Asp Asn Glu Gln Cys Leu Asp Glu His Ile Ala Arg
            530                 535                 540

Ile Ser Ala Asp Ile Ala Gly Gly Leu Ile Val Gln Ala Val Glu
545                 550                 555                 560

His Ile Phe Ser Ser Leu Lys Ser Thr
                565

<210> SEQ ID NO 31
<211> LENGTH: 571
<212> TYPE: PRT
<213> ORGANISM: Rivularia sp. PCC 7116
```

<400> SEQUENCE: 31

```
Met Asn Thr Val Arg Leu Thr Lys Asn Thr Val Ser Gln Lys Ser Phe
1               5                   10                  15

Ser Phe Leu Asn Asn Ser Asp Ala Ser Val Ile Val Gly Asp Arg Gln
                20                  25                  30

Leu Thr Ile Glu Glu Val Val Ser Val Ala Arg Tyr Arg Ala Arg Val
            35                  40                  45

Lys Leu Thr Glu Asn Leu Glu Lys Leu Ala Asn Val Gln Ala Ser Cys
        50                  55                  60

Asp Phe Ile Arg Asp Ala Val Glu Ser Gly Pro Ile Tyr Gly Val
65                  70                  75                  80

Thr Thr Gly Phe Gly Gly Met Ala Asn Val Val Ile Ser Pro Glu Ser
                85                  90                  95

Ala Thr Leu Leu Gln Asn Asn Leu Met Cys Tyr His Lys Val Gly Ala
                100                 105                 110

Gly Asn Lys Leu Pro Leu Ala Asp Val Arg Ala Ala Met Leu Leu Arg
            115                 120                 125

Ala Asn Ser His Val Ala Gly Ala Ser Gly Ile Arg Leu Glu Leu Ile
        130                 135                 140

Lys Arg Met Leu Ile Phe Leu Asn Ala Gly Val Thr Pro His Val Pro
145                 150                 155                 160

Glu Phe Gly Ser Ile Gly Ala Ser Gly Asp Leu Thr Pro Leu Ala Tyr
                165                 170                 175

Ile Ser Gly Ala Leu Ile Gly Leu Asn Ser Ser Tyr Ile Val Asp Phe
            180                 185                 190

Asp Gly Glu Glu Met Asp Ala Pro Thr Ala Leu Gln Lys Leu Gly Leu
        195                 200                 205

Glu Pro Leu Gln Leu Leu Pro Lys Glu Gly Leu Ala Met Met Asn Gly
210                 215                 220

Thr Ser Val Met Thr Gly Ile Ala Ala Asn Cys Val Gln Asp Thr Arg
225                 230                 235                 240

Ile Leu Leu Ala Leu Ser Val Ala Thr His Ala Leu Thr Ile Gln Gly
                245                 250                 255

Leu Glu Gly Thr Asn Gln Ser Phe His Glu Tyr Ile His Lys Leu Lys
            260                 265                 270

Pro His Ser Gly Gln Ile Trp Ala Ala Ser Gln Met Leu Glu Leu Leu
        275                 280                 285

Ala Gly Ser Gly Leu Ile Arg Asp Glu Leu Asp Gly Ser His Asp Tyr
290                 295                 300

Arg Gly Lys Asn Pro Ile Gln Asp Arg Tyr Ser Leu Arg Cys Leu Pro
305                 310                 315                 320

Gln Tyr Met Gly Pro Ile Val Asp Gly Ile Glu Asp Ile Ala Lys Gln
                325                 330                 335

Val Glu Ile Glu Ile Asn Ser Val Thr Asp Asn Pro Leu Ile Asp Val
            340                 345                 350

Glu Asn Gln Ala Ser Tyr His Gly Gly Asn Phe Leu Gly Gln Tyr Ile
        355                 360                 365

Gly Val Gly Met Asp Arg Leu Arg Tyr His Ile Gly Met Leu Ala Lys
370                 375                 380

His Leu Asp Val Gln Ile Ala Tyr Leu Val Ala Pro Glu Phe Asn Asn
385                 390                 395                 400

Gly Leu Ser Pro Ser Leu Val Gly Asn Gln Gln Arg Thr Val Asn Met
```

```
            405                 410                 415
Gly Leu Lys Gly Leu Gln Ile Thr Gly Asn Ser Ile Met Pro Leu Leu
        420                 425                 430

Thr Phe Tyr Gly Asn Ser Ile Ala Asp Arg Phe Pro Thr His Ala Glu
        435                 440                 445

Gln Tyr Asn Gln Asn Ile Asn Ser Gln Gly Phe Ala Ser Ala Asn Leu
        450                 455                 460

Ala Arg Thr Ser Val Glu Ile Phe Gln Gln Tyr Ile Ala Leu Ala Leu
465                 470                 475                 480

Met Phe Gly Val Gln Ser Val Asp Leu Arg Thr Tyr Ala Ile Ala Gly
        485                 490                 495

His Tyr Asp Ala Arg Ala Thr Leu Ser Pro Ala Thr Gln Asp Leu Tyr
        500                 505                 510

Met Ala Val Arg Asn Val Val Gly Arg Pro Pro Ser Lys Glu Arg Ala
        515                 520                 525

Tyr Ile Trp Asp Asp Asn Glu Gln Gly Leu Asp Ser His Ile Ser Lys
        530                 535                 540

Ile Ala Asp Asp Ile Ala Tyr Gly Gly Gln Ile Val Thr Ala Ile Ser
545                 550                 555                 560

Glu Val Leu Ser Ala Leu Lys Ser Val Asn Asn
        565                 570

<210> SEQ ID NO 32
<211> LENGTH: 565
<212> TYPE: PRT
<213> ORGANISM: Oscillatoria sp. PCC 6506

<400> SEQUENCE: 32

Met Ser Thr Asn Leu Thr Glu Pro Ile Ser Gln Lys Leu Leu Gln Trp
1               5                   10                  15

Leu Glu Pro Asn Leu Ser Ala Val Ile Val Gly Asn Arg Arg Leu Ser
            20                  25                  30

Val Glu Glu Val Ala Arg Val Ala Arg Cys Gly Thr Arg Val Arg Leu
        35                  40                  45

Asn Asp Glu Ser Asp Val Ala Glu Arg Val Gln Ala Ser Cys Asp Tyr
    50                  55                  60

Ile Thr Asp Ala Val Glu Ser Gly Lys Ala Ile Tyr Gly Val Thr Thr
65                  70                  75                  80

Gly Phe Gly Gly Met Ala Asn Thr Glu Ile Ala Pro Glu Glu Ala Ala
                85                  90                  95

Ser Leu Gln Asn Asn Leu Ile Trp Phe Leu Lys Ala Gly Ala Gly Gln
            100                 105                 110

Lys Leu Pro Thr Ala Cys Val Arg Ala Ala Met Leu Leu Arg Ile Asn
        115                 120                 125

Ser His Leu Gln Gly Ala Ser Gly Ile Arg Leu Glu Leu Ile Lys Arg
    130                 135                 140

Met Ile Val Phe Leu Asn Ala Gly Val Thr Pro His Val Cys Glu Leu
145                 150                 155                 160

Gly Ser Ile Gly Ala Ser Gly Asp Leu Val Pro Leu Ala Gln Ile Thr
                165                 170                 175

Gly Ala Leu Ile Gly Leu Asp Asp Ser Phe Thr Val Asp Phe Asn Gly
            180                 185                 190

Arg Glu Met Ser Ala Ile Gln Ala Leu Glu Leu Leu Asp Leu Pro Lys
        195                 200                 205
```

Ile Asp Leu Arg Pro Lys Glu Gly Leu Ala Met Val Asn Gly Thr Ser
    210                 215                 220

Val Met Thr Gly Ile Ala Ala Asn Cys Val Arg Asp Ser Gln Val Met
225                 230                 235                 240

Leu Ala Leu Ala Met Gly Thr His Ala Leu Met Ile Gln Gly Leu Gly
                245                 250                 255

Ala Thr Asn Gln Ser Phe His Pro Phe Ile His Lys Leu Lys Pro His
            260                 265                 270

Phe Gly Gln Val Trp Ala Ala Ser Gln Met Val Glu Leu Ala Gly
        275                 280                 285

Ser Cys Leu Asn Arg Asp Glu Leu Asp Gly Gln His Asp Ala Arg Gly
290                 295                 300

Glu His Pro Ile Gln Asp Arg Tyr Ser Leu Arg Cys Leu Pro Gln Tyr
305                 310                 315                 320

Ile Gly Pro Ile Val Asp Gly Ile Ala Glu Ile Ala Gln Gln Ile Glu
                325                 330                 335

Val Glu Val Asn Ser Val Thr Asp Asn Pro Leu Ile Asp Thr Glu Asn
            340                 345                 350

Gln Ala Ser Tyr His Gly Gly Asn Phe Leu Gly Gln Tyr Val Gly Val
        355                 360                 365

Gly Met Asp Arg Leu Arg Tyr Leu Leu Gly Leu Leu Ala Lys His Leu
370                 375                 380

Asp Val Gln Ile Ala Leu Leu Ala Ala Pro Glu Phe Asn Asn Gly Leu
385                 390                 395                 400

Ser Pro Ser Leu Val Gly Asn Thr Ser Arg Lys Val Asn Met Gly Leu
                405                 410                 415

Lys Gly Leu Gln Ile Ala Gly Asn Ser Ile Met Pro Leu Leu Thr Phe
            420                 425                 430

Tyr Gly Asn Ser Ile Ala Asp Arg Phe Pro Thr His Ala Glu Gln Phe
        435                 440                 445

Asn Gln Asn Ile Asn Ser Gln Gly Phe Ala Ser Ala Asn Leu Ala Arg
450                 455                 460

Arg Ser Ile Glu Leu Phe Gln Gln Tyr Met Ala Ile Ser Leu Met Phe
465                 470                 475                 480

Ala Val Gln Ala Val Asp Leu Arg Thr His Glu Val Ala Gly His Tyr
                485                 490                 495

Asp Ala Arg Glu Cys Leu Ser Pro Leu Ser Leu Pro Leu Tyr Glu Ala
            500                 505                 510

Val Arg Glu Val Val Gly Gln Pro Pro Asn Val Asp Arg Ser Tyr Ile
        515                 520                 525

Trp Asn Asp Asn Glu Gln Ser Leu Asp Ile His Ile Ala Met Ile Ala
530                 535                 540

Ala Asp Ile Ala Gln Glu Gly Arg Ile Val Gln Ala Val Asn Gln Ile
545                 550                 555                 560

Leu Ser Ser Leu Lys
                565

<210> SEQ ID NO 33
<211> LENGTH: 559
<212> TYPE: PRT
<213> ORGANISM: Gloeocapsa sp. PCC 7428

<400> SEQUENCE: 33

Met Asn Thr Ala Val Gln Thr Gln Ala Ser Thr Asn Leu Asn Ala Asp
1               5                   10                  15

```
Thr Ile Leu Leu Gly Asp Arg Asn Leu Thr Ile Asp Glu Val Val Ser
                20                  25                  30

Val Ala Arg His Gly Ala Lys Val Asn Ile Ser Thr Ala Asp Asn Val
            35                  40                  45

Ala Gln Arg Ile Gln Ala Ser Cys Asp Tyr Ile Ala Glu Ala Val Ala
50                  55                  60

Thr Gly Arg Pro Ile Tyr Gly Val Thr Ser Gly Phe Gly Gly Met Ala
65                  70                  75                  80

Asn Val Val Ile Ser Arg Glu Tyr Ala Asp Leu Leu Gln His Asn Leu
                85                  90                  95

Val Trp Tyr His Lys Val Gly Ala Gly Arg Lys Leu Pro Leu Thr Asp
                100                 105                 110

Val Arg Ala Ala Met Leu Leu Arg Val Asn Ser His Leu His Gly Ala
            115                 120                 125

Ser Gly Ile Arg Arg Glu Ile Val Gln Arg Met Glu Met Phe Leu Asn
130                 135                 140

Ala Arg Val Thr Pro His Val Pro Glu Tyr Gly Ser Ile Gly Ala Ser
145                 150                 155                 160

Gly Asp Leu Thr Pro Leu Ser Tyr Ile Thr Gly Ala Leu Ile Gly Leu
                165                 170                 175

Asp Asp Arg Tyr Lys Val Asp Phe Asp Gly Glu Glu Ile Asp Ala Ile
            180                 185                 190

Thr Ala Leu Glu Arg Leu Gly Leu Pro Gln Leu Gln Leu Gln Ala Lys
        195                 200                 205

Glu Gly Leu Ala Met Met Asn Gly Thr Ser Val Met Thr Gly Ile Ala
210                 215                 220

Ala Asn Cys Val Tyr Asp Thr Arg Leu Leu Met Ala Leu Thr Met Gly
225                 230                 235                 240

Ala His Ala Leu Ile Leu Gln Gly Leu Asn Gly Thr Asn Gln Ser Phe
                245                 250                 255

His Pro Phe Ile His Lys Leu Lys Pro His Pro Gly Gln Lys Trp Ala
            260                 265                 270

Ala Ser Thr Met Leu Asp Leu Leu Ala Gly Ser Arg Leu Ile Arg Glu
        275                 280                 285

Glu Leu Asp Gly Thr His Glu Tyr Arg Gly Gln Ala Pro Ile Gln Asp
290                 295                 300

Arg Tyr Ser Leu Arg Cys Leu Ala Gln Tyr Met Gly Pro Ile Val Asp
305                 310                 315                 320

Gly Val Ser Gln Val Ala Gln Gln Val Glu Ile Glu Met Asn Ser Ala
                325                 330                 335

Thr Asp Asn Pro Leu Ile Asp Val Glu Asn Gln Ala Ser Tyr His Gly
            340                 345                 350

Gly Asn Phe Leu Gly Gln Tyr Ile Gly Met Gly Met Asp His Leu Arg
        355                 360                 365

Tyr Tyr Ile Gly Met Met Ala Lys His Leu Asp Val Gln Ile Ala Tyr
370                 375                 380

Leu Val Ala Pro Glu Phe Asn Asn Gly Leu Pro Ala Ser Leu Val Gly
385                 390                 395                 400

Asn Lys Glu Arg Ile Val Asn Met Gly Leu Lys Gly Leu Gln Ile Thr
                405                 410                 415

Gly Asn Ser Ile Met Pro Leu Leu Ser Phe Tyr Gly Asn Ser Ile Ala
            420                 425                 430
```

```
Asp Arg Tyr Pro Thr His Ala Glu Gln Tyr Asn Gln Asn Ile Asn Ser
        435             440             445

Gln Gly Phe Ala Ala Ala Asn Leu Thr Arg Asn Ala Val Glu Ile Phe
    450             455             460

Gln Gln Tyr Met Ala Ile Ala Leu Met Phe Gly Val Gln Ala Val Asp
465             470             475             480

Leu Arg Thr Tyr Ala Tyr Ala Gly His Tyr Asp Ala Ser Glu Cys Leu
            485             490             495

Ser Pro Thr Thr Arg Arg Leu Tyr Gln Ala Val Arg Glu Val Val Gly
            500             505             510

Gln Pro Ser Ser Ala Thr Arg Pro Tyr Ile Trp Asp Asp Arg Glu Gln
        515             520             525

Pro Leu Asp Glu His Ile Ala Lys Ile Ala Ala Asp Ile Ala Ala Glu
        530             535             540

Gly Val Ile Val Ala Ala Val Lys Asp Leu Leu Thr Ser Leu Lys
545             550             555
```